&

US008338116B2

(12) United States Patent
Fang et al.

(10) Patent No.: US 8,338,116 B2
(45) Date of Patent: *Dec. 25, 2012

(54) LABEL FREE BIOSENSORS AND CELLS

(75) Inventors: Ye Fang, Painted Post, NY (US); Ann M. Ferrie, Painted Post, NY (US); Norman H. Fontaine, Painted Post, NY (US); Joydeep Lahiri, Painted Post, NY (US); Po Ki Yuen, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/281,996

(22) Filed: Oct. 26, 2011

(65) Prior Publication Data

US 2012/0071351 A1    Mar. 22, 2012

Related U.S. Application Data

(62) Division of application No. 11/887,809, filed as application No. PCT/US2006/013539 on Apr. 5, 2006, now Pat. No. 8,076,090.

(60) Provisional application No. 60/668,908, filed on Apr. 5, 2005.

(51) Int. Cl.
G01N 33/567    (2006.01)
G01N 21/76    (2006.01)
C12Q 1/02    (2006.01)
(52) U.S. Cl. ............... 435/7.21; 435/29; 436/172
(58) Field of Classification Search .................. None
See application file for complete search history.

(56) References Cited

U.S. PATENT DOCUMENTS

| | | | | |
|---|---|---|---|---|
| 4,815,843 A | 3/1989 | Tiefenthaler et al. | ......... | 356/128 |
| 5,305,074 A | 4/1994 | Feldman | ......... | 356/345 |
| 5,738,825 A | 4/1998 | Rudigier et al. | ......... | 422/82.11 |
| 5,830,766 A | 11/1998 | Attridge et al. | ......... | 436/518 |
| 6,233,471 B1 | 5/2001 | Berner et al. | ......... | 600/345 |
| 6,340,598 B1 | 1/2002 | Herron et al. | ......... | 436/518 |
| 6,707,561 B1 | 3/2004 | Budach et al. | ......... | 356/521 |
| 6,727,071 B1 | 4/2004 | Dunlay et al. | ......... | 435/7.21 |
| 6,818,886 B2 | 11/2004 | Tiefenthaler | ......... | 250/282 |
| 6,867,869 B2 | 3/2005 | Budach et al. | ......... | 356/521 |
| 6,870,630 B2 | 3/2005 | Budach et al. | ......... | 356/521 |
| 6,893,705 B2 | 5/2005 | Thomas et al. | ......... | 428/141 |
| 6,985,664 B2 | 1/2006 | Caracci et al. | ......... | 385/130 |
| 7,064,844 B2 | 6/2006 | Budach et al. | ......... | 356/521 |
| 7,105,347 B2 | 9/2006 | Fang et al. | ......... | 435/455 |
| 7,264,973 B2 | 9/2007 | Lin et al. | ......... | 436/518 |
| 7,286,221 B2 | 10/2007 | Caracci et al. | ......... | 356/300 |
| 7,627,201 B2 | 12/2009 | Tiefenthaler | ......... | 385/12 |
| 7,927,822 B2 | 4/2011 | Genick et al. | ......... | 435/7.2 |
| 2002/0127565 A1 | 9/2002 | Cunningham et al. | ......... | 435/6 |
| 2002/0160534 A1 | 10/2002 | Herron et al. | ......... | 436/518 |
| 2002/0164824 A1 | 11/2002 | Xiao et al. | ......... | 436/524 |
| 2002/0168295 A1 | 11/2002 | Cunningham et al. | ......... | 422/82.05 |
| 2003/0012692 A1 | 1/2003 | Lemee et al. | ......... | 422/57 |
| 2003/0017580 A1 | 1/2003 | Cunningham et al. | ......... | 435/287.2 |
| 2003/0017581 A1 | 1/2003 | Li et al. | ......... | 435/287.2 |
| 2003/0026891 A1 | 2/2003 | Qiu et al. | ......... | 427/58 |
| 2003/0027327 A1 | 2/2003 | Cunningham et al. | ......... | 435/287.2 |
| 2003/0027328 A1 | 2/2003 | Cunningham et al. | ......... | 435/287.2 |
| 2003/0032039 A1 | 2/2003 | Cunningham et al. | ......... | 435/6 |
| 2003/0059855 A1 | 3/2003 | Cunningham et al. | ......... | 435/7.9 |
| 2003/0068657 A1 | 4/2003 | Lin et al. | ......... | 435/7.9 |
| 2003/0077660 A1 | 4/2003 | Pien et al. | ......... | 435/7.1 |
| 2003/0092075 A1 | 5/2003 | Pepper | ......... | 435/7.9 |
| 2003/0113766 A1 | 6/2003 | Pepper et al. | ......... | 435/6 |
| 2003/0124516 A1 | 7/2003 | Chung et al. | ......... | 435/5 |
| 2003/0138208 A1 | 7/2003 | Pawlak et al. | ......... | 385/37 |
| 2003/0194755 A1 | 10/2003 | Schnabel et al. | ......... | 435/7.23 |
| 2003/0211461 A1 | 11/2003 | Kariv et al. | ......... | 435/4 |
| 2004/0009540 A1 | 1/2004 | Soohoo et al. | ......... | 435/7.23 |
| 2004/0023310 A1 | 2/2004 | Kariv et al. | ......... | 435/7.2 |
| 2004/0033539 A1 | 2/2004 | Schnabel et al. | ......... | 435/7.21 |
| 2004/0053209 A1 | 3/2004 | Kariv et al. | ......... | 435/4 |
| 2004/0091397 A1 | 5/2004 | Picard | ......... | 422/99 |
| 2004/0132172 A1 | 7/2004 | Cunningham et al. | ......... | 435/287.2 |
| 2004/0151626 A1 | 8/2004 | Cunningham et al. | ......... | 422/58 |
| 2004/0223881 A1 | 11/2004 | Cunningham et al. | ......... | 422/82.05 |
| 2004/0235198 A1 | 11/2004 | Marx et al. | ......... | 436/527 |
| 2004/0263841 A1 | 12/2004 | Caracci et al. | ......... | 356/300 |
| 2005/0070027 A1 | 3/2005 | Gollier et al. | ......... | 436/518 |
| 2005/0100904 A1 | 5/2005 | Yoshizato et al. | ......... | 435/6 |
| 2005/0158880 A1 | 7/2005 | Ostuni et al. | ......... | 438/1 |
| 2005/0236554 A1 | 10/2005 | Fontaine et al. | ......... | 250/208.1 |
| 2006/0063276 A1 | 3/2006 | Jiang et al. | ......... | 436/518 |
| 2006/0205058 A1 | 9/2006 | Frutos et al. | ......... | 435/287.1 |
| 2006/0205092 A1 | 9/2006 | Lackritz et al. | ......... | 436/525 |

(Continued)

FOREIGN PATENT DOCUMENTS

WO    WO 01/57530    8/2001

(Continued)

OTHER PUBLICATIONS

D.R. Alessi et al., "PD 098059 Is a Specific Inhibitor of the Activation of Mitogen-activated Protein Kinase Kinase in Vitro and in Vivo", *The Journal of Biological Chemistry*, Nov. 17, 1995, vol. 270, No. 46, pp. 27489-27494.

M. Azzi et al., "β-Arrestin-mediated activation of MAPK by inverse agonists reveals distinct active conformations for G protein-coupled receptors", *PNAS*, Sep. 30, 2003, vol. 100, No. 20, pp. 11406-11411.

Z. Bajzer et al., "Binding, Internalization, and Intracellular Processing of Proteins Interacting with Recycling Receptors", *The Journal of Biological Chemistry*, Aug. 15, 1989, vol. 264, No. 23, pp. 13623-13631.

J.G. Baker et al., "Influence of Agonist Efficacy and Receptor Phosphorylation on Antagonsit Affinity Measurements: Differences between Second Messenger and Reporter Gene Responses", *Mol. Pharmacol.*, 2003, vol. 64, No. 3, pp. 679-688.

(Continued)

*Primary Examiner* — Rebecca E. Prouty
*Assistant Examiner* — Paul Martin
(74) *Attorney, Agent, or Firm* — John L. Haack

(57)    ABSTRACT

Disclosed are compositions and methods for using label free optical biosensors for performing cell assays. In certain embodiments the assays can be performed in highthough put methods and can be multiplexed.

9 Claims, 76 Drawing Sheets

U.S. PATENT DOCUMENTS

2006/0223051 A1  10/2006  Fang et al. .................... 435/4

FOREIGN PATENT DOCUMENTS

| WO | WO 02/08762    | 1/2002  |
|----|----------------|---------|
| WO | WO 2004/044171 | 5/2004  |
| WO | WO 2005/017507 | 2/2005  |
| WO | WO 2006/107967 | 10/2006 |
| WO | WO 2007/015878 | 2/2007  |
| WO | WO 2007/018872 | 2/2007  |

OTHER PUBLICATIONS

D.W. Barnes, "Epidermal Growth Factor Inhibits Growth of A431 Human Epidermoid Carcinoma in Serum-free Cell Culture", *The Journal of Cell Biology*, Apr. 1982, vol. 93, pp. 1-4.

O. Beske et al., "A Novel Encoded Particle Technology that Enables Simultaneous Interrogation of Multiple Cell Types", *The Society of Biomolecular Screening*, 2004, vol. 9, No. 3, pp. 173-185.

Brecht et al., "Optical Probes and Transducers*", *Biosensors and Bioelectronics*, vol. 10, 1995, pp. 923-936.

W. Budach et al., "Planar Waveguides as High-Performance Sensing Platforms for Fluorescence-Based Multiplexed Oligonucleotide Hybridization Assays", *Anal. Chem.*, 1999, vol. 71, pp. 3347-3355.

P. Burke et al., "Regulation of Epidermal Growth Factor Receptor Signaling by Endocytosis and Intracellular Trafficking", *Molecular Biology of the Cell*, Jun. 2001, vol. 12, pp. 1897-1910.

K. Choudhuri et al., "T-cell receptor triggering is critically dependent on the dimensions of its peptide-MHC ligand", *Nature*, vol. 436, Jul. 28, 2005, pp. 578-582.

Clerc et al., "Direct Immunosensing With an Integrated-Optical Output Grating Coupler", *Sensors & Actuators B*, vol. 40, 1997, pp. 53-58.

B. Cunningham et al., "Label-Free Assays on the BIND System", *The Society for Biomolecular Screening*, 2004, vol. 9, No. 6, pp. 481-490.

Y. Danjo et al., "Actin 'purse string' filaments are anchored by E-cadherin-mediated adherens junctions at the leading edge of the epithelial wound, providing coordinated cell movement", *Journal of Cell Science*, 1998, vol. 111, pp. 3323-3331.

R.J. Daly, "Take Your Partners, Please—Signal Diversification by the erbB Family of Receptor Tyrosine Kinases", Growth Factors, vol. 16, pp. 255-263, (1999).

H. Daub et al., "Role of transactivation of the EGF receptor in signalling by G-protein-coupled receptors", *Nature*, Feb. 8, 1996, vol. 379, pp. 557-560.

Drews, "Drug Discovery: A Historical Perspective", *Science*, Mar. 17, 2000, vol. 287, pp. 1960-1964.

G.L. Duveneck et al., "Novel Bioaffinity Sensors for Trace Analysis Based on Luminescence Excitation by Planar Waveguides", *Sensors and Actuators B*, vol. 38-39, 1997, pp. 88-95.

G.L. Duveneck et al., "Review on Fluorescence-Based Planar Waveguide Biosensors", *Proc. SPIE*, vol. 3858, 1999, pp. 59-71.

G.L. Duveneck et al., "Two-Photon Fluorescence Excitation of Macroscopic Areas on Planar Waveguides", *Biosensors and Bioelectronics*, vol. 18, 2003, pp. 504-510.

P.L. Edmiston et al., "Dipole Orientation Distributions in Langmuir-Blodgett Films by Planar Waveguide Linear Dichroism and Fluorescence Anisotropy", *J. Phys. Chem.*, 1996, vol. 100, pp. 775-784.

Ye Fang et al., "Cellular functions of cholesterol probed with optical biosensors", *Biochimica et Biophysica Acta*, vol. 1763, 2006, pp. 254-261.

Y. Fang et al., "Characteristics of Dynamic Mass Redistribution of Epidermal Growth Factor Receptor Signaling in Living Cells Measured with Label-Free Optical Biosensors", *Anal. Chem.*, vol. 77, 2005, pp. 5720-5725.

Y. Fang et al., "G-Protein-Coupled Receptor Microarrays", *ChemBioChem*, Oct. 4, 2002, vol. 3, No. 10, pp. 987-991.

Y. Fang, "Label-Free Cell-Based Assays with Optical Biosensors in Drug Discovery", *Assay and Drug Development Technologies*, vol. 4, No. 5, 2006, pp. 583-595.

Y. Fang et al., "Non-Invasive Optical Biosensor for Assaying Endogenous G Protein-Coupled Receptors in Adherent Cells", *Journal of Pharmacological and Toxicological Method*, vol. 55, 2007, pp. 314-322.

Y. Fang et al., "Optical biosensor differentiates signalling of endogenous $PAR_1$ and $PAR_2$ in A431 cells", *BMC Cell Biology*, 2007, vol. 8, No. 24, pp. 1-12.

Ye Fang et al., "Optical Biosensor Provides Insights for Bradykinin $B_2$ Receptor Signaling in A431 Cells", *FEBS Letters*, vol. 579, 2005, pp. 6365-6374.

Y. Fang et al., "Probing cytoskeleton modulation by optical biosensors", *FEBS Letters*, vol. 579, 2005, pp. 4175-4180.

Y. Fang et al., "Resonant Waveguide Grating Biosensor for Living Cell Sensing", *Biophysical Journal*, vol. 91, Sep. 2006, pp. 1925-1940.

A.R. French et al., "Postendocytic Trafficking of Epidermal Growth Factor-Receptor Complexes Is Mediated Through Saturable and Specific Endosomal Interactions", *The Journal of Biological Chemistry*, Jun. 3, 1994, vol. 269, No. 22, pp. 15749-15755.

I. Giaever et al., "Monitoring fibroblast behaviour in tissue culture with an applied electric field", *Proc. Natl. Acad. Sci.*, Jun. 1984, vol. 81, pp. 3761-3764.

A. Glading et al., "Epidermal Growth Factor Receptor Activation of Calpain Is Required for Fibroblast Motility and Occurs via an ERK/MAP Kinase Signaling Pathway", *The Journal of Biological Chemistry*, Jan. 28, 2000, vol. 275, No. 4, pp. 2390-2398.

H.M. Grandin et al., "Waveguide Excitation Fluorescence Microscopy: A New Tool for Sensing and Imaging the Biointerface", *Biosensors and Bioelectronics*, vol. 21, 2006, pp. 1476-1482.

A. Graness et al., "Protein-tyrosine-phosphatase-mediated epidermal growth factor (EGF) receptor transinactivation and EGF receptor-independent stimulation of mitogen-activated protein kinase by bradykinin in A431 cells", *Biochem. J.*, 2000, vol. 347, pp. 441-447.

A. Grakoui et al., "The Immunological Synapse: A Molecular Machine Controlling T Cell Activation", *Science*, vol. 285, Jul. 9, 1999, pp. 221-227.

S.A. Green et al., "Sustained Activation of a G Protein-coupled Receptor via 'Anchored' Agonist Binding", *The Journal of Biological Chemistry*, vol. 271, No. 39, pp. 24029-24035, (1996).

A. Gschwind et al., "Cell communication networks: epidermal growth factor receptor transactivation as the paradigm for interrreceptor signal transmission", *Oncogene*, 2001, vol. 20, pp. 1594-1600.

M. Halter et al., "Enhanced Optical Waveguide Light Mode Spectroscopy Via Detection of Fluorophore Absorbance", *Review of Scientific Instruments*, vol. 77, 2006, pp. 103105-1-103105-6.

M. Hide et al., "Real-Time Analysis of Ligand-Induced Cell Surface and Intracellular Reactions of Living Mast Cells Using a Surface Plasmon Resonance-Based Biosensor", *Analytical Biochemisny*, vol. 302, 2002, pp. 28-37.

W.R. Holland et al., "Waveguide Mode Enhancement of Molecular Fluorescence", *Optics Letters*, vol. 10, No. 8, Aug. 1985, pp. 414-416.

R. Horváth et al., "Effect of patterns and inhomogeneities on the surface of waveguides used for optical waveguide lightmode spectroscopy applications", *Applied Physics B*, 2001, vol. 72, pp. 441-447.

R. Horváth et al., "Reverse-symmetry waveguides: theory and fabrication", *Applied Physics B*, 2002, vol. 74, pp. 383-393.

C.E. Jordan et al., "Surface Plasmon Resonance Imaging Measurements of DNA Hybridization Adsorption and Streptavidin/DNA Multilayer Formation at Chemically Modified Gold Surfaces", *Anal. Chem.*, 1997, pp. 4939-4947.

P. Lalanne et al., "Highly Improved Convergence of the Coupled-Wave Method for TM Polarization", *J. Opt. Soc. Am. A*, vol. 13, No. 4, Apr. 1996, pp. 779-784.

M.A. Lemmon et al., "Regulation of signal transduction and signal diversity by receptor oligomerization", *Trends Biochem. Sci.*, 1994, vol. 19, pp. 459-463.

G. Liapakis et al., "Synergistic Contributions of the Functional Groups of Epinephrine to Its Affinity and Efficacy at the $\beta_2$ Adrenergic Receptor", *Mol. Pharmacol.*, 2004, vol. 65, No. 5, pp. 1181-1190.

G. Liapakis et al., "The Forgotten Serine", *The Journal of Biological Chemistry*, vol. 275, No. 48, pp. 37779-37788, (2000).

Y. Liu et al., "Structural basis for selective inhibition of Src family kinases by PP1", *Chemistry & Biology*, 1999, vol. 6, No. 9, pp. 671-678.

E. Livnch et al., "Reconstitution of Human Epidermal Growth Factor Receptors and Its Deletion Mutants in Cultured Hamster Cells", *The Journal of Biological Chemistry*, Sep. 25, 1986, vol. 261, No. 27, pp. 12491-12497.

L. Lorenzelli, et al., "Bioelectrochemical signal monitoring of in-vitro cultured cells by means of an automated microsystem based on solid state sensor-array", *Biosensors and Bioelectronics*, 2003, vol. 18, pp. 621-626.

Z. Lu et al., "Epidermal Growth Factor-Induced Tumor Cell Invasion and Metastasis Initiated by Dephosphorylation and Downregulation of Focal Adhesion Kinase", *Molecular and Cellular Biology*, Jun. 2001, vol. 21, No. 12, pp. 4016-4031.

Ma et al., "From the Analyst's Couch: Value of Novelty?", *Nature Reviews, Drug Discovery*, vol. 1, Aug. 2002, pp. 571-572.

Morhard et al., "Immobilization of Antibodies in Micropatterns for Cell Detection by Optical Diffraction", *Sensors and Actuators B*, vol. 70, 2000, pp. 232-242.

K. Mossman et al., "Micropatterned supported membranes as tools for quantitative studies of the immunological synapse", *Chemical Society Reviews*, vol. 36, 2007, pp. 46-54.

B.S. Negrutskii et al., "A sequestered pool of aminoacyl-tRNA in mammalian cells", *Proc. Natl. Acad. Sci. USA*, 1992, vol. 89, pp. 3601-3604.

B.S. Negrutskii et al., "Supramolecular organization of the mammalian translation system", *Proc. Natl. Acad. Sci. USA*, 1994, vol. 91, pp. 964-968.

P.M. Nellen et al., "Integrated Optical Input Grating Couplers as Biochemical Sensors", *Sensors and Actuators*, 1988, vol. 15, pp. 285-295.

Y. Nong et al., "Glycine binding primes NMDA receptor internalization", *Nature*, Mar. 20, 2003, vol. 422, pp. 302-307.

Pierce et al., "Seven-Transmembrane Receptors", *Nature Reviews, Molecular Cell Biology*, vol. 3, Sep. 2002, pp. 639-650.

G. Powis et al., "Wortmannin, a Potent and Selective Inhibitor of Phosphatidylinositol-3-kinase[1]", *Cancer Research*, May 1, 1994, vol. 54, pp. 2419-2423.

Ramsden et al., "Kinetics of Adhesion and Spreading of Animal Cells", *Biotechnology and Bioengineering*, vol. 43, 1994, pp. 939-945.

H. Resat et al., "An Integrated Model of Epidermal Growth Factor Receptor Trafficking and Signal Transduction", *Biophysical Journal*, Aug. 2003, vol. 85, pp. 730-743.

C. Rosette et al., "Ultraviolet Light and Osmotic Stress: Activation of the JNK Cascade Through Multiple Growth Factor and Cytokine Receptors", *Science*, Nov. 15, 1996, vol. 274, pp. 1194-1197.

M.D. Salik et al., Resonant Excitation Analysis of Waveguide Grating Couplers, *Optics Communications*, vol. 193, Jun. 15, 2001, pp. 127-131.

J. Schlessinger, "Cell Signaling by Receptor Tyrosine Kinases", *Cell*, Oct. 13, 2000, vol. 103, pp. 211-225.

B. Schoeber et al., "Computational modelling of the dynamics of the MAP kinase cascade activated by surface and internalized EGF receptors", *Nature Biotechnology*, Apr. 2002, vol. 20, pp. 370-375.

M.A. Simmons, "Functional Selectivity, Ligand-Directed Trafficking, Conformation-Specific Agonism: What's in a Name?", *Molecular Interventions*, Jun. 2005, vol. 5, Issue 3, pp. 154-157.

"Signal Pathway Identification and Deconvolution", http://www.cellkey.com/apps2.html (accessed Oct. 24, 2008).

E.A. Smith et al., "Surface Plasmon Resonance Imaging as a Tool to Monitor Biomolecular Interactions in an Array Based Format", *Applied Spectroscopy*, 2003, vol. 57, No. 11, pp. 320A-332A.

K. Solly et al., "Application of Real-Time Cell Electronic Sensing (RT-CES) Technology to Cell-Based Assays", *ASSAY and Drug Development Technologies*, 2004, vol. 2, No. 4, pp. 363-372.

G. Swaminath et al., "Probing the $\beta_2$ Adrenoceptor Binding Site with Catechol Reveals Differences in Binding and Activation by Agonists and Partial Agonists", *The Journal of Biological Chemistry*, vol. 280, No. 23, pp. 22165-22171, (2005).

Tiefenthaler et al., "Intregrated Optical Switches and Gas Sensors", *Optics Letters*, Apr. 1984, vol. 10, No. 4, pp. 137-139.

K. Tiefenthaler et al., "Sensitivity of grating couplers as integrated-optical chemical sensors", *J. Opt. Soc. Am. B*, Feb. 1989, vol. 6, No. 2, pp. 209-220.

P.K. Tien, "Integrated optics and new wave phenomena in optical waveguides", *Reviews of Modern Physics*, Apr. 1977, vol. 49, No. 2, pp. 361-454.

J.D. Urban et al., "Functional Selectivity and Classical Concepts of Quantitative Pharmacology", *The Journal of Pharmacology and Experimental Therapeutics*, vol. 320, No. 1, pp. 1-13, (2007).

E. Verdonk et al., "Celllular Dielectric Spectroscopy: A Label-Free Comprehensive Platform for Functional Evaluation of Endogenous Receptors", *ASSAY and Drug Development Technologies*, 2006, vol. 4, No. 5, pp. 609-619.

P.J. Verveer, et al., "Quantitative Imaging of Lateral ErbB1 Receptor Signal Propagation in the Plasma Membrane", *Science*, Nov. 24, 2000, vol. 290, pp. 1567-1570.

G. Voirin et al., "$Si_3N_4/SiO_2/Si$ Waveguide Grating for Fluorescent Biosensors", *Proc. SPIE*, vol. 3620, 1999, pp. 109-116.

J. Vörös et al., "Feasibility study of an online toxicological sensor based on the optical waveguide technique", *Biosensor & Bioelectronics*, 2000, vol. 15, pp. 423-429.

J. Vörös et al., "Optical Grating Coupler Biosensors", *Biomaterials*, vol. 23, 2002, pp. 3699-3710.

Z.H. Wang et al., "A Label-Free Multisensing Immunosensor Based on Imaging Ellipsometry", *Anal. Chem.*, 2003, vol. 75, pp. 6119-6123.

L.C. Waters et al., "Microchip Device for Cell Lysis, Multiplex PCR Amplification, and Electrophoretic Sizing", *Anal. Chem.*, 1998, vol. 70, pp. 158-162.

R. Wetzker et al., "Transactivation joins multiple tracks to the ERK/MAPK cascade", *Nature Reviews Molecular Cell Biology*, Aug. 2003, vol. 4, pp. 651-657.

A.D. Zechnich et al., "Possible Interactions With Terfenadine or Astemizole", *West J. Med.*, Apr. 1994, vol. 160, No. 4, pp. 321-325.

P.N. Zeller et al., "Single-Pad Scheme for Integrated Optical Fluorescence Sensing", *Biosensors & Bioelectronics*, vol. 15, 2000, pp. 591-595.

"Zeptosens—Bioanalytical Solutions", http://www.zeptosens.com/en/ (accessed Oct. 24, 2008).

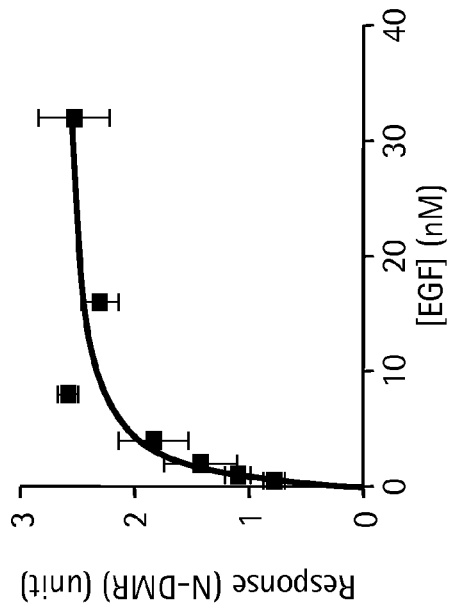
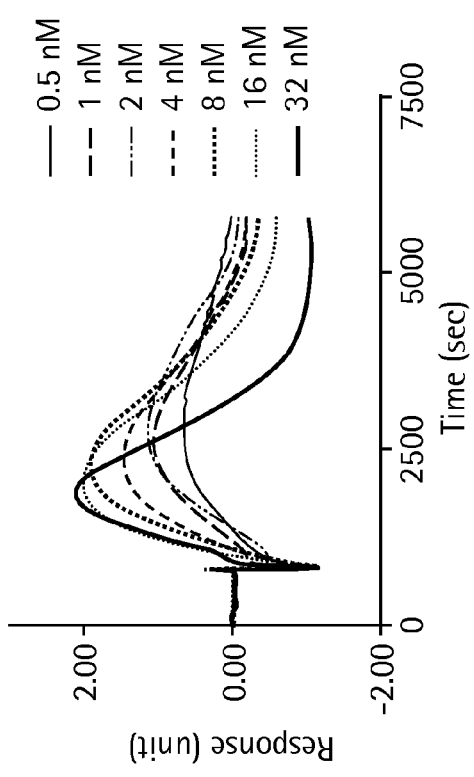
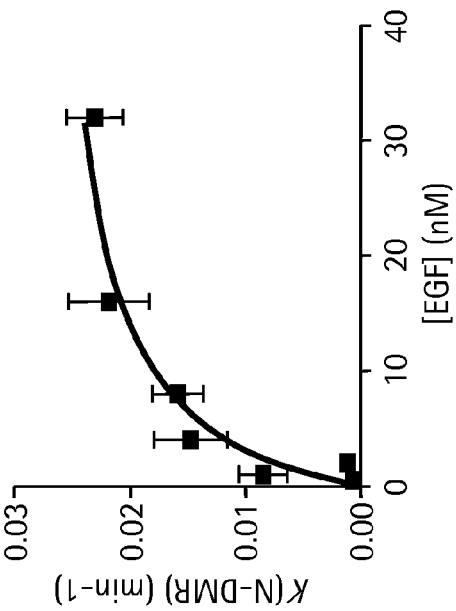
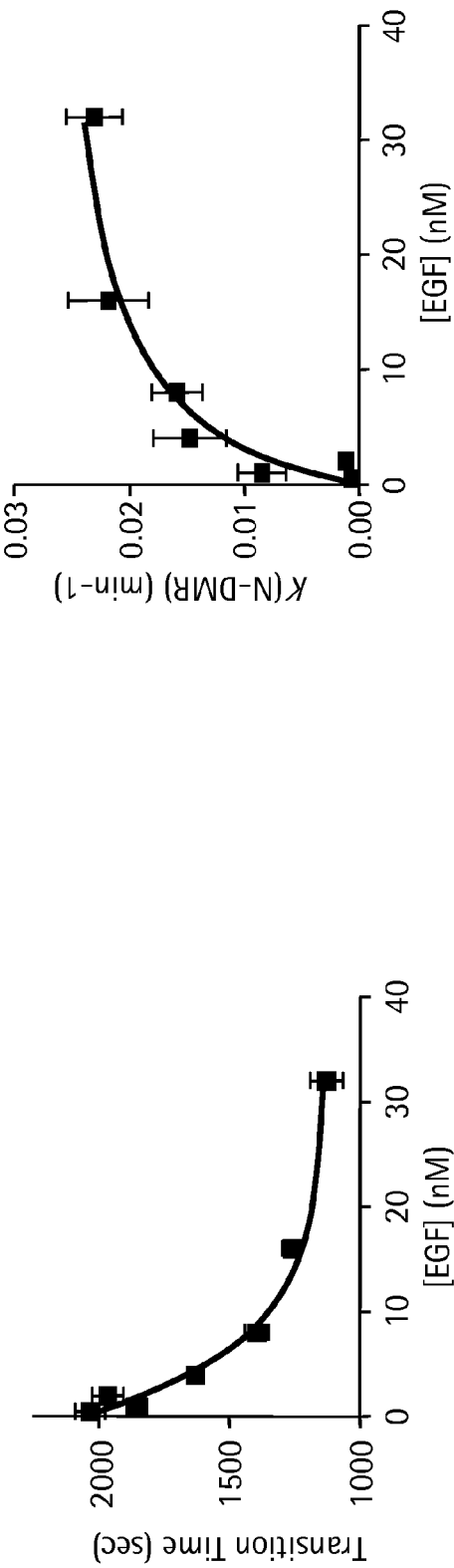
FIG. 7A
FIG. 7B
FIG. 7C
FIG. 7D

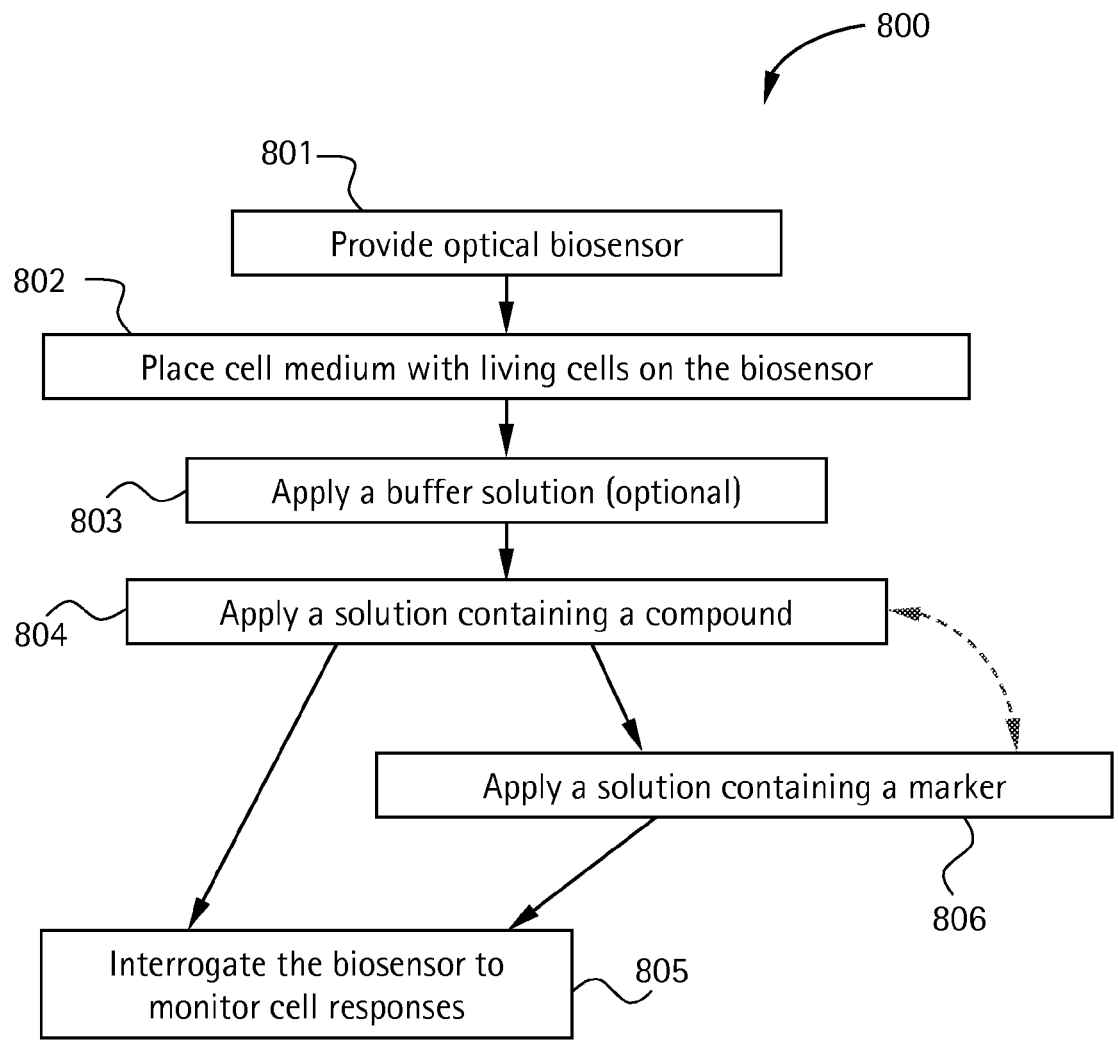

Prior Art

FIG. 14

Cholesterol efflux

FIG. 35A
FIG. 35B
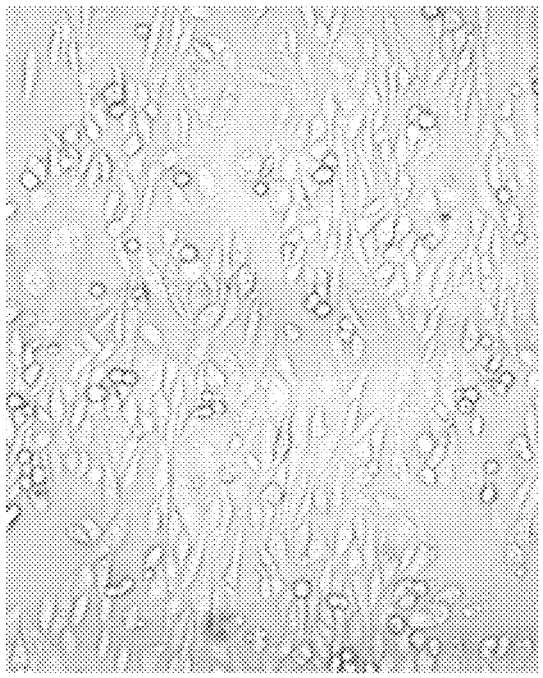
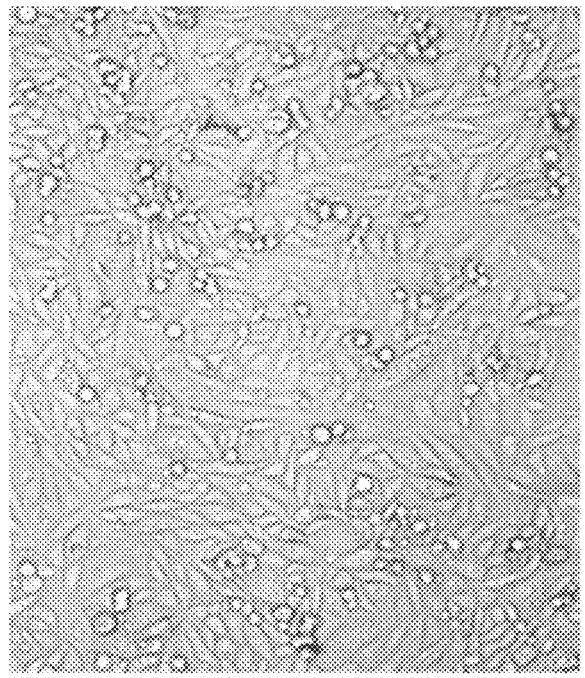

Initial seeding numbers of CHO cells 0 min 15 min

30min 0 min 15 min

30min

Compound effect on saponin acting on CHO cells

LABEL FREE BIOSENSORS AND CELLS

I. CROSS-REFERENCE TO RELATED APPLICATIONS

This application is a divisional of U.S. patent application Ser. No. 11/887,809, filed on Apr. 5, 2006, now U.S. Pat. No. 8,076,090, granted on Dec. 13, 2011, which is a 371 of PCT/US2006/013539 filed Apr. 5, 2006 and which claims the benefit of priority to U.S. Provisional Application No. 60/668,908, filed on Apr. 5, 2005, the content of which is relied upon and incorporated herein by reference in its entirety, and claims the benefit of priority under 35 U.S.C. §120 is hereby claimed.

II. BACKGROUND

The drug discovery and development process that ultimately brings new drugs to market is a complex and costly process. Traditionally, the early stages of drug discovery utilized affinity binding assays that generally were done in vitro and provided limited information on the ability of a potential drug compound to illicit the effect on the target of interest. Many of these potential leads fail when tested either in cell-based assays or animal model-based validation assays at the preclinical/clinical trials, resulting in high attrition rates. More recently, innovative cell-based technologies including high-content screening technologies have gained popularity in the pharmaceutical and biotech industries. These assay technologies provide functional, kinetic cell-based information on the cellular consequences of target-compound interaction. The data obtained include information on signal transduction pathways, drug mechanisms of action, efficacy, selectivity and cytotoxicity. Most of the existing cell-based technologies that require the use of fluorescent labels or luminescence labels for imaging-based detection are generally focused on evaluating discrete intracellular events (e.g., $Ca^{2+}$ flux, cAMP generation and accumulation, target translocation, reporter gene generation, etc). Because of the complexity of cell function, cellular responses generally result from integration of multitude signals, and thus assay technologies based on a given single-cellular response or signal tend to fail to generate information regarding the overall integrated cellular response to drug stimulation. The use of labels or the use of artificial enhancements (e.g., transfection or RNAi knockout) or the use of a reporte gene system, for example, could contribute in an adverse way to elucidating the real cellular physiology of the target of interest. For these reasons, there is a continuing need for being able to assay the effect of molecules on living cells, such as assaying whether the molecule effects a particular signaling pathway, such as a G protein coupled receptor (GPCR) or epidermal growth factor receptor (EGFR), or whether the molecule causes the cell to proliferate or causes the cell to die or stop growing. The use of label free or label independent detection (LID) biosensors is desirable because the biosensors bypass the need for often complex labeling strategies and detection mechanisms. Label free biosensors are more convenient for high through put methods. Disclosed are methods and systems for using label free biosensors to perform any type of cell assay, including assaying signal transduction pathways and cell proliferation and death.

III. SUMMARY

Disclosed are methods and compositions related to label free biosensors and their uses with cells.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows an example of a specific detection scheme of an optical waveguide grating (OWG) microplate after live cells become adherent on the sensor surface. The image showed a resonant band image of 5 columns of 7 sensors after cell culture with a cell confluency of ~95% obtained using an arrayed angular interrogation system. The arrayed angular interrogation system consists of a launch system for generating an array of light beams such that each illuminates an OWG sensor and a receiving system for receiving all responses from the light beams reflected from these sensors. This system allows simultaneously measuring responses of adherent cells from multiplex systems. This example is for a 5×7, but one can utilize a 6×7, or 7×7, or any configuration that fits with the light generation and receiving systems. These measurements can be taken in real time with a time resolution of ~3 sec, for example. The broken circle indicates that the cell density is not even across this sensor, as confirmed by light microscopic imaging.

FIG. 2a shows optical biosensors for cell assays based on stimulation-induced directional mass redistribution within adherent layer of cells. The example shown is an optical waveguide grating sensor, consisting of a thin film of $Nb_2O_5$ with a high refractive index ($n_F$=2.36) and a thickness of $d_F$ (75 nm) on a glass substrate of an index of $n_s$=1.50, an adlayer of cells on the waveguide film with an overall refractive index of $n_A$=1.37, and a surrounding medium with an index of ~1.33 ($n_c$). The OWG biosensor is an evanescent-wave sensor, based on the resonant coupling of light into a waveguide by means of a diffraction grating. A laser illuminates the waveguide at varying angles and light is coupled into the waveguide only at specific angles, determined by the effective refractive index (N) of a guided mode. Ligand-induced target activation leads to recruitment of target-interacting component(s) to the target, movement of the resulted target complexes, and potentially the remodeling of cell cytoskeleton structure (i.e., morphological changes). When such movements or changes occur in the very periphery of an OWG sensor surface on which the cells are cultured, a DMR signal, as indicated by the arrow, is generated at certain time and can be monitored in real time. The ligand-induced directional mass redistribution within adherent cell layer leads to a change in effective refractive index, which, in turn, results in angle shift of the out-coupled light. FIG. 2b A three-layer configuration for detecting the stimulation-mediated vertical mass redistribution within the sensing volume. The bottom portion of cells is viewed to consist of multiple equal-spaced and homogenous thin layers, each layer has its own refractive index $n_i$, protein concentration $C_i$, distance $Z_i$ (away from the sensor surface). A grating with a periodicity of Λ is embedded with the waveguide film with a refractive index of $n_F$ and a thickness of $d_F$. The waveguide film is deposited on the top surface of a substrate with a refractive index of $n_s$.

FIG. 3 The phase shift as a function of asymmetrically lateral redistribution of cellular contents mediated by stimulation. The guided light, propagating in the planar waveguide, is viewed as zigzag waves. The inhomogeneity of lateral mass distribution within the sensing volume results in broadening, and even splitting of the resonant peak of a given mode.

FIG. 4 shows the intensity of the evanescent wave of a guided mode of the sensor as a function of distance away from the sensor surface.

FIG. 5 shows an alternative symmetry of OWG sensors. In this so-called reverse symmetry waveguide configuration, it consists of a waveguide film (e.g., Nb$_2$O$_5$) supported by typically a 1-100 micron thick layer of nanoporous silica with or without a glass bottom support. The nanoporous silica has an effective refractive index of ~1.1 and the refractive index of the silica is lower than the refractive index of the cover medium, which are generally aqueous solution for our applications in the present invention.

FIG. 6 shows parameters on which cell assays can be based using an OWG biosensor. Shown in 6A is a typical time-dependent response of an adherent layer of exemplary quiescent A431 cells of ~95% confluency induced by 8 nM EGF, as obtained using the angular interrogation system. As shown in the graph of 6A, six parameters that can define the kinetics of the stimulation-induced directional mass redistribution within the cells are 1) overall dynamics (i.e., shape), 2) phases of the response (e.g., in this specific example, there are three phases: Positive-Directional Mass Redistribution (P-DMR), net-zero Directional Mass Redistribution (net-zero DMR) and Negative-Directional Mass Redistribution (N-DMR)), 3) kinetics of each phases, 4) total duration time of both P- and N-DMR phases, 5) total amplitudes of both P- and N-DMR phases, and 6) transition time τ from the P- to N-DMR phase. FIG. 6B shows a typical resonant peak, obtained using TM$_0$ mode, of exemplary A431 cells of ~90% confluency and illustrates four additional parameters: 7) peak position, 8) intensity, 9) shape and 10) width at half maximum (PWHM). FIG. 6C shows a typical TM$_0$ resonant band image of a biosensor with biosensors, a biosensor #5, on which exemplary A431 cells were cultured with a confluency of ~95%. The data was obtained using an arrayed angular interrogation system and illustrates 5 five additional features: 11) band shape, 12) position, 13) intensity, 14) distribution and 15) width. All of these parameters can be used independently or together for any given application of any cell assays using biosensors as disclosed herein. The use of the parameters in any subset or combination can produce a signature for a given assay or given variation on a particular assay, such as a signature for a cell receptor assay, such as a specific signature for an EGF receptor based assay.

FIG. 7 shows dose dependent responses of quiescent A431 cells induced by EGF. (A) Real time kinetics, obtained in parallel using our system, of the cell responses induced by different concentrations of EGF. The final concentrations of EGF are indicated in the graph. (B) The amplitudes of the N-DMR signals, calculated based on the difference between the transition phase and the end phase as indicated in FIG. 7A, as a function of EGF concentration. A typical saturation curve was obtained. (C) The time τ for the transition from the P-DMR to the N-DMR event as a function of EGF concentration. (D) The value of κ, obtained using non-linear regression, of the N-DMR event was plotted as a function of EGF concentration.

FIG. 8 shows a method for screening and classifying compounds against a particular target or signaling pathway based on directional mass redistribution. In this figure, a marker can be an activator or deactivator of a particular target or signaling pathway or function of the cell that leads to or prevents a directional mass redistribution event or signal. The broken arrow indicates that the two steps can be interchangeable or combined together. Both steps 804 and 806 can be considered a stimulatory event as discussed herein.

FIG. 9 shows a schematic drawing of a biological cell with various typical components. The cell consists of a cytoplasm (typically 10-30 μM) containing numerous organelles. The largest organelle is the nucleus, whose size ranges typically between 3 and 10 μm. The nucleus is filled with proteins, the most important one being chromatin. Mitochondria are small organelles comprised of a series of folded membranes with sizes typically ranging from 0.5-1.5 μm. Other cell components include endoplasmic reticulum (ER) (typically 0.2-1 μm), lysomes (typically 0.2-0.5 μm), peroxisomes (typically 0.2-0.5 μm), and endosomes (typically ~100 nm).

Figure 12:
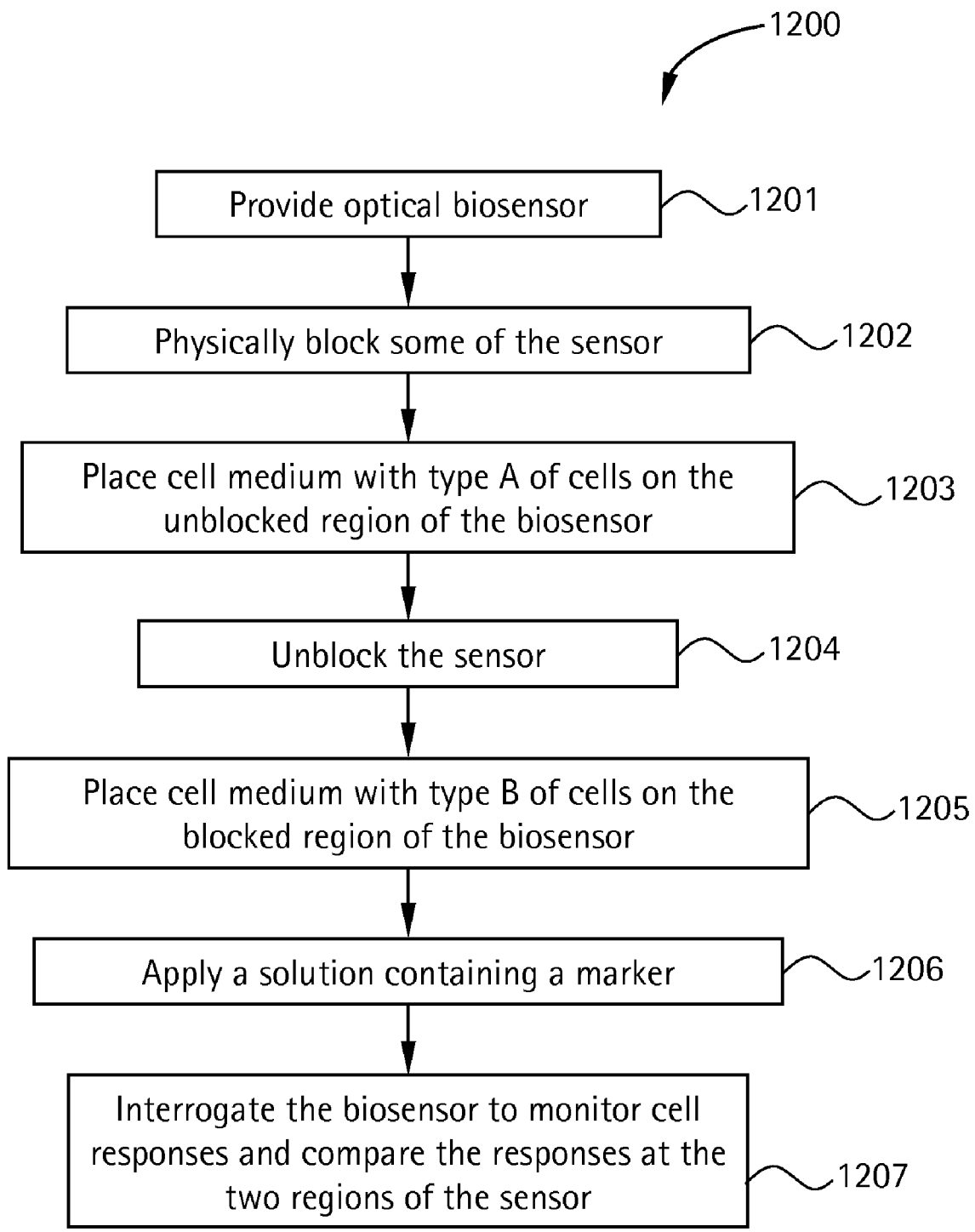

FIG. 12 shows a method for target identification and evaluation based on directional mass redistribution. Note: (1) a marker in this situation is an activator or deactivator of a particular target that leads to or prevents a directional mass redistribution event or signal, (2) The responses obtained can be used to identify the level of the target in the specific cells, or evaluate the target in a particular signaling pathway or a given type of disease cells, and (3) 1206 could be considered a stimulatory event as disclosed herein.

Figure 13:
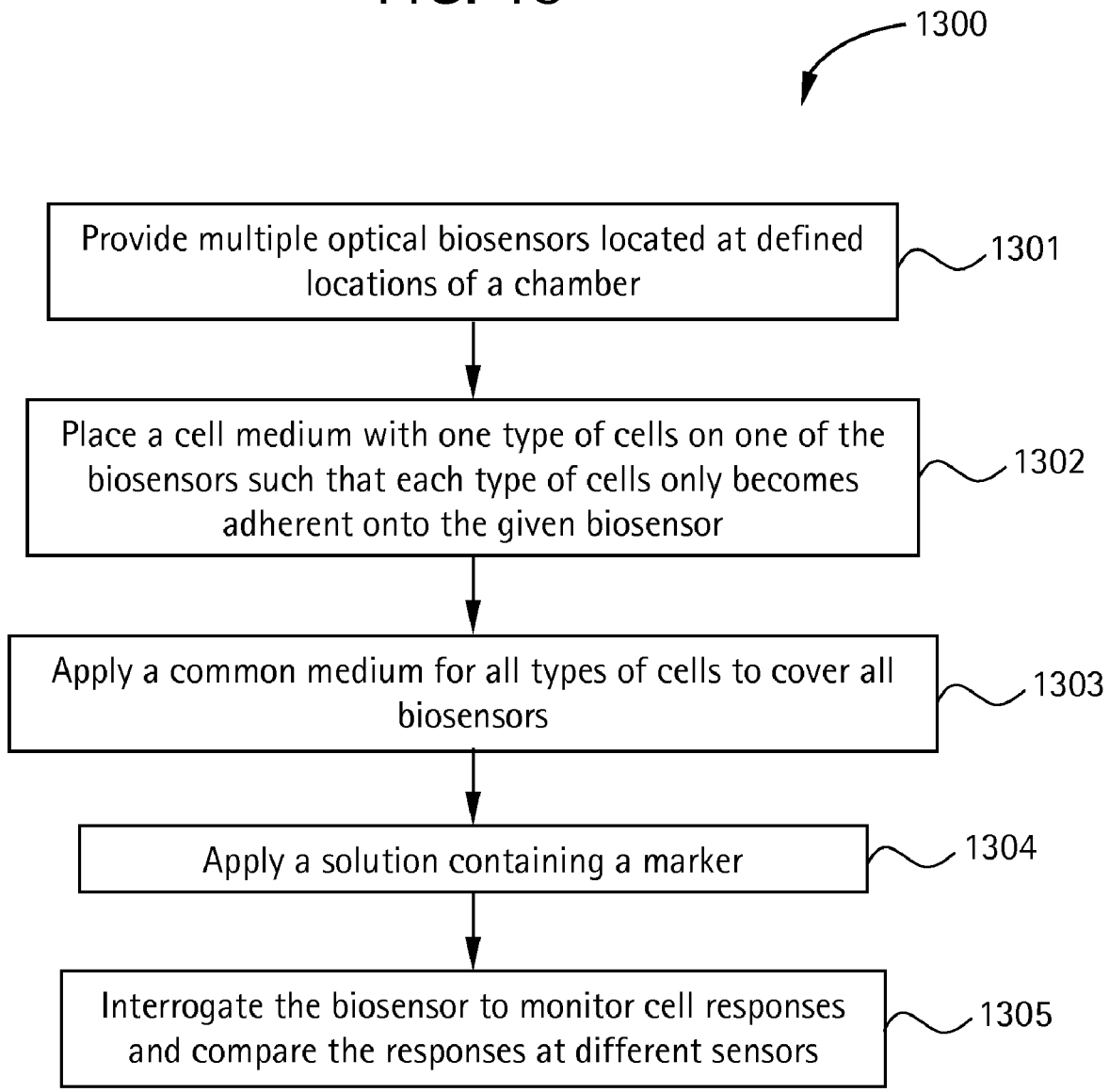

FIG. 13 shows an alternative method for target identification and evaluation based on directional mass redistribution. Note: (1) a marker in this situation is an activator or deactivator of a particular target that leads to or prevent a directional mass redistribution event or signal, (2) The responses obtained can be used to identify the level of the target in the specific cells, or evaluate the target in a particular signaling pathway or a given type of disease cells, and (3) both 1303 and 1304 could be considered a stimulatory event as disclosed herein.

Figure 14:
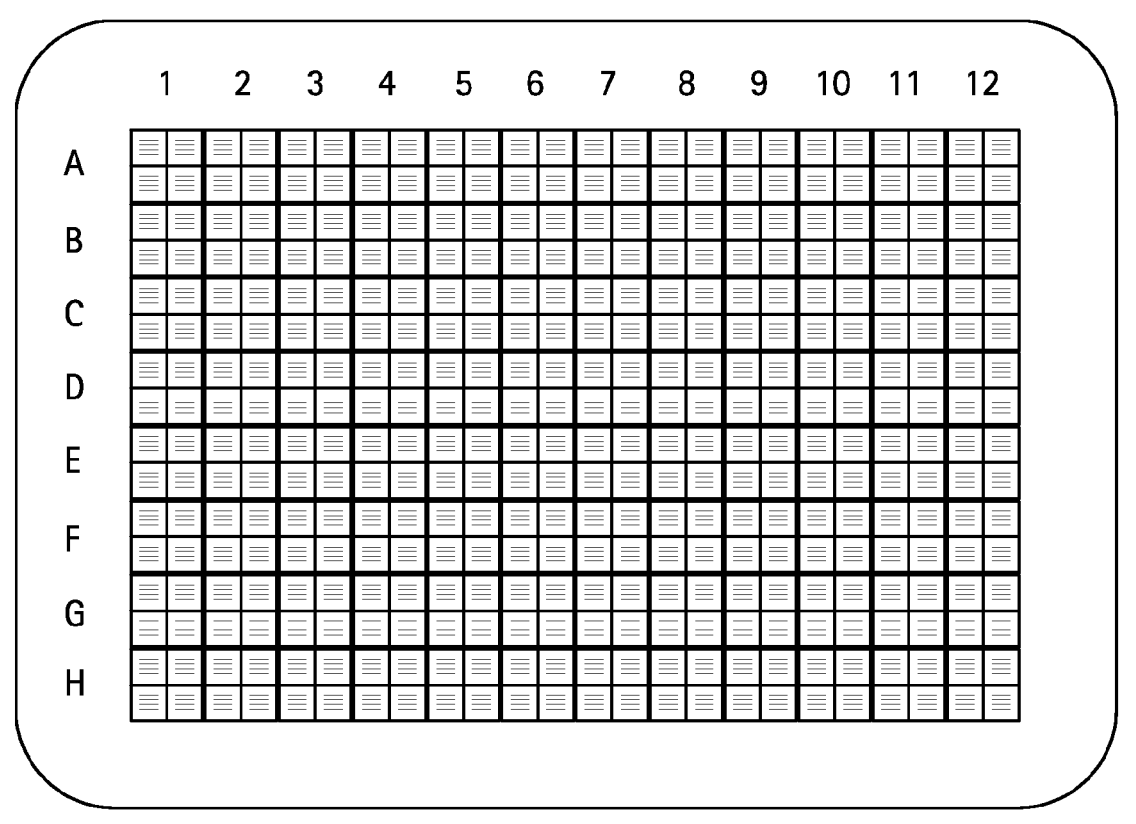

FIG. 14 shows an optical LID biosensor microplate that can be used, for example, in the alternative method showed in FIG. 13. This particular microplate is a multi-compartment plate and has an optical biosensor-embedded multi-compartment within each well. In this 96 well microplate, each well contains four compartments; each compartment has one waveguide grating substrate embedded, and can be used to host a single type of cells or a target of interest. The four compartments are separated by inner walls, the height of the inner walls (preferably between 100 microns and 2 millimeters) is much lower than those of each well (which is typical the height of any given microplate), such that each well having four compartments can be used to examine simultaneously the effect of one drug candidate on multiple targets or multiple types of cells, whatever different target may be in each compartment. The gray lines represent a waveguide grating-based biosensor.

Figure 15:
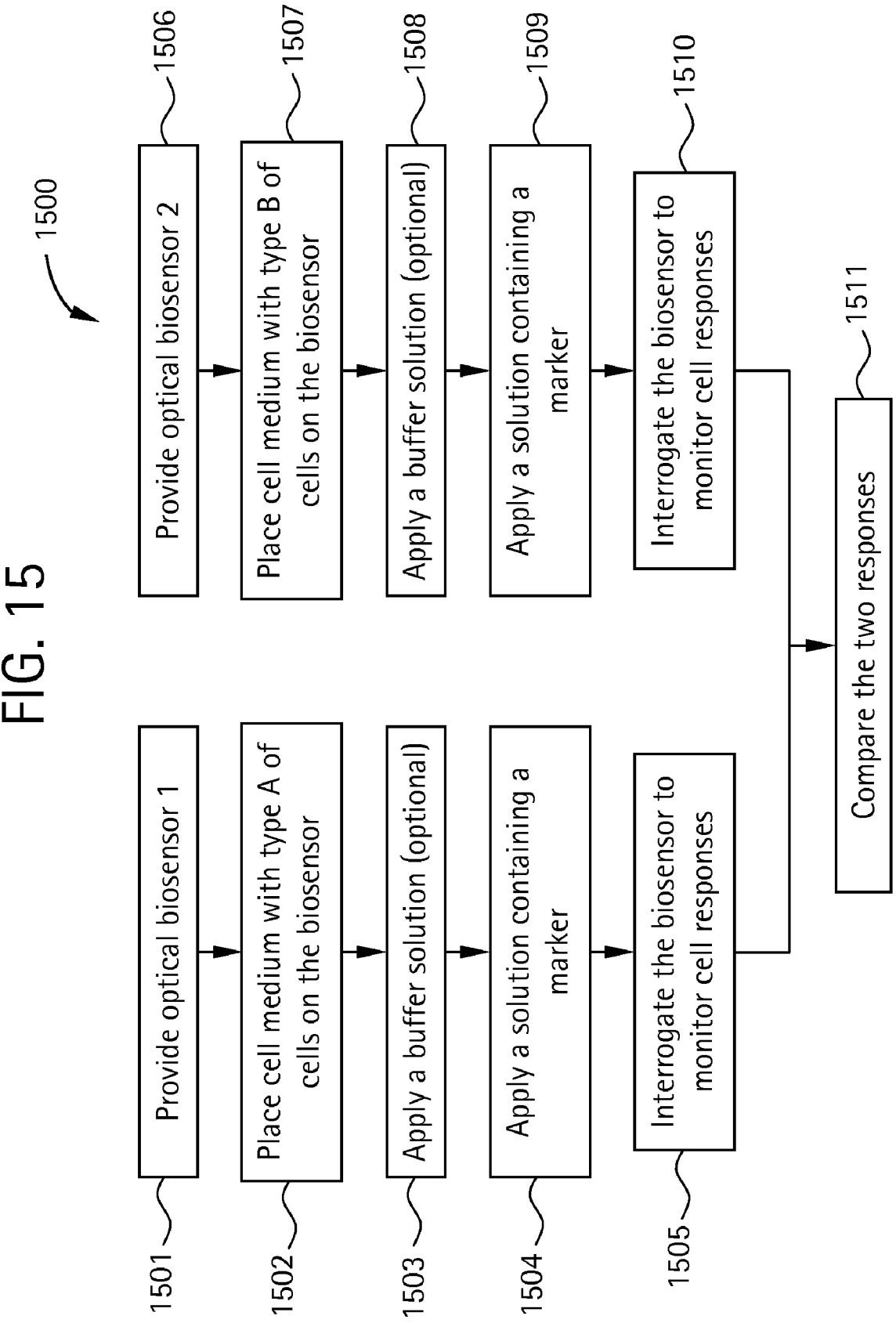

FIG. 15 shows an alternative method for target identification and evaluation based on directional mass redistribution. Note: (1) a marker in this situation is an activator or deactivator of a particular target that leads to or prevents a directional mass redistribution event or signal, (2) The responses obtained can be used to identify the level of the target in the specific cells, or evaluate the target in a particular signaling pathway or a given type of disease cells, and (3) 1503, 1504, 1508, and 1509 can be considered stimulatory events as disclosed herein.

Figure 10:
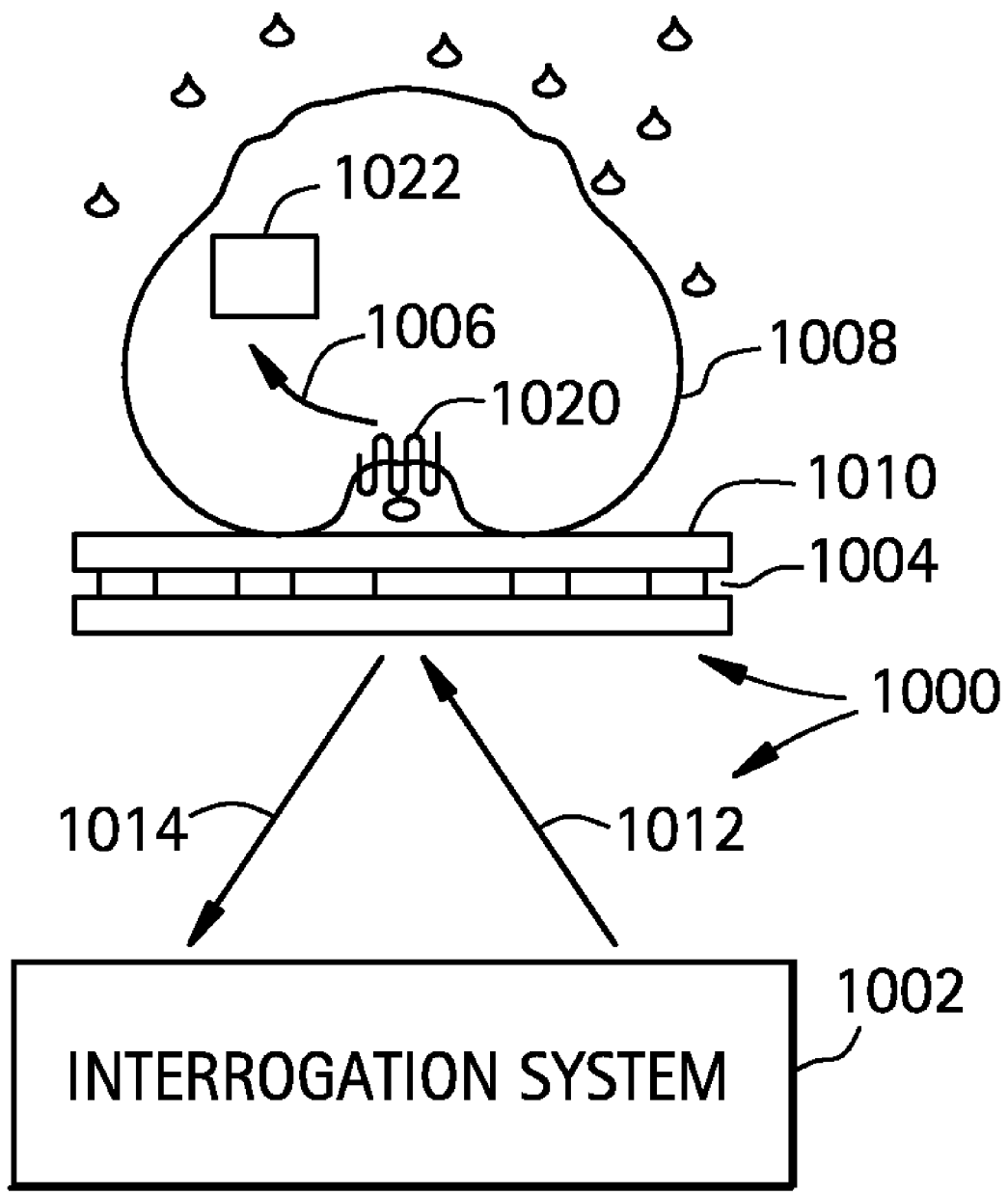
FIG. 10 shows a diagram showing an optical LID system being used to monitor a mass redistribution (e.g. GPCR translocation) within a living cell in accordance with methods and systems disclosed herein.
Figure 16:
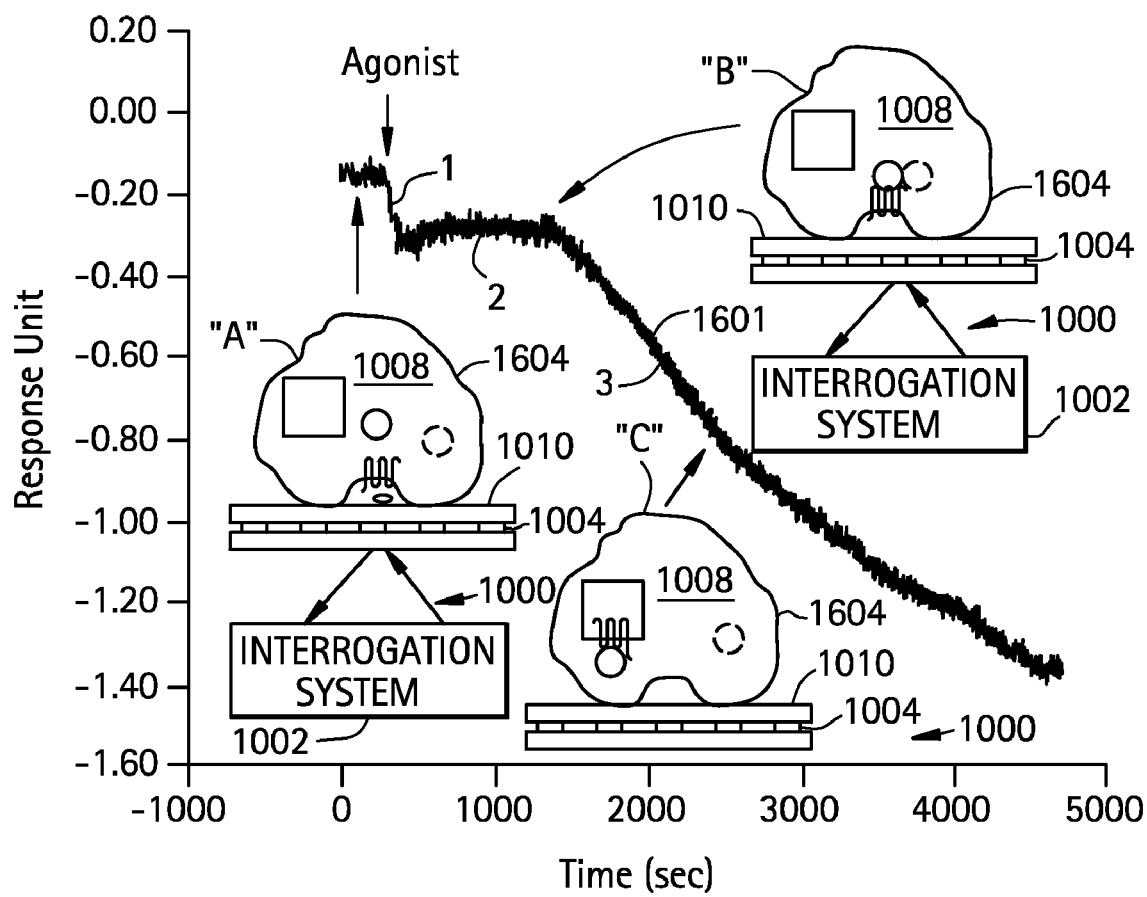

FIG. 16 shows a diagram that shows the different states associated with cell modulation by a stimulatory event, such as the GPCR translocation within the living cell that can be identified by analyzing the time dependent optical response output from an optical LID system, for example, like that shown in FIG. 10.

Figure 17:
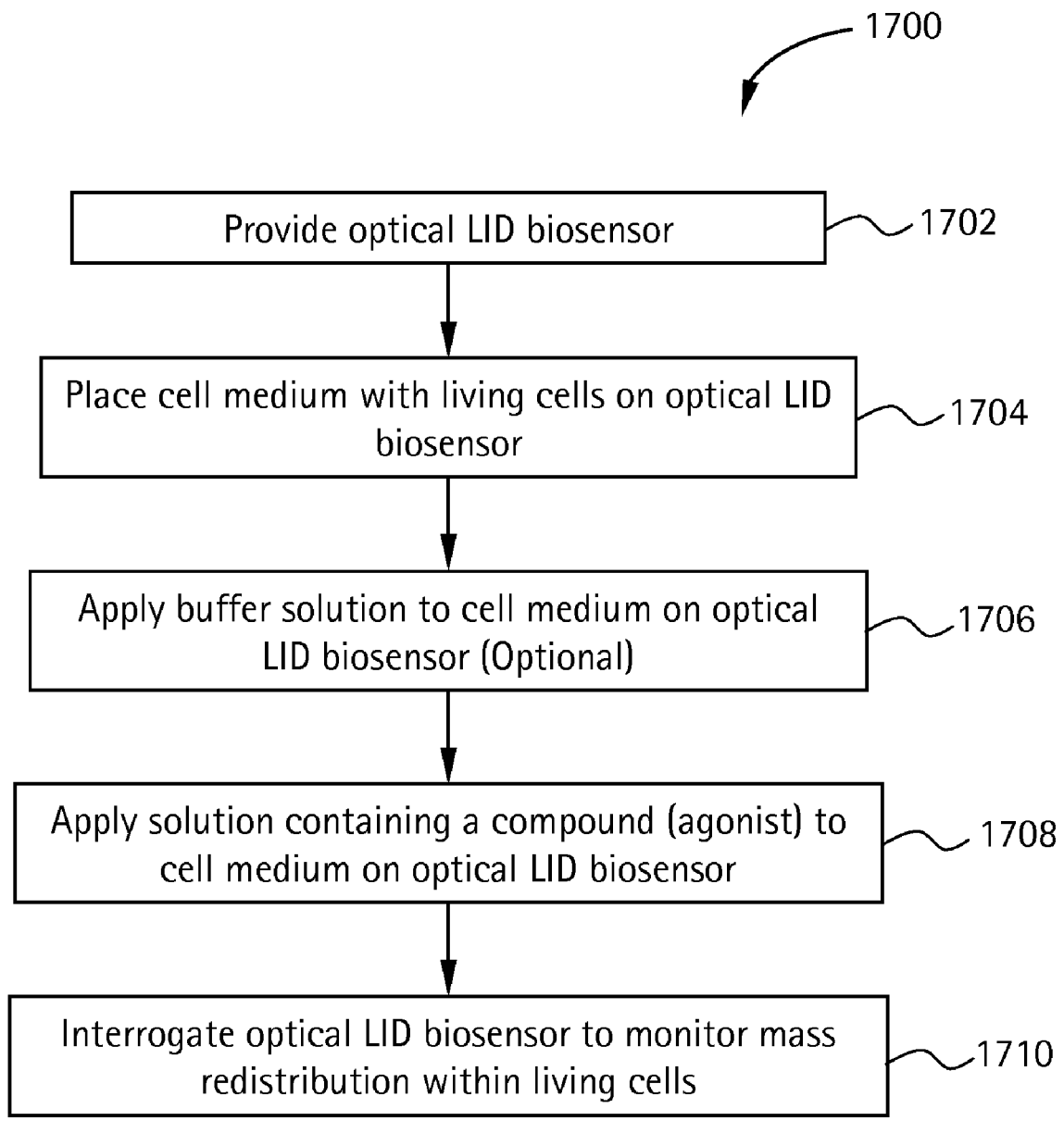

FIG. 17 shows a flowchart illustrating the basic steps of a method for monitoring in real time a stimulatory event, such as an agonist-induced mass redistribution of a cell receptor, including GPCR translocation within living cells, using an optical LID biosensor as disclosed herein. 1706 and 1708 can be considered stimulatory events as disclosed herein.

Figure 18:
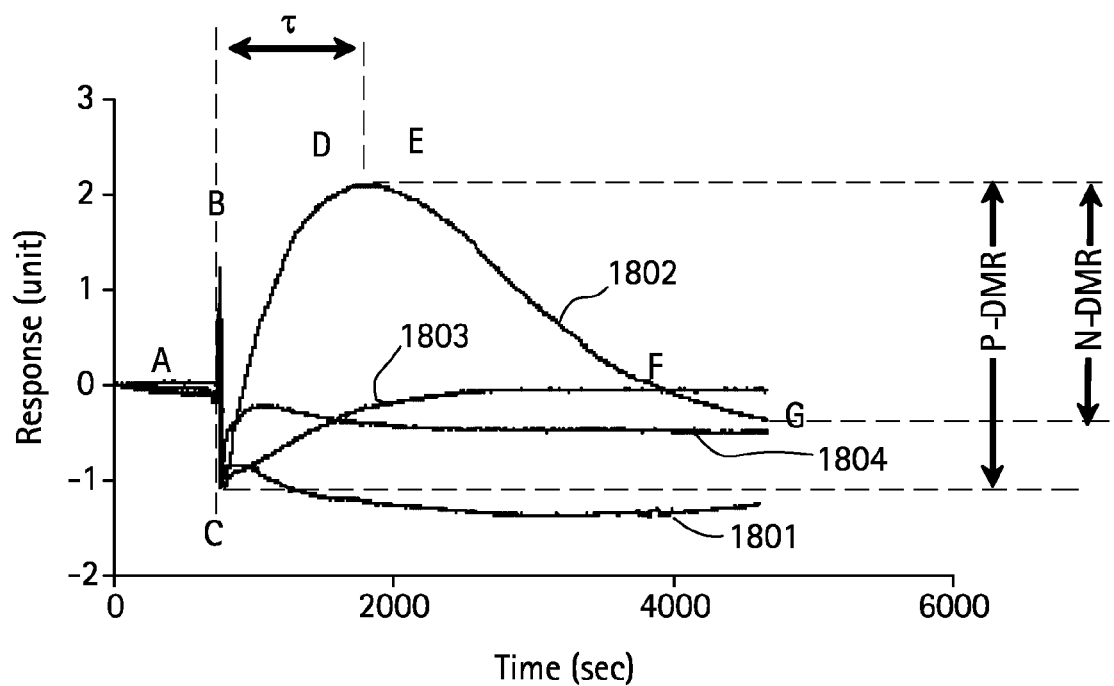

FIG. 18 shows an example of target identification based on directional mass redistribution. Note: (1) The example shown in this graph is EGF-induced DMR responses of a cancel cell line A431 in comparison with another cell line CHO; (2) EGF-induced DMR responses of an adherent layer of A431 cells of ~95% confluency cultured under three different conditions as indicated in the figure were compared with that of an adlayer of Chinese hamster ovary cells of ~95% confluency cultured in 0.1% fetal bovine serum (FBS) for 20 hours. Before addition of 50 µl 4× solution of EGF (32 nM), the cells covered by 100 µl the medium were subject to treatment with 25 µl regular Hank's balanced salt solution (HBSS) at least twice, separated by 15 minutes such that the cells reach a steady state, as indicated by a prolonged net-zero response; (3) The stimulatory event is an activator (i.e., cognate ligand, EGF) of a particular target (EGFR) that leads to a directional mass redistribution event or signal; and (4) The A431 cell endogenously over-expresses epidermal growth factor receptor (EGFR) (~1,700,000 copies per cell). In contrast, the CHO does not endogenously express EGFR. 1801 represents the output data for the CHO cells. 1802 represents the output data for A431 cells in 0.1% fetal calf serum (FCS) for 20 hours. 1803 represents the output data for A431 cells in 10% FCS. 1804 represents the output data for A431 cells in 0.1% FCS for 4 hours.

Figure 19:
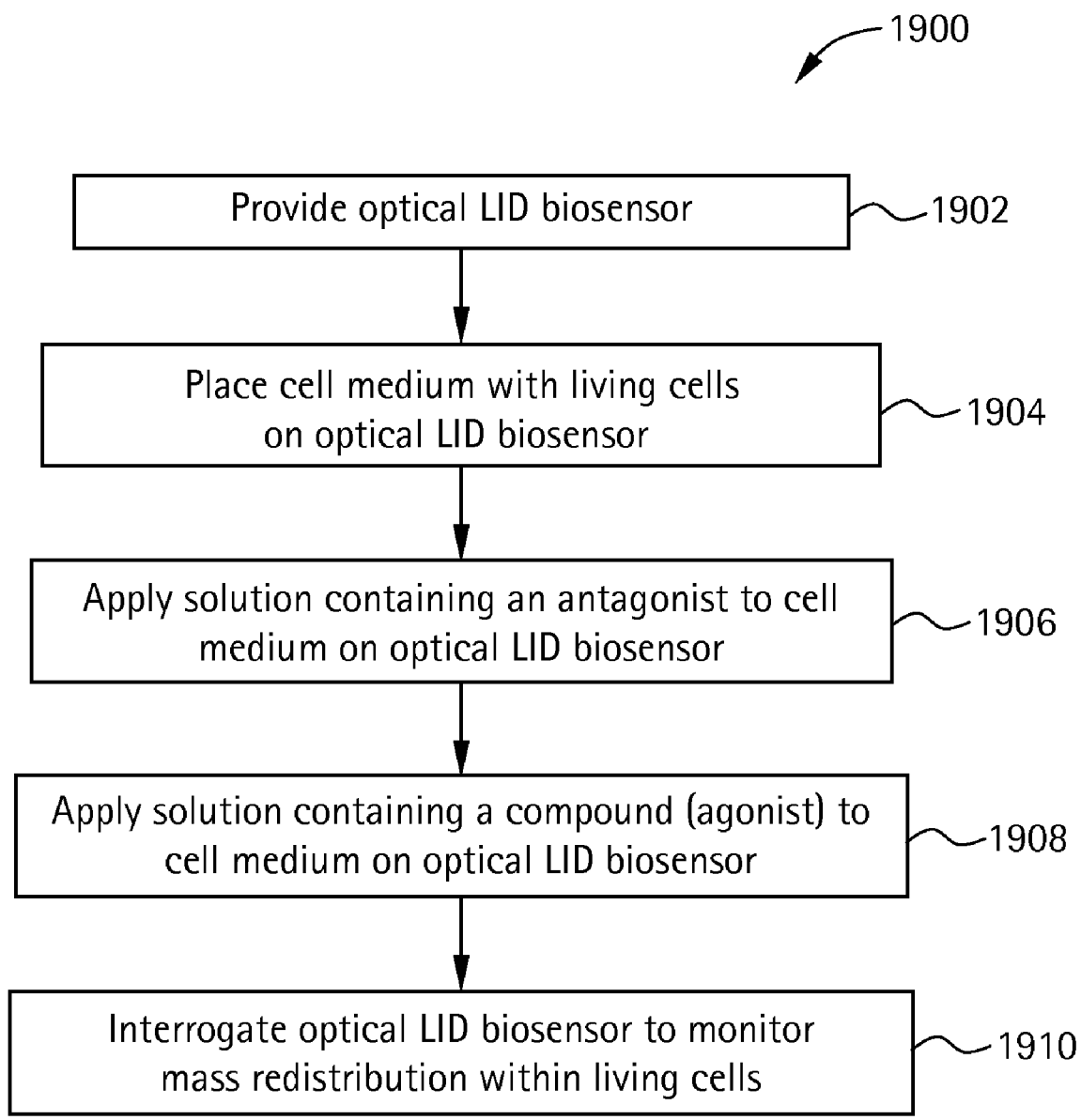

FIG. 19 shows a flowchart illustrating the basic steps of a method for screening a stimulatory event, such as an agonist event, against a target, such as a GPCR, based on mass redistribution within living cells using an optical LID biosensor as disclosed herein.

Figure 20:
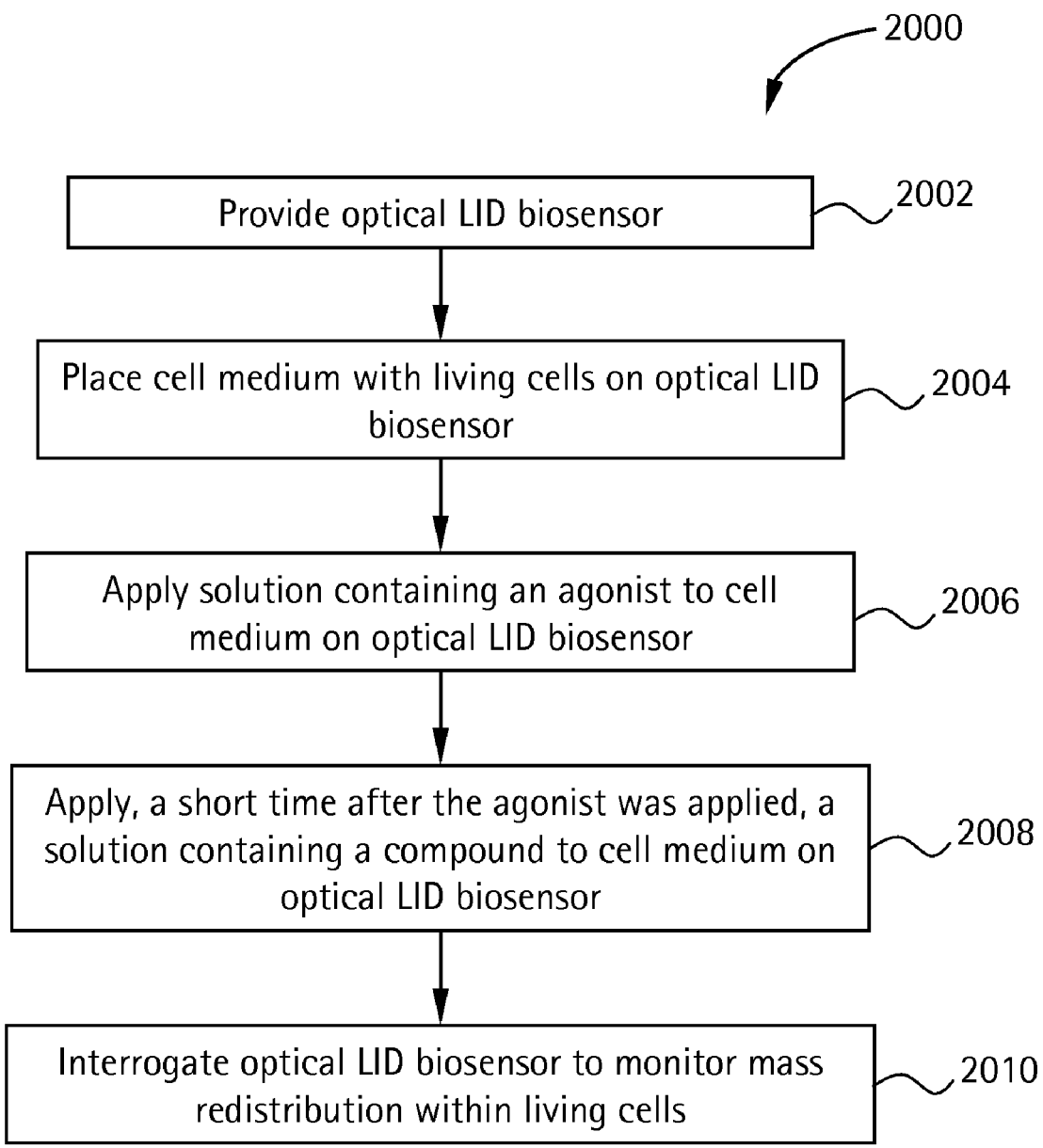

FIG. 20 shows a flowchart illustrating the basic steps of a method for screening a stimulatory event, such as an antagonist event, against a target of a cell, such as a receptor, such as a GPCR, based on mass redistribution within living cells using an optical LID biosensor as disclosed herein. 2006 and 2008 can be considered stimulatory events as disclosed herein.

Figure 21:
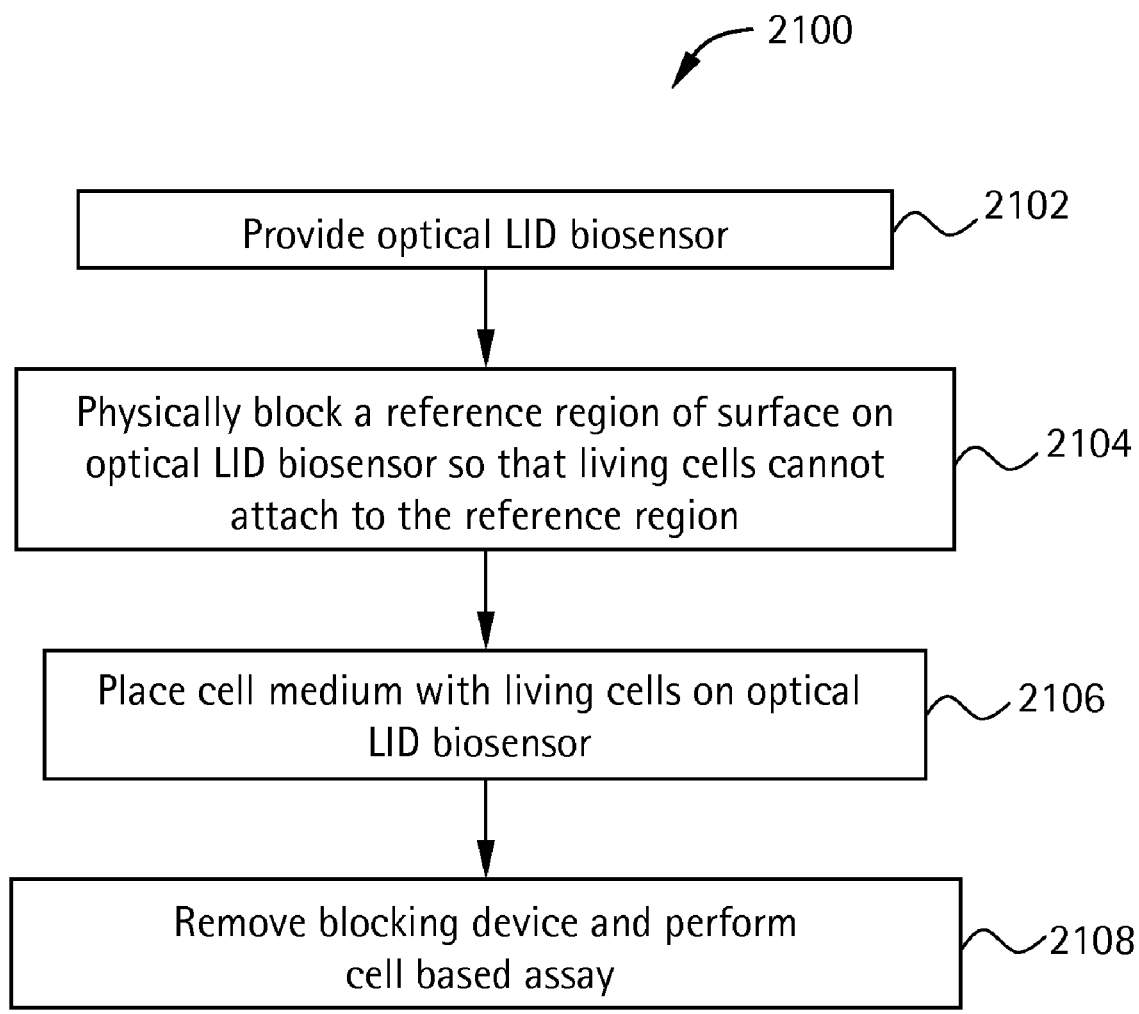

FIG. 21 shows a flowchart illustrating the basic steps of a method for creating a self-referencing optical LID biosensor that can be used in any one of the methods disclosed herein.

Figure 22:
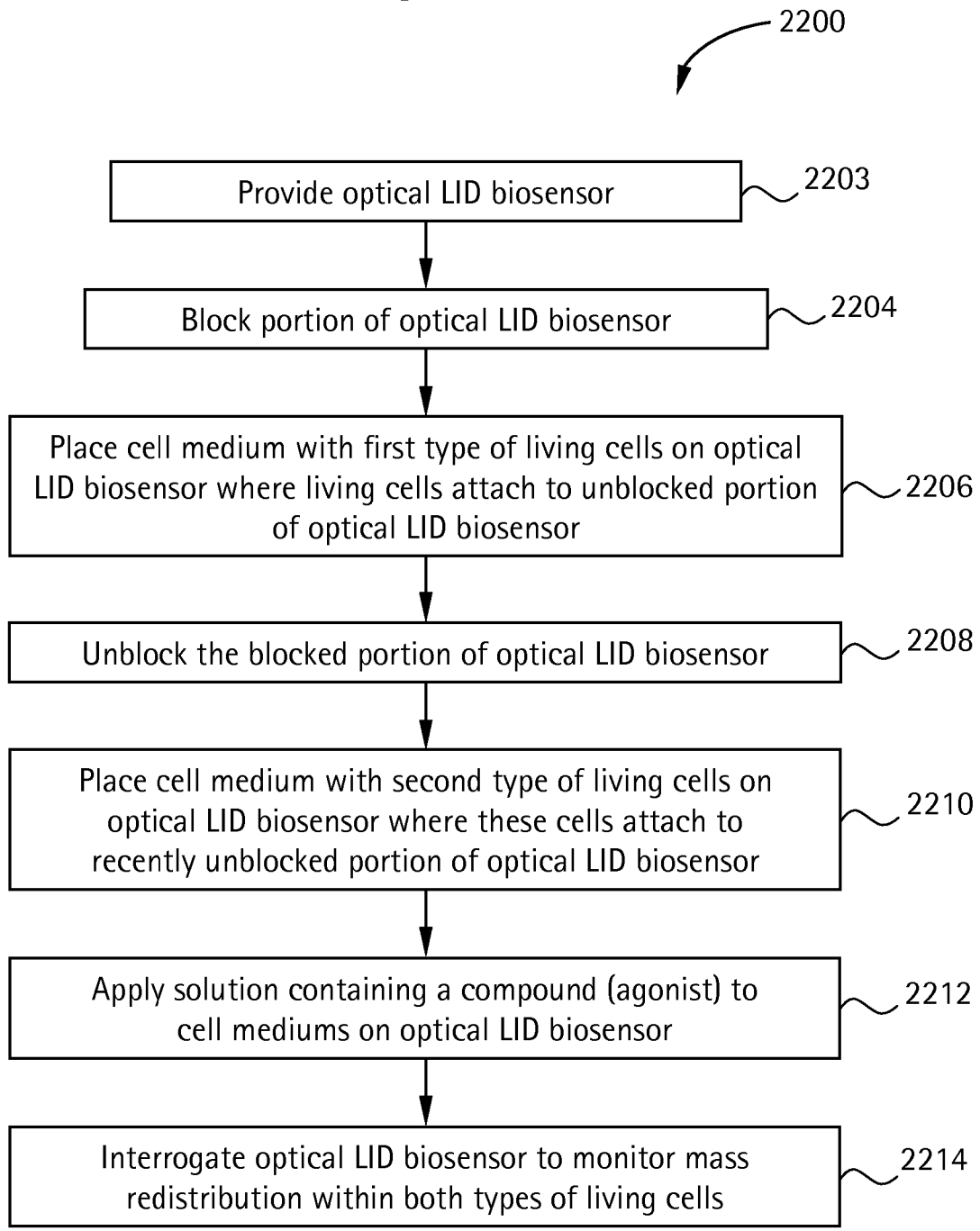

FIG. 22 shows a flowchart illustrating the basic steps of another method for creating a self-referencing optical LID biosensor that hosts two types of cells adherent at spatially separated regions within the same sensor and which can be used in any one of the methods disclosed herein. 2212 can be considered a stimulatory event as disclosed herein.

Figure 23:
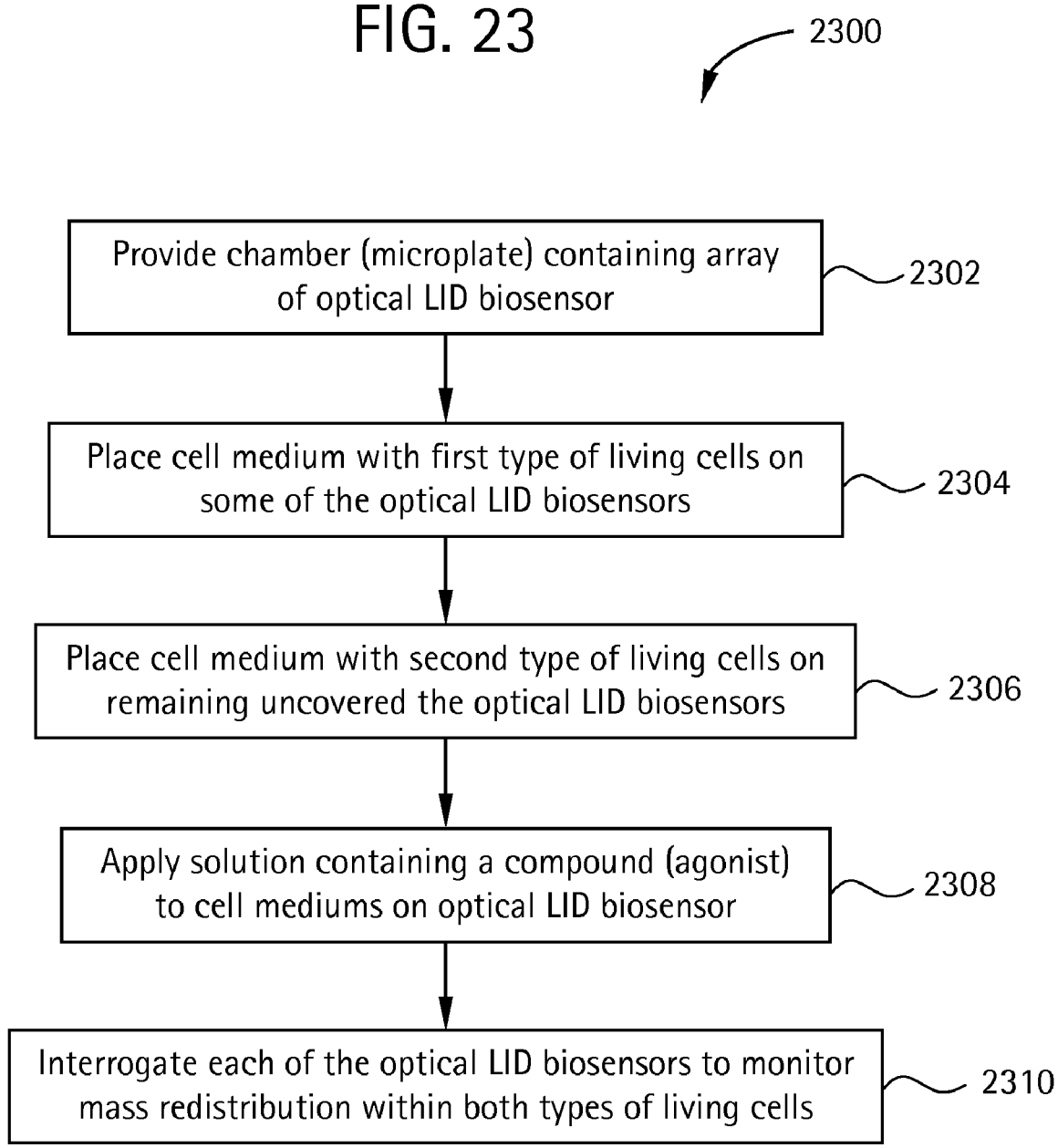

FIG. 23 shows a flowchart illustrating the basic steps of a method for monitoring a stimulatory event, such as an agonist-induced receptor event, such as a GPCR receptor, via mass redistribution within multiple types of living cells using an optical LID biosensor as disclosed herein. 2308 can be considered a stimulatory event as disclosed herein.

Figure 24:
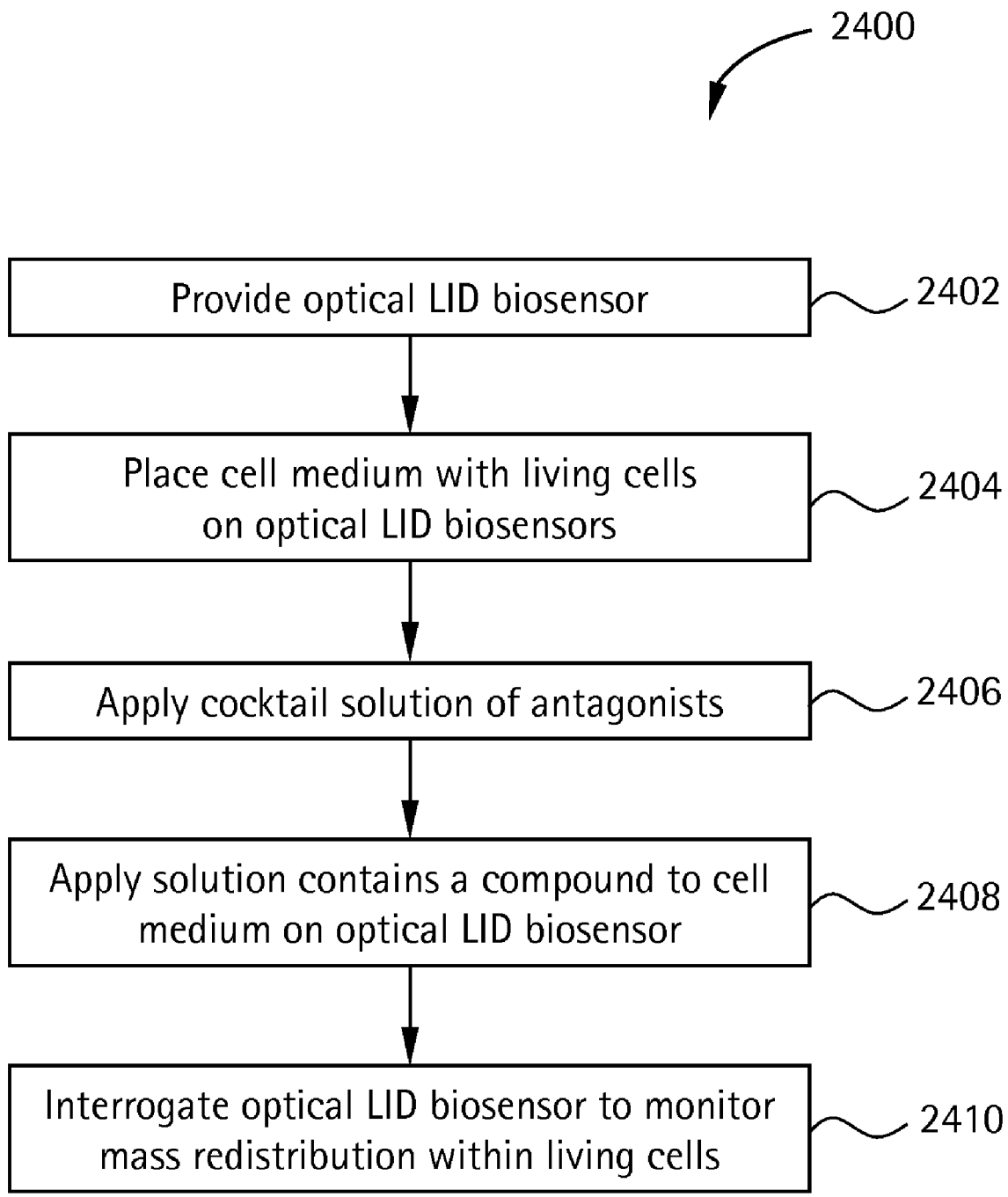

FIG. 24 shows a flowchart illustrating the basic steps of a method for screening a panel of compounds, such as potential agonists or antagonists for a particular receptor, such as against multiple GPCRs within a single type of living cell based on mass redistribution using an optical LID biosensor as disclosed herein. 2406 and 2408 can be considered a stimulatory event.

Figure 25:
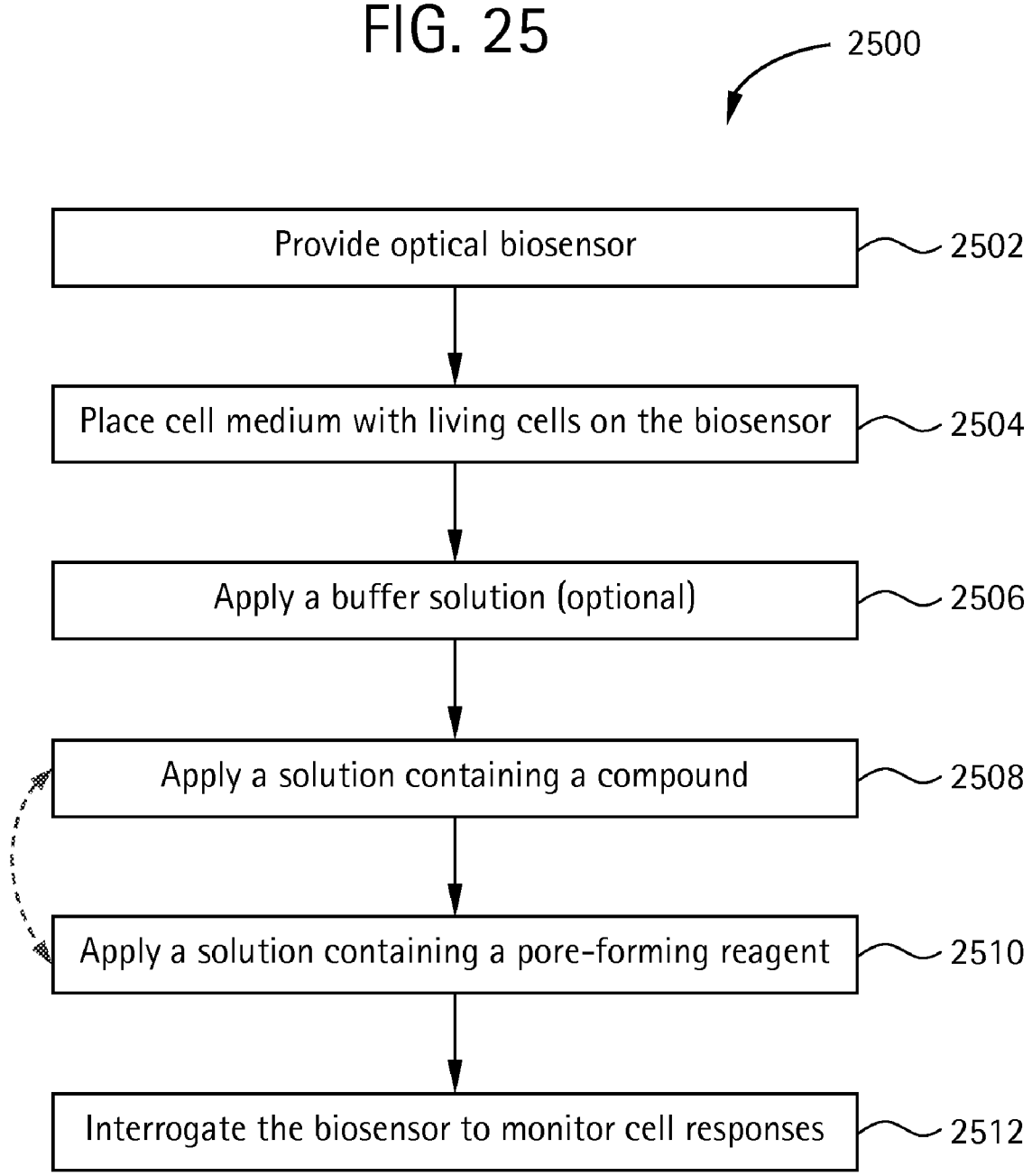

FIG. 25 shows a method to screen modulators that interfere with cytoskeleton structures of cells. 2506, 2508, and 2510 can be considered a stimulatory event.

Figure 26:
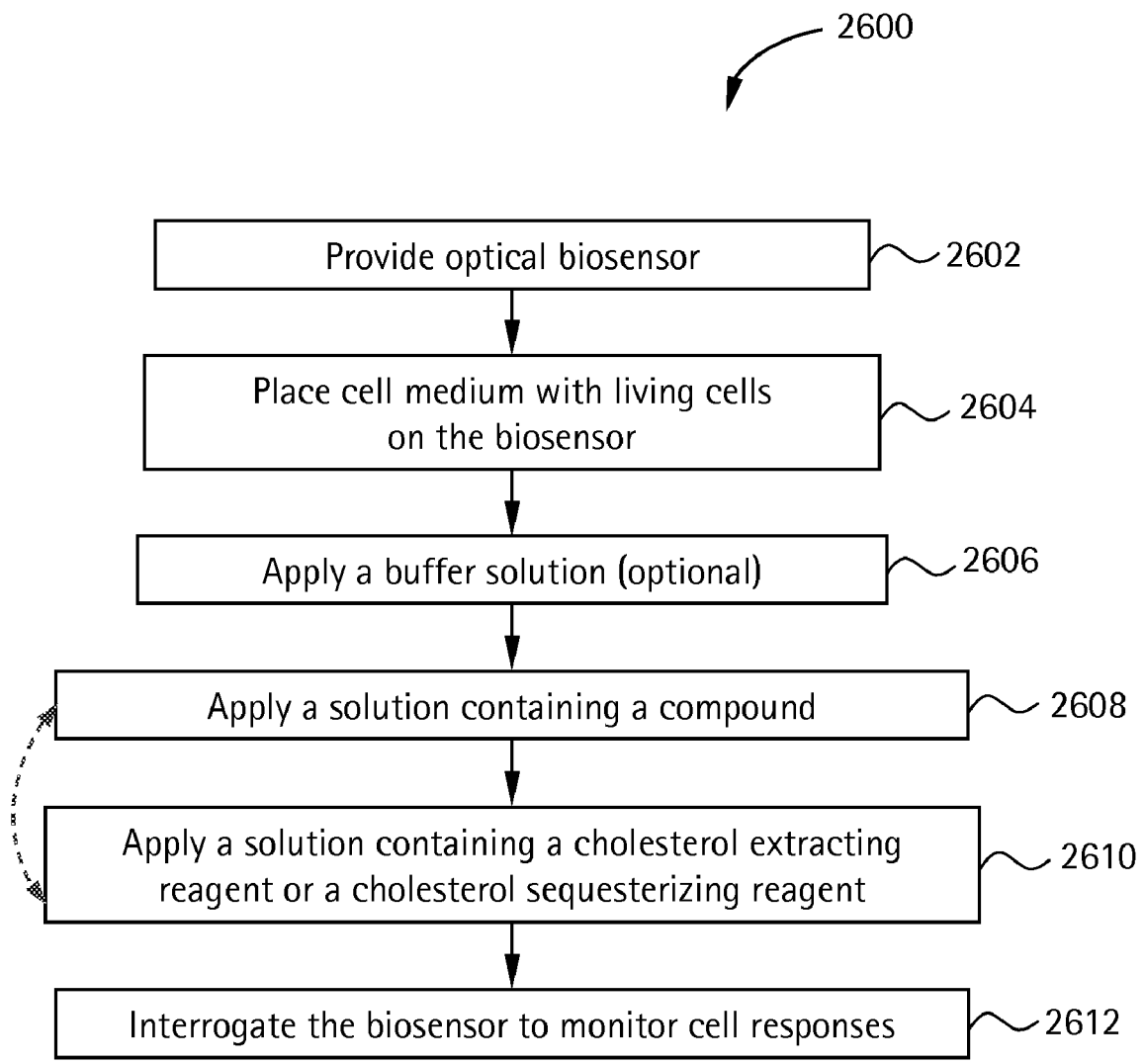

FIG. 26 shows an example of a method to screen modulators that interfere with cholesterol effluxing. 2606, 2608, and 2610 can be considered a stimulatory event.

Figure 27:
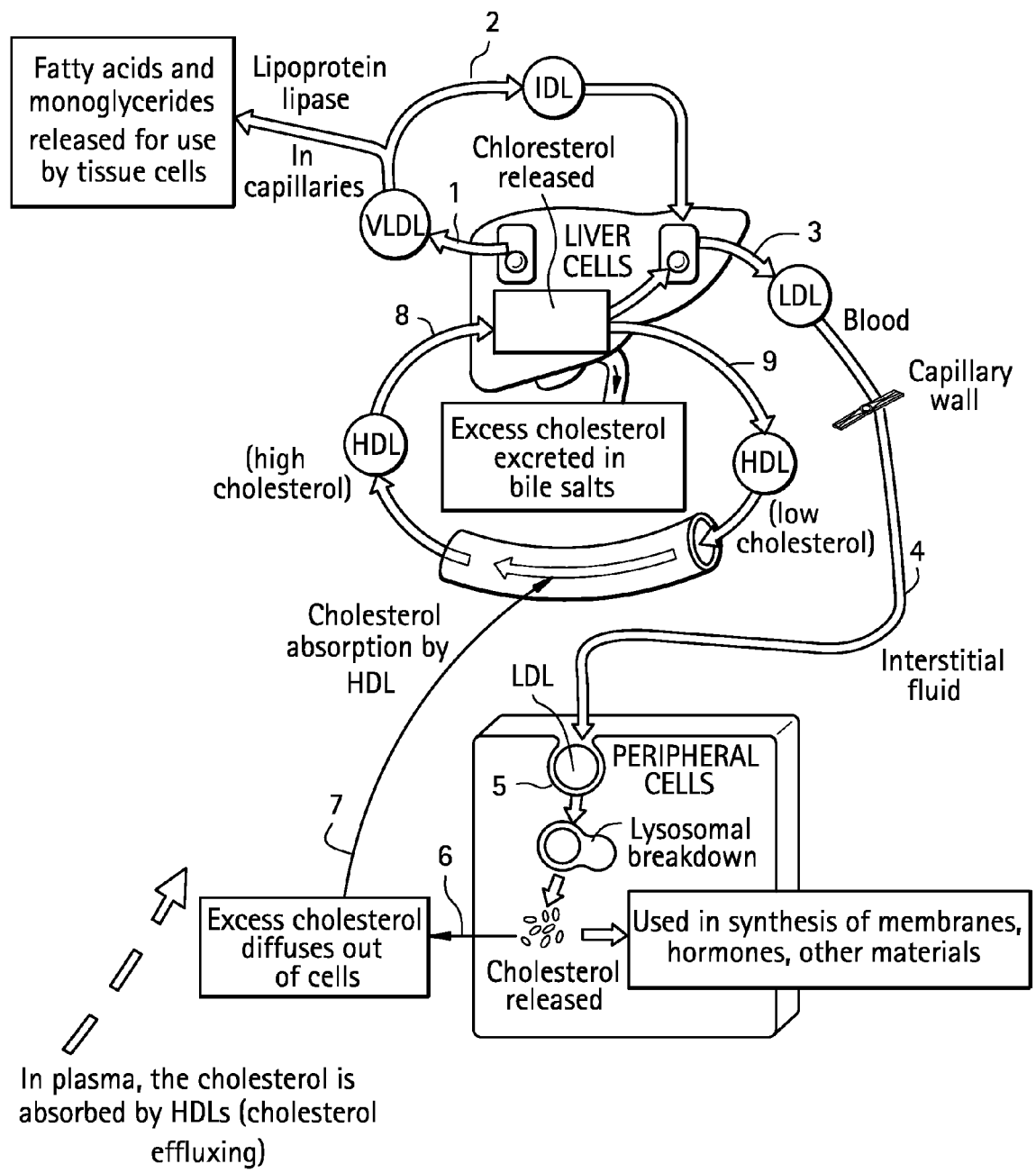

FIG. 27 shows a schematic drawing showing the lipid signaling and transport in the body.

Figure 28A:
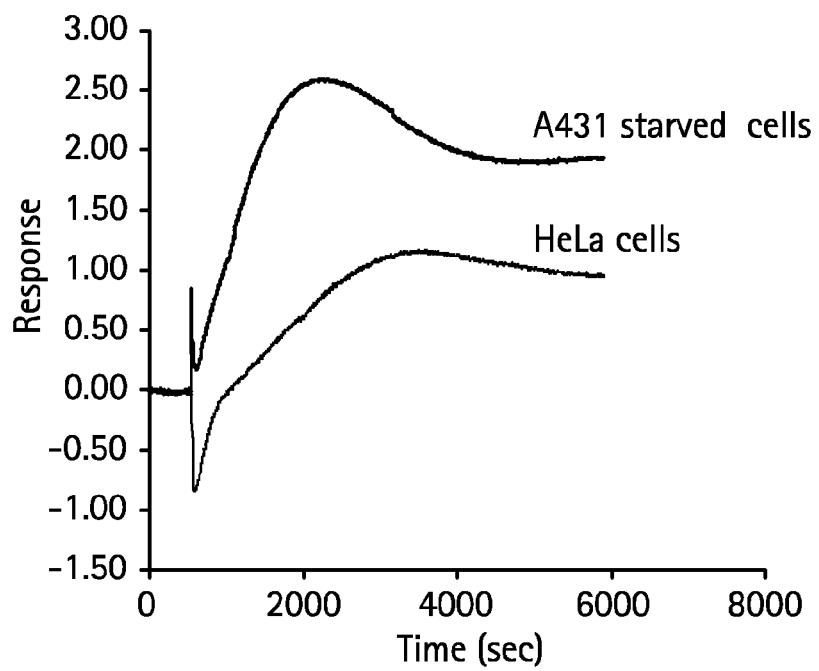
Figure 28B:
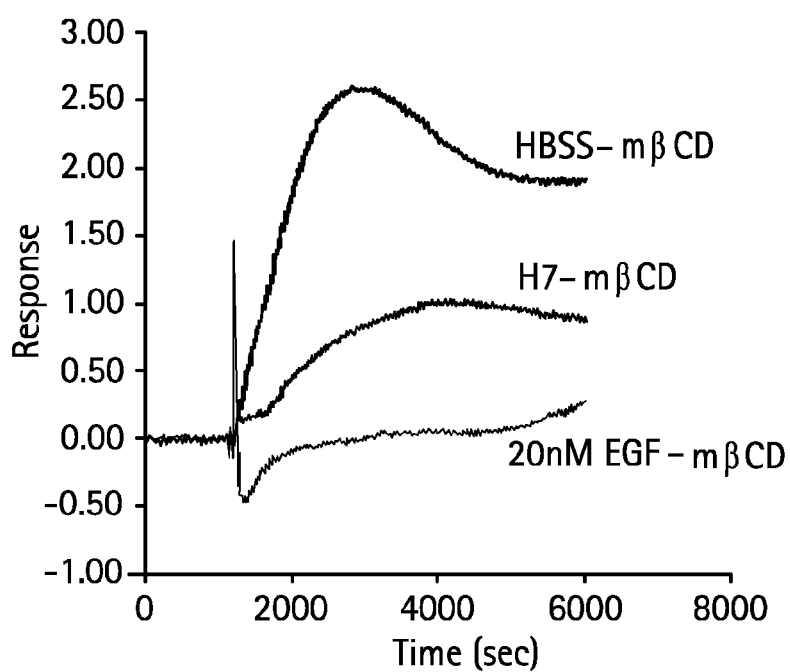

FIG. 28(A) shows time-dependent responses of methyl-beta-cyclodextrin (mβCD) on adlayer of quiescent A431 cells or HeLa cells on LID sensors. FIG. 28(B) shows the effect of compound (20 nM EGF or 1000 nM H7) on mβCD-induced responses of quiescent A431 cells. The quiescent A431 cells were pretreated with corresponding compound for at least 40 minutes before introduction of mβCD solution.

Figure 29:
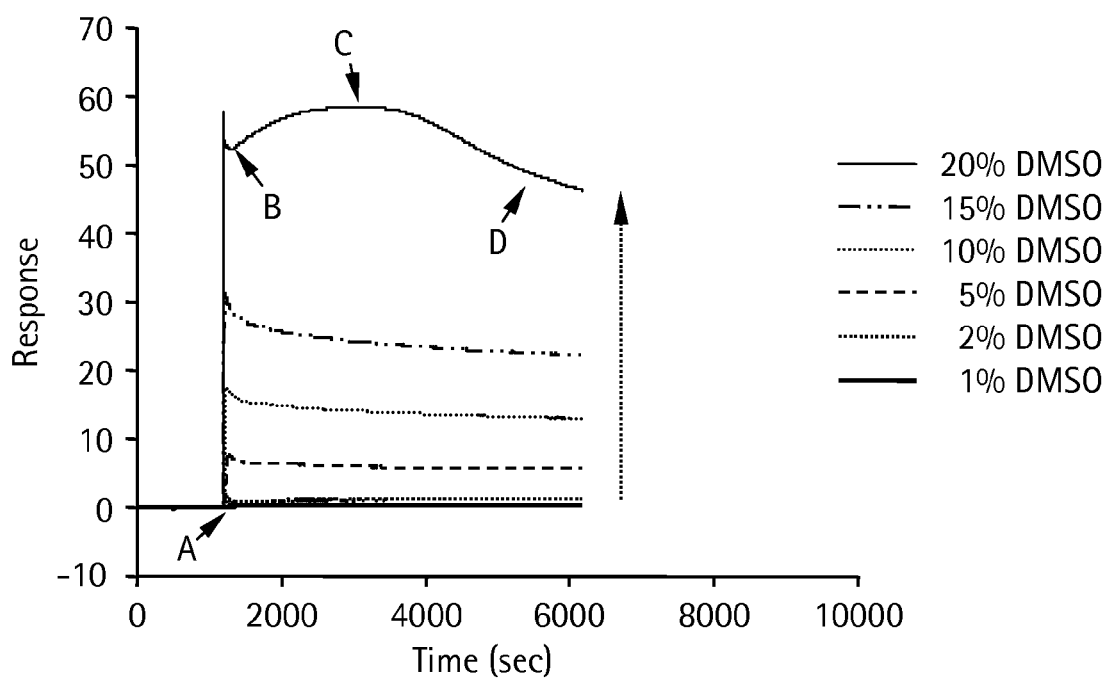

FIG. 29 shows a DMSO-induced dose-response and time-dependent response of a CHO cell layer adherent on a waveguide based biosensor. At 20% DMSO, four events are observed: (A) large response signal due to the bulk index change right after the introduction of DMSO solution; (B) a small decreased signal probably due to the mixing of the two fluids in the well; (C) a slow and steady increased signal probably because DMSO penetrates and replaces the biofluid inside the cells; and (D) a prolong decreased signal due to the loss of proteins or other biological molecules of cells caused by the toxicity of high concentration of DMSO.

Figure 30:
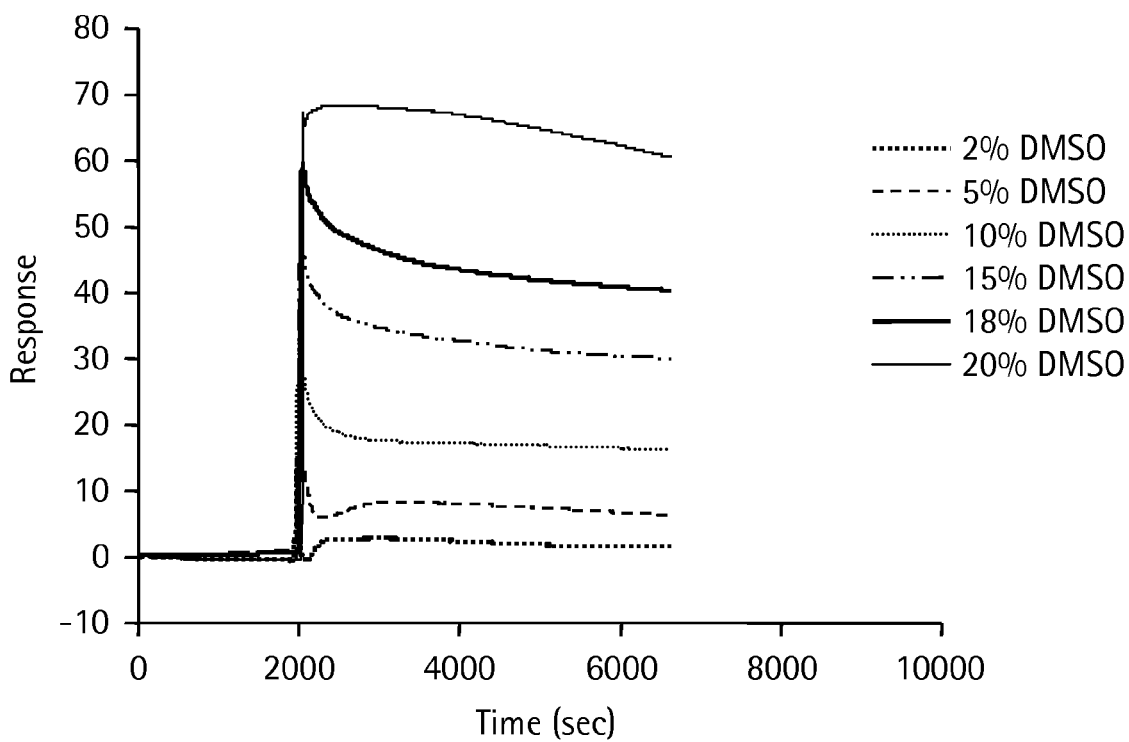

FIG. 30 shows a DMSO-induced dose-response and time-dependent response of A431 cell layer adherent on a waveguide based biosensor. The responses observed were similar to those on CHO cell layers.

Figure 31A:
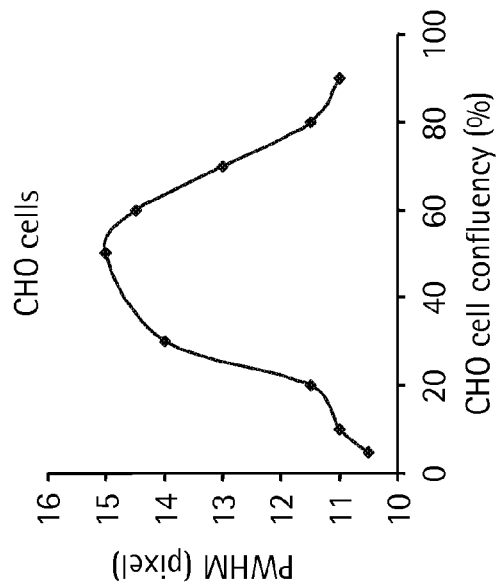
Figure 31B:
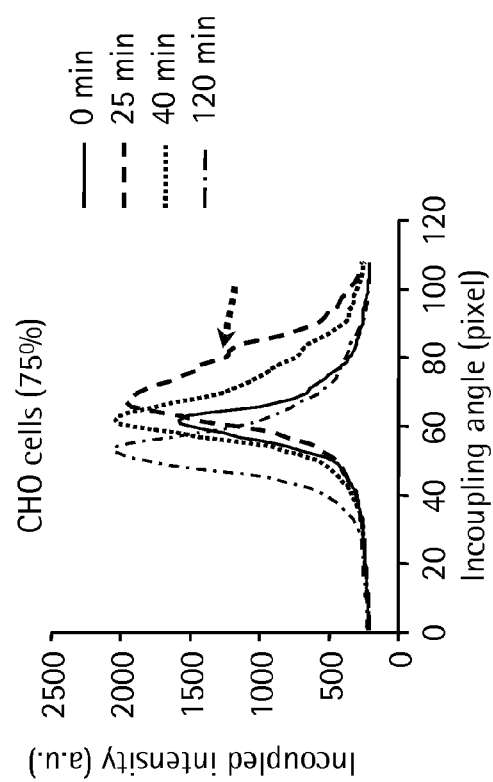

FIG. 31A shows the intensity of the incoupled light as a function of the incident angle for a layer of CHO cells with different confluencies (30%, 50% and 90%) cultured on a $Nb_2O_5$-based optical waveguide biosensors. The coupling mode is transverse magnetic ($TM_0$) mode. FIG. 31B The width of the peak at half-maximum (PWHM) using $TM_0$ mode is calculated and plotted as a function of CHO cell confluency.

Figure 32A:
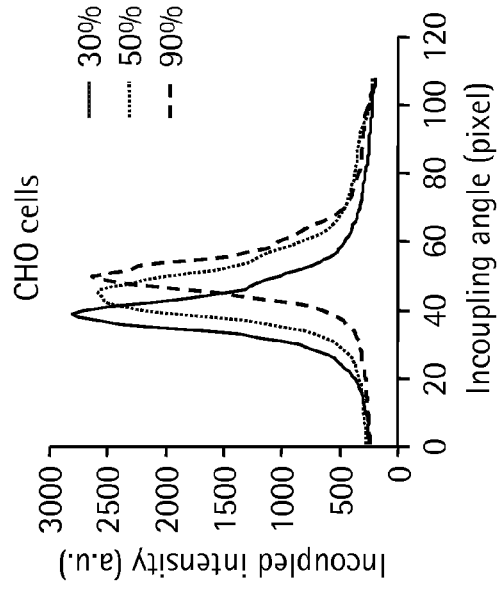
Figure 32B:
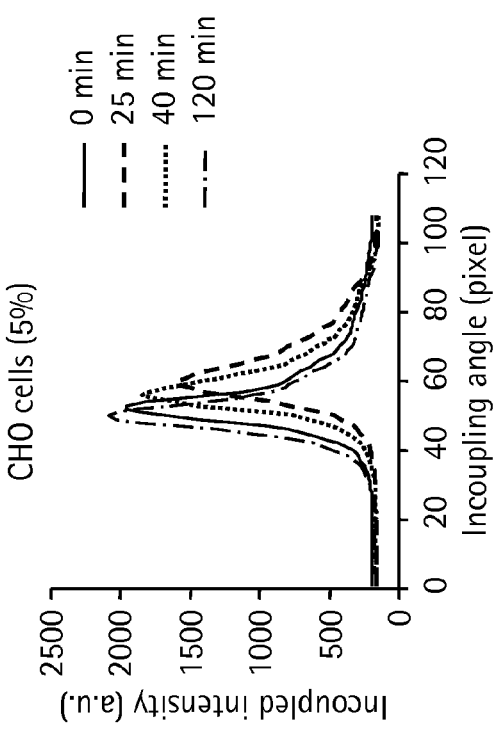

FIG. 32A and FIG. 32B shows the $TM_0$ mode resonant peaks of a layer of CHO cells with two different confluencies, 5% and 75%, respectively, cultured on waveguide grating sensors. FIG. 32B the resonant peak spectra were recorded at different times after addition of DMSO (with a final concentration of 18%). The broken arrow in the right graph shows the broadening and splitting of the resonance peak at the time of 25 min after DMSO treatment.

Figure 33:
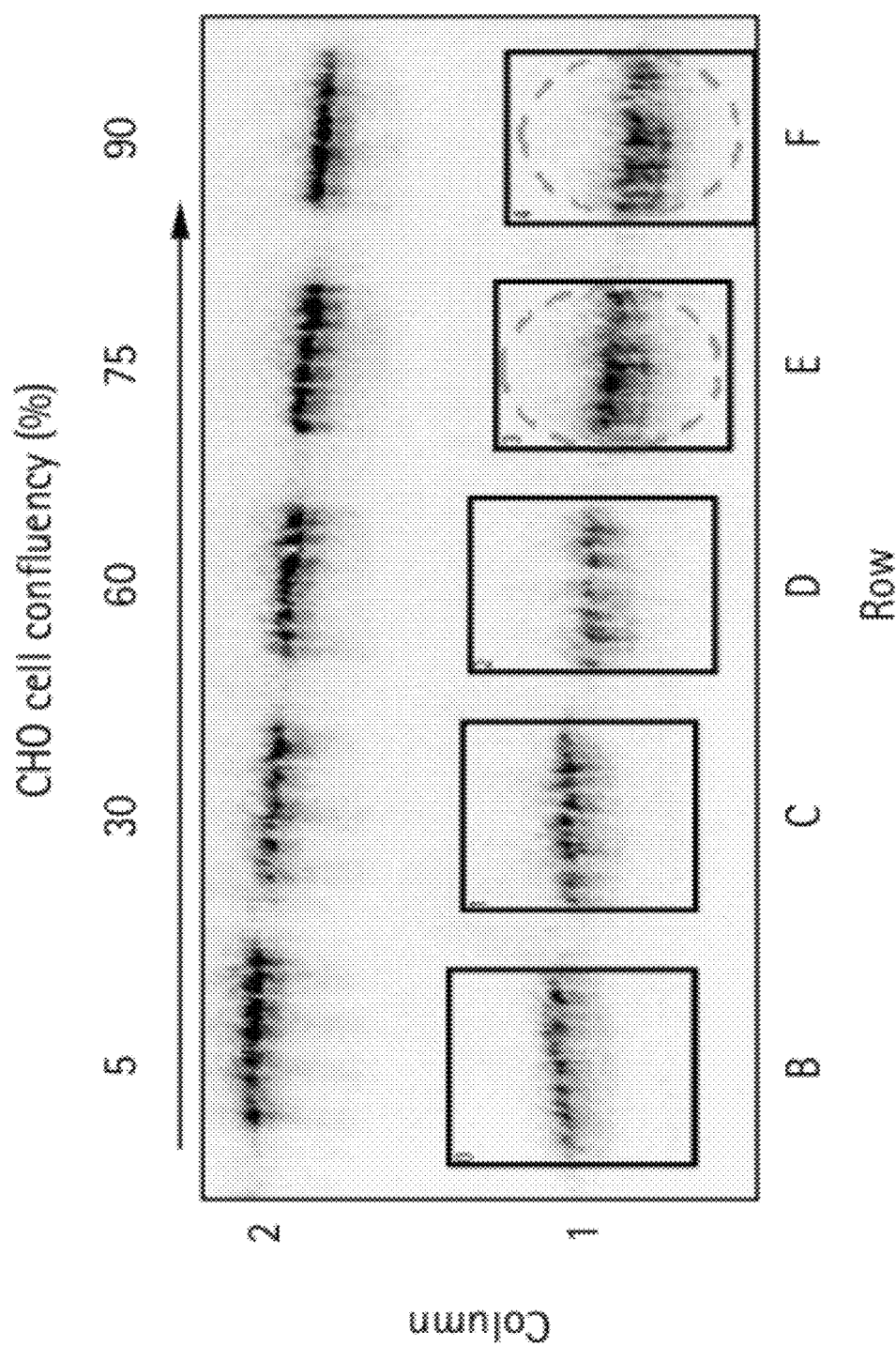

FIG. 33 shows a $TM_0$ mode resonance band image of the whole sensors, each sensor was covered by a layer of CHO cells at different confluencies (as indicated in the Figure). The images are taken after 25 min treatment with buffer (column 2), and with 18% DMSO (column 1).

Figure 34:
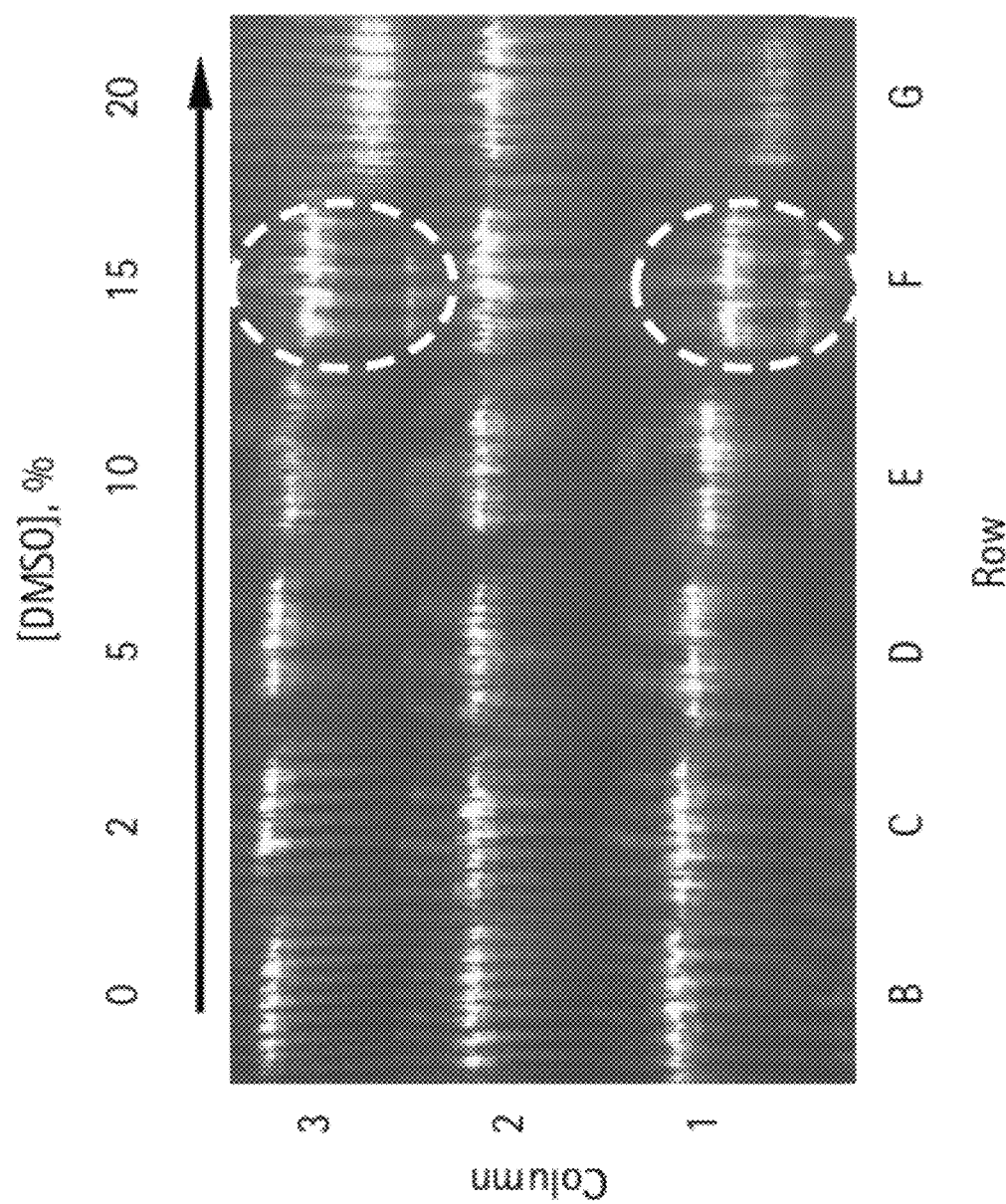

FIG. 34 shows a $TM_0$ mode resonance band image of the whole sensors, each sensor was covered by a layer of CHO cells at same confluency (~95%). The images are taken after a 25 min treatment with buffer (column 2), and with different concentrations of DMSO (column 1, and column 3, as indicated in the Figure). The circles indicate the peak splitting induced by the toxicity of DMSO of ~15% on CHO cells.

FIG. 35A and FIG. 35B show phase contrast images of CHO cells cultured on a waveguide grating sensor area and outside the sensor area, respectively.

Figure 36B:
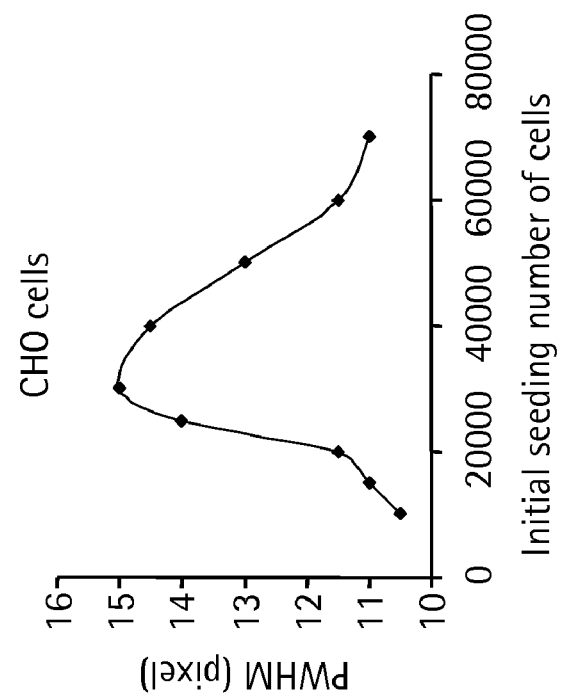
Figure 36A:
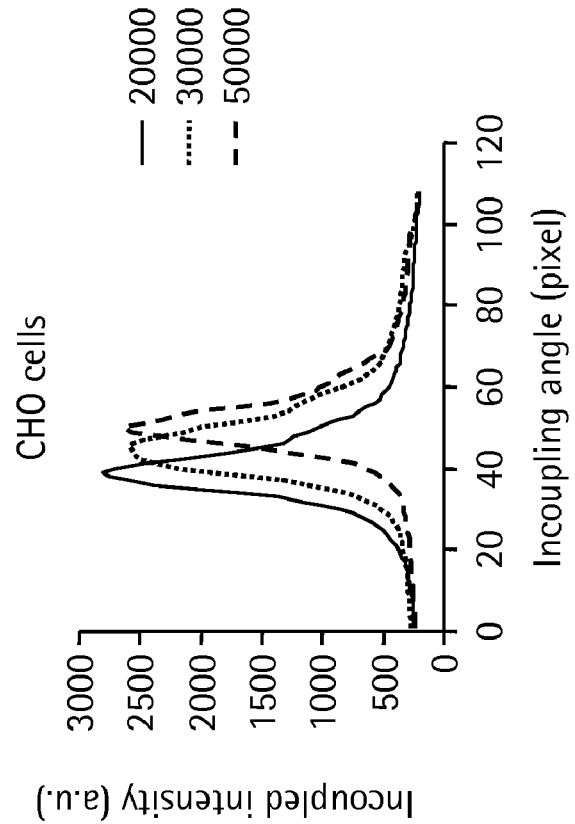

FIG. 36A shows the intensity of the incoupled light of the $TM_0$ mode as a function of the incident angle for CHO cells after cultured on $Nb_2O_5$-based optical waveguide biosensors for 36 hours. Different initial seeding numbers of cells are used to study the proliferation rate of CHO cells. The coupling mode is transverse magnetic ($TM_0$) mode. FIG. 36B shows that the width of the peak at half-maximum (PWHM) using $TM_0$ mode is calculated and plotted as a function of initial seeding numbers of CHO cells.

Figure 37:
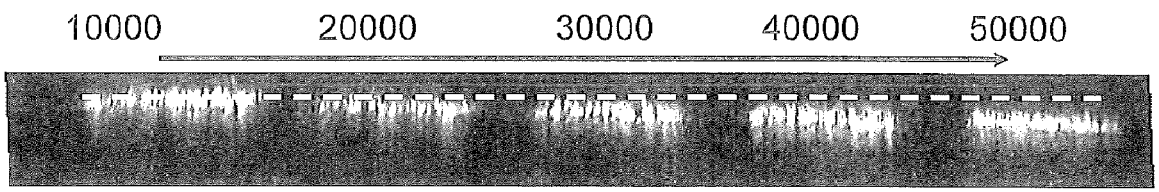

FIG. 37 shows a monitoring of CHO cells proliferation at different initial cell seeding numbers on the waveguide grating biosensors. The shape and position of the $TM_0$ mode resonance images of the whole sensors is observed to be dependent on initial seeding cell numbers, indicating that the proliferation rate of CHO cells depends on initial seeding cell numbers.

Figure 38:
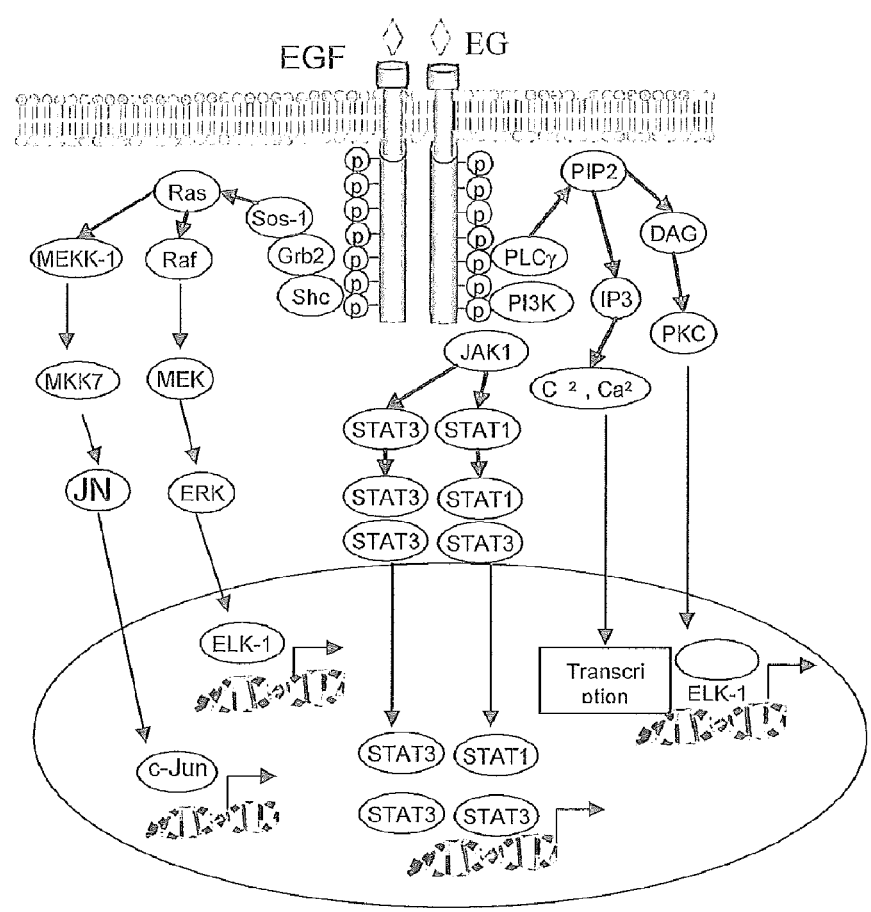

FIG. 38 shows epidermal growth factor receptor (EGFR) signaling pathways. The epidermal growth factor (EGF) family of receptor tyrosine kinases consists of four receptors, EGF-R (ErbB1), ErbB2 (Neu), ErbB3, and ErbB4. Members of the EGFR family contain a cytoplasmic tyrosine kinase domain, a single transmembrane domain, and an extracellular domain that is involved in ligand binding and receptor dimerization. Binding of ligand to EGFR leads to formation of homodimers or heterodimers of the receptor with other family members. Each dimeric receptor complex will initiate a distinct signaling pathway by recruiting different Src homology 2 (SH2)-containing effector proteins. Dimerization results in autophyosphorylation initiating a diverse array of downstream cellular signaling pathways. The activated EGF-R dimer complexes with the adapter protein, Grb, coupled to the guanine nucleotide releasing factor, SOS. The Grb-SOS complex can either bind directly to phosphotyrosine sites in the receptor or indirectly through Shc. These protein interactions bring SOS in close proximity to Ras, allowing for Ras activation. This subsequently activates the ERK and JNK signaling pathways that, in turn, activate transcription factors, such as c-fos, AP-1, and Elk-1, that promote gene expression and contribute to cell proliferation. EGF=epidermal growth factor, EGFR=epidermal growth factor receptor, Shc=src homology domain consensus, grb2=growth factor receptor-bound protein 2, SOS=mammalian son of sevenless, Raf=Ras activated factor, MEK=MAP kinase kinase, MAPK=mitogen activated protein kinase, PI3K=phosphatidylinositol 3' kinase, PIP2=phosphatidyl inositol 3,4-diphosphate, PIP3=phosphatidyl inositol 3,4,5 triphosphate, PLCγ=phospholipase-γ, DAG=diacyl glycerol, IP3=inositol 3,4,5 triphosphate, PKC=protein kinase C.

Figure 39:
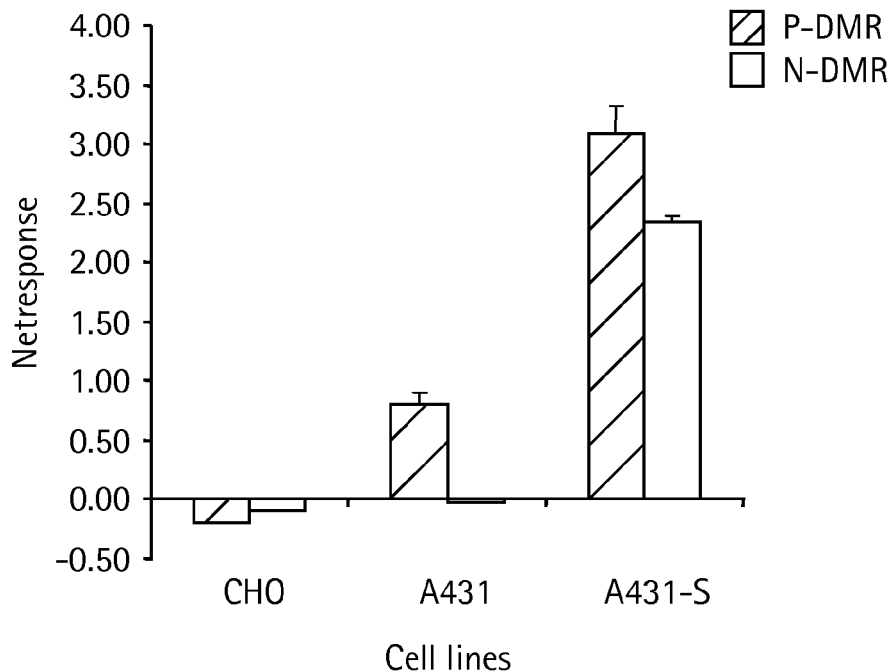

FIG. 39 shows the net responses of the P-DMR and N-DMR events observed for the EGF-induced responses of proliferating (indicated as A431) and quiescent A431 cells (indicated as A431-S), in comparison with quiescent CHO cells (indicated as CHO).

Figure 40:
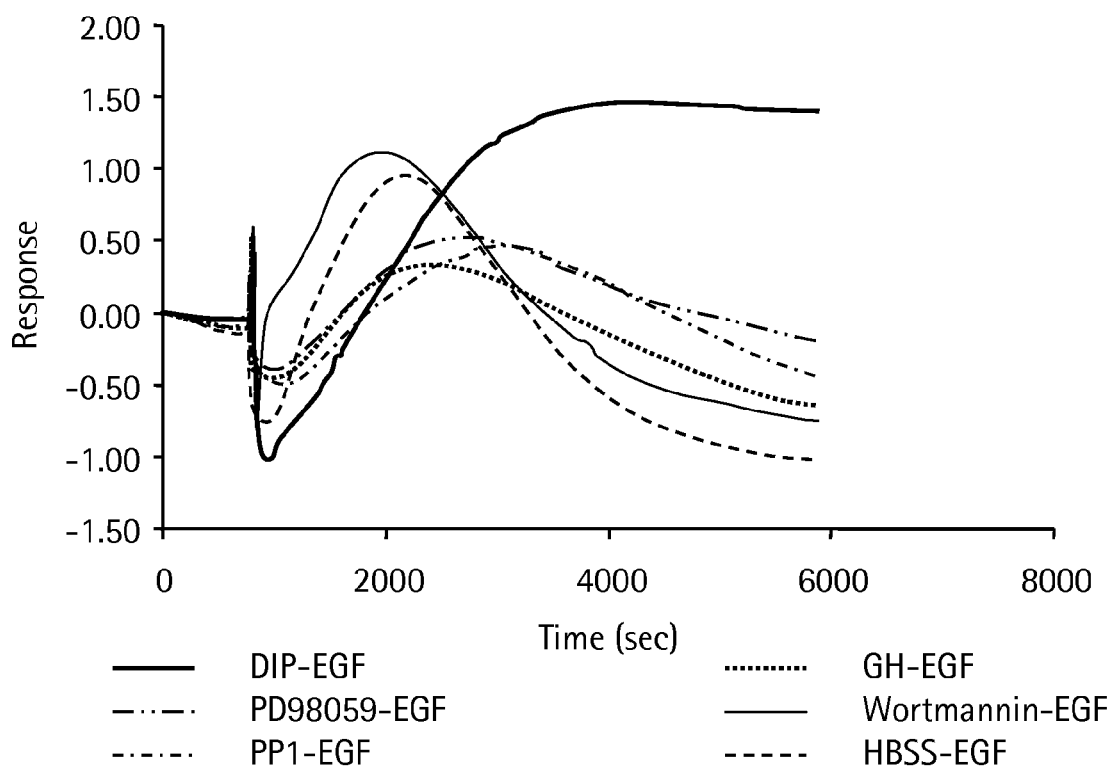

FIG. 40 shows the effect of a 30-minute pretreatment of a layer of starved A431 cells with different compounds on the time-dependent response after the addition of 16 nM EGF. The final concentrations of the compounds are 0.5 μg/ml, 0.1 mM, 1 μM, 0.1 μM, and 50 μM for growth hormone (GH), PD98059, PP1, wortmannin, and dynamin inhibitory peptide (DIP), respectively.

Figure 41:
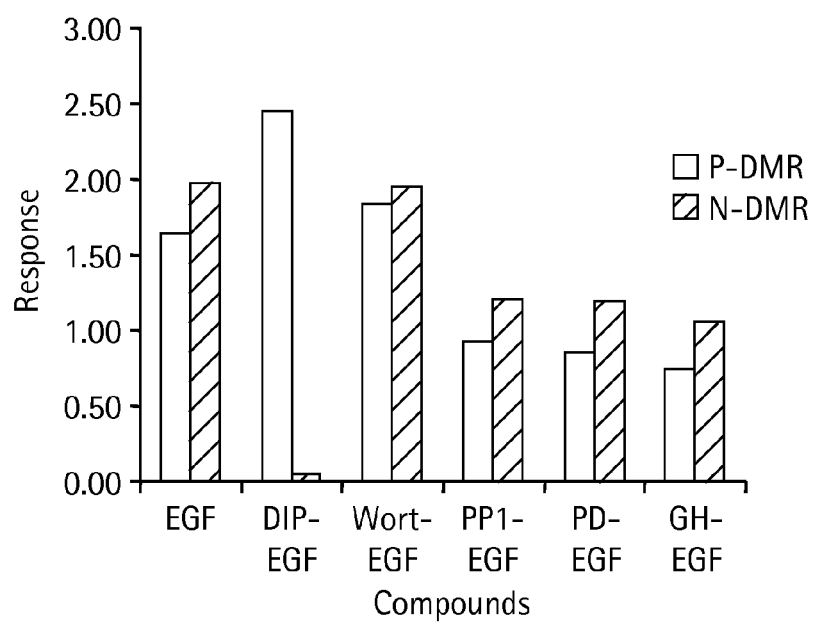

FIG. 41 shows the net responses of the P-DMR and N-DMR signals for a layer of starved A431 cells, cultured on waveguide biosensors, in response to stimulation with 16 nM EGF.

Figure 42A:
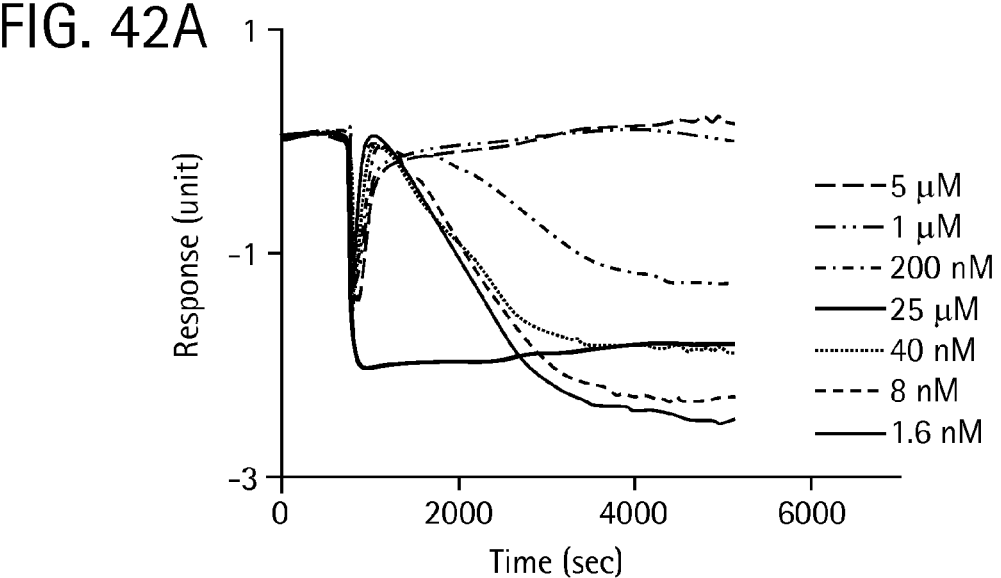
Figure 42B:
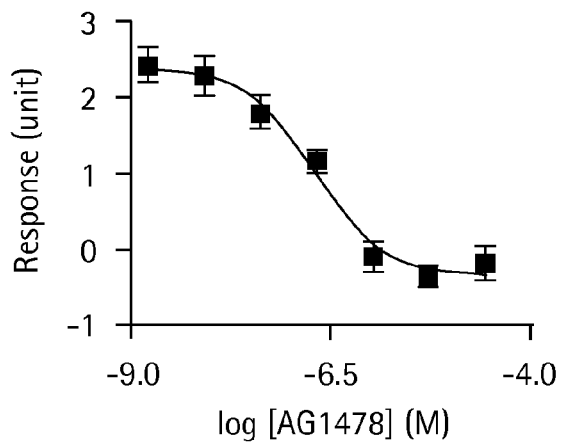

FIG. 42 shows a dose dependent suppression of the EGF-induced responses of quiescent A431 cells induced by AG1478. (A) Pretreatment of quiescent A431 cells with different concentrations of AG1478 led to a dose dependent alternation of the response induced by 32 nM EGF. (B) The amplitudes of the N-DMR signals as a function of AG1478 concentration.

Figure 43:
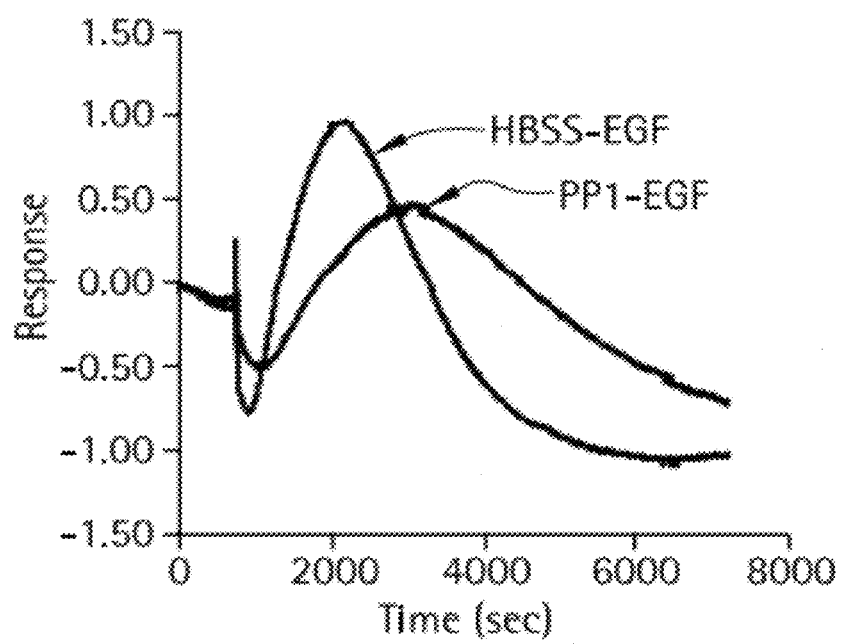

FIG. 43 shows the effect of a Src kinase inhibitor PP1 on the EGF-induced DMR response of quiescent A431 cells.

Figure 44:
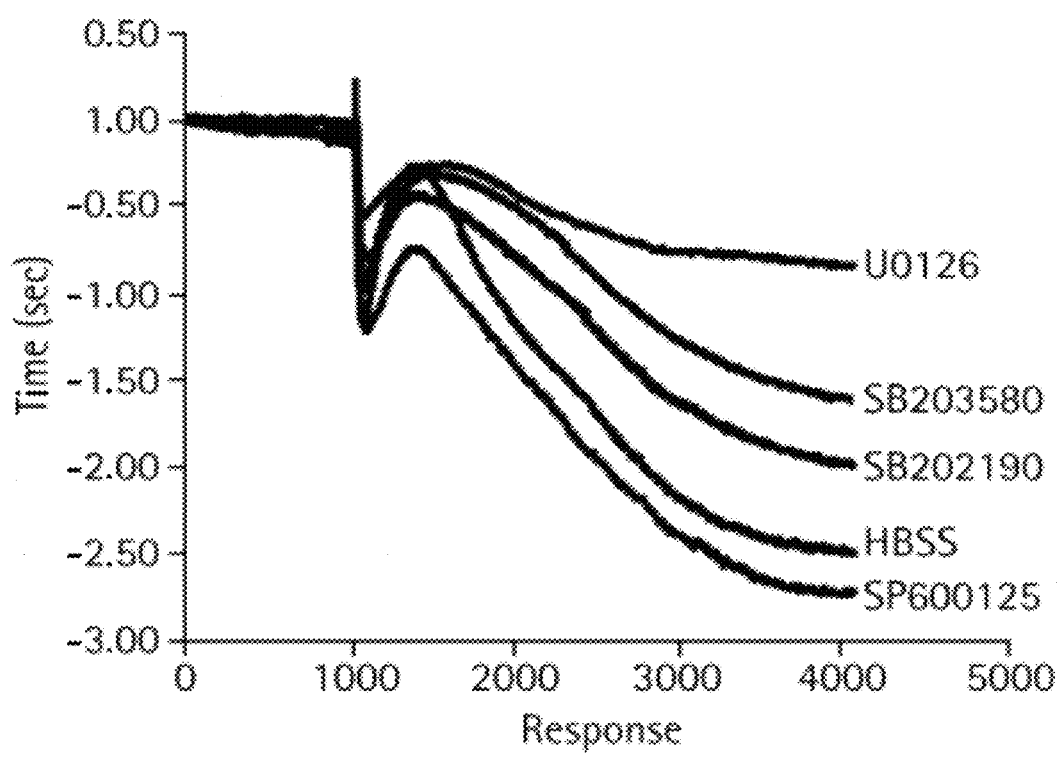

FIG. 44 shows the effect of Ras/MAPK pathway modulators on 32 nM EGF-induced response of the quiescent A431 cells.

Figure 45:
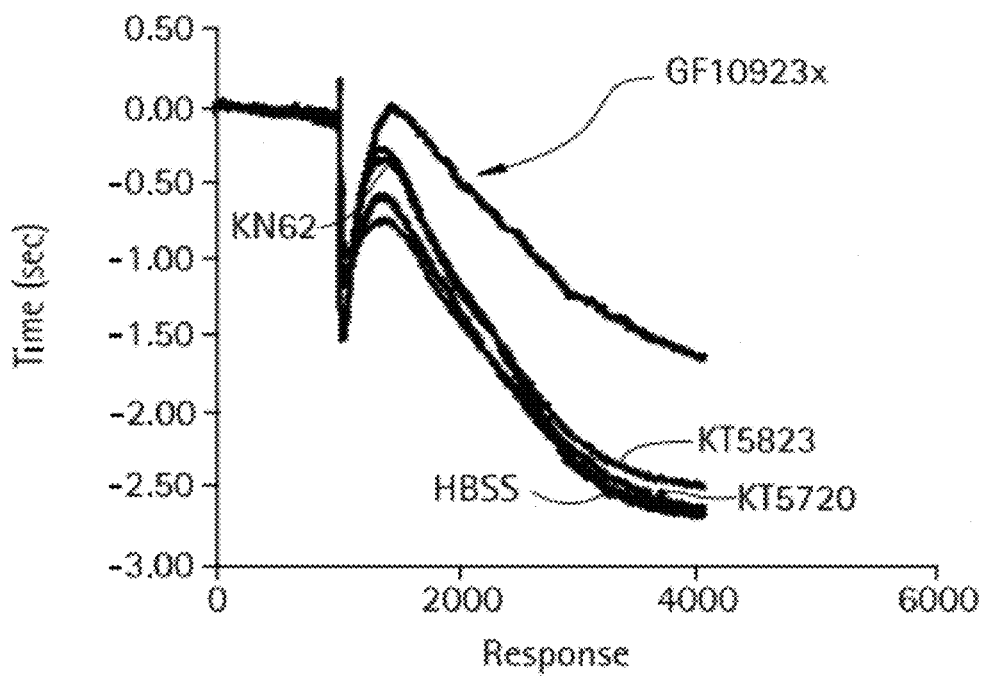

FIG. 45 shows the effect of protein kinase inhibitors on 32 nM EGF-induced response of the quiescent A431 cells.

Figure 46:
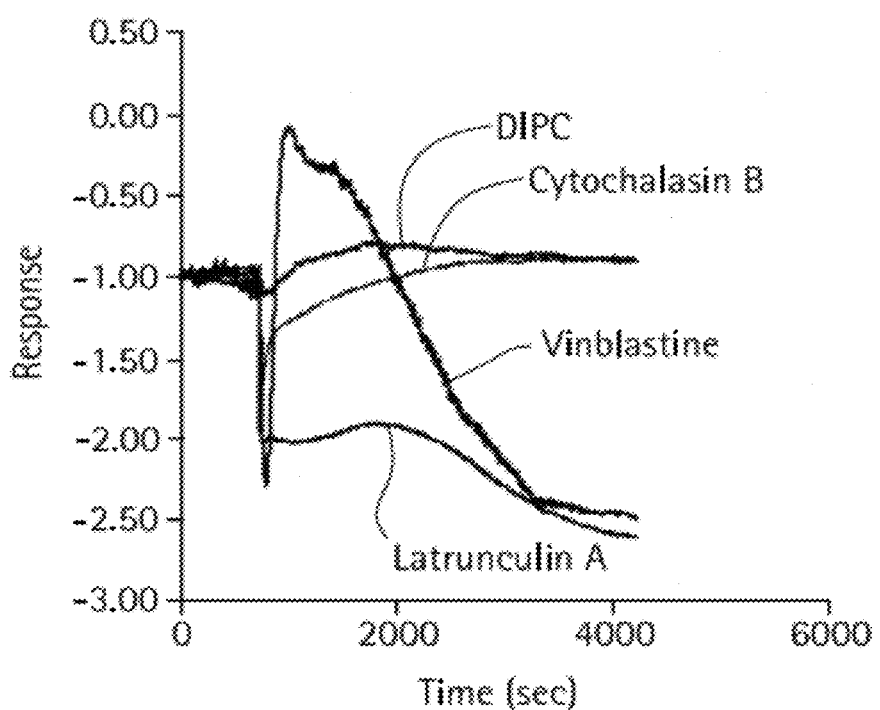

FIG. 46 shows the effect of cytoskeleton modulators on 32 nM EGF-induced response of the quiescent A431 cells.

Figure 47:
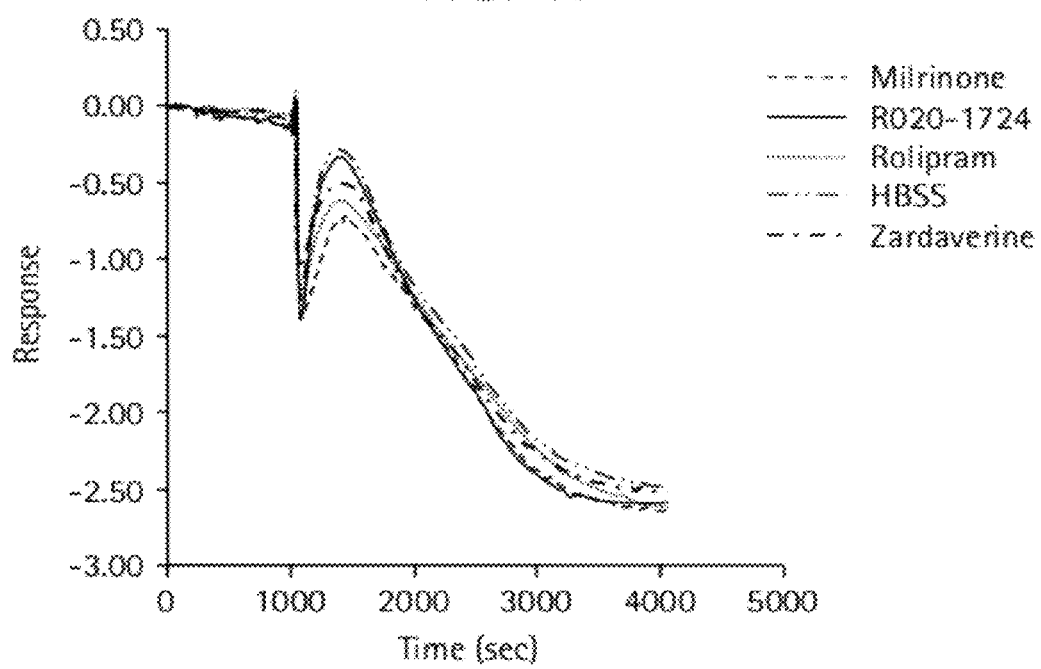

FIG. 47 shows the effect of phosphodiesterase and other inhibitors on 32 nM EGF-induced response of the quiescent A431 cells.

FIG. 48 shows two major contributors to the overall DMR signal induced by EGF of quiescent A431 cells observed using the optical biosensor. EGF induced EGFR internalization, cell morphology changes, and directional mass redistribution in A431 cells at room temperature (22° C.). (FIG. 48A) Fluorescence image of proliferating A431 (10% FBS) after staining with 8nM tetramethylrhodamine labeled EGF (TMR-EGF) and sequent stripped away the surface-bound TMR-EGF with an acidic solution at 4°C. (FIG. 48B) Fluorescence image of quiescent A431 (0.1% FBS) after staining with TMR-EGF. (FIG. 48C) Fluorescence image of quiescent A431 (0.1% FBS) after staining and sequent stripped away the surface-bound TMR-EGF with an acidic solution at 4° C. (FIG. 48D) Quiescent A431 cells before treated with 16 nM EGF for the indicated times were examined using fluorescence microscopy with a 32× magnification after fixation and stained with Texas red-labeled phalloidin. (F*ig*.48E) Quiescent A431 cells 15 min after treated with 16 nM EGF were examined using fluorescence microscopy with a 32× magnification after fixation and stained with Texas red®-labeled phalloidin. (F*ig*.48F) Quiescent A431 cells 30 min after treated with 16 nM EGF were examined using fluorescence microscopy with a 32× magnification after fixation and stained with Texas red®-labeled phalloidin.

Figure 49A:
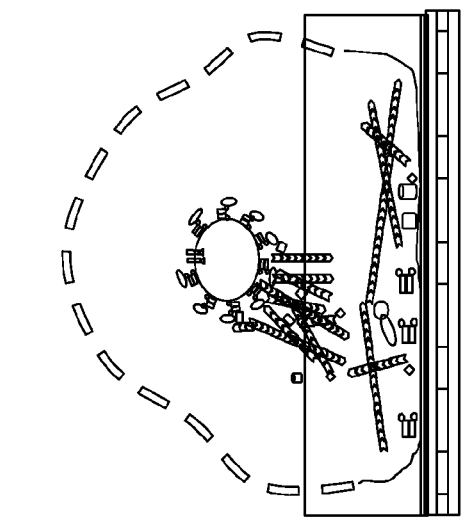
Figure 49B:
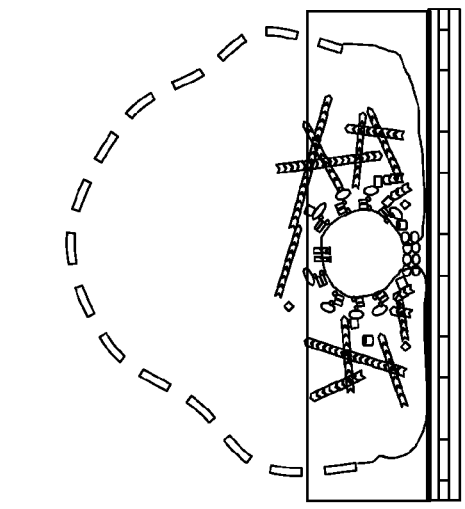
Figure 49C:
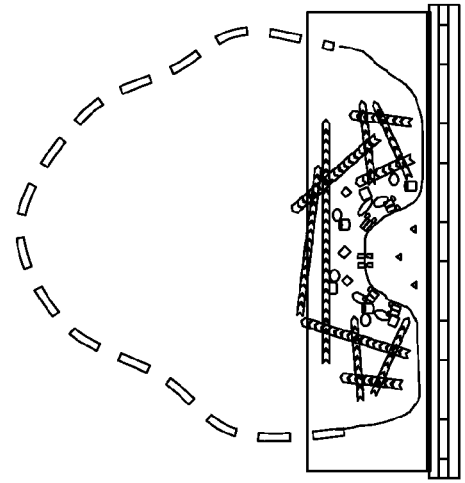

FIGS. 49A to 49C show a schematic sequence of one possible mechanism for EGF-induced DMR signals—receptor endocytosis.

Figure 50:
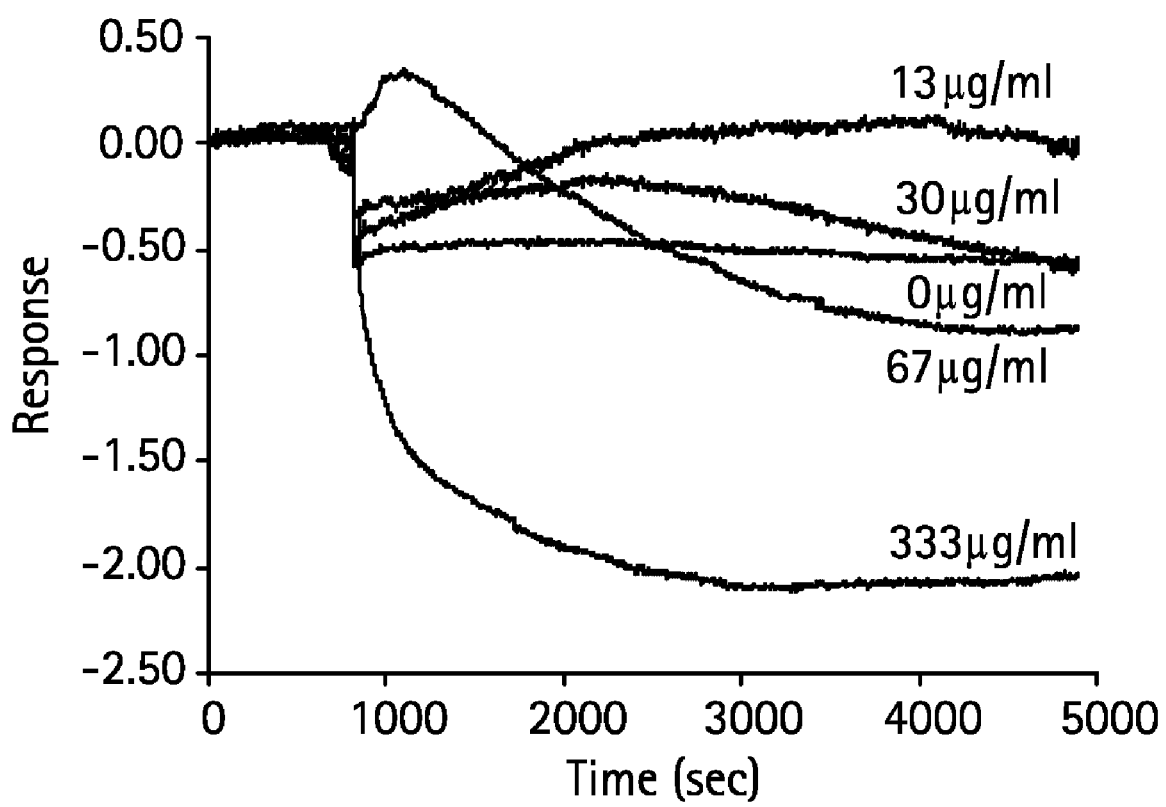

FIG. 50 shows dose dependent responses of Chinese hamster ovary (CHO) cells adherent on a LID sensor surface before, and after addition of saponin.

Figure 51:
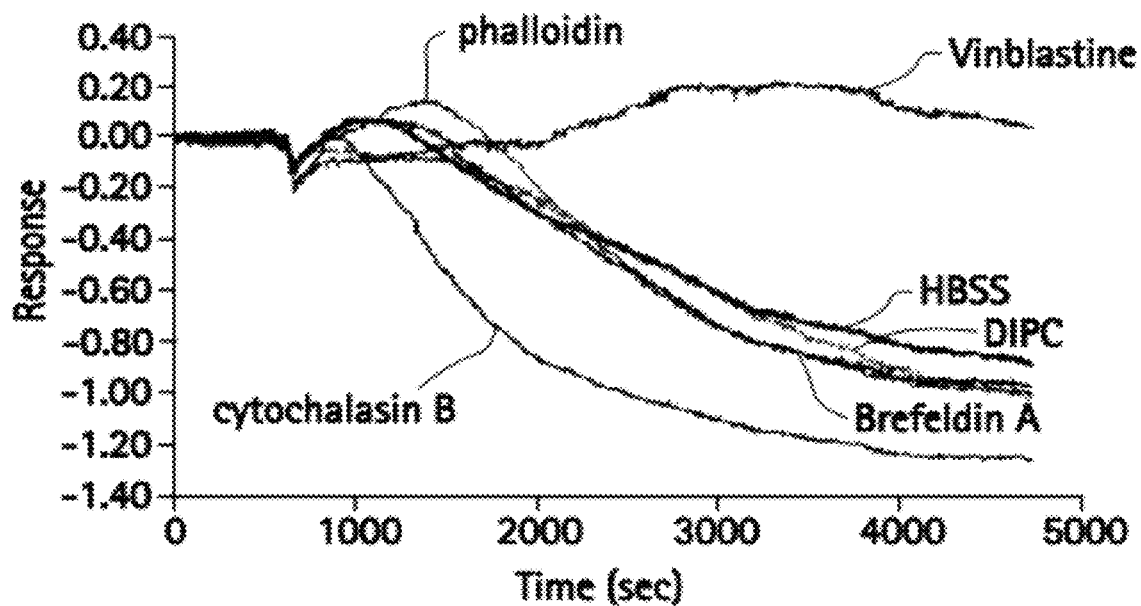

FIG. 51 shows real time responses of CHO cells after pre-treatment with different compounds and followed by saponin treatment.

Figure 52:
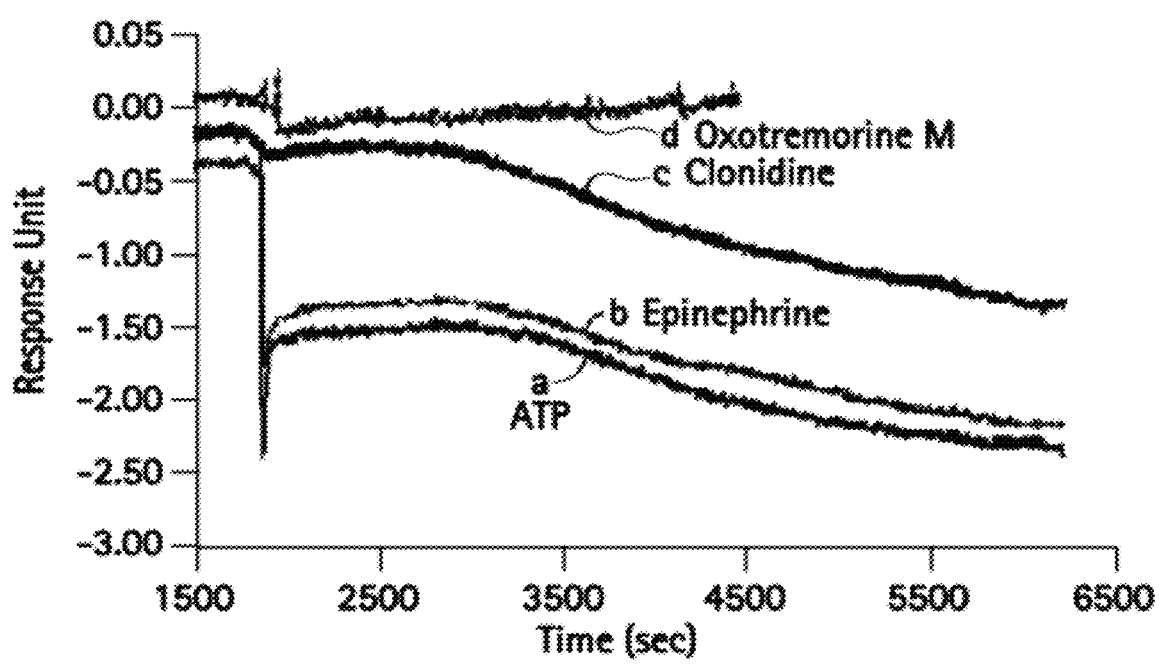

FIG. 52 shows a time-dependent LID response of Chinese Hamster Ovary (CHO) cells before and after compound addition.

Figure 53:
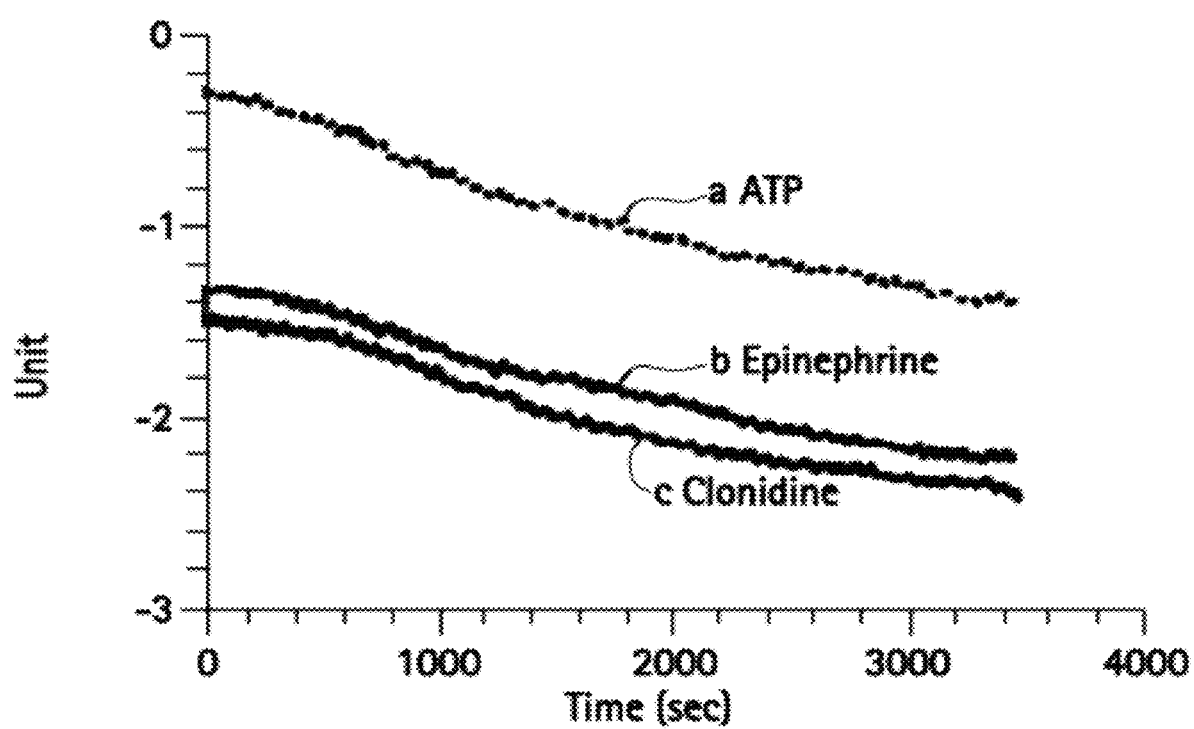

FIG. 53 shows the different kinetics of the mass redistribution due to agonist-induced GPCR activation.

Figure 54:
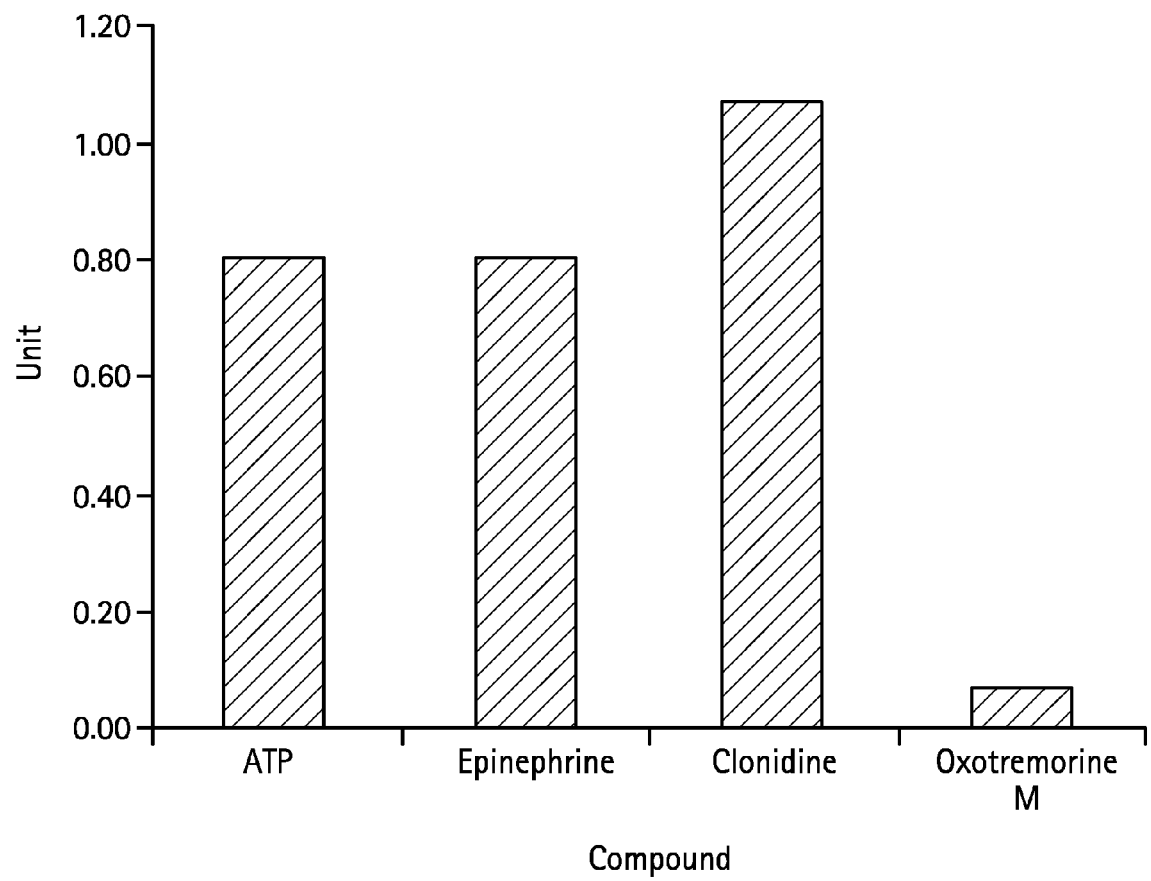

FIG. 54 shows compound-dependant total responses of agonist-induced mass changes in the Stage 3 as highlighted in FIG. 16.

Figure 55:
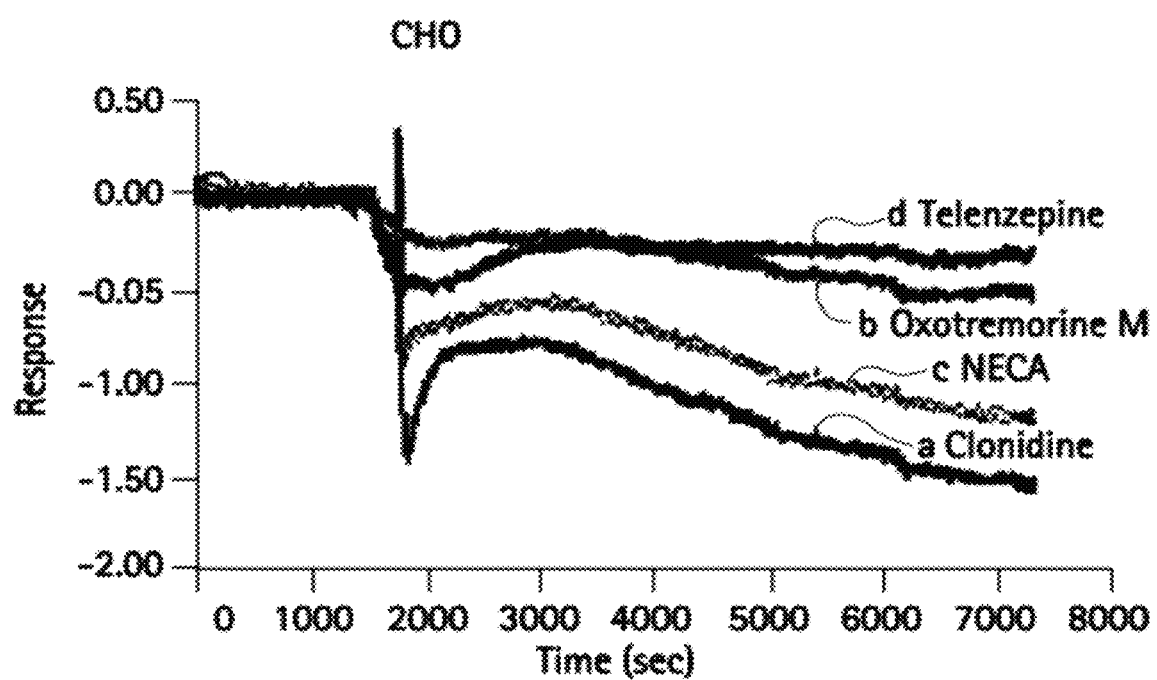

FIG. 55 shows a time-dependent LID response of Chinese Hamster Ovary (CHO) cells before and after compound addition. The compound concentration used is 10 μM for all compounds.

Figure 56:
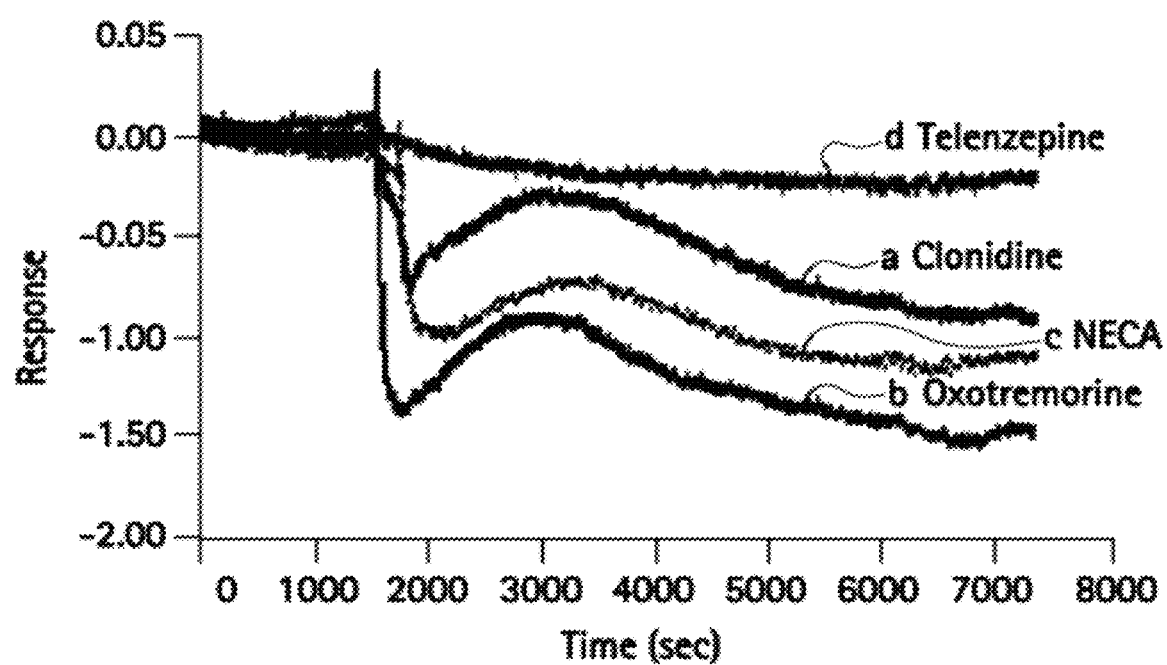

FIG. 56 shows a time-dependent LID response of engineered Chinese Hamster Ovary (CHO) cells with over-expressed rat muscarnic receptor subtype 1 (thus this cell line is termed as M1 CHO) before and after compound addition. The compound concentration used is 10 μM for all compounds.

Figure 57:
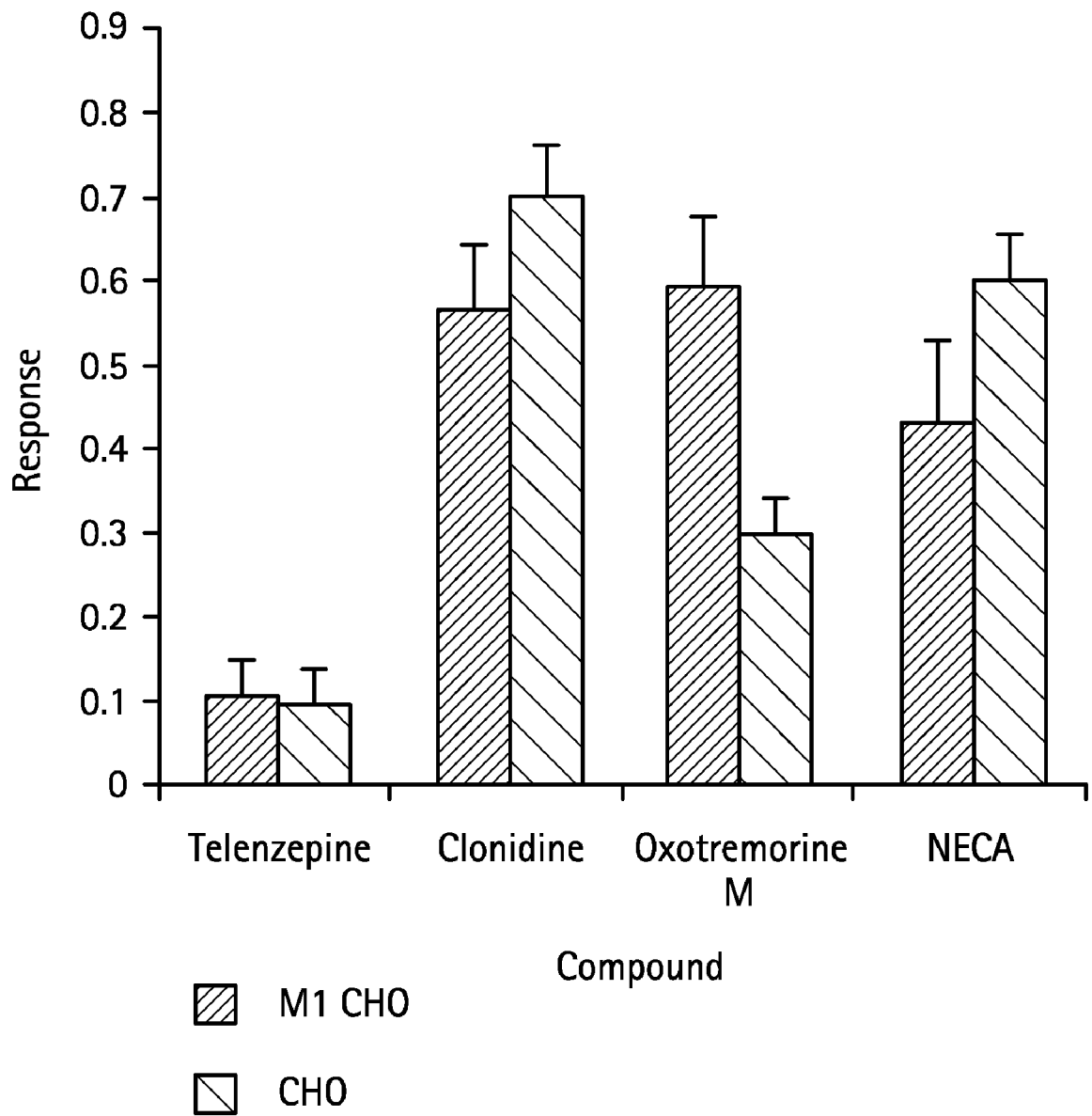

FIG. 57 compares the compound-dependant total responses in the Stage 3 as highlighted in FIG. 16 for two distinct cell lines.

Figure 58:
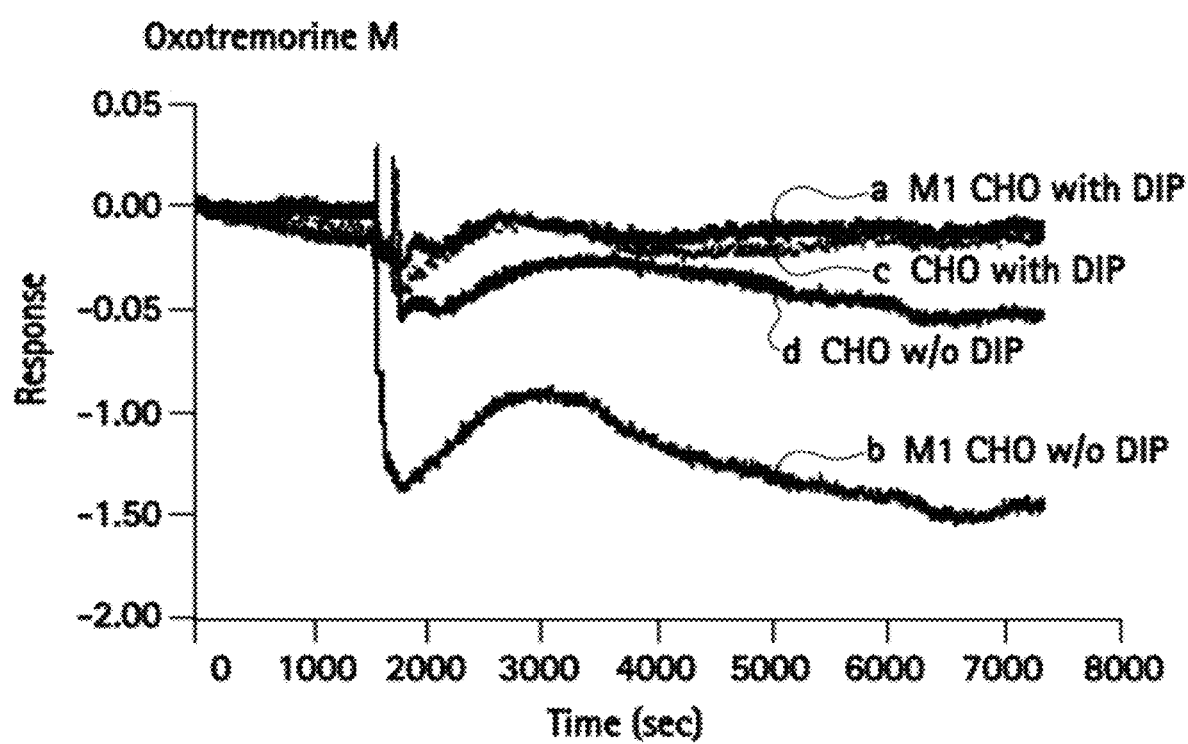

FIG. 58 shows a time-dependent LID response of two types of cells (CHO and M1 CHO) before and after addition of oxotremorine M (10 µM). Before the compound addition, the cells are pre-incubated either HBSS buffer (Invitrogen) (referred to "without DIP") or with dynamin inhibitory peptide (DIP) at a concentration of 50 µM for 45 minutes.

Figure 59:
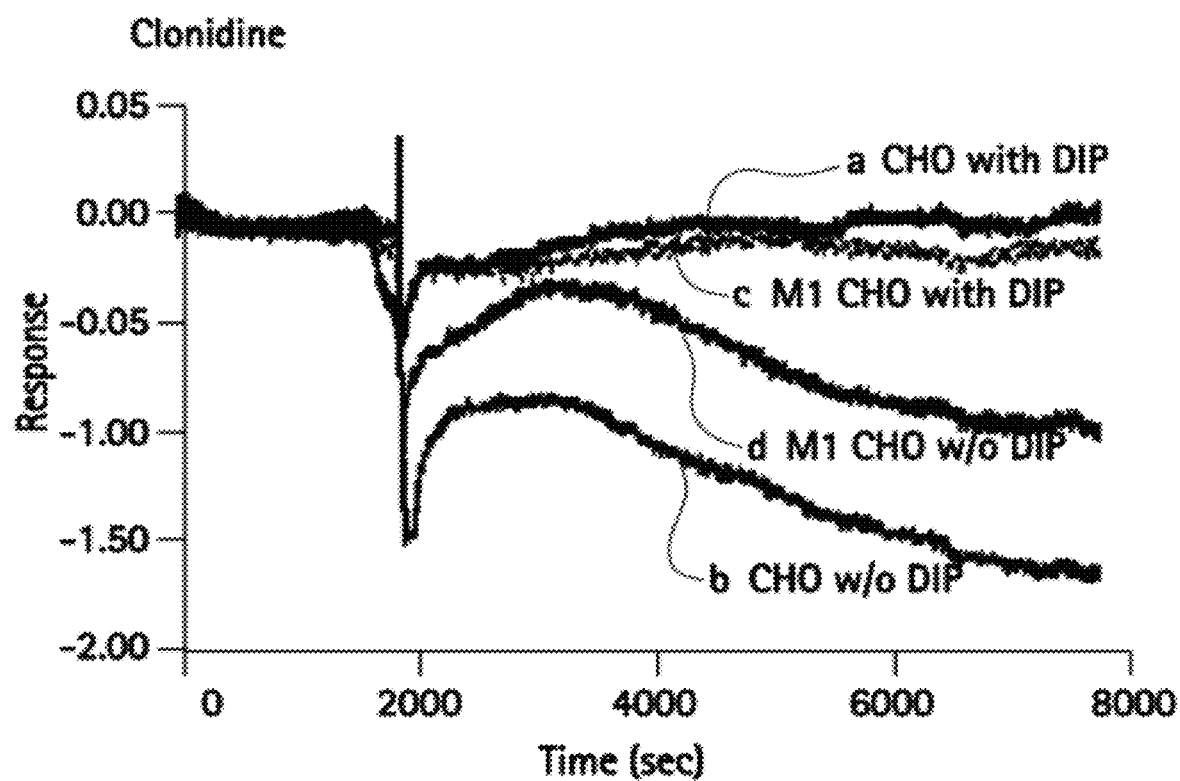

FIG. 59 shows a time-dependent LID response of two types of cells (CHO and M1 CHO) before and after addition of clonidine (10 µM). Before the compound addition, the cells are pre-incubated either HBSS buffer (Invitrogen) (referred to "without DIP") or with dynamin inhibitory peptide (DIP) at a concentration of 50 µM for 45 minutes.

Figure 60:
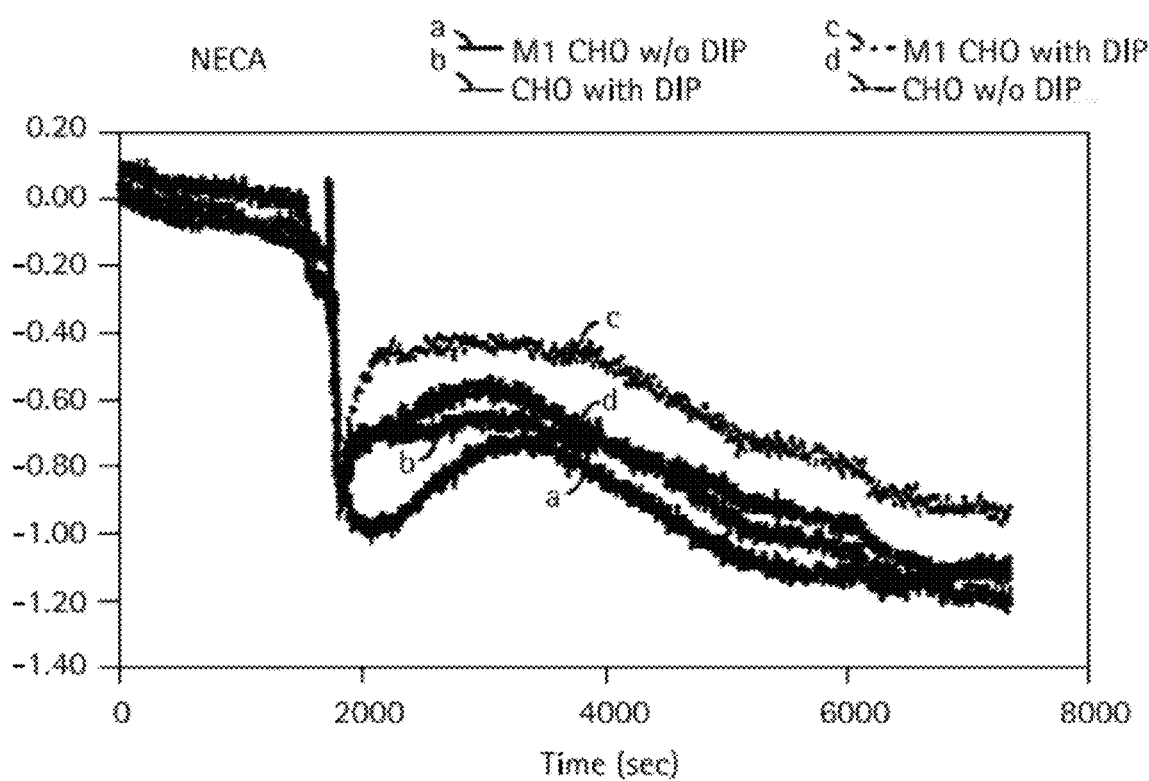

FIG. 60 shows a time-dependent LID response of two types of cells (CHO and M1 CHO) before and after addition of NECA (10 µM). Before the compound addition, the cells are pre-incubated either HBSS buffer (Invitrogen) (referred to "without DIP") or with dynamin inhibitory peptide (DIP) at a concentration of 50 µM for 45 minutes.

Figure 61A:
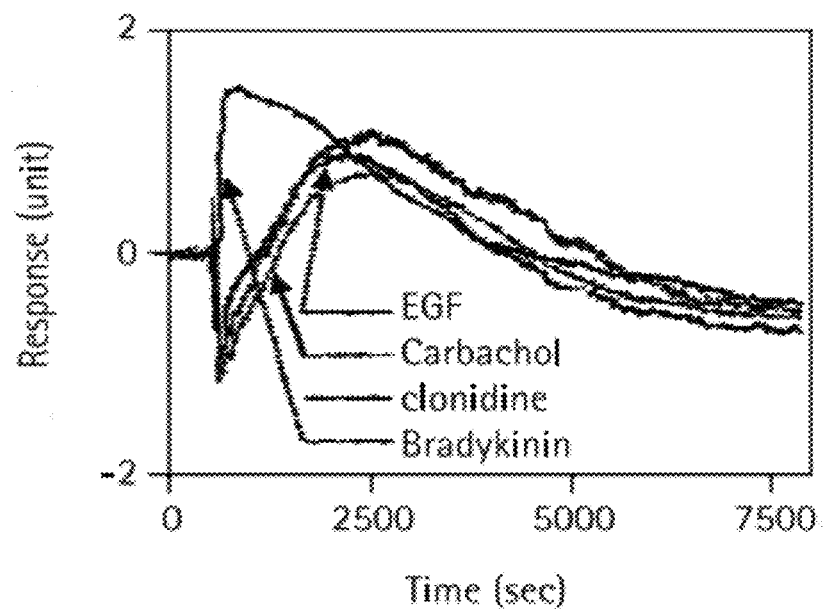
Figure 61B:
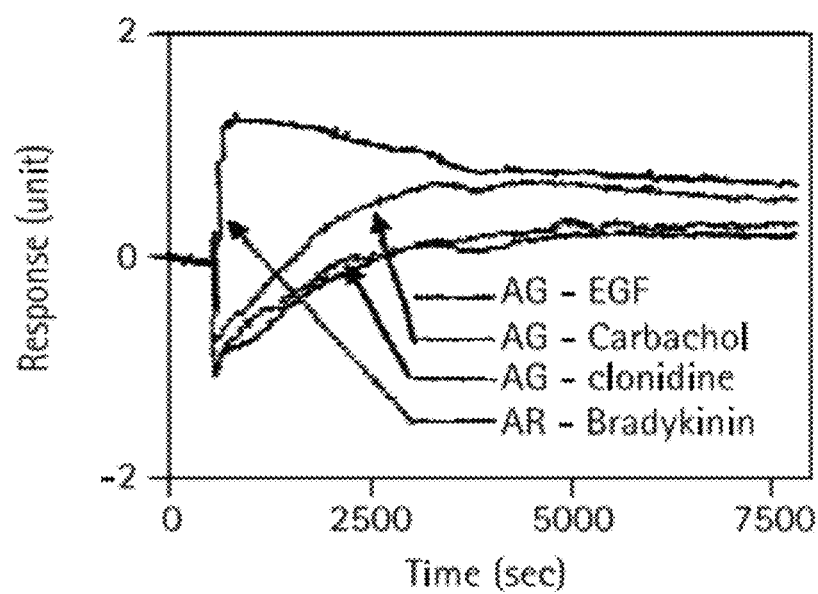

FIG. 61A shows a GPCR agonist-induced directional mass redistribution within adlayer of quiescent A431 cells. Three GPCR agonists, bradykinin (100 nM), carbachol (10 µM) and clonidine (1 µM), induced time-dependent responses of quiescent A431 cells, in comparison with that induced by EGF (8 nM). FIG. 61B shows the FIG. 61A experiment with the exception of Pretreatment of A431 with 10 µM AG1478 on the GPCR agonist- and EGF-induced responses.

Figure 62:
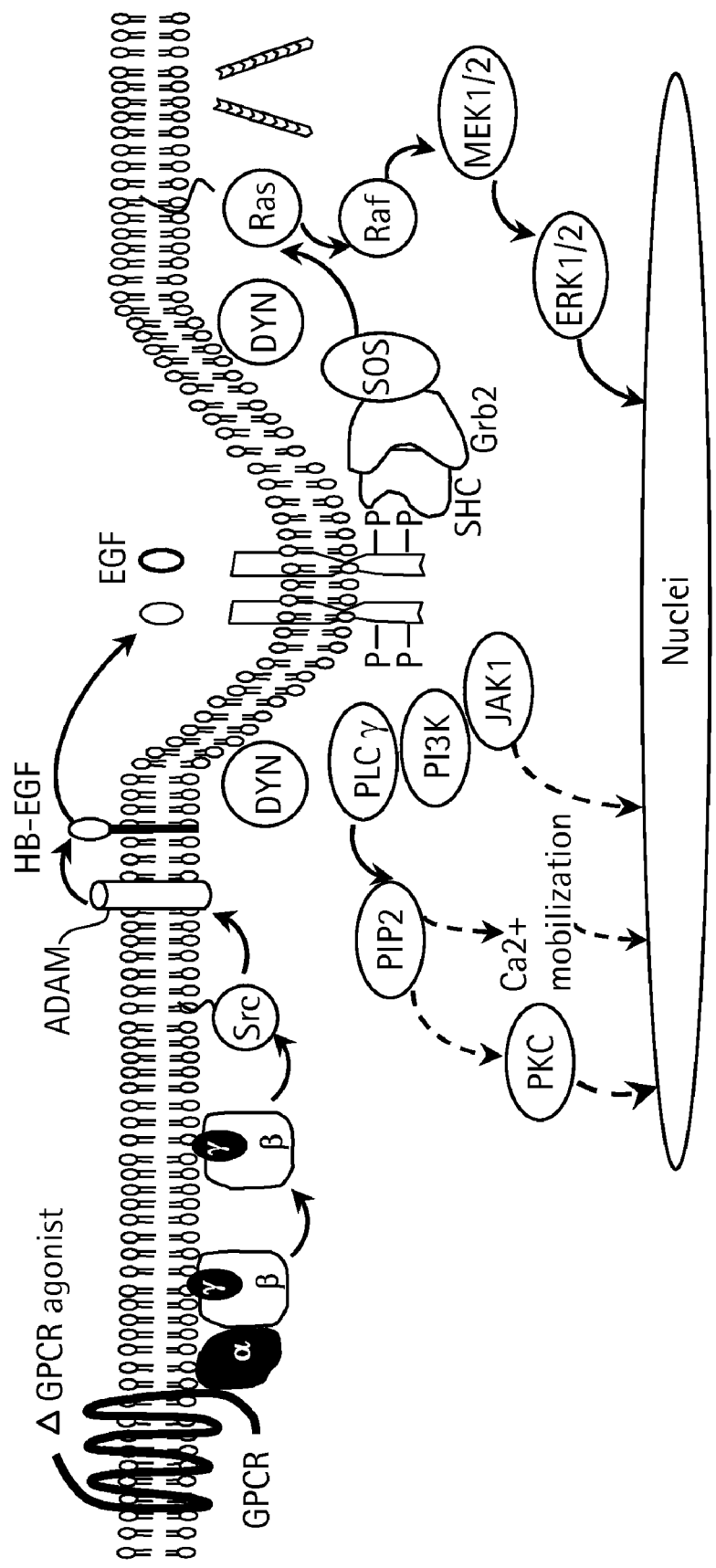

FIG. 62 shows a schematic drawing shows the mechanism of EGF-induced EGFR activation and one possible mechanism of G protein-coupled receptor (GPCR) agonist-induced EGFR transactivation. The GPCR agonist induced EGFR transactivation could also be through other mechanisms: such as protein kinase C pathway, or PI3K pathway. The bradykinin-induced DMR response of quiescent A431 cells, as showed in FIG. 61, could be through protein kinase C pathway.

FIG. 63 shows four classes of optical signatures induced by GPCR agonists. The optical signature is related to dynamic mass redistribution within the bottom portion of quiescent A431 cells, as monitored in real time with resonant waveguide grating biosensors. (a) $G_q$-type DMR signal, as exampled by thrombin (40 unit/ml). (b) $G_s$-type DMR signal, as exampled by epinephreine (25 nM). (c) $G_i$-type DMR signal, as exampled by α-MSH (α-melanocyte stimulating hormone) (40 nM). (d) Net-zero DMR signal, as exampled by neurotensin (40 nM). The solid arrows (the same in the rest figures) indicated the time when the agonist solution was introduced.

Figure 64:
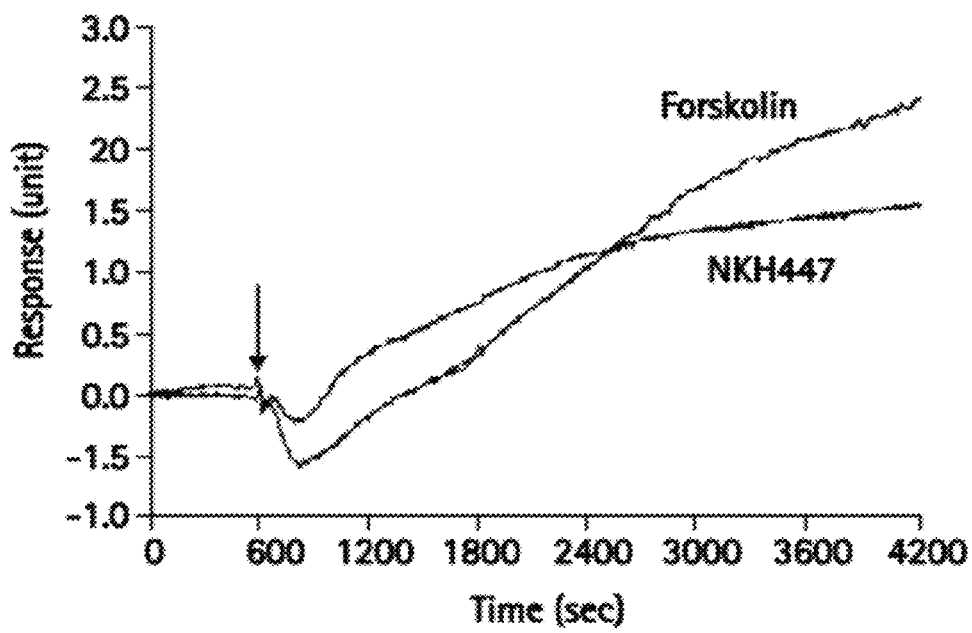

FIG. 64 shows the optical signatures of quiescent A431 cells induced by adenylate cyclase activators forskolin and NKH447.

Figure 65:
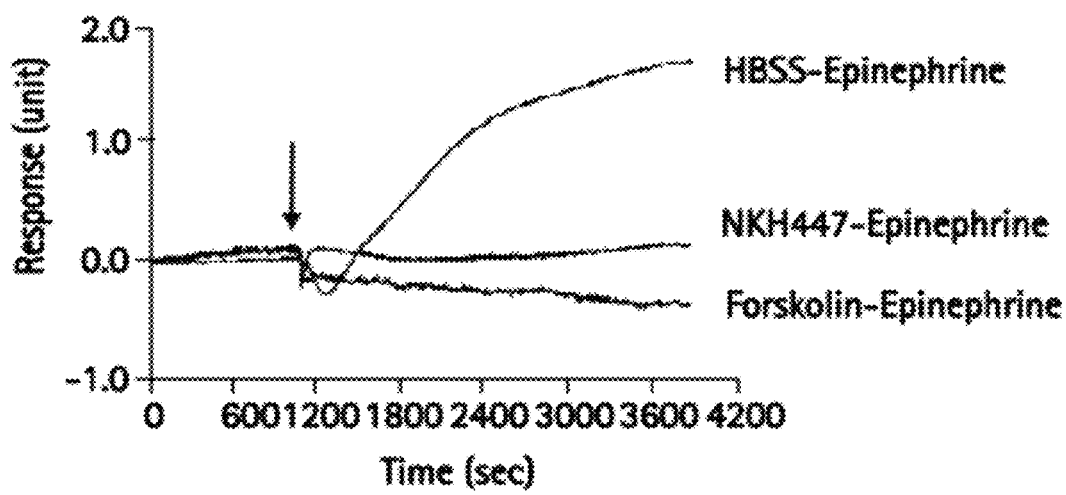
Figure 66A:
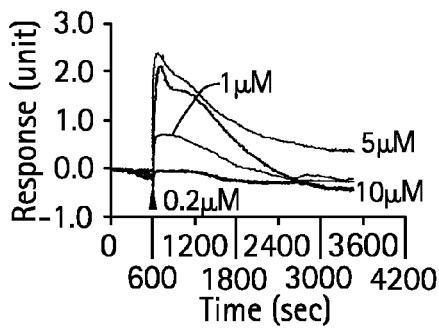
Figure 66B:
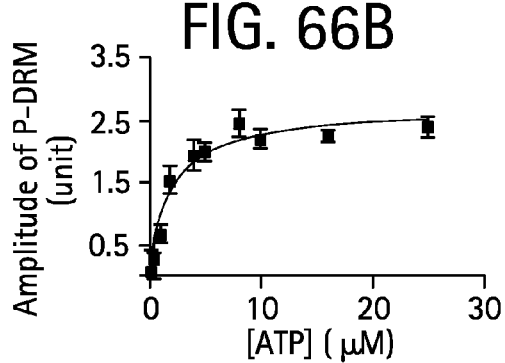
Figure 66C:
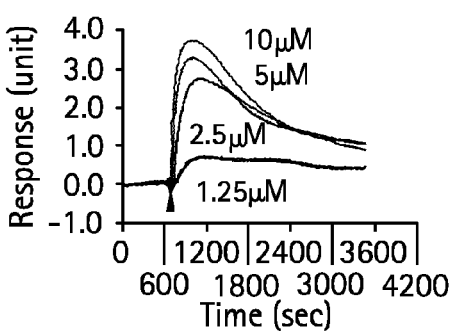
Figure 66D:
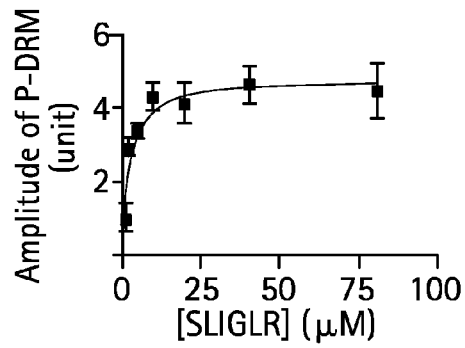
Figure 66E:
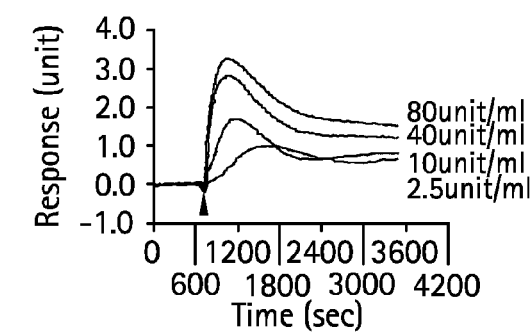
Figure 66F:
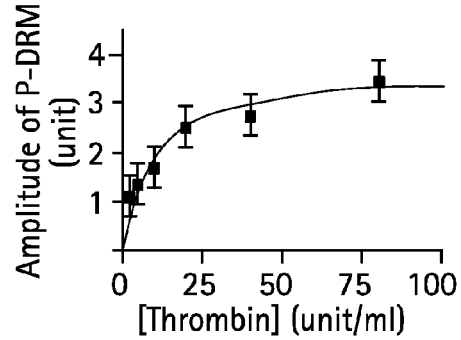
Figure 66G:
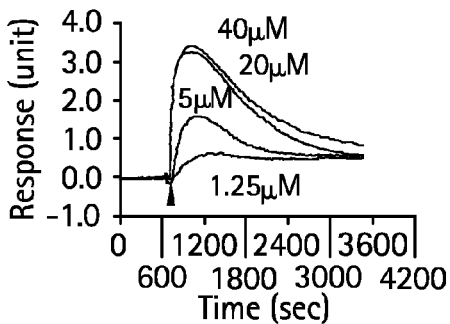
Figure 66H:
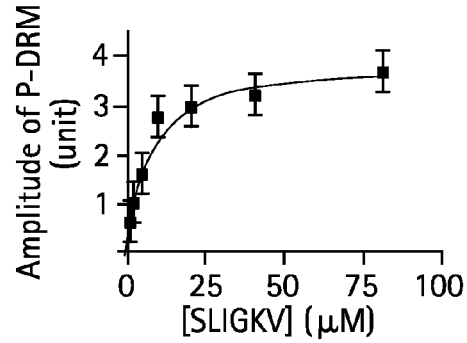
Figure 67A:
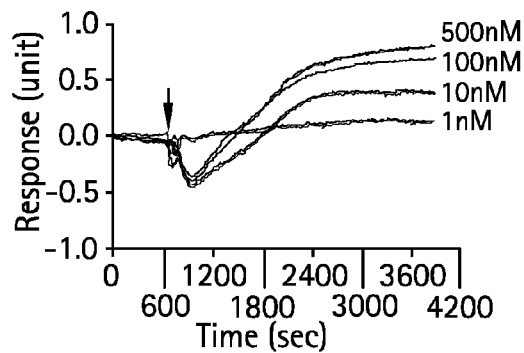
Figure 67B:
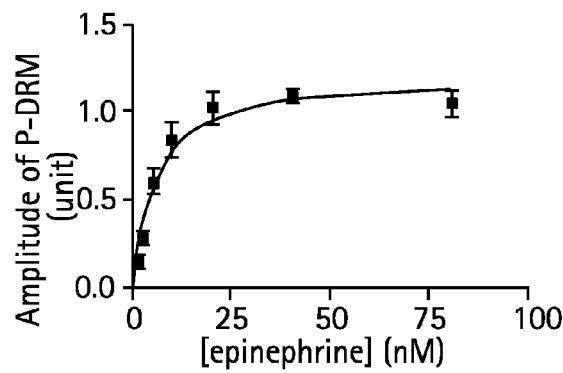
Figure 67C:
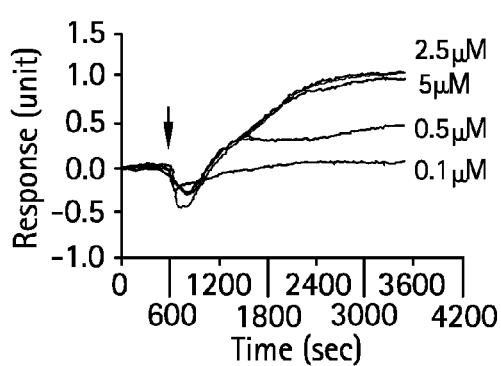
Figure 67D:
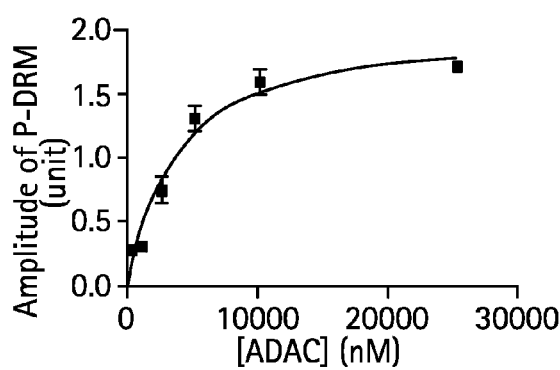
Figure 67E:
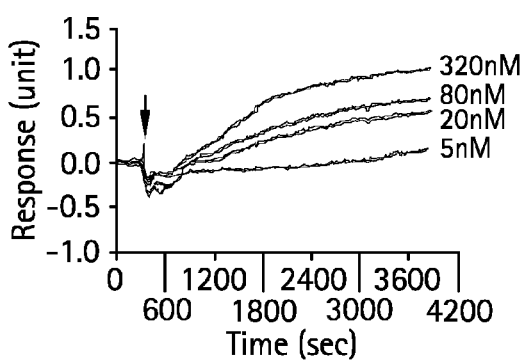
Figure 67F:
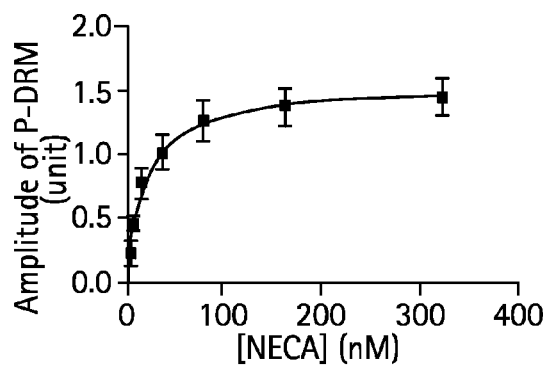

FIG. 65 shows the pretreatment of quiescent A431 cells with forskolin and NKH447 completely abolished the DMR response mediated by 25 nM epinephreine. The pretreatment of cells with the HBSS only was used as positive controls.

FIG. 66 shows the efficacies of agonists that trigger the $G_q$-type signature. The dose-dependent kinetic responses and the corresponding saturation curves were plotted for ATP (a, b), SLIGLR-amide (c, d), thrombin (e, f), and SLIGKV-amide (g, h), respectively. The final concentrations were indicated in the graphs.

FIG. 67 shows the efficacies of agonists that trigger the $G_s$-type signature. The dose-dependent kinetic responses and the corresponding saturation curves were plotted for epinephreine (a, b), adenosine amine cogener (ADCA) (c, d), and NECA (e, f), respectively.

Figure 68A:
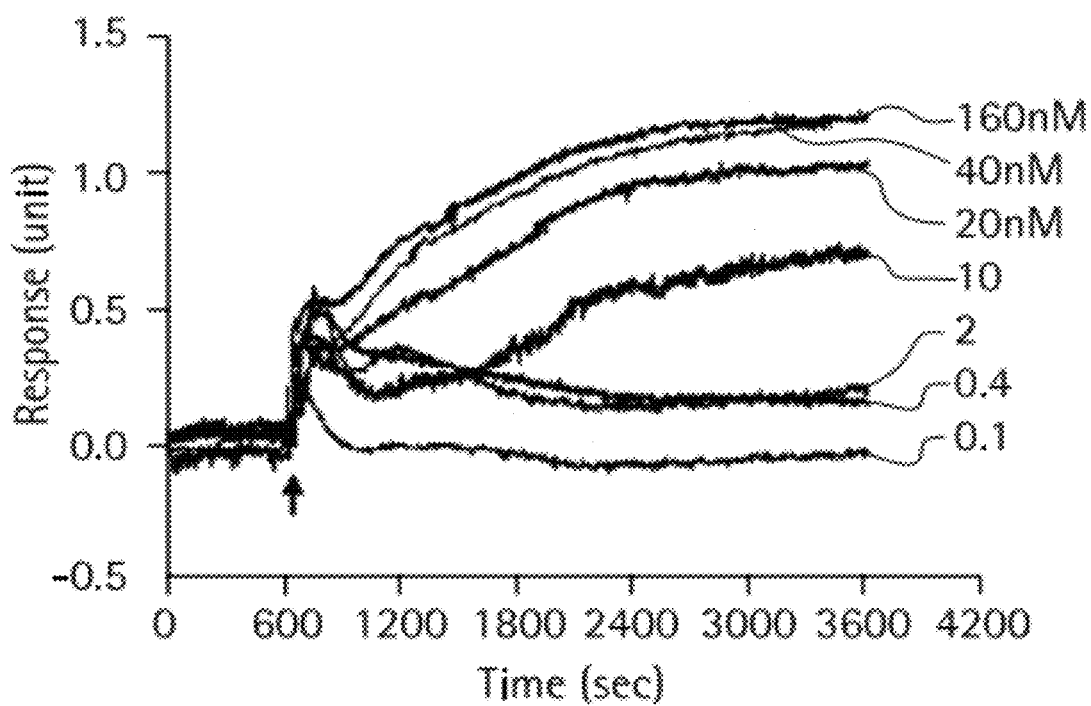
Figure 68B:
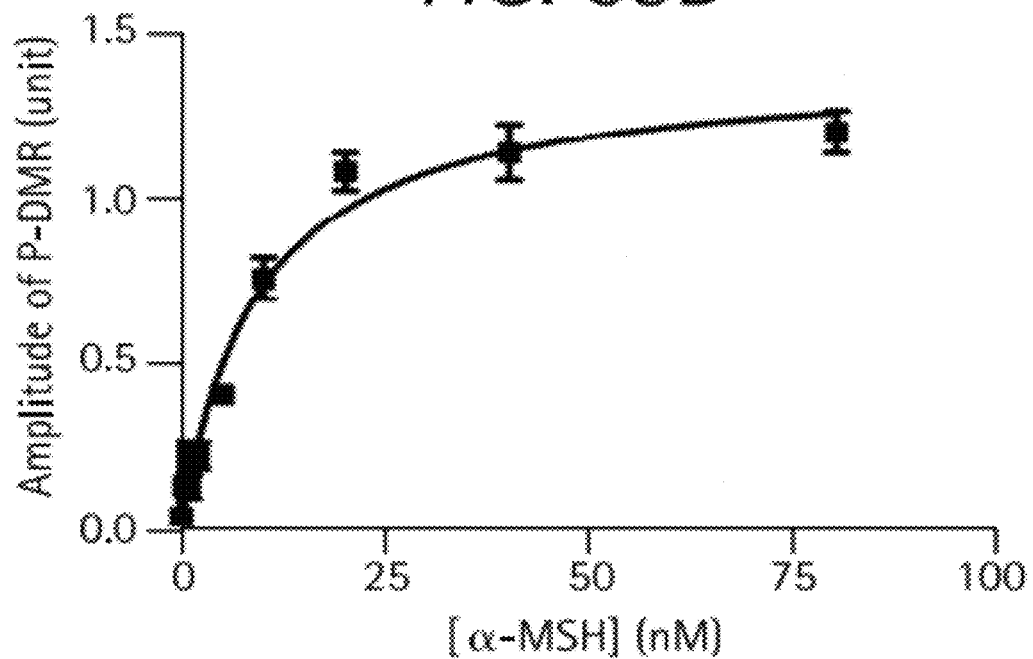

FIGS. 68A and 68B, respectively, show the dose-dependent kinetic responses, and the saturation curve of quiescent a431 cells induced by α-MSH (α-melanocyte stimulating hormone).

Figure 69A:
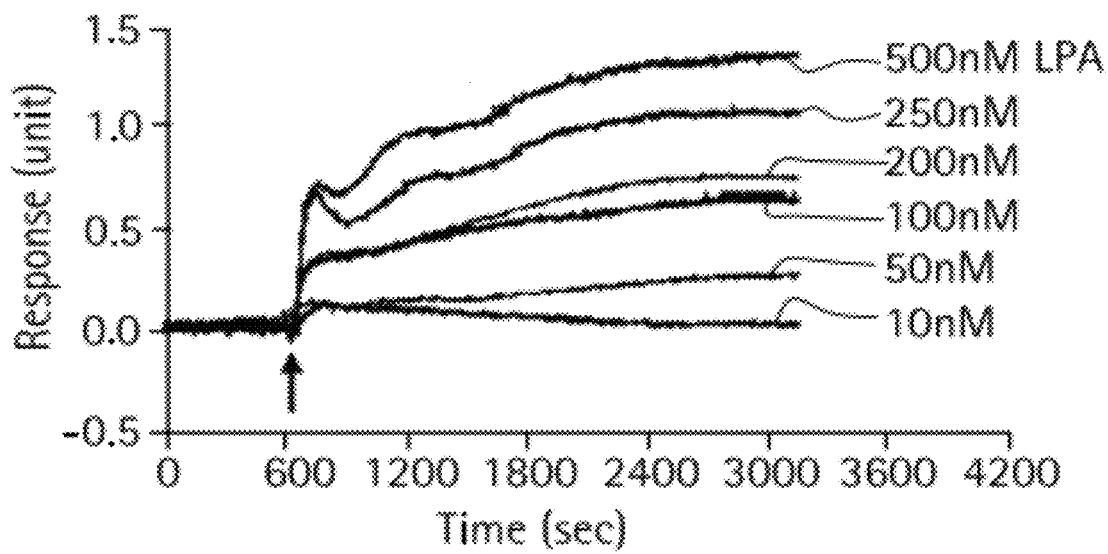
Figure 69B:
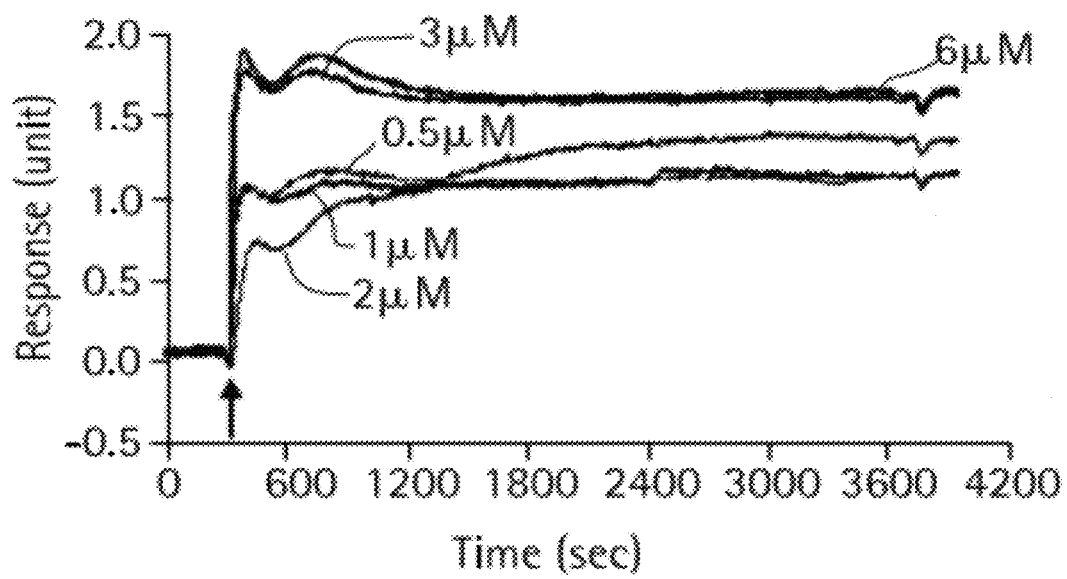

FIG. 69 shows the switching of optical signatures induced by LPA (oleoyl-L-α-lysophosphatidic acid) from low doses (a) to high doses (b).

Figure 70A:
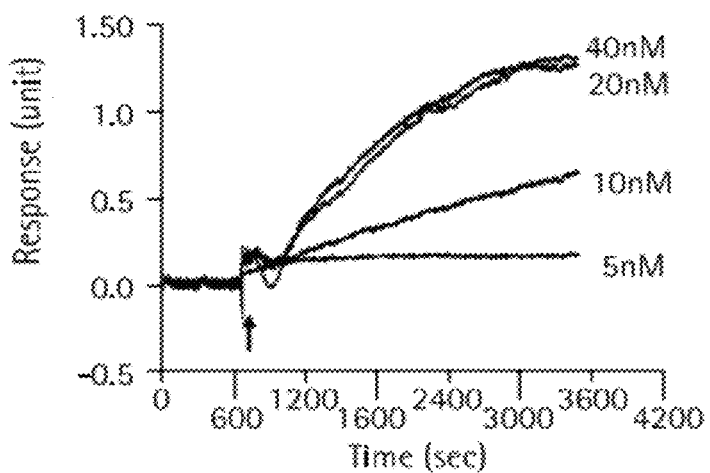
Figure 70B:
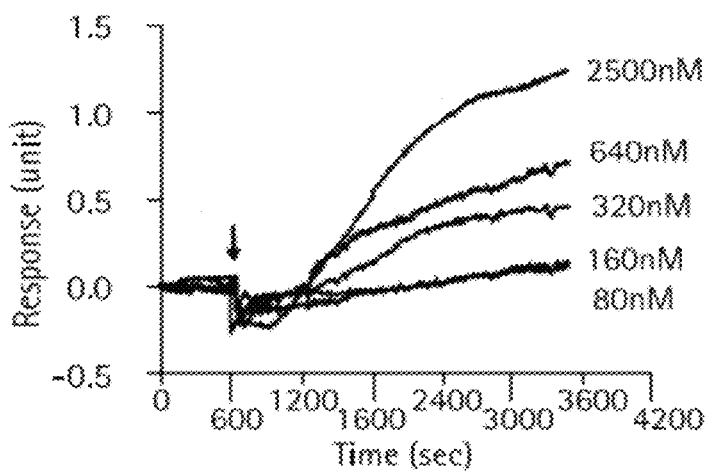
Figure 70C:
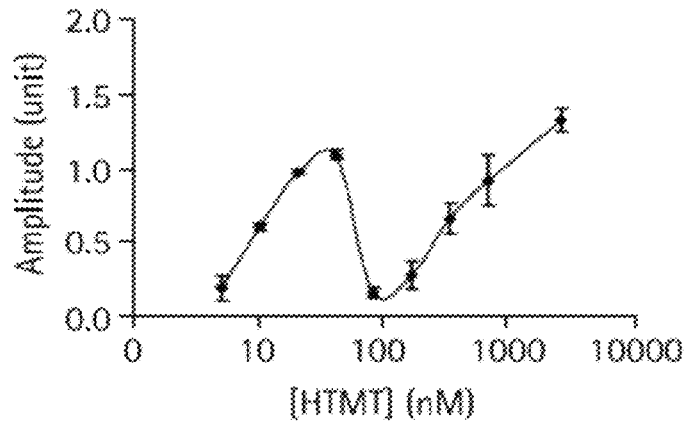

FIG. 70 shows the switching of optical signatures induced by HTMT from low doses (a) to high doses (b). The total amplitudes of the P-DMR signals were plotted as a function of HTMT concentration (c), in order to visualize the switching.

Figure 71:
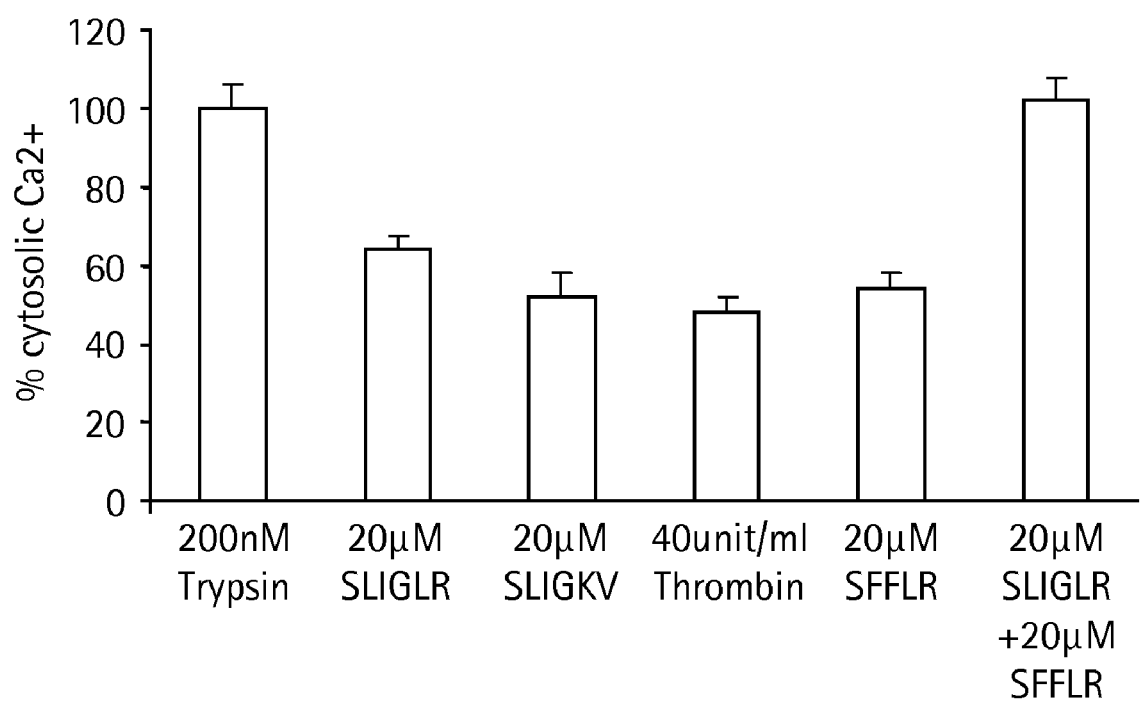

FIG. 71 shows the maximum percentage increases in intracellular $Ca^{2+}$ level, measured with the fluorescence intensity of $Ca^{2+}$ obtained with Fluo-3, were plotted as a function of PAR agonist.

Figure 72A:
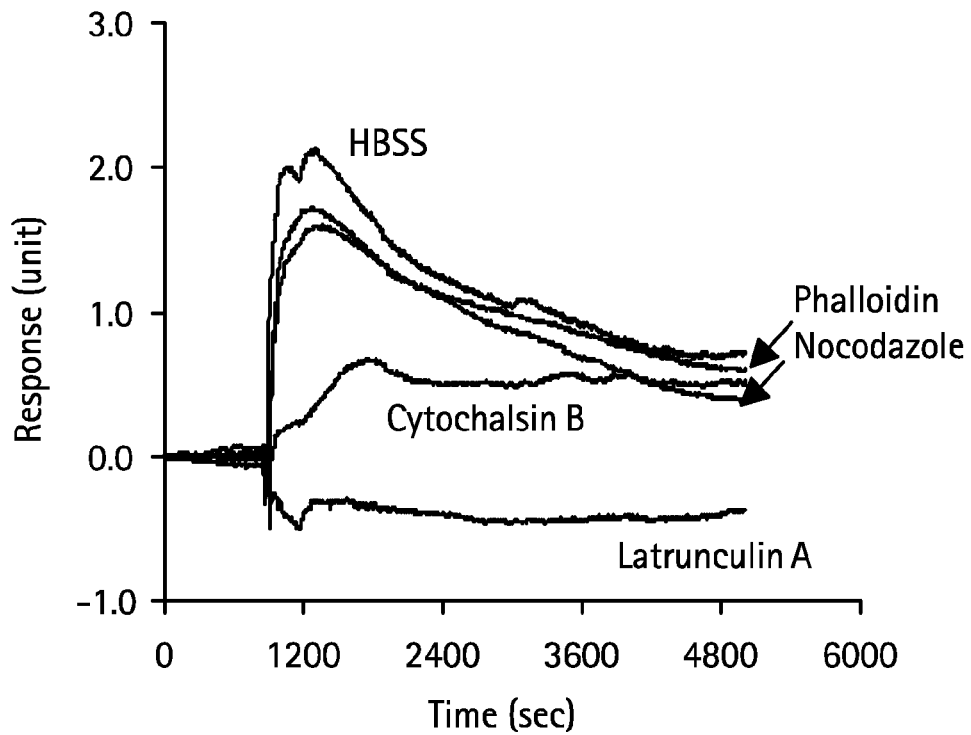
Figure 72B:
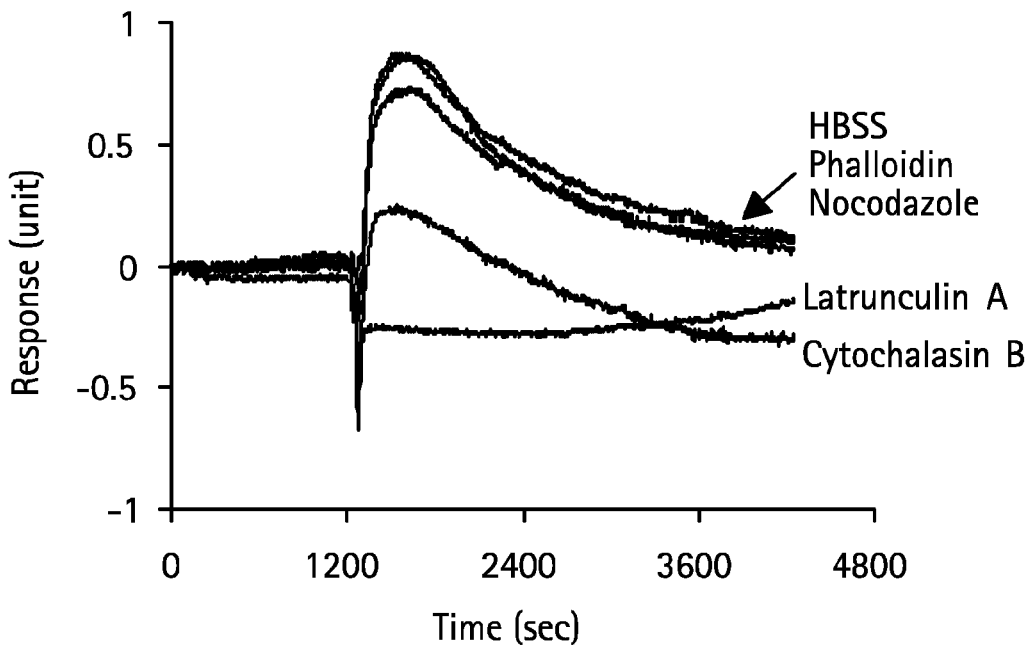

FIG. 72 shows the effect of cytoskeletal modulators on the DMR signals mediated by 100 nM trypsin (a) and 40 unit/ml thrombin (b). The modulators used to pretreat the cells include latrunculin A, cytochalasin B, phalloidin, and nocodazole; each at 10 µM. The cells pretreated with the vehicle only (i.e., HBSS) were used as controls.

Figure 73A:
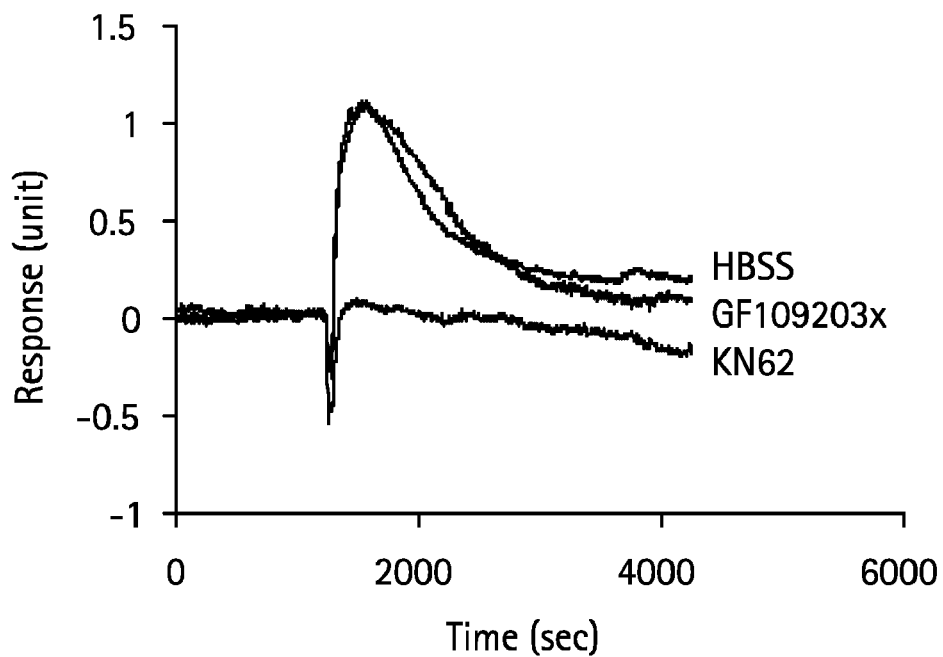
Figure 73B:
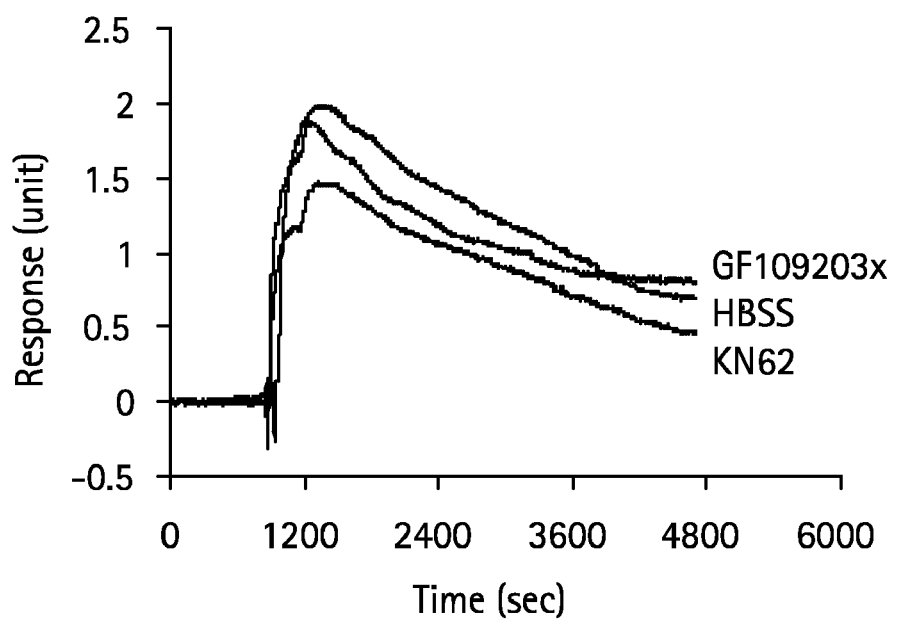

FIG. 73 shows the effect of kinase inhibitors on the DMR signals mediated by 200 nM trypsin (a) and 40 unit/ml thrombin (b). The kinase inhibitors were GF109203x (10 µM) and KN-62 (10 µM).

Figure 74:
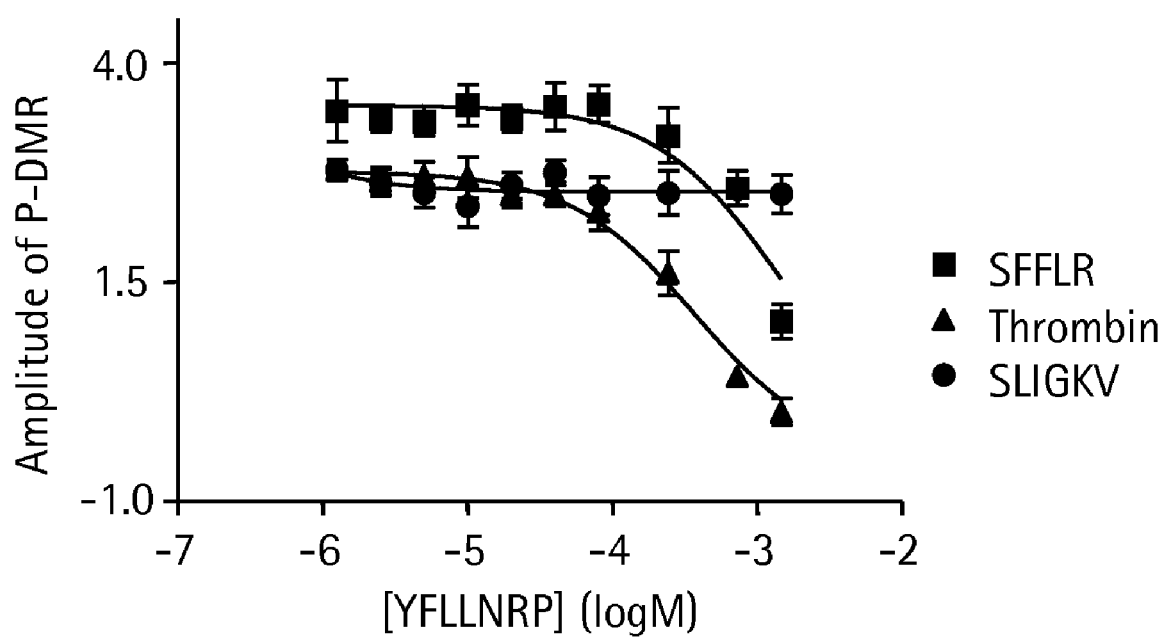
Figure 75A:
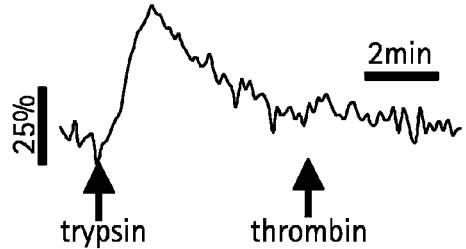
Figure 75E:
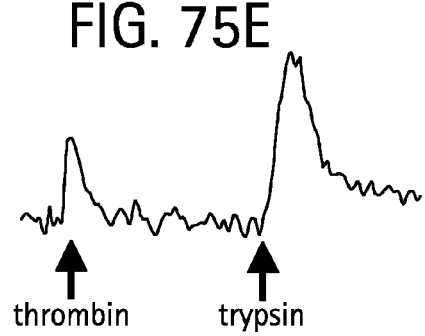
Figure 75B:
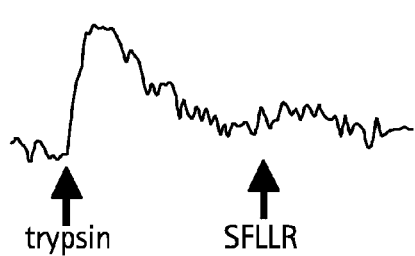
Figure 75F:
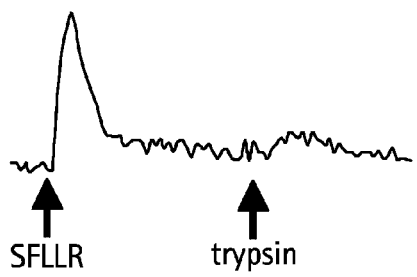
Figure 75C:
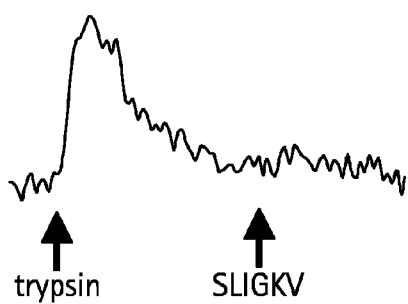
Figure 75G:
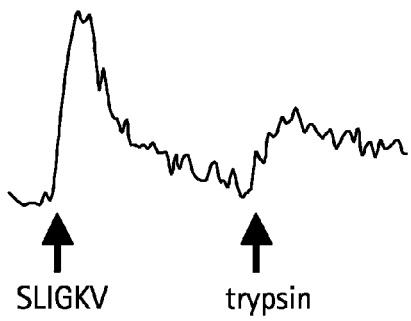
Figure 75D:
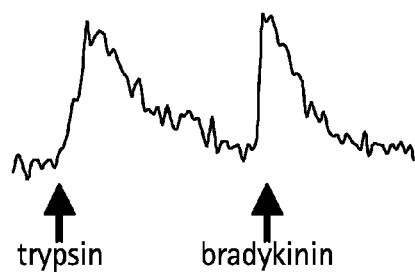
Figure 75H:
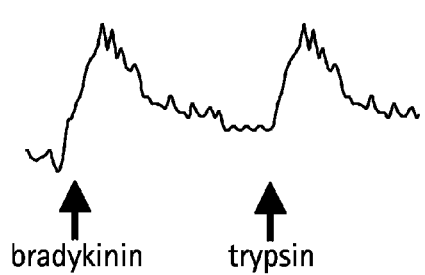
Figure 76A:
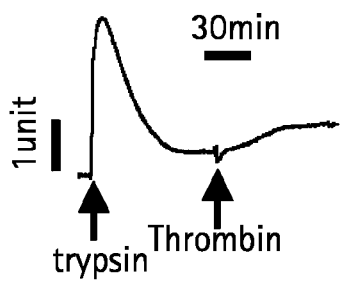
Figure 76B:
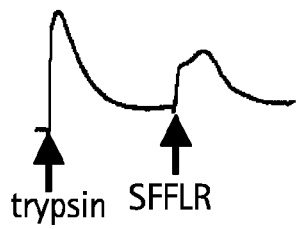
Figure 76C:
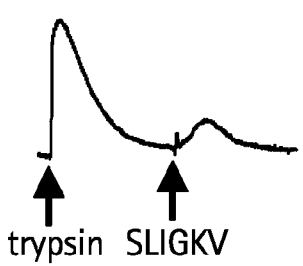
Figure 76D:
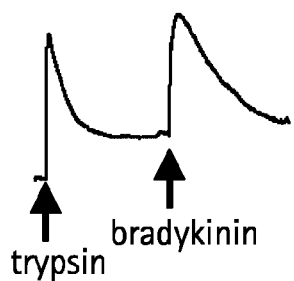
Figure 76E:
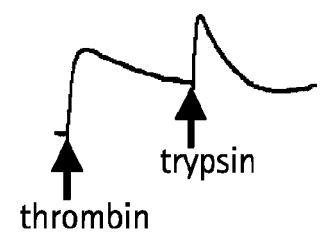
Figure 76F:
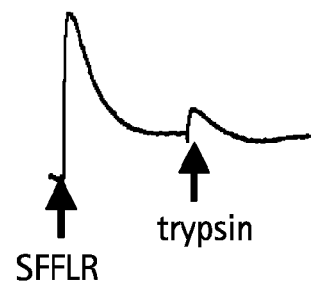
Figure 76G:
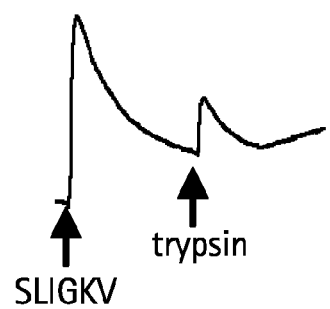
Figure 76H:
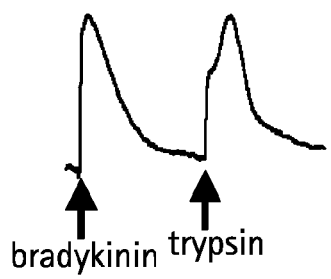

FIG. 74 shows the effect of YFFLNRP on the DMR responses mediated by thrombin (40 unit/ml), SFFLR-amide (20 µM) and SLIGKV-amide (20 µM), as plotted as the amplitudes of the P-DMR events as a function of YFFLNRP concentration.

FIG. 75 shows cross desensitization of $Ca^{2+}$ signaling mediated by PARs. After preceding treatment with trypsin, A431 cells were stimulated with thrombin (a), SFFLR-amide (b), SLIGKV-amide (c), and bradykinin (d). On the other hand, A431 cells were pre-stimulated with thrombin (e), SFFLR-amide (f), SLIGKV-amide (g), and bradykinin (h) before stimulated with trypsin. The final concentrations were 40 unit/ml, 200 nM, 20 µM, 20 µM, and 100 nM for thrombin, trypsin, SFFLR-amide, SLIGKV-amide, and bradykinin, respectively. The time interval between two stimulations is about 6 min. The solid arrows indicated the time when the solution was added (the same in other figures).

FIG. 76 shows cross desensitization of dynamic mass redistribution signals mediated by PARs. After preceding treatment with trypsin, A431 cells were stimulated with thrombin (a), SFFLR-amide (b), SLIGKV-amide (c), and bradykinin (d). On the other hand, A431 cells were pre-stimulated with thrombin (e), SFFLR-amide (f), SLIGKV-amide (g), and bradykinin (h) before being stimulated with trypsin. The final concentrations were 40 unit/ml, 200 nM, 20 µM, 20 µM, and 100 nM for thrombin, trypsin, SFFLR-amide, SLIGKV-amide, and bradykinin, respectively. The time interval between the two stimulations was about 1 hour.

Figure 77A:
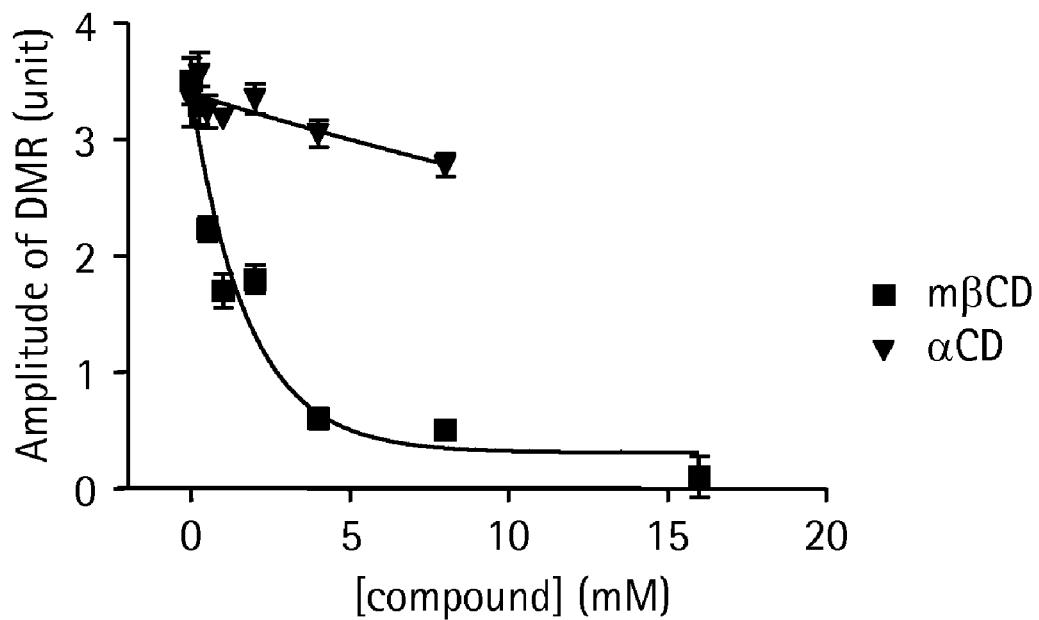
Figure 77B:
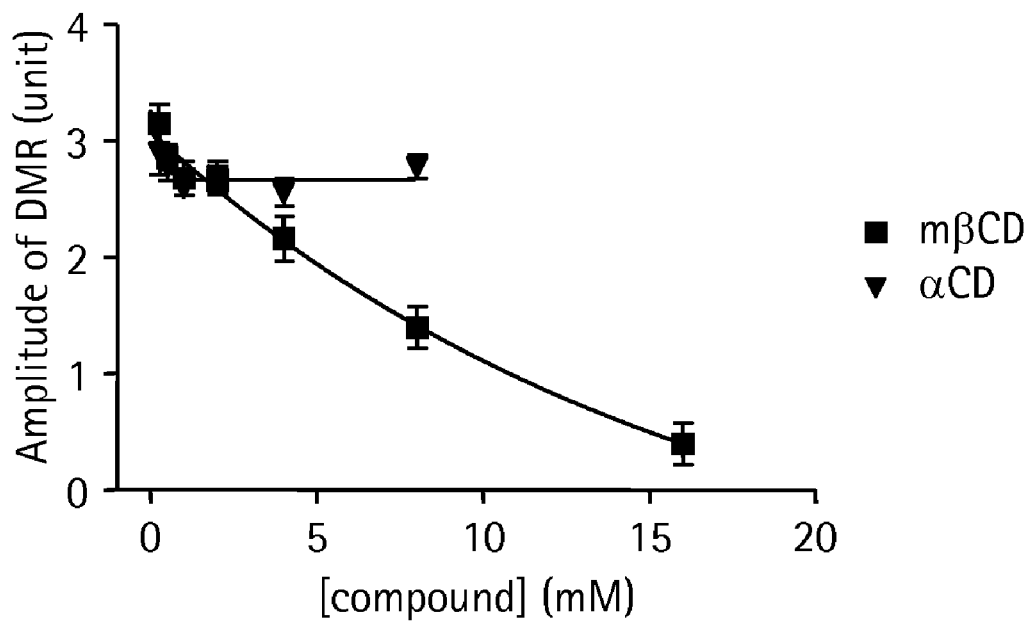

FIG. 77 shows the effect of cholesterol depletion by mβCD on the amplitudes of both P- and N-DMR signals mediated by 40 unit/ml thrombin (a) and 200 nM trypsin (b). In comparison, the effect of αCD (α-cyclodextrin) was also included.

Figure 78:
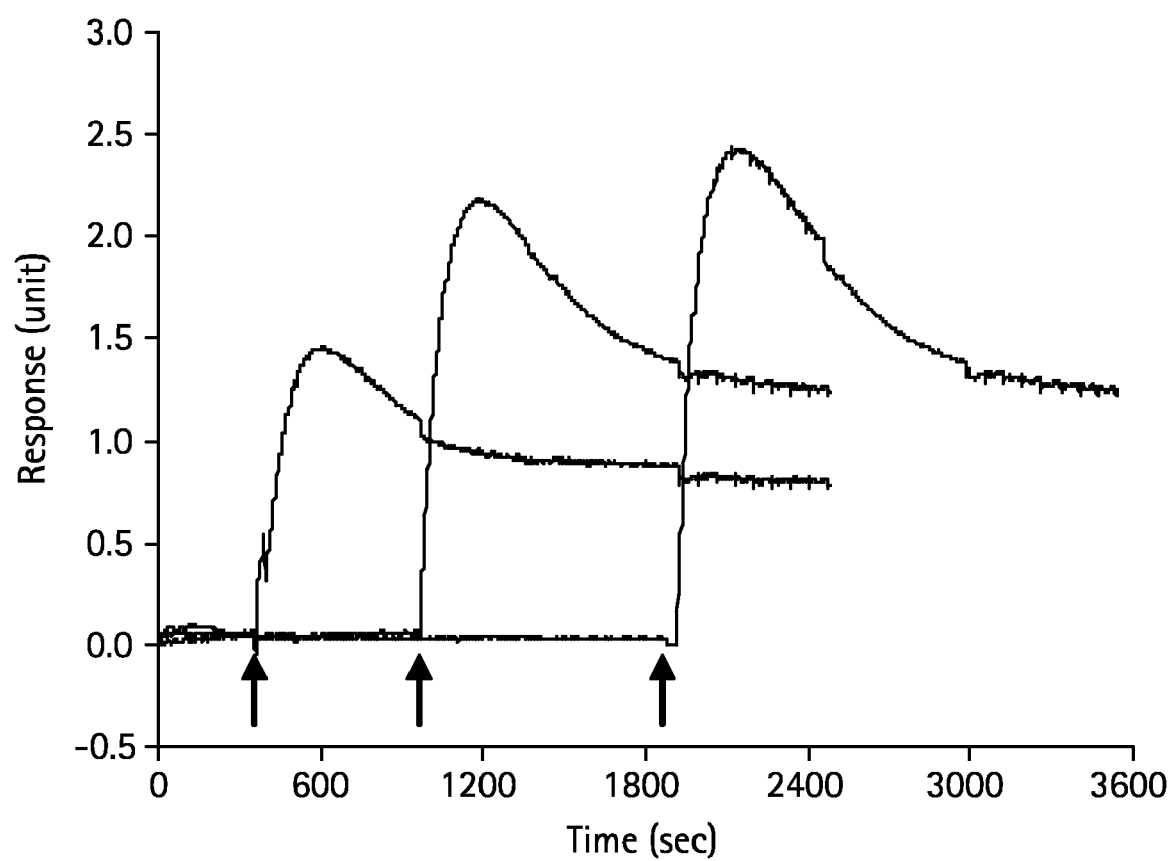

FIG. 78 shows the functional recovery of PAR signaling. After the cell surface cholesterol was removal by mβCD and the cells were washed, a thrombin solution was added separately into each well at specific time. The DMR signals were recorded in real time. Each graph is an average of 7 independent responses.

Figure 79A:
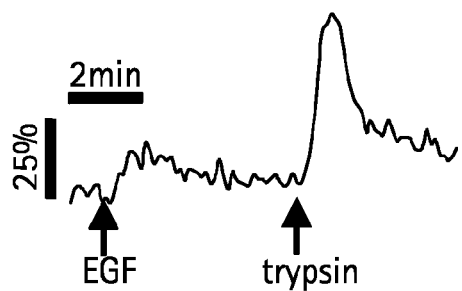
Figure 79B:
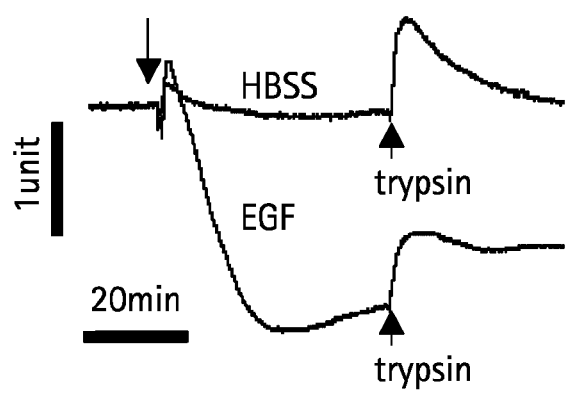

FIG. 79 shows the effect of preceding EGF stimulation on PAR signaling. (a) The trypsin-mediated $Ca^{2+}$ mobilization. (b) The trypsin-mediated DMR signal. (c) The thrombin-mediated DMR response. The final concentrations were 100 nM EGF, 100 nM trypsin, and 40 unit/ml thrombin. The cell responses with the pretreatment with HBSS buffer only were also included as control.

FIG. 80 shows the multi-parameters of quiescent A431 cells in response to 1 mM hydrogen peroxide as a function of time. (A) the shift in the incident angle; (B) the normalized PWHM; (C) the normalized peak intensity; (D) the normalized peak area. The arrows indicated the time when the solution was added.

Figure 81A:
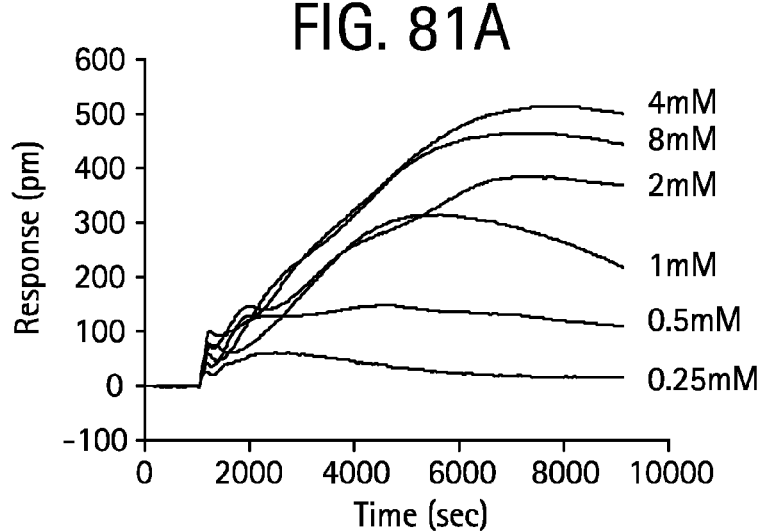
Figure 81B:
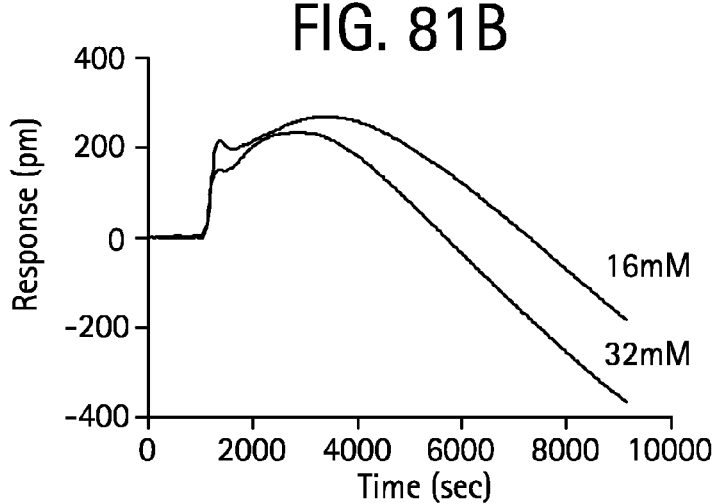

FIGS. 81A and 81B show the dose dependent responses of quiescent A431 cells adherent on a LID sensor surface before, and after addition of hydrogen peroxide.

Figure 82:
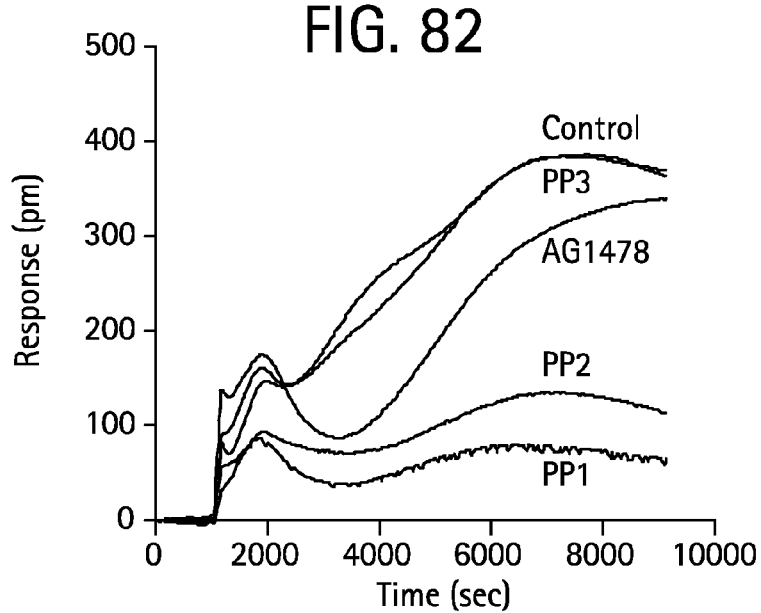

FIG. 82 shows the effect of src inhibitors on the DMR signal of quiescent A431 cells mediated by 1 mM $H_2O_2$.

Figure 83:
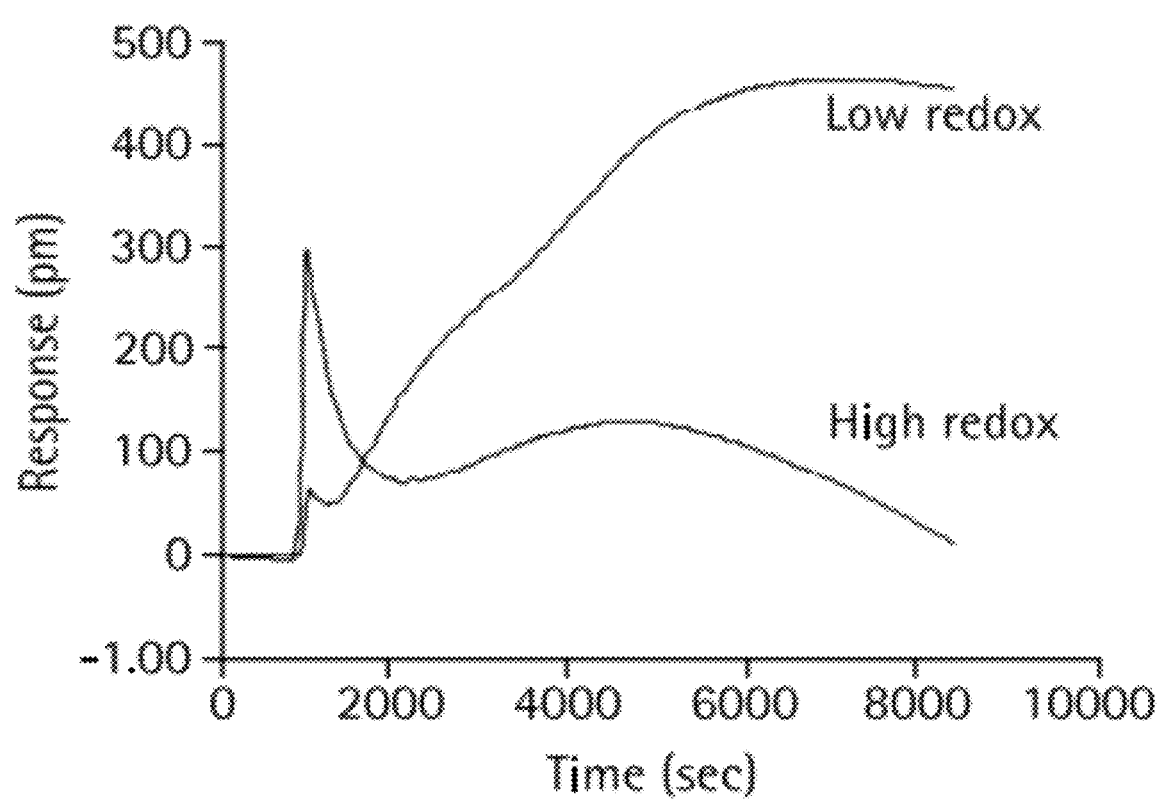

FIG. 83 shows the effect of different redox states of quiescent cells on the DMR responses mediated by 4 mM $H_2O_2$.

FIG. 84 shows the responses of quiescent A431 cells to EGF stimulation. (A) The dynamic shift in the incident angle as a function of time. (B) The normalized PWHM as a function of time. (C) Staining pattern of actin filaments of untreated A431 with TR-phalloid. (D) Staining pattern of actin filaments of A431 after treated with 16 nM EGF for 15 min and subsequently stained with Texas Red-phalloid. The bar represents 40 μM.

Figure 85A:
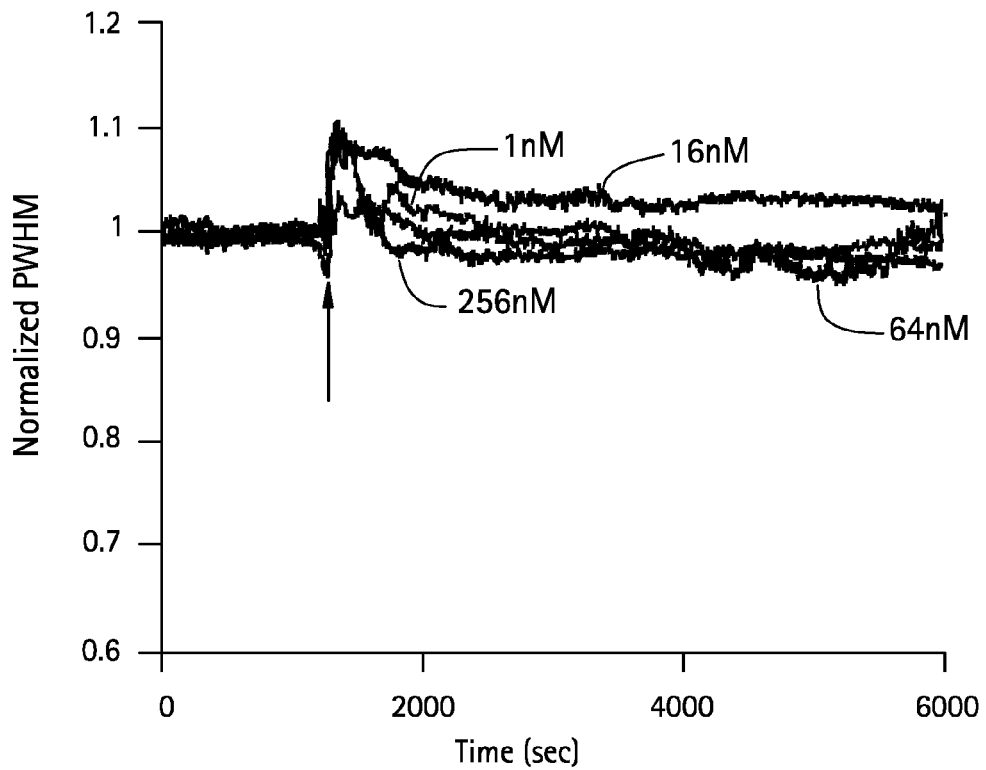
Figure 85B:
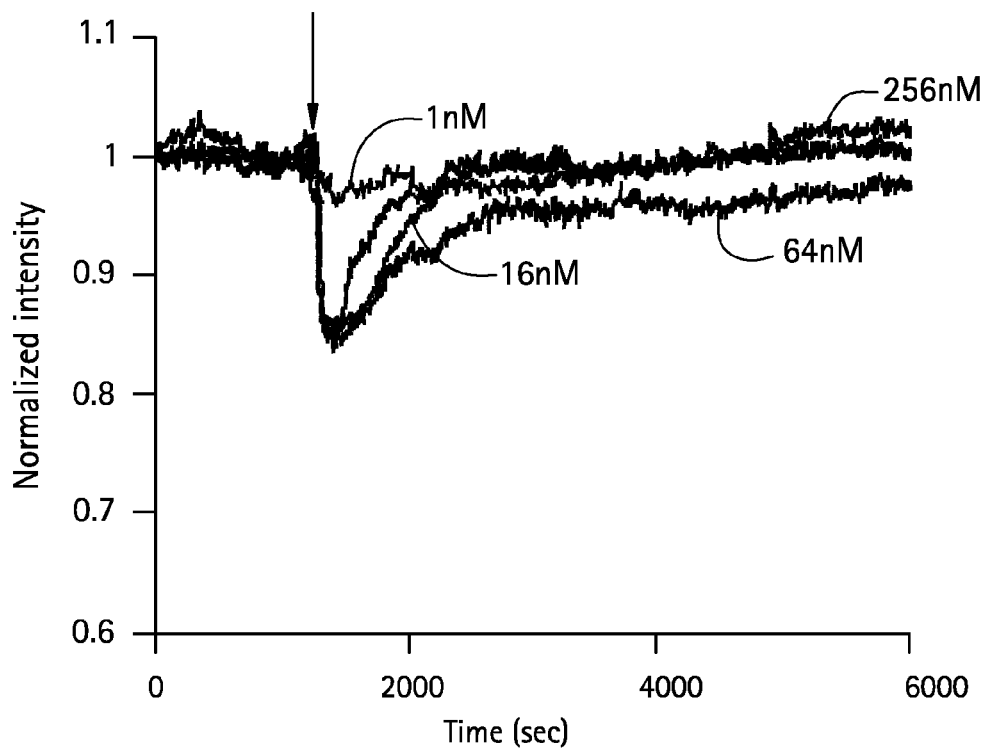

FIG. 85 shows optical signatures of quiescent A431 cells mediated through bradykinin $B_2$ receptor signaling by bradykinin: The PWHM (A) and the intensity (B) of the resonant peak of the $TM_0$ mode. The arrows indicated the time when a bradykinin solution was added.

Figure 86:
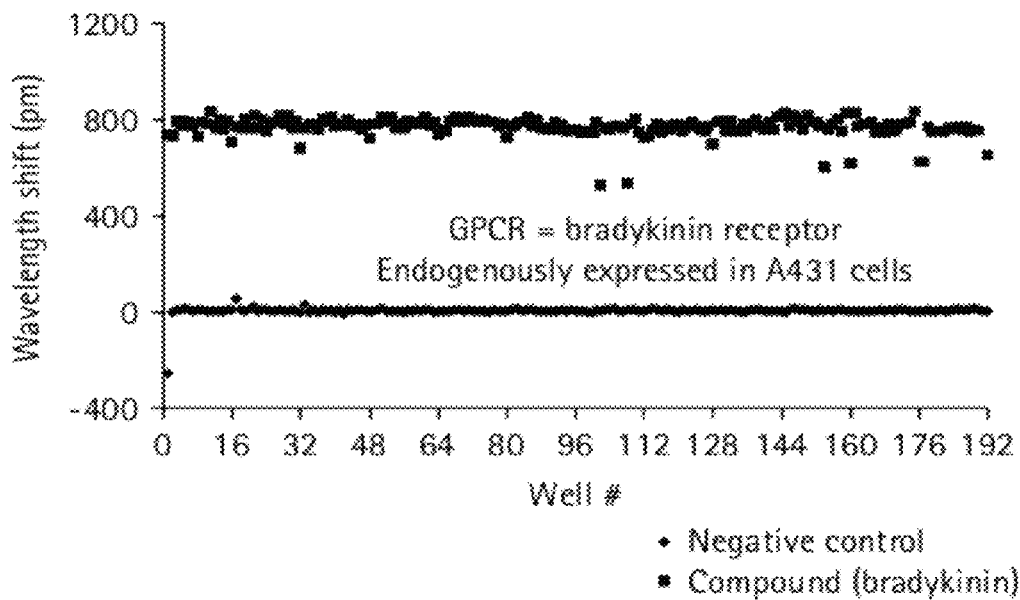

FIG. 86 shows the wavelength shift between two time points during the assay as a function of compounds. The two time points were right before the compound addition (the baseline point), and 5 minutes after the compound addition (the measured point). The difference between two endpoints reflects the total amplitude of the P-DMR event mediated by bradykinin—a bradykinin $B_2$ receptor agonist. The $B_2$ receptor is endogenously expressed in A431 cells. The cells become quiescent before the bradykinin stimulation. In this example, a 384 well Coring Epic biosensor plate was used. Each well contains A431 cells with a confluency of ~90%. Half of the wells were treated with bradykinin at 100 nM, whereas other half of the wells were treated with the buffer HBSS only.

Figure 87:
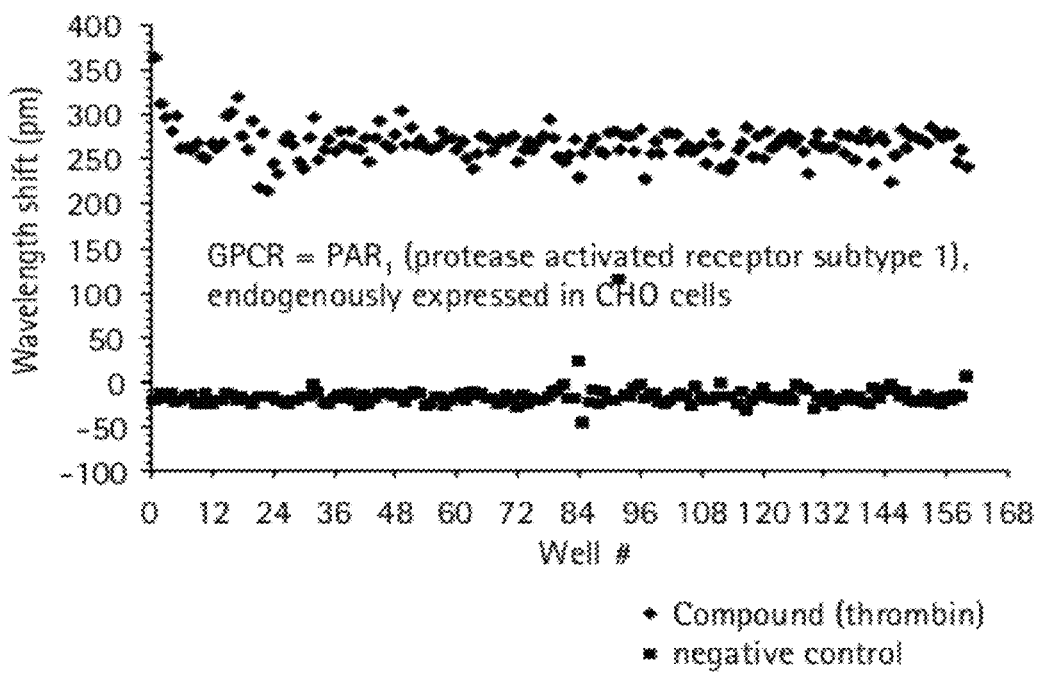

FIG. 87 shows the wavelength shift between two time points during the assay as a function of compounds. The two time points were right before the compound addition (the baseline point), and 5 minutes after the compound addition (the measured point). The difference between two endpoints reflects the total amplitude of the P-DMR event mediated by thrombin—a PAR1 receptor agonist. The PAR1 receptor is endogenously expressed in CHO cells. The cells become partially quiescent by culturing the cells in the DMEM medium for 4 hours before the thrombin stimulation. In this example, a 384 well Coring Epic biosensor plate was used. Each well contains CHO cells with a confluency of ~90%. Half of the wells were treated with thrombin at 40 unit/ml, whereas other half of the wells were treated with the buffer HBSS only.

Figure 88:
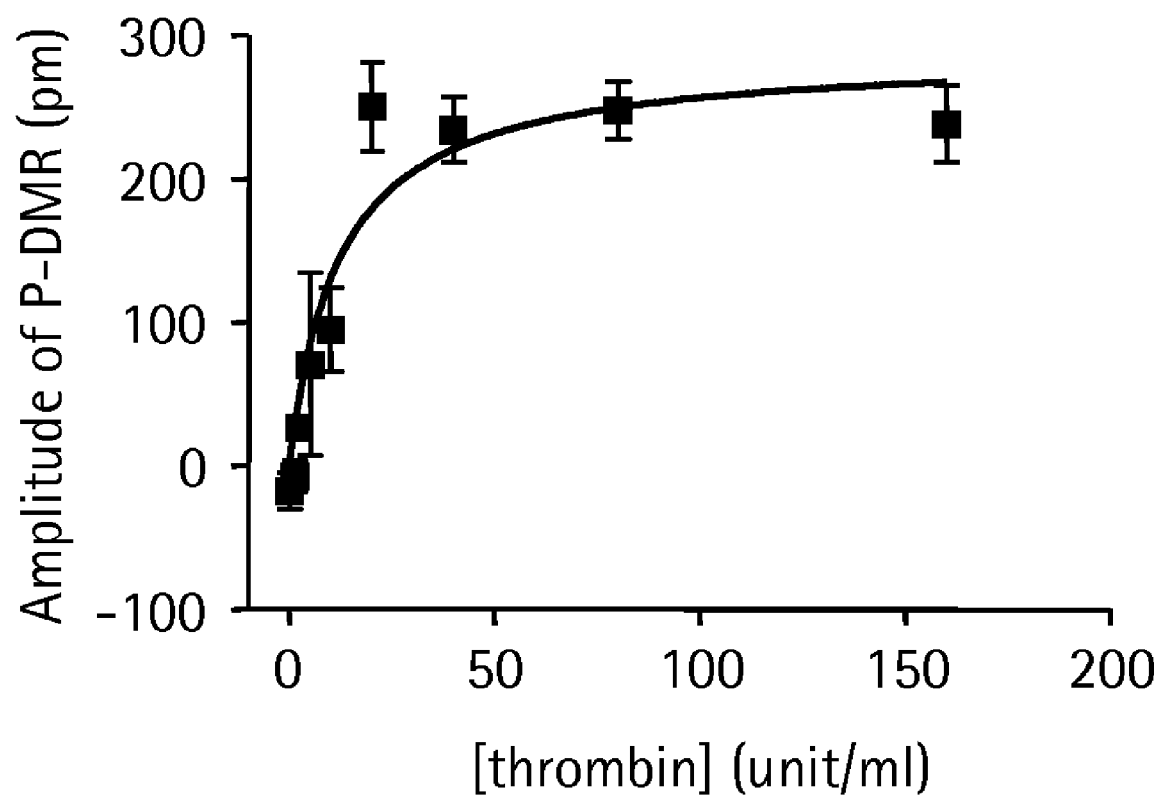

FIG. 88 shows the wavelength shift between two time points during the assay as a function of thrombin concentration. The two time points were right before the compound addition (the baseline point), and 5 minutes after the compound addition (the measured point). The CHO cells were treated with thrombin at different doses.

V. DETAILED DESCRIPTION

Before the present compounds, compositions, articles, devices, and/or methods are disclosed and described, it is to be understood that they are not limited to specific synthetic methods or specific biotechnology methods unless otherwise specified, or to particular reagents unless otherwise specified, as such may, of course, vary. It is also to be understood that the terminology used herein is for the purpose of describing particular embodiments only and is not intended to be limiting.

I. Definitions

As used in the specification and the appended claims, the singular forms "a," "an" and "the" include plural referents unless the context clearly dictates otherwise. Thus, for example, reference to "a marker or stimulatory event" includes mixtures of two or more such markers or stimulatory events, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that any number between the range and making the range is also disclosed, such as between 10 and 15, 10, 11, 12, 13, 14, and 15 are disclosed.

"Optional" or "optionally" means that the subsequently described event or circumstance may or may not occur, and that the description includes instances where said event or circumstance occurs and instances where it does not.

"Adhere" and "Adherent" or other forms of this word refer to two items coming into contact such that the two items have an affinity, such as sticking, to one another. An adherent layer of cells on a substrate would be a layer of cells that, for example, would be adhered to the surface, such that when gently washed with a buffer the cells would not become unadherent. It is understood that contact or other forms of this word means two or more items being in proximity to one another such that they are considered to be touching. Contact does not typically require a sticking. Contact can occur without having an adherence, for example. Attach or other forms of this word refer to a condition between two or more items that is more permanent than adhere. It does not require, for example, covalent attachment, but could. Thus, in order of the required strength of the bond between two or more items, contact is less than adhere which is less than attach. It is understood that these words have distinct meanings, but that unless there is explicit indication to the contrary or the skilled artisan would clearly understand it to be the contrary, these words, can be interchanged within the description for which they are found in this specification. For example, if a sentence includes, "and the cells became adhered to the biosensor" it is understood that "and the cells became contacted to the biosensor" and "and the cells became attached to the biosensor" are also disclosed. It is also understood that there can be a variety of adhered, contacted or attached items, such as cells or proteins.

"Amplitude" can refer to the amount or size of a particular response. For example, the output data from a biosensor can produce a resonant peak that has a particular amplitude, such as intensity.

"Biological diffusion limited" refers to a process that is limited by the diffusion of molecules in solution, and/or the penetration or uptake of the molecules into the cells and subsequent diffusion inside the cells before reaching the target. For example, when a compound or stimulus-containing a solution is introduced to a medium which is pre-existed to cover the cells adherent on the surface of a biosensor, the compound or stimulus molecules have to diffuse in the resulted mixture (the medium and the solution) and take a certain time to reach the cells. Afterwards, depending on the target with which that the compound or stimulus will interact, the compound or stimulus molecules might have to take extra-time to reach the target determined by the penetration or uptake of the molecules by the cell.

"Bulk index" refers to the absolute refractive index of a solution or a medium, determined by the compositions of the solution or the medium. "Bulk index change" refers to the resulted changes in refractive index of a mixture solution when two solutions are mixed together, or a solution is added into and mixed with a medium or another solution.

"Guided mode" or "coupling mode" refers to a specific mode of light coupled into the waveguide substrate. There are two basic types of guided waves (or modes) in a planar waveguide: TEm (transverse electric or s-polarized) and TMm (transverse magnetic or p-polarized), where m=0, 1, 2, ... is the mode number. Because the optical waveguide grating (OWG) biosensor is an evanescent-wave sensor and based on the resonant coupling of light into a waveguide by means of a diffraction grating. There might be some different numbers of modes for each of the two basic modes, for example, $TM_0$, $TM_1$, $TM_2$ ... and $TE_0$, $TE_1$, $TE_2$, .... The specific mode that can be coupled into the waveguide substrate is dependent on the waveguide configuration and effective refractive index of the given mode, which is determined by the refractive index of the cellular material and bulk solution that lies in the evanescent tail of that mode.

"Dose-dependent response" refers to a response, usually of a biosensor output or biosensor parameter, that changes with a change in dose (amount) of a stimulatory event such as addition of a compound.

"Incoupled light" refers to the light of certain bandwidth that is used to illustrate the biosensor and thus coupled into the waveguide film.

"Label free biosensors" Many aspects of the disclosed compositions, methods and techniques involve the use of label free biosensors. As used herein, label free biosensor refers to any sensor that can detect and/or generate a signal from an event or change (such as mass redistribution) in a cell without the need of labels such as fluorescent molecules. Label free biosensors generally comprise an optical transducer that converts an event in a cell into a quantifiable signal. Such signal generation can be accomplished in many ways. For example, direct surface sensing methods include surface plasmon resonance (SPR) (Jordan & Corn, "Surface Plasmon Resonance Imaging Measurements of Electrostatic Biopolymer Adsorption onto Chemically Modified Gold Surfaces", Anal. Chem., 1997, 69:1449-1456), grating couplers (Morhard et al., "Immobilization of Antibodies in Micropatterns for Cell Detection by Optical Diffraction," Sensors and Actuators B, 2000, 70, 232-242), ellipsometry (Jin et al., "A Biosensor Concept Based on Imaging Ellipsometry for Visualization of Biomolecular Interactions", Analytical Biochemistry, 1995, 232, 69-72), evanescent wave devices (Huber et al., "Direct Optical Immunosensing (Sensitivity and Selectivity)," Sensors and Actuators B, 1992, 6, 122-126), and reflectometry (Brecht & Gauglitz, "Optical Probes and Transducers," Biosensors and Bioelectronics, 1995, 10, 923-936). The instrumentation typically used to interrogate SPR or waveguide grating sensors utilizes an optical beam with the appropriate spectral or angular content, such that when this beam is reflected by the sensing surface, the resonant angle or wavelength response becomes dominant in the output response.

Many label free biosensors are known examples of which are described elsewhere herein. Examples of label free biosensors include non-contact biosensors, label independent detection biosensors, label free optical biosensors, optical non-contact biosensors, optical-based biosensors, optical biosensors, optical label independent detection biosensors, waveguide grating-based biosensors, optical waveguide lightmode spectroscopy biosensors, evanescent wave devices. Various label free biosensors and their use are described and referred to herein. Some particular methods and modes of the use of label free biosensors are described in the context of particular label free biosensors in order to provide more specific examples of label free biosensors and their use. To avoid unnecessary duplication, such descriptions are not repeated for every type of label free biosensor. However, it is to be understood that when the use of particular biosensors in particular methods or modes is described such use is illustrative of the use of any label free biosensor in such methods and modes unless the context or nature of the use would exclude one or more types of label free biosensor. Such use of any and all biosensors in any and all methods and modes described herein (unless the context or nature of the use would exclude one or more types of label free biosensor) is specifically contemplated and should be considered specifically disclosed. Thus, for example, if analysis of EGF-induced EGFR signaling in a cell using a particular grating coupler biosensor is described, then analysis of EGF-induced EGFR signaling in a cell using any other appropriate label free biosensor is considered disclosed. Thus, for example, analysis of EGF-induced EGFR signaling in a cell using a surface plasmon resonance-based biosensor would be considered disclosed.

"Time-dependent response" is a response, usually of a biosensor output or biosensor parameter, that changes over time.

"Starvation medium" is any medium which decreases the proliferation capacity of a culture of cells. When the starvation medium is used for incubating the cells or culturing the cells, the resulted cells become quiescent.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

II. Compositions and Methods

The disclosed compositions, methods, and techniques relate to the field of label free optical biosensors including waveguide grating-based biosensors for cell-based assay and techniques. The methods and systems in general can relate to the direct optical-sensor field and, specifically, to systems and methods for using an optical label independent detection (LID) biosensor (e.g., waveguide grating-based biosensor) to monitor, for example, in real time, compound-induced mass redistribution in living cells, including G protein coupled receptor (GPCR) agonisms and antagonisms, Epidermal Growth Factor Receptor activity, cytoskeleton reorganization, cell death and cell proliferation, as well as cell signaling, desensitization, and translocation within living cells, as well as morphological changes of adherent cells, cell deadhension, cell movements, and cells cultured on a biosensor. Direct optical sensor (DOS) technologies refers to those that utilize an optical transducer to convert the molecular recognition or cellular event into a quantifiable signal without exciting the fluorescent or luminescent label(s). The technologies that rely on the excitation and subsequent emission or luminescences of such labels are referred to as indirect optical technologies, which can also be used in certain embodiments of the disclosed methods. Also disclosed are methods for screening the activity of compounds against cells, for example against receptors on cells, such as the GPCR or the EGFR or PDGFR or cytokine receptor.

Disclosed are compositions and methods that utilize label free biosensors, such as waveguided grating-based biosensors, for monitoring and measuring directional mass redistribution (DMR) and which can couple this DMR with a particular cell state or cellular event or cell activity. It is understood that disclosed are "cell-biosensor" and "cell-biosensor-reagent" compositions which can be any of the compositions disclosed herein in combination. For example, disclosed is a cell-biosensor-reagent composition comprised of A431 cells, a biosensor, and EGF.

For example, in certain disclosed assays, label free optical biosensors can be used to assay the toxicity or proliferative effect of a compound or compound or composition to a cell, and to measure the occurrence of cell signal transduction events mediated, for example, through cell surface receptors, such as receptor tyrosine kinases (RTKs), such as epidermal growth factor receptor (EGFR) or platelet derived growth factor receptor (PDGF), or G protein-coupled receptors (GPCRs), or through internal signaling events, such as various signaling pathways or cytoskeleton rearrangement events. Label free optical biosensors as disclosed herein can be used to assay the stimulation-mediated translocation of a protein target or substrate recruitment, for example, to the nucleus, or to the membrane, or to the cytosol, or to other organelles (e.g., endosomes, endoplasmic reticulum (ER) or gogli or nuclei), or throughout various recycling pathways, or the uptake from extracellular space (e.g., ligand binding, gene transfection or protein transduction, phagocytosis, endocytosis, etc). In other examples, label free optical biosensors can be used to monitor the redistribution of a particular target or a target complex among different functional compartments and/or among defined microenvironments in response to stimulation, or to measure the de novo synthesis of a particular target, or to examine the stimulation-mediated release from a particular compartment(s) or location(s) (e.g., Ca mobilization due to agonist-induced Gq-coupled receptors or Ca ionophores). In this context, target is used as a molecule or cell component that is to be tracked or is part of an assay. In other examples label free optical biosensors can be used to monitor the transport of a target molecule or a target complex (e.g., bacteria, or viruses, or phages, or lipid particles, or exosome particles, etc.) from one cell to another cell (e.g., through gap junction or ion channel), or either from or to the surrounding environment through, for example, a process known as excytosis or a control release process such as apoptosis or diffusion through artificial holes at the cell surface membrane. These compositions and methods in certain embodiments can be adapted to high throughput methods by adoption and identification of a point during data collection whereby a determination can be made by collection of only one, two, or three, for example, separate points of data, which are predictive of the type of cell event occurring during monitoring, which can be due to, for example, a stimulatory event.

In certain embodiments, the disclosed compositions, methods, and techniques relate to the use and the methods of use of waveguide grating-based biosensors for monitoring adsorption, distribution and/or toxicity of compounds acting on living cells adherent on biosensors.

In certain embodiments, the disclosed compositions, methods, and techniques relate to methods of using of optical waveguide lightmode spectroscopy (OWLS) or resonant peak spectrum, or resonant band imaging of a given guided mode in combination with angular or wavelength interrogation to screen inhibitor or activator of cell proliferation. This method is applicable for high throughput screening.

In certain embodiments, the disclosed compositions, methods, and techniques relate to methods of using optical waveguide lightmode spectroscopy (OWLS) or resonant peak spectroscopy of a given mode or resonant band imaging of a given mode that is applicable for high throughput screening compound toxicity, as well as the other methods disclosed herein.

The disclosed compositions, methods, and techniques can use optical-based biosensors to monitor the adsorption, distribution, and/or toxicity of compounds acting on a living cell layer that is adherent on an optical biosensor. In another embodiment, the disclosed compositions, methods, and techniques provide methods for screening or monitoring the adsorption, distribution and/or toxicity of compounds acting on multiple types of cells adherent on spatially addressable regions of an optical sensor, or multiple biosensors located within a single well.

The disclosed compositions, methods, and techniques disclose a real time and label free assays for compound adsorption, distribution and/or toxicity screening and profiling. These methods can be used in multiple different assays (e.g., ADME/Tox, functional assays) and in fact, can integrate multiple different assays into a single assay format.

In certain embodiments, the disclosed compositions, methods, and techniques provide label-free measurements that are suitable for high throughput screening of the effect of compounds on cell proliferation. In certain embodiments, the disclosed compositions, methods, and techniques utilize optical waveguide lightmode spectroscopy (OWLS) or resonant peak spectroscopy of a given mode or resonant band imaging of a given guided mode, rather than wavelength or angular shift alone, for high throughput screening inhibitors or activators of cell proliferation. This method uses the dependence of the peak-width-at-half-maximum (PWHM) of incoupled peak of a given sensor on cell density. In certain embodiments of the disclosed compositions, methods, and techniques, the images of the incoupling resonance bands of the whole sensors in a microplate can be collected at the same time and used as a high throughput means to screen compounds for their effects on cell proliferation.

Disclosed are methods of screening modulators of cell signaling pathways using optical biosensors. The methods can be applied to, for example, RTKs or GPCR, at the cell surface as well as to signaling events occurring within the cell.

Disclosed are methods of screening modulators of cytoskeleton components using optical biosensors. The methods are based on measuring release of macromolecules from a permeabilized cell induced by modulators of cytoskeleton components. Specifically, the methods utilize special chemicals or biologicals (e.g., saponin, streptolysin O, or the like) to render the plasma membrane of living cells sufficiently porous which permits soluble proteins inside the cells to diffuse away. Treatment of cells with cytoskeleton-disrupting modulators lead to further release biological molecules including proteins and RNAs that are sequestered by cytoskeleton, resulting in the loss in mass which can be detected by optical biosensors.

Provided is a discussion of optical biosensors, such as label free optical biosensors, such as optical waveguide light mode spectroscopy and waveguide grating-based biosensors and how they can be used in different configurations and combinations. This is followed by a discussion of mass redistribution and how this can be related to optical biosensors. Also provided is a discussion of exemplary cell assays that can be performed using the optical biosensors disclosed herein as well as additions and modifications to these assays, such as performing an assay first using an label free optical biosensor, but then having a particular type of label coupled to one or more reagents in the assay which can be then used in a secondary or additional assay.

Disclosed are methods that can be used to perform a label free functional cell assay, such as a GPCR cell-based assay, which enables compound screening and profiling. The disclosed methods allow one to study an endogenous GPCR in living cells without needing to genetically engineer the cell to over-express a receptor of interest, although, in certain embodiments, a cell having an over-expressed GPCR of interest is preferably used in order to achieve high sensitivity and optimal assay results.

The disclosed methods are capable of performing multiplexed cell-based assays using a single sensor or using multiple sensors for comparison of the function of a compound among at least two different types of cells originated from distinct parental cells or same parental cell (i.e., a given specific type of cells). The methods can offer an advantage of increased throughput.

Disclosed are methods that can be used to perform multiplexed assays using a single sensor or using multiple sensors for confirming the involvement of a particular cellular target in the signaling or cellular events measured in response to stimulation. The methods can use a single sensor with at least two distinct regions: one without modification and another with modification; or can use at lease two sensors within a same chamber or separated chambers: one without modification and another with modification. The modified areas of sensors, for example, can have printed or deposited spots containing reagents/genes or interference RNA (RNAi) or antisense oligonucleotides or antisense/antigene peptide nucleic acid (PNA) or proteins or antibody such that when cells are cultured onto and overlaid with these regions, the adherent cells uptake these reagents/materials and become transfected. Such methods are referred to as positional surface-mediated transfection. Once transfected with these materials, a particular target in the cell becomes either over-expressed through the surface-mediated gene transfection or protein delivery, or can be down-regulated through antisense/ antigene suppression or RNA interference or knockout or antibody blockage. US2004/0023391A1 and U.S. Pat. No. 6,544,790, which are herein incorporated in their entireties, but at least for material related to methods for delivery to cells. The positional surface-mediated transfection allows the detection of stimulation-induced responses of a particular type of cells with and without the specific target. The positional surface mediated transfection can be considered a stimulatory event. Therefore, the present methods can be used to confirm the involvement of the specific cellular target in the signal or cellular events measured using the label free optical biosensors. The deposition or printing of the materials onto the sensor surface can be achieved using state-of-the-art methods, including, but not limited to, contact printing such as pin printing technology (US5807522 A or U.S. Pat. No. 6,101,946 A) or microstamping methods (U.S. Pat. No. 5,731,152), capillary dispensing devices (U.S. Pat. No. 5,807, 522) and micropipetting devices (U.S. Pat. No. 5,601,980) or non-contact printing such as piezo-driven printing or micro/ nanodispenser devices (US6656432 B1, EP0895082 B1 or U.S. Pat. No. 6,399,396 B1).

Disclosed are methods to perform label-free biosensor-based cell assays that utilize multiple penetration depths. Also, disclosed are devices that allow one to perform such assays in simplexed or multiplexed assay formats.

According to the OWLS, the PWHM changes of the TM modes are more sensitive to surface inhomogeneities than that of the TE mode. The PWHM increases when the cells start to spread on the surface, reaches its maximum at about 50% cell coverage, and decay back to the original level afterwards.

Disclosed herein it has been shown that the adsorption, distribution and toxicity of a compound to a highly confluent cell layer near the cell-sensor interface can be monitored in real time, as documented by compound toxicity-induced wavelength or angular shifts using optical biosensors.

Disclosed are methods to study the cellular functions of reactive oxygen species (ROS) probed with optical biosensors. Also, disclosed are methods to evaluate the redox states of cultured cells, as well as to screen modulators that affect the redox states of cultured cells as well as the ROS signaling. Reactive oxygen species are molecules like hydrogen peroxide, ions like the hypochlorite ion, radicals like the hydroxyl radical, and the superoxide anion which is both ion and radical. Substances that have the ability to oxidize other substances are said to be oxidative and are known as oxidizing agents, oxidants or oxidizers. Oxidants are usually chemical substances with elements in high oxidation numbers (e.g., $H_2O_2$, $MnO_4^-$, $CrO_3$, $Cr_2O_7^{2-}$, $OsO_4$) or highly electronegative substances that can gain one or two extra electrons by oxidizing a substance ($O_2$, $O_3$, $F_2$, $Cl_2$, $Br_2$). Reactive oxygen species are formed by several different mechanisms: (1) the interaction of ionizing radiation with biological molecules; (2) as an unavoidable byproduct of cellular respiration (e.g., some electrons passing "down" the respiratory chain leak away from the main path (especially as they pass through ubiquinone) and go directly to reduce oxygen molecules to the superoxide anion); (3) synthesized by dedicated enzymes in phagocytic cells like neutrophils and macrophages (e.g., NADPH oxidase (in both type of phagocytes); or myeloperoxidase (in neutrophils only)). ROS are essential, but it is important that the attempt to limit the production of ROS not succeed too well. Because ROS have important functions to perform in the cell. Examples are (1) The cells of the thyroid gland must make hydrogen peroxide in order to attach iodine atoms to thyroglobulin in the synthesis of thyroxine. (2) Macrophages and neutrophils must generate ROS in order to kill some types of bacteria that they engulf by phagocytosis. (3) Neutrophils (but not macrophages) also kill off engulfed pathogens by using the enzyme myeloperoxidase which catalyzes the reaction of hydrogen peroxide (made from superoxide anions) with chloride ions to produce the strongly antiseptic hypochlorite ion. (4) Much biological energy is stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide ($NAD^+$), which then contributes to the creation of a proton gradient, which drives the synthesis of adenosine triphosphate (ATP) and is maintained by the reduction of oxygen. In animal cells, mitochondria perform similar functions. The term redox state is often used to describe the balance of $NAD^+$/NADH and $NADP^+$/NADPH in a biological system such as a cell or organ. The redox state is reflected in the balance of several sets of metabolites (e.g., lactate and pyruvate, beta-hydroxybutyrate and acetoacetate) whose interconversion is dependent on these ratios. An abnormal redox state can develop in a variety of deleterious situations, such as hypoxia, shock, and sepsis. It is understood that the flux and effect of all of the molecules, compounds, and compositions discussed in this paragraph can be identified, or otherwise used in the methods disclosed herein.

Disclosed are methods to examine the cross communication among family members of targets such as GPCRs, RTKs, and others, as well as among distinct classes of targets such as between a GPCR and a RTK. Cells need to communicate with one another, whether they are located close to each other or far apart. Extracellular signaling molecules regulate interactions between cells. The basic mechanism requires a ligand (signaling molecule) to interact with its receptor so as to convert the extracellular signal to an intracellular signal. This process is called signal transduction and can occur in several forms. First, if a signal is needed to communicate with the entire organism; the signaling molecule is secreted into the bloodstream. For example, endocrine signaling requires a cell to synthesize and secrete a hormone into the circulatory system. That hormone is then recognized by a specific target cell protein (receptor) either on the plasma membrane or within the cytoplasm. Second, in other situations the signal is required to act locally. For example, paracrine signaling molecules (local mediators) can be released by a neighboring cell, diffuse locally through the ECM, and stimulate a close target cell. For example, growth and differentiation factors are thought to act primarily as paracrine signaling molecules. A third form of communication is neuronal signaling. This type of signal transduction can occur over long distances, however the delivery is by way of long cellular processes called axons. Neuronal signals can act on target cells or on other neuronal cells. The signal travels through the axon as an electrical impulse that upon reaching the axon terminus it is converted into a chemical signal called a neurotransmitter. The fourth style of signal transduction is the most short-range of all. It typically does not require the release of a secreted molecule. For example, contact-dependent signaling requires the transduction to be completed when the signaling molecule anchored in the plasma membrane of the signaling cell to bind to the receptor molecule embedded in the plasma membrane of the target cell. Contact-dependent signaling can also occur in the form of a cell interacting with the extracellular matrices. Each cell is able to respond to a limited set of signals due to its specialized function as well as its limited types of receptors. Additionally, each cell responds to a signal molecule differently. In this case, for example, the neurotransmitter, acetylcholine can stimulate one type of muscle cell to contract (skeletal) or inhibit contraction in another (cardiac). Acetylcholine can also stimulate certain cells to secrete the contents of their secretory vesicles. Alternatively, similar receptors can activate different intracellular signaling pathways, or the ligand binds to different receptors. In a linear model, signaling pathways can be viewed that the main flow of information is sequential and goes through a linear chain of intermediate steps from the receptor to a particular cell function. However, because of the complexity of cell biology, instead of the linear information flow, the signaling mediated by a stimulation consists of a number of modules that are connected by feedback involving a diffusion step (diffusible feedback systems) or that are physically linked to complexes of signaling proteins and/or scaffolding proteins. For example, a diffusible feedback module can be seen in the positive and negative feedback loops by which calcium and the inositol-trisphosphate receptor regulate cytosolic calcium concentration. These positive and negative feedback loops play important roles in signaling cross-communications. For example, signaling of many mitogenic GPCRs has been demonstrated to cross-communicate with EGFR signaling in either a negative or positive way. The activation of these GPCRs also leads to the activation of EGFR in the same cells, either through protein kinase C or β-arrestin which acts an adaptor protein.

Disclosed are methods to screen modulators against a specific target or a class of targets in a high throughput format, based on at least two endpoint measurements.

a) Use of OWLS for Monitoring Cell Health

The present compositions, methods, and techniques disclose the use of optical waveguide lightmode spectroscopy or resonant peak spectrum of a given guided mode or resonant band imaging for high throughput screening compound toxicity. Disclosed are measurements that are suitable for high throughput screening compound toxicity using optical-based biosensors. The disclosed methods, compositions, and techniques, can be used to monitor the health of a cell or cell population. The term "health" refers to the overall state of the cell in terms of viability and cell function. There are many ways in which a cell can display negative effects on its health, such as a decrease in cell division, a decrease in cell function, such as protein or mRNA production, a decrease in cell signaling, and/or an increase in proteins related to cell death, for example. Traditionally, cell health evaluation used fluorescence staining methods or other means to examine cell membrane integrity, or the function of a particular target protein (e.g., mitochondrial dehydrogenases), or the synthesis of a particular gene product, or the incorporation of a labeled nucleotide into the DNA or RNA, or the integrity of chromosome in the nuclei of the cell. In certain embodiments, the methods utilize the dependence of the peak-width-at-half-maximum (PWHM) of incoupled peaks of a given sensor on cell density, cell death patterns and cell layer inhomogeneities that are modified due to the toxicity of a compound. Compound toxicity results in the formation of three populations of cells, viable, affected and dead cells, on the waveguide film surface. The resulted increased inhomogeneities of the surface lead to resonance peak broadening, and even splitting. The resonance peak broadening and splitting can be used as a signature for compound toxicity. Either the resonance peak spectra or the whole sensor resonance images can be collected and analyzed at certain time after cells are exposed to a compound.

The disclosed compositions, methods, and techniques provide methods to monitor the adsorption, distribution and toxicity of a compound acting on a cell layer cultured on an optical sensor. The methods can involve the real-time measurements of the angular or wavelength shifts for a layer of cells in response to a compound administered to or incubated with the cell, due to the mass redistribution in the cell layer, using optical biosensors. These methods are useful for studying the kinetics and mechanisms of cell toxicity and apoptosis. Also disclosed are high through-put methods.

2. High Through Put Methods for Monitoring Cell Health

In certain embodiments, these methods utilize an optical interrogation system that can simultaneously monitor multiple waveguide grating biosensors, and/or obtain resonant peak spectra of a given guided mode of multiple biosensors, and/or visualize resonant band images of a given guided mode of multiple biosensors. For example, an optical angular interrogation system, as disclosed in U.S. patent application Ser. No. 10/602,304, filed Jun. 24, 2003, having publication no. US-2004-0263841, published Dec. 30, 2004 and U.S. patent application Ser. No. 11/019,439, filed Dec. 21, 2004, and U.S. Patent App. for "OPTICAL INTERROGATION SYSTEM AND METHOD FOR 2-D SENSOR ARRAYS" by N. Fontaine et al., filed on Apr. 5, 2005, all of which are herein incorporated in their entireties by reference but at least for biosensors and their uses.

U.S. patent application Ser. No. 10/602,304, having publication no. US-2004-0263841 and U.S. patent application Ser. No. 11/019,439, filed Dec. 21, 2004, and U.S. Patent App. for "OPTICAL INTERROGATION SYSTEM AND METHOD FOR 2-D SENSOR ARRAYS" by N. Fontaine et al., filed on Apr. 5, 2005 provide a launch system for generating an array of light beams such that each illuminates an RWG sensor with a dimension of ~200 µm×3000 µm and a receive system for receiving all responses, as indicated by the angles of the light beams reflected from these sensors. This system allows, for example, up to 7×7 sensors to be simultaneously sampled at a rate of 3 seconds (an example was shown in FIG. 1). This means that cell health evaluation for 96 samples in a 96 well microplate can be done within several seconds. Another exemplary system, as disclosed in U.S. application Ser. No. 10/993,565, filed Nov. 18, 2004 by N. Fontaine et al. and "METHOD FOR ELIMINATING CROSSTALK BETWEEN WAVEGUIDE GRATING-BASED BIOSENSORS LOCATED IN A MICROPLATE AND THE RESULTING MICROPLATE" by Y. Fang et al., filed on Apr. 5, 2005 (Both of which are incorporated in their entireties and at least for material related to biosensors, scanning devices, and microplates) uses an arrayed optical fibers for generating an arrayed light such that each illuminates one biosensor and receives the responses from the same biosensors; and uses the controlled scanning module to collect responses from multiple areas within a single sensor as well as from multiple biosensors within a microplate in a sequential manner. Such system allows the cell health evaluation to be done within about 30 seconds.

3. Optical Based Biosensors

Optical-based biosensors have been used to detect a variety of biomolecular interactions including oligonucleotides, antibody-antigen interactions, hormone-receptor interactions, and enzyme-substrate interactions. There have been relatively few of reports describing the use of optical label free techniques for cell-based studies. For example, optical waveguide grating-based biosensor has been used to investigate the adhesion and spreading of animal cells (J. J. Ramsden, et al., "Kinetics of Adhesion and Spreading of Animal Cells," Biotechnol. Bioeng. 1994, 43, 939-945); and surface plasmon resonance (SPR) has been used for studying ligand-induced intracellular reactions of living cells (M. Hide, et al, "Real-time Analysis of Ligand-Induced Cell Surface and Intracellular Reactions of Living Mast Cells Using a Surface Plasmon Resonance-Based Biosensor," Anal. Biochem. 2002, 302, 28-37).

Optical-based biosensors generally consist of two components: a highly specific recognition element and an optical transducer that converts the molecular recognition event into a quantifiable signal. Direct surface sensing methods include surface plasmon resonance (SPR) (Jordan & Corn, "Surface Plasmon Resonance Imaging Measurements of Electrostatic Biopolymer Adsorption onto Chemically Modified Gold Surfaces," Anal. Chem., 1997, 69:1449-1456), grating couplers (Morhard et al., "Immobilization of Antibodies in Micropatterns for Cell Detection by Optical Diffraction," Sensors and Actuators B, 2000, 70, 232-242), ellipsometry (Jin et al., "A Biosensor Concept Based on Imaging Ellipsometry for Visualization of Biomolecular Interactions," Analytical Biochemistry, 1995, 232, 69-72), evanescent wave devices (Huber et al., "Direct Optical Immunosensing (Sensitivity and Selectivity)," Sensors and Actuators B, 1992, 6, 122-126), and reflectometry (Brecht & Gauglitz, "Optical Probes and Transducers," Biosensors and Bioelectronics, 1995, 10, 923-936). The instrumentation typically used to interrogate SPR or waveguide grating sensors utilizes an optical beam with the appropriate spectral or angular content, such that when this beam is reflected by the sensing surface, the resonant angle or wavelength response becomes dominant in the output response. A common feature is that both SPR and grating coupler (i.e., OWG or RWG) technologies are sensitive to refractive index changes at/near the sensor surface.

Figure 1:
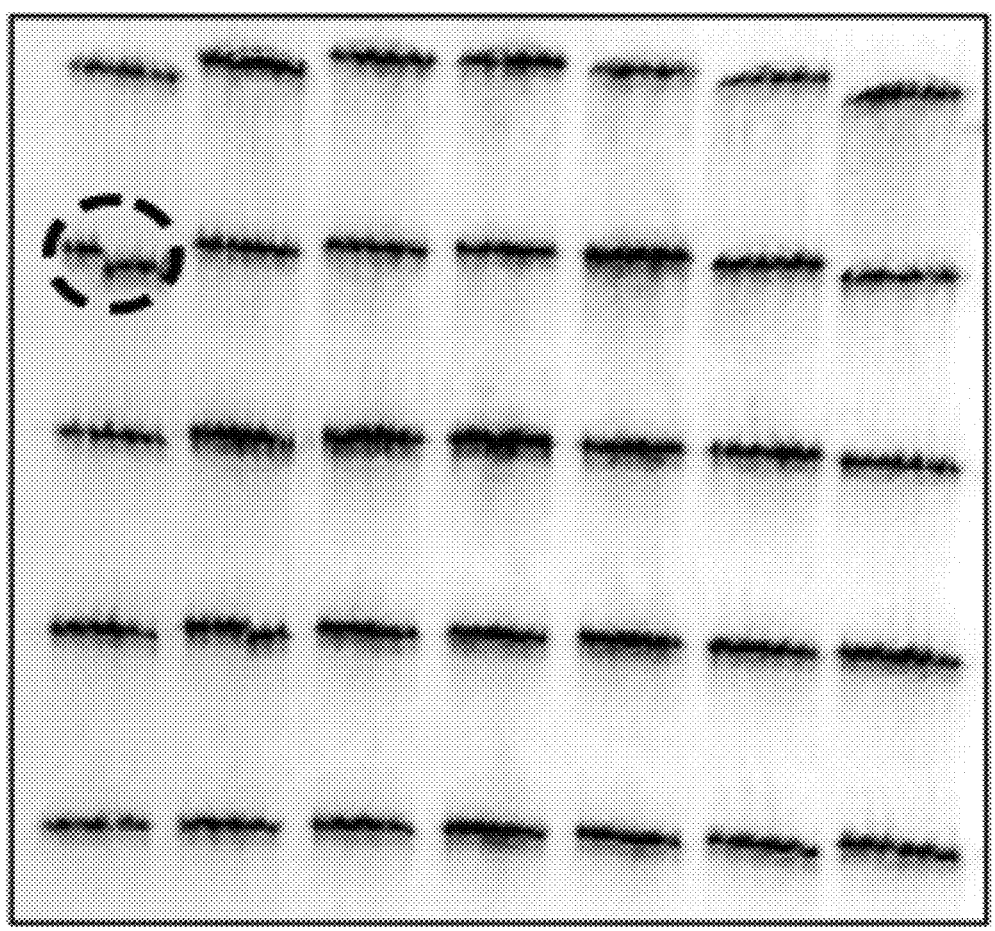

One major application of this technology as a biosensor is to monitor in situ the interfacial behaviors of specific analytes under the conditions of different surface properties and different solution characteristics. This technology allows label free detection, unlike most of the current technologies which requires specific labels for readout the interaction signals. The disadvantages associated with the labeling is that labeling is not only labor-intensive and costly, but also has potential to interference with the biological properties of target biologicals or compounds such that the data interpretation would be difficult and false information might be generated from assays. However, as disclosed herein, these disadvantages can be reduced when non-labeling visualization techniques are used or when labeling is used in conjunction with the non-labeling techniques disclosed herein. It is also understood that any of the sensors disclosed herein can be used in a variety of ways, including in a multiplex manner, for example, such that the multiplexing is done in using multi-well plates, such as a modified 96 well microplate. As disclosed herein, the label free biosensors, such as a RWG or OWG biosensor can be used in conjunction with cells and activities of the cells can be monitored. The cells can be cultured on the biosensors such that the cultured cells are adherent to the biosensor, much like when cells are cultured on a conventional plate and become adherent to the bottom surface of the plate. When the cells are cultured on the disclosed biosensors there is a change in the output of the biosensor. FIG. 1 shows an example of the output of cultured cells on the system. FIG. 2 shows a diagram of an optical waveguide grating sensor. In this figure the cells are cultured on top of the sensor. When a light source, such as a laser, is directed at the sensor at varying angles, at a specific set of angles the light will be coupled into the sensor. At other angles the light will either be directly reflected or pass through the sensor. As disclosed herein, upon cell manipulation such as stimulation of a receptor at the surface of the cell, there is a mass redistribution that takes place within the cell. This mass redistribution causes a number of things, one of which is a change in the angle at which the light will couple into the sensor. This change in angle can be utilized to identify events taking place within the cell, and it is understood as described herein that particular events can have a signature profile with respect to the output associated with the biosensor based on the mass redistribution that takes place within the cell.

Unlike conventional cell proliferation assays that generally require labels and lengthy incubation steps, certain embodiments of the disclosed compositions, methods, and techniques provide methods based on optical waveguide lightmode spectroscopy (OWLS) or resonant peak spectroscopy of a given guided mode or resonant band imaging of a given guided mode that do not require any labels. Furthermore, in certain embodiments the disclosed compositions, methods, and techniques eliminate any extra treatment steps including reagent reaction and washing steps. In addition, in certain embodiments, the disclosed compositions, methods, and techniques, such as the cell proliferation assays can be carried out under standard culture conditions in the absence and presence of compounds of interest only, without the interference of any other reagents which are generally required for almost all conventional methods. The presence of other reagents could result in the misinterpretation of assays results: (J. J. Ramsden, et al., "Kinetics of Adhension and Spreading of Animal Cells", Biotechnol. Bioeng. 1994, 43, 939-945) as these reagents themselves could have a direct effect on cell proliferation; (M. Hide, et al., "Real-time Analysis of Ligand-Induced Cell Surface and Intracellular Reactions of Living Mast Cells Using a Surface Plasmon Resonance-Based Biosensor," Anal. Biochem. 2002, 302, 28-37) compounds to be screened could have an effect on these reagents, rather than cell proliferation. For example, compounds that inhibit cellular mitochondrial dehydrogenases directly could result in the suppression of the conversion of MTT, thereby leading to false positives when a MTT assay is used to screen modulators against another particular target of interest.

In certain embodiments, the disclosed compositions, methods, and techniques provide ultra high throughput screening approaches to "fish out" inhibitors and activators, unlike other current label free cell proliferation assays including optical waveguide sensing approach which involves the real-time measurements of the angular or wavelength shifts due to cell proliferation. Because cell proliferation is generally a slow process (e.g., it takes many hours, days or even weeks) and generally requires 37° C. incubation, label free proliferation assays other than those disclosed herein which generally collects signals at room temperature are difficult to be implemented for high throughput screening.

The methods disclosed herein can provide accurate measurements without any extra reagents, and are easy to use and integrate with other functional screening. For example, there can be no need to store or manipulate radioactive or other substances (e.g., light-sensitive fluorescent compounds).

While others have used optical waveguide-based biosensors for cell proliferation assays, their use of optical waveguide-based biosensors monitored the wavelength shift of the sensors due to attachment of cells in the presence of different concentrations of a compound for a given number of starting cells (Cunningham, B. T., et al., "Label-Free Assays on the BIND System," J. Biomol.Screening 2004, 9, 481-490 and U.S. Patent Application Publication No. US20030068657A1 for "Label-free methods for performing assays using a colorimetric resonant reflectance optical biosensor" SRU Biosystems LLC by Lin, Bo et al.). These methods can be used, in certain situations, for examining $IC_{50}$s of a compound on cell proliferation. However, these methods are not suitable for high throughput screening, as the methods disclosed herein are. Disclosed herein, waveguide-based biosensors can be used to not only monitor the agonist-induced directional mass redistribution due to the activation of G protein coupled receptor (GPCR) or receptor tyrosine kinase such as EGFR in living cells, but also to study signaling pathways or cellular mechanism that lead to directional mass redistribution.

a) OWLS and Cell Toxicity

According to the OWLS, patterns and inhomogeneities on the surface of the waveguide can produce broadening and fine structure in the incoupled peak spectra. Instead of one sharp resonance peak of each mode for homogeneous surface immobilization on the sensor, these fine structures for sensors with inhomogeneous attachment of biologicals or materials observed experimentally and theoretically include, but not limited to, at least one shoulder (i.e., secondary) peak appearing with the main resonance peak of each mode, and well-separate double (or more) peak for each mode (see Horvath, R., et al. "Effect of patterns and inhomogeneities on the surface of waveguides used for optical waveguide lightmode spectroscopy applications", Appl. Phys. B. 2001, 72, 441-447; Voros, J., Graf, R. et al., "Feasibility Study of an Online Toxicological Sensor Based on the Optical Waveguide Technique," Biosensors & Bioelectronics 2000, 15, 423-429 the references therein are incorporated). Previously, researchers have observed that during cell attachment and spreading on the waveguide, the incoupled peaks are broadened, while regular microstructures on the grating produce shifts and splitting of the peaks. The broadening of the resonance peaks has been used as fingerprint of cell attachment and spreading.

4. Optical Biosensors and Mass Redistribution in Cells

The instrumentation typically used to interrogate SPR or waveguide grating sensors utilizes an optical beam with an appropriate spectral or angular content, such that when this beam is reflected by the sensing surface, the resonant angle or wavelength response becomes dominant in the output beam. Specifically, a planar optical waveguide used as a sensor consists of a substrate, a waveguiding film and a cover medium, where the cover medium is the substance to be characterized by determining the refractive index. The planar waveguide-based biosensors can be used to detect changes in the media surrounding the waveguide as the eletromagnetic field propagating in the waveguide will extend into the surrounding media as an evanescent eletromagnetic field (the depth is referred to the penetration depth or sensing volume). When mass redistribution occurs within the sensing volume, a response change is observed as an angular or spectral change in the reflected beam. The angular shift can be measured to obtain the kinetics of the mass redistribution response signal. In addition, because of that, distinct cellular responses would contribute differently to the overall mass redistribution signals. For example, cell detachment from the extracellular matrices occurs at/near the sensor surface, and therefore could lead to significantly greater responses than those occurring inside the cells.

Figure 9:
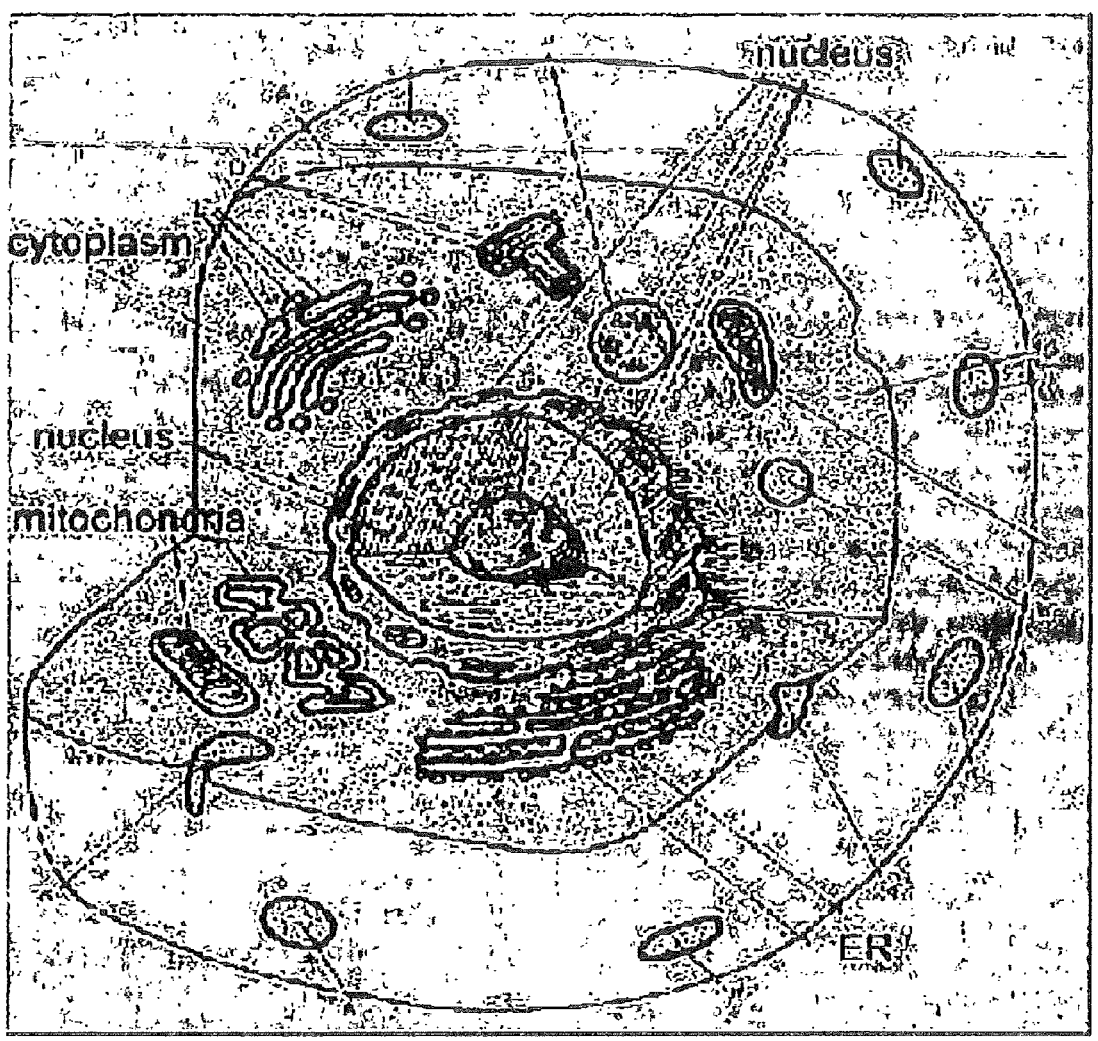

Biological cells are complex structures with components ranging in size from nanometers to tens of microns, as illustrated in FIG. 9. The cell consists of a cytoplasm (typically 5-30 μM) containing numerous organelles. The largest organelle is the nucleus, whose size ranges typically between 3 and 10 μm. The nucleus is filled with DNA-protein complexes and proteins, the most important one being chromatin. Mitochondria are small organelles comprised of a series of folded membranes with sizes typically ranging from 0.5-1.5 μm. Other cell components include endoplasmic reticulum (ER) (typically 0.2-1 μm), lysomes (typically 0.2-0.5 μm), peroxisomes (typically 0.2-0.5 μm), endosomes (typically ~100 nm), and golgi.

a) Optical Waveguide Grating-Based Surface Sensing Technology

Resonant waveguide grating sensors (RWG) and optical waveguide grating (OWG) can be used interchangeably. The RWG biosensor is an evanescent-wave sensor, based on the resonant coupling of light into a waveguide by means of a diffraction grating. The RWG-based surface sensing technology takes advantage of the evanescent field, which penetrates less than a wavelength out of the waveguide surface, to selectively respond to the adsorption of immobilized chemical and biological molecules over a given spectral bandwidth.

An example of an optical LID biosensor, such as 1004 FIG. 10, is a SPR sensor 1004 or a waveguide grating based sensor 1004. Other optical-based biosensors can also be used such as ellipsometry devices, evanescent wave devices, and reflectometry devices. For a more detailed discussion about the structure and operation of these two types of optical LID biosensors, such as 1004, are provided in U.S. Pat. No. 4,815,843 entitled "Optical Sensor for Selective Detection of Substances and/or for the Detection of Refractive Index Changes in Gaseous, Liquid, Solid and Porous Samples" and K. Tiefenthaler et al. "Integrated Optical Switches and Gas Sensors" Opt. Lett. 10, No. 4, April 1984, pp. 137-139, which are both herein incorporated in their entireties at least for material related to biosensors. In particular, optical biosensors disclosed in U.S. Patent App. 60/701,445, filed Jul. 20, 2005, for "Label-Free High Throughput Biomolecular Screen System and Method" and U.S. patent application Ser. No. 11/019,439, filed Dec. 21, 2004, and U.S. Patent App. for "OPTICAL INTERROGATION SYSTEM AND METHOD FOR 2-D SENSOR ARRAYS" by N. Fontaine et al., filed on Apr. 5, 2005, all of which are herein incorporated in their entireties by reference but at least for biosensors and their uses.

(1) Symmetry Waveguide Grating Biosensors

An example of a symmetry waveguide grating biosensor is a grating coupler or coupled biosensors. Examples of grating coupled biosensors can be found in Jordan & Corn, "Surface Plasmon Resonance Imaging Measurements of Electrostatic Biopolymer Adsorption onto Chemically Modified Gold Surfaces," Anal. Chem., 1997, 69:1449-1456; Morhard et al., "Immobilization of antibodies in micropatterns for cell detection by optical diffraction," Sensors and Actuators B, 2000, 70, 232-242; and Tiefenthaler, K., and W. Lukosz, "Sensitivity of grating couplers as integrated optical chemical sensors" J. Opt. Soc. Am.B, 1989, 6, 209-220 and are herein incorporated by reference in their entireties but at least for material related to grating coupled biosensors.

Figure 2A:
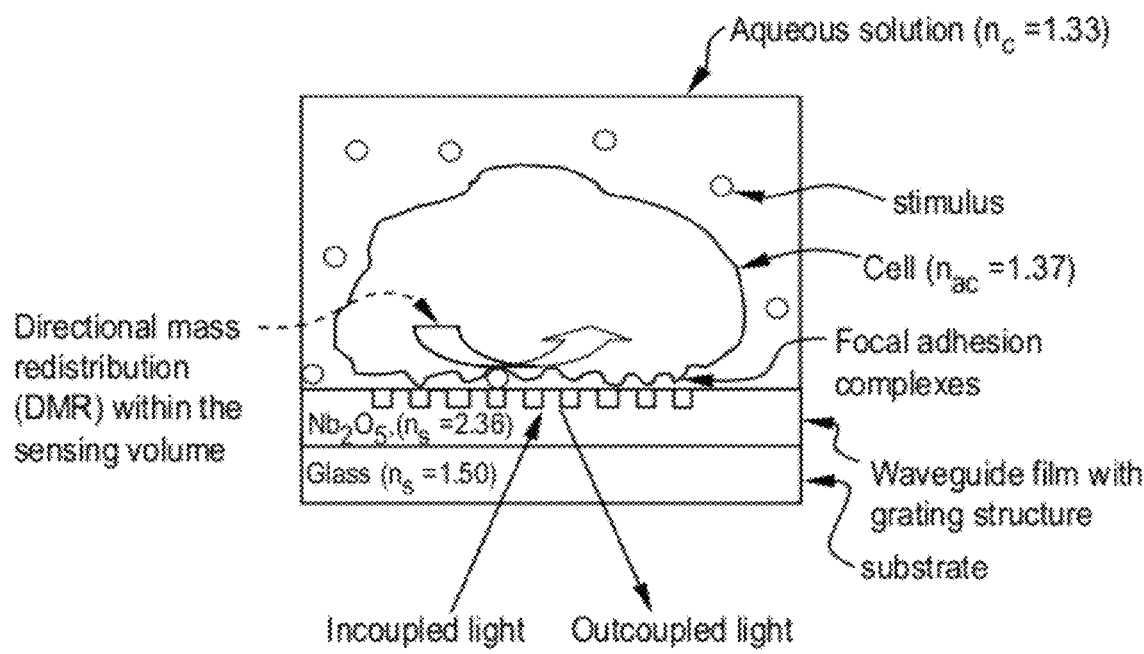

Grating coupler biosensors are evanescent-wave sensors based on the resonant coupling of light into a waveguide by means of a diffraction grating. The grating coupler sensor consists of the combination of a waveguide and diffraction grating. FIG. 2a shows a classical four layer waveguide biosensor consisting of a thin film of a high refractive index (e.g., $n_F$~2.36 for $Nb_2O_5$) material with a thickness of $d_F$ on a substrate of lower index (e.g., $n_s$~1.50 for 1737 glass). Immobilized on the waveguide film is an adlayer of biologicals with a refractive index ($n_A$) around 1.4 and a thickness $d_A$, and on top of the entire sensor structure is the cover medium, being the biological solution with index ($n_c$) around 1.35. In this conventional configuration, the refractive index of the waveguide thin film is at least 1% higher than that of the substrate of lower index, for example, by 1%, 5%, 10%, 20%, 30%, 50%, 70%, or 100%. The refractive index of the substrate of lower index is higher than that of the cover medium, for example, by 5%, 7%, 10%, 15%, 20%, 30%, or 50%. The refractive index of the cover medium, generally aqueous medium for cell-based assay applications, is typically around 1.32, 1.35, and 1.38.

The guided waves or modes in planar waveguide are $TE_m$ (transverse electric or s-polarized) and $TM_m$ (transverse magnetic or p-polarized), where m=0, 1, 2, . . . is the mode number. A given guided mode refers to, for example, $TM_0$, $TE_0$, $TM_1$, $TE_1$, etc. A laser illuminates the waveguide at varying angles and light is coupled into the waveguide only at specific angles determined by the effective refractive index of the guided mode, denoted as N. Since the evanescent tails of the light mode propagates in the substrate and cover media but still along the film, the light modes experience or sense all three media at the same time. It means that the refractive index experienced by the traveling light modes is a weighed mixture of the three refractive indices. The effective refractive index N can be calculated numerically from the mode equation, which can be written in the following form for a four layer waveguide assuming that the thickness of the thin adlayer is less than the wavelength of the light ($d_A \ll \lambda$) [Tiefenthaler, K., and W. Lukosz, "Sensitivity of grating couplers as integrated optical chemical sensors" J. Opt. Soc. Am.B, 1989, 6, 209-220]:

$$0 \cong \pi m - k(n_F^2 - N^2)^{0.5} \left( d_F + d_A \frac{n_A^2 - n_C^2}{n_F^2 - n_C^2} \left[ \frac{(N/n_C)^2 + (N/n_A)^2 - 1}{(N/n_C)^2 + (N/n_F)^2 - 1} \right]^\sigma \right) + \arctan\left[ \left(\frac{n_F}{n_S}\right)^2 \left(\frac{N^2 - n_S^2}{n_F^2 - N^2}\right)^{0.5} \right] + \arctan\left[ \left(\frac{n_F}{n_C}\right)^2 \left(\frac{N^2 - n_C^2}{n_F^2 - N^2}\right)^{0.5} \right] \quad (1)$$

Here, k=2π/λ, where λ is the vacuum wavelength of the guided light. σ is a mode type number which equals 1 for TE and 0 for TM modes.

If light is coupled into the waveguide by a surface-relief grating, N can be calculated from the incoupling angle:

$$(\pm)N = N_{air} \sin(\theta) + l\lambda/\Lambda \quad (2)$$

Where $N_{air}$=1.0003 is the refractive index of air, θ the angle of incidence measured in air, λ the wavelength, Λ the grating period and l=±1, ±2, . . . the diffraction order. The plus and minus signs on the left side of this equation hold for guided modes propagating in the +x and −x directions, respectively.

The induced effective refractive index change ΔN in the waveguide in the grating area lead to changes Δθ as described in following equation:

$$\Delta N = n_{air} \cos(\theta) \Delta\theta \quad (3)$$

Since the laser light is coupled to and propagates parallel to the surface in the plane of a waveguide film, this creates an electromagnetic field (i.e., an evanescent wave) in the liquid adjacent to the interface. The amplitude (Em) of the evanescent wave decays exponentially with increasing distance d from the interface:

$$E_m(d) = E_m(0)\exp\left(\frac{-d}{\Delta Z_C}\right) \quad (4)$$

with $$\Delta Z_C = \frac{1-\sigma}{k(N^2 - n_C^2)^{0.5}} + \frac{\sigma[(N/n_F)^2 + (N/n_C)^2 - 1]^{-1}}{k(N^2 - n_C^2)^{0.5}} \quad (5)$$

is the penetration depth of the waveguide mode with high intensity into cover medium.

A given mode type propagates only as a guide wave if two conditions need to be fulfilled: (a) the refractive index of the waveguide film has to be at least 1% larger than the surrounding substrate and cover medium refractive indices; and (2) the thickness of the waveguide film is larger than a well-defined value, call the cut-off thickness $d_C$:

$$d_C = \frac{1}{k(N_F^2 - n_{max}^2)^{0.5}}\left(\pi m + \arctan\left(\left(\frac{n_F}{n_{min}}\right)^{2\sigma}\left(\frac{n_{max}^2 - n_{min}^2}{n_F^2 - n_{max}^2}\right)^{0.5}\right)\right) \quad (6)$$

Where $n_{min} = \min\{n_s, n_C\}$ and $n_{max} = \max\{n_s, n_C\}$. It is known that when the film thickness approaches the cut-off thickness, the effective refractive index, N, of the mode approaches $n_{max}$. Furthermore, equation 5 implies that the penetration depth goes to infinity at the cut-off point on the side of the film that has the bigger refractive index, which the penetration depth will be finite on the other side. The $d_{eff}$ will be also infinite in this case.

Again, the exponentially decaying evanescent field from light propagating in waveguide sensors only penetrates the cover medium to a depth of 50-200 nm with high intensity, when the waveguide grating biosensors fall into the conventional waveguide configuration. This value is dependent upon the refractive indices of the media present at the interface, the illumination wavelength as well as the grating structure. When the incident angle equals the critical value, $d_c$ goes to infinity, and the wavefronts of refracted light are normal to the surface.

Figure 4:
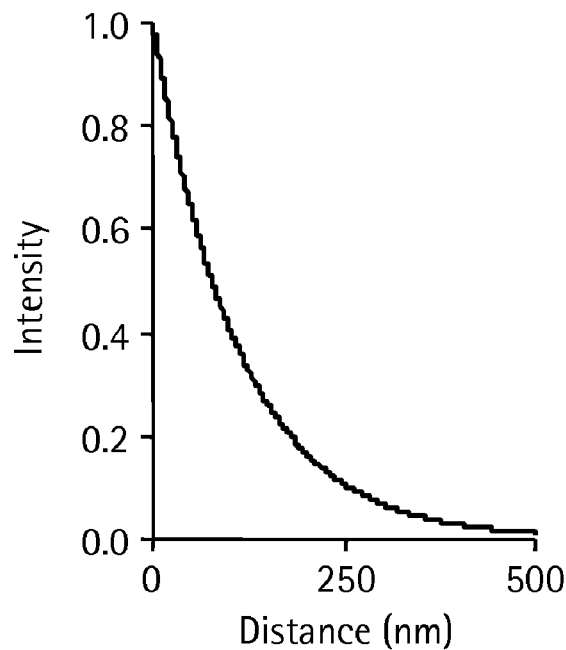

Considering a four-layer waveguide with following parameters: $n_F$=2.37 ($Nb_2O_5$ layer), $n_s$=1.51 (1737 glass), $n_c$=1.333 (aqueous solution), $n_A$=1.37 (cells), $d_A$=500 nm (average thickness of cultured cells), $d_F$=157 nm, wavelength 830 nm, grating period 530 nm, we have: (1) The cut-off thickness is 27 nm for $TE_0$ mode and 69 nm for $TM_0$, and 252 nm for $TE_1$ mode and 294 nm for $TM_1$ mode, suggesting that this sensor only supports $TE_0$ and $TM_0$ mode. (2) The penetration depth is 78 nm for $TE_0$ mode, and 112 nm for $TM_0$ mode. This means that (1) only the bottom portion of the adlayer of cells we was monitored, as highlighted in FIG. 2a by the broken arrow inside the cell; (2) target or complex of certain mass contributes more to the overall response when the target or complex is closer to the sensor surface as compared to when it is further from the sensor surface, as shown in FIG. 4. FIG. 4 shows the intensity of the evanescent wave penetrated into the medium decays exponentially with increasing distance. Because of its higher sensitivity, the $TM_0$ was used in most of exemplary studies in the present application unless specified.

(2) Reverse Symmetry Waveguide Grating biosensors

Figure 5:
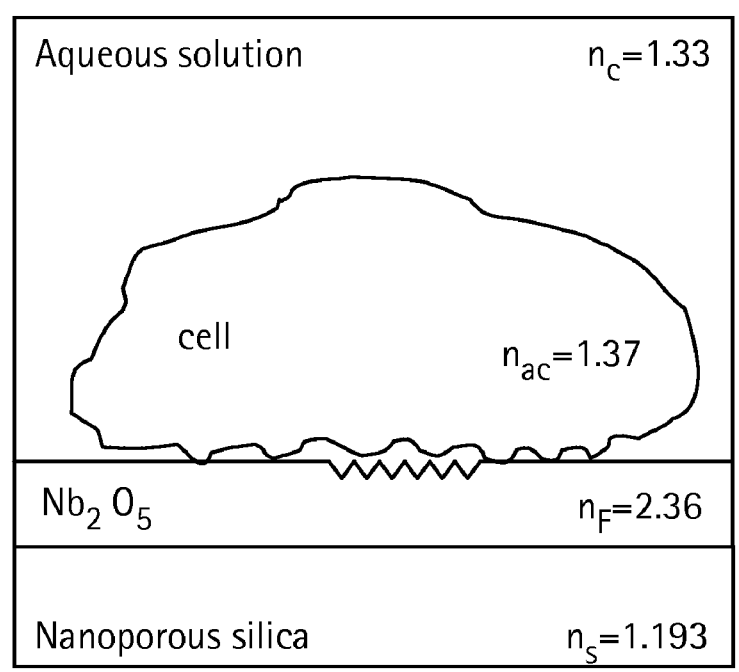

In the abovementioned waveguide sensors with conventional configurations, the substrate refractive index (e.g, glass substrate, typically $n_s$~1.5) is always higher than the aqueous cover medium refractive index (typically ~1.33). The exponentially decaying evanescent field from light propagating in such symmetry waveguide sensors only penetrates the cover medium to a short depth (typically ~50-200 nm). The evanescent tail on the substrate side is much longer and more intense than on the cover medium side. This limits the response to analytes, as the sensitivity depends on the fraction of the mode power propagating in the analyte adlayer. Reversal of the mode profile would overcome this limitation and permit larger (longer) penetration depths, thereby allowing analysis of morphology or intracellular components. Horvath et al. (US20030109055A1 and Horvath, R., Lindvold, L. R., and Larsen, N. B. "Demonstration of Reverse Symmetry Waveguide Sensing in Aqueous Solutions,", Applied Physics B, 2002, 74, 383-393; references therein are incorporated) have demonstrated the feasibility of so-called reverse symmetry waveguides. The principle of reverse symmetry waveguide is based on making the refractive index of the waveguide substrate less than the refractive index of the medium covering the waveguiding film (i.e., typically 1.33 for aqueous solution), as shown in FIG. 2a. As shown in FIG. 5, the reverse symmetry can be realized by three different geometries: (1) thin waveguide film deposited on a microstructured support; (2) thin waveguide film deposited on a mesoporous or nanoporous support in which the refractive index of such nanoporous substrates is around 1.15; and thin waveguide film deposited on nanostructured support. By using such reverse configurations, the cover medium penetration depth significantly exceeds that of the conventional waveguide, when film thickness approaches the cut-off thickness of the two waveguides. Furthermore, by controlling the film thickness the probing depth can also be controlled with no upper limit.

(3) Optical Detection Systems

In certain embodiments, the optical detection system can be either angular interrogation, or wavelength interrogation, or their variation systems, for example, the arrayed angular interrogation system or the scanning wavelength interrogation system (U.S. patent application Ser. No. 10/993,565, filed Nov. 18, 2004 by N. Fontaine, et al. and "METHOD FOR ELIMINATING CROSSTALK BETWEEN WAVEGUIDE GRATING-BASED BIOSENSORS LOCATED IN A MICROPLATE AND THE RESULTING MICROPLATE" by Y. Fang, et al., filed on Mar. 31, 2005 (Both of which are incorporated in their entireties and at least for material related to biosensors, scanning devices, and microplates), when optical waveguide biosensors are used. U.S. patent application Ser. No. 10/602,304, filed Jun. 24, 2003 having publication no. US-2004-0263841, published Dec. 30, 2004 and U.S. application Ser. No. 11/019,439, filed Dec. 21, 2004, and U.S. Patent App. for "OPTICAL INTERROGATION SYSTEM AND METHOD FOR 2-D SENSOR ARRAYS" by N. Fontaine, et al., filed on Mar. 31, 2005, all of which are herein incorporated in their entireties by reference but at least for biosensors and their uses.

Examples of a plate which can be used with a specific configuration of the OWG biosensor(s) in microplate is a 96 well Corning's Epic® biosensor microplate in which each well contains an optical waveguide grating (OWG) biosensor embedded in the bottom surface of a glass support substrate.

Because the evanescent field of the guided mode projects into the cover liquid, the waveguide mode is exquisitely sensitive to the cover environment. When cellular events occur at the waveguide surface (e.g., controlled releasing of biological materials from permeabilized cells), the resulted change the effective index of the cover medium because of the loss of mass, the propagation constant of the waveguide mode must also change in accordance with Maxwell's electromagnetic equations. As a result of the phase-matching condition for the waveguide grating structure mentioned above, the preferred coupling angle (or wavelength) of input light must change in accordance with the waveguide propagation constant change. These macroscopic physical changes can be monitored to indicate the microscopic cellular event.

b) Optical Waveguide Lightmode Spectroscopy (OWLS) Theory

Grating coupler biosensors are evanescent-wave sensors based on the resonant coupling of light into a waveguide by means of a diffraction grating. The guided modes propagate in the planar waveguide by total internal reflection which can be described by the zigzag wave model. After having passed a full zigzag, the phase difference between the ordinary wave and the twice-reflected wave is a function of the $\chi$ component of the wave-vector of the light in the film ($\beta$) only for a given waveguide structure and fixed polarization and wavelength. Determined by self-consistency criteria, the value of $\beta$ can be calculated numerically from the mode equation (Horvath, R., et al., "Effect of Patterns and Inhomogeneities on the Surface of Waveguides Used for Optical Waveguide Lightmode Spectroscopy Applications," Appl. Phys. B. 72, 441-447):

$$\pi m \cong d_F(k^2 n_F^2 - \beta^2)^{0.5} - \arctan\left[\left(\frac{n_F}{n_S}\right)^{2\rho}\left(\frac{\beta^2 - k^2 n_S^2}{k^2 n_F^2 - \beta^2}\right)^{0.5}\right] - \arctan\left[\left(\frac{n_F}{n_C}\right)^{2\rho}\left(\frac{\beta^2 - k^2 n_C^2}{k^2 n_F^2 - \beta^2}\right)^{0.5}\right] \quad (7)$$

Here $k=2\pi/\lambda$, where $\lambda$ is the vacuum wavelength of the guided light. $\rho$ is a mode type number which equals 1 for TE and 0 for TM modes. $n_F$, $n_s$ and $n_c$ are the refractive indices of the film, substrate and cover medium, respectively. The mode propagation direction in the waveguide is $\chi$, and m=0, 1, 2 . . . is the mode index of mth-guide mode. In the zigzag wave model, each ray represents a plane wave (P. K. Tien., "Integrated Optics and New Wave Phenomena in Optical Waveguides," Rev. Mod. Phys. 1977, 49, 361). If the light is coupled into the waveguide, it is only necessary to consider the coupling at those points where the zigzag wave strikes the film surface, and at these points simple ray optics can be used.

Figure 3:
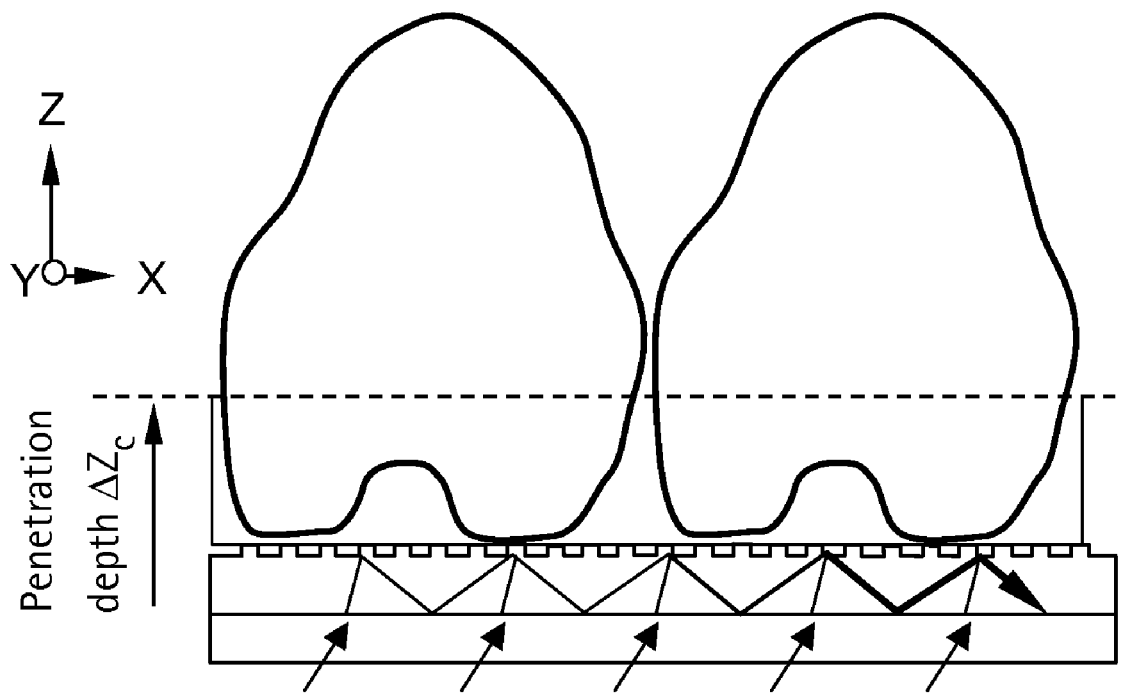

As shown in FIG. 3, provided that the phase shift during one zigzag is $\Phi(\beta)$, the amplitude of the wave after the nth zigzag, $(A_n(\beta))$, will be given by a geometrical series:

$$A_n(\beta) = A_0(\beta) \sum_{j=0}^{n-1} e^{ij\Phi(\beta)} \quad (8)$$
$$= A_0(\beta) G(\beta)$$

Here i denotes the imaginary unit, and $$G(\beta) = \frac{e^{in\Phi(\beta)} - 1}{e^{i\Phi(\beta)} - 1} \quad (9)$$

and $$\Phi(\beta_m) = 2\pi m, m = 0, 1, 2 \ldots \quad (10)$$

Assuming that the whole grating length is illuminated, the coupling length L equals the grating length, the total number, n, of the full zigzags can be calculated:

$$n = \frac{L\sqrt{k^2 n_F^2 - \beta^2}}{2 d_F \beta} \quad (11)$$

Illuminating the grating at angle $\alpha_o$, the waveguide mode with $\beta_0$ is generated:

$$\beta_0 = k n_{air} \sin(\alpha_0) + 2\pi/\Lambda \quad (12)$$

Where $n_{air}$ is the refractive index of the air and $\Lambda$ is the grating periodicity. Because of the finite width of the grating and laser beam, when illuminating the grating under angle $\alpha_o$ with a plane wave, the diffracted light can be described using a plane wave distribution. This leads to a peak at $\beta_o$ with a Peak Width at Half Maximum (PWHM) of approximately $2\pi/L$, calculated from the optical uncertainty principle (Tiefenthaler, K. and Lukosz, W, J., "Sensitivity of grating couplers as integrated-optical chemical sensors", J. Opt. Soc. Am. B. 1989, 6, 209-220).

The intensity of the coupled light after the nth section ($I_n(\beta)$) is proportional to the absolute square of the amplitude of the light: $|G(\beta)|^2 \beta IG(\beta)$. The relation between the coupled light intensity, $I(\alpha)$, and the incident angle, which can also be measured using optical waveguide lightmode spectroscopy (OWLS) technique, can be calculated using following equation:

$$I(\alpha) = \int I_d(\beta, \alpha) IG(\beta) d\beta \quad (13)$$

Where $I_d(\beta,\alpha)$ is the intensity distribution of the first-order diffraction:

$$I_d(\beta, \alpha) = \left| \frac{\sin\left(0.5L\beta - 0.5L\left(kn_{air}\sin(\alpha) + \frac{2\pi}{\Lambda}\right)\right)}{\beta - \left(kn_{air}\sin(\alpha) + \frac{2\pi}{\Lambda}\right)} \right|^2 \quad (14)$$

c) Vertical Mass Redistribution and Lateral Mass Redistribution

Living cells are highly dynamic and most organelles travel extensively within cells, for example, in response to activation of signaling molecules or pathways. For example, microtubules can transport organelles over long distances. A stimulus can result in the submicron movement of densely packed organelles in the very periphery of a sensor surface on which the cells are cultured; such movement leads to mass redistribution within the cell. Such movements in response to signal simulation can be called "trafficking" or "translocation" or "redistribution". Such a trafficking or translocation or redistribution event is generally associated with mass redistribution. The mass redistribution can be detected by optical biosensors; and the signal relating to mass redistribution is referred to as directional mass redistribution (DMR) signal.

Since stimulation could lead to dynamic redistribution of cellular contents in three-dimension, monitoring the cell responses with the changes in incident angle or wavelength may not be sufficient for cell sensing with the biosensors. To simplify the analysis, the dynamic mass redistribution can be divided into two types: vertical mass redistribution which occurs perpendicular to the sensor surface, and lateral or horizontal mass redistribution that occurs parallel to the sensor surface. It is understood that a specific stimulatory event may result in one of these mass redistribution or the other, or both.

As implicated by the dynamic changes in the incident angle or resonant wavelength, the DMR signal is primarily resulted from the redistribution of cellular contents that occurs perpendicular to the sensor surface, since the biosensors are mostly sensitive to the mass redistribution parallel to the direction of the evanescent wave of the sensors. Such DMR is also referred to vertical mass redistribution. Specifically, a stimulatory event-induced mass redistribution in the direction that is parallel to the sensor surface and perpendicular to the direction of the evanescent wave of the sensors can lead to the change in homogeneity of the mass within the cell layer, and thus result in a change in the resonant peak, a resonant band image, and/or the OWLS spectrum. Such change(s) can be detected and used as signature for the effect of stimulatory events or compounds on the stimulatory event-induced cell responses. Such mass redistribution is referred to lateral mass redistribution.

As shown in FIGS. 2 and 3, cells are directly cultured onto the surface of a resonant waveguide grating (RWG) biosensor. Exogenous signals mediate the activation of specific cell signaling, in many cases resulting in dynamic redistribution of cellular contents, equivalent to dynamic mass redistribution. When occurring within the sensing volume (i.e., penetration depth of the evanescent wave), the DMR can be manifested and thus monitored in real time by a RWG biosensor—a label free technology that is sensitive to change in local refractive index in the vicinity of the sensor surface. Because of its ability for multi-parameter measurements, the biosensor has potentials to provide high information content for cell sensing. These parameters include the angular shift (one of the most common outputs), the intensity, peak-width-at-half-maximum (PWHM), and area of the resonant peaks. In addition, because of the unique design of our angular interrogation system which uses a light beam of ~200 μm×3000 μm to illuminate each sensor, the resonant band image of each sensor can provide additional useful information regarding to the uniformity of cell states (e.g., density and adhesion degree) as well as the homogeneity of cell responses for cells located at distinct locations across the entire sensor.

The RWG biosensor exploits the evanescent-wave that is generated by the resonant coupling of light into a waveguide via a diffraction grating. The guided light can be viewed as one or more mode(s) of light that all have directions of propagation parallel with the waveguide, due to the confinement by total internal reflection at the substrate-film and medium-film interfaces. The waveguide has higher refractive index value than its surrounding media. Because the guided light mode has a transversal amplitude profile that covers all layers, the effective refractive index N of each mode is a weighed sum of the refractive indices of all layers:

$$N = f_N(n_F, n_S, n_C, n_{ad}, d_F, d_{ad}, \lambda, m, \sigma) \quad (15)$$

Here, $n_F$, $n_S$, $n_C$, and $n_{ad}$ is refractive index of the waveguide, the substrate, the cover medium, and the adlayer of cells, respectively. $d_F$ and $d_{ad}$ is the effective thickness of the film, and the cell layer, respectively. $\lambda$ is the vacuum wavelength of the light used. m=0, 1, 2, . . . is the mode number; and σ is the mode type number which equals to 1 for TE (transverse electric or s-polarized) and 0 for TM modes (transverse magnetic or p-polarized).

Optical sensing of adherent cells is unique and quite challenging, because of the nature of cells interacting with surfaces and the complexity of cell structure and functions. Some types of cells are known to be adherent on a surface, primarily through three types of contacts: focal contacts, close contacts and extracellular matrix (ECM) contacts. The focal contacts are narrow regions of an adherent cell membrane (e.g., 0.2 μM×10 μm) that come within 10-15 nm of the substrate surface. The close contacts refer to regions of the cell membrane separated from the substrate of 1-50 nm, whereas the ECM contacts designate regions of the cell membrane separated from the substrate by 100 nm or more. Thus, one can appreciate that the sensor still is able to sense the cover medium, even when the cell confluency is high (~95%). However, it is known that living cells contain ~70% water, and most of intracellular bio-macromolecules are highly organized by the matrices of filament networks and spatially restricted to appropriate sites in mammalian cells. Furthermore, the height of the cells is typically beyond the wavelength of incident light (here λ=830 nm), while the penetration depth is generally much smaller than the height of cells. Thus, the biosensor for cell sensing can be viewed as a three-layer configuration: the substrate, the waveguide, and the cell layer.

The value of effective refractive index N can be calculated numerically from the mode equation for a given mode of a three-layer waveguide [Tiefenthaler, K., and W. Lukosz, "Sensitivity of grating couplers as integrated optical chemical sensors" J. Opt. Soc. Am.B, 1989, 6, 209-220]:

$$0 \cong \pi m - k d_F (n_F^2 - N^2) + \\ \arctan\left[\left(\frac{n_F}{n_S}\right)^{2\sigma}\left(\frac{N^2 - n_S^2}{n_F^2 - N^2}\right)^{0.5}\right] + \arctan\left[\left(\frac{n_F}{n_C}\right)^{2\sigma}\left(\frac{N^2 - n_C^2}{n_F^2 - N^2}\right)^{0.5}\right] \quad (16)$$

Here, the wave vector k=2π cm/A.

The guided light modes propagate parallel to the surface of a plane waveguide, thus creating an electromagnetic field (i.e., an evanescent wave) extending into low-refractive index mediums surrounding both sides of the film with a characteristic of exponential decaying. The amplitude ($E_m$) of the evanescent wave decays exponentially with increasing distance z from the interface:

$$E_m(d) = E_m(0) \exp\left(\frac{-z}{\Delta Z_C}\right) \quad (17)$$

with:

$$\Delta Z_C = \frac{1 - \sigma}{k(N^2 - n_C^2)^{0.5}} + \frac{\sigma[(N/n_F)^2 + (N/n_C)^2 - 1]^{-1}}{k(N^2 - n_C^2)^{0.5}} \quad (18)$$

is the penetration depth of the evanescent tail of the waveguide mode that extends into the cover medium. Based on the configuration of the biosensors used and the uniqueness of cell properties, the penetration depth of the $TM_0$ mode used here is ~120 nm, meaning that we only monitored the bottom portion of the cells.

The translocation of proteins and/or molecular assemblies is common to many cell responses triggered by exogenous signals. The translocation enables the precise control in the amplitude, duration and kinetics of cell signaling through a specific target. In addition, in some cases exogenous stimuli could also cause changes in cell status such as the adhesion degree and cytoskeletal structure. When such changes occur within the sensing volume, the mode index N is altered due to the interaction between the cover medium and the evanescent tail.

Figure 2B:
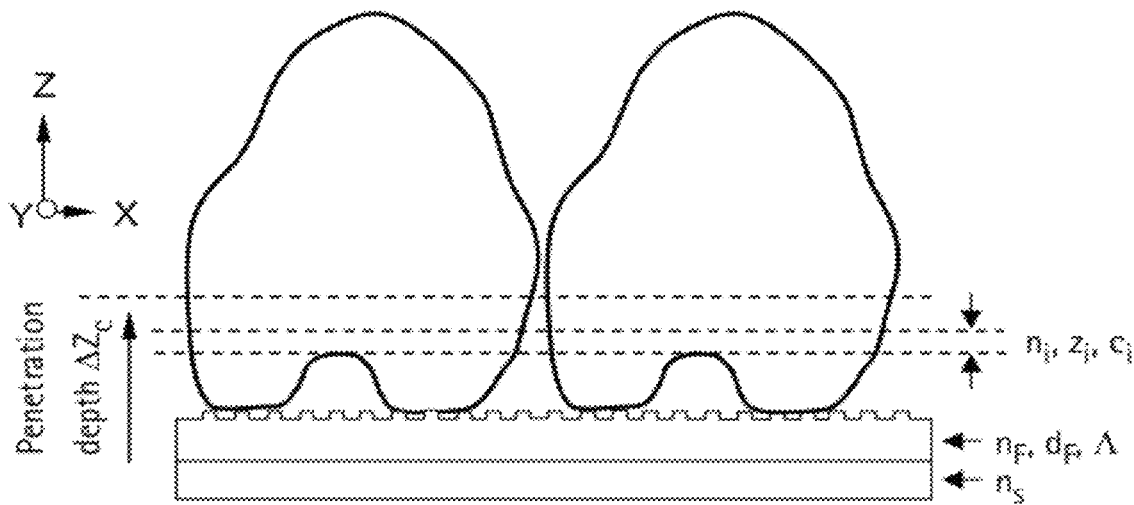

For the redistribution of cellular contents in a direction that is perpendicular to the sensor surface but parallel to the evanescent tail of the guided modes (referred to vertical mass redistribution), one can divide the bottom portion of adherent cells into multiple equal-spaced and homogenous thin layers, assuming that the degree and configurations of adhesion are similar for cells being probed with the light beam at a given time. Each layer has its own refractive index $n_i$ and is away from the sensor surface by a distance of $z_i$ (FIG. 2b). All layers could be considered to have equal volume, because the unit area A is considered to be constant and determined by the spatial resolution of the optical biosensor which is limited to the physical size of incident light beam as well as the propagation length of the guided wave in the waveguide. The refractive index of a given volume within cells is largely determined by the concentrations of bio-molecules, mainly proteins [Beuthan J, O. Minet, J. Helfmann, M. Herrig, and G. Muller. 1996. The spatial variation of the refractive index in biological cells. Phys. Med. Biol. 41:369-382):

$$n_i = n_o + \alpha C_i \tag{19}$$

Here $n_o$ is the index of the solvent, which is constant and approximately equals to water in cells. $\alpha$ is the specific refraction increment, and is about 0.0018 for protein, and 0.0016 for other solutes found in cells such as sodium. $C_i$ is the concentration of solutes (in g/100 ml) in the layer i. While the specific refraction increments are similar for proteins and other solutes, proteins primarily account for the refractive index of each layer because their concentrations in terms of weight per volume are considerably greater than other solutes. Thus, the refractive index changes $\Delta n_i$ of the homogeneous layer i approximately form a piece-wise continuous function:

$$\Delta n_i = \alpha \Delta C_i \tag{20}$$

The weighed index change $\Delta n_c$ within the sensing volume is the integration of $\Delta n_i$ with a weighed factor $\exp(-z/\Delta Z_c)$:

$$\Delta n_C = \frac{\int_0^\infty \Delta n(z) e^{\left(\frac{-z}{\Delta Z_C}\right)} dz}{\int_0^\infty e^{\left(\frac{-z}{\Delta Z_C}\right)} dz} \tag{21}$$

Integrated from $z=0$ to $z=\infty$, after substituting expression (7) for $\Delta n(z)$ and rearrangement, we have:

$$\Delta n_C = \alpha \sum_i \Delta C_i \left[ e^{\frac{-z_i}{\Delta Z_C}} - e^{\frac{-z_{i+1}}{\Delta Z_C}} \right] \tag{22}$$

Since in most cases $\Delta n_c$ is a small portion of the refractive index of the cells sensed by the biosensors (generally less than 20%), thus to first order the change in effective refractive index is, $$\Delta N = S(C) \Delta n_c \tag{23}$$

where S(C) is the sensitivity to the cover medium (i.e., the cells):

$$S(C) = \partial N / \partial N_c \tag{24}$$

$$= \frac{n_C}{N} \left[ \frac{n_F^2 - N^2}{n_F^2 - n_C^2} \right] \frac{\Delta z_C}{d_{\mathit{eff}}} \left[ 2 \frac{N^2}{n_C^2} - 1 \right]^\sigma$$

with $d_{\mathit{eff}}$ being the effective waveguide thickness given by:

$$d_{\mathit{eff}} = d_F + \Sigma \Delta z_C \tag{25}$$

Inserting Eqs. 9 and 11 into Eq. 12, we obtain, for the detected signal:

$$\Delta N = \frac{n_C}{N} \left[ \frac{n_F^2 - N^2}{n_F^2 - n_C^2} \right] \frac{\Delta z_C}{d_{\mathit{eff}}} \left[ 2 \frac{N^2}{n_C^2} - 1 \right]^\sigma \alpha \sum_i \Delta C_i \left[ e^{\frac{-z_i}{\Delta Z_C}} - e^{\frac{-z_{i+1}}{\Delta Z_C}} \right] \tag{26}$$

The eq. 26 suggests: (i) changes of the effective refractive index, thus the optical signature relating to the shift in the incident angle measured, is primarily sensitive to the vertical mass redistribution within the sensing volume; (ii) changes of the effective refractive index is directly a function of changes in protein concentration due to protein relocation, rather than ion mobilization such as $Ca^{2+}$ influx and $Ca^{2+}$ flux, mediated by a stimulation; (iii) the relocation of a target or complex of certain mass towards the sensor surface contributes more to the overall response than that moving away from the surface; (iv) the optical signature is an integrated signal that is a sum of contributions from mass redistribution occurring at different distances away from the sensor surface. Because of the complex nature of cell signaling, the activation of distinct cell signaling mediated through different targets might result in similar overall DMR signal. However, because of the participation of unique sets of cellular targets for a specific signaling event, the inhibition profiles mediated by a predetermined set of selective inhibitors might provide a means to classify the specificity of cell signaling being activated by a particular stimulus.

As discussed above, the shift in the incident angle or resonant wavelength is largely determined by vertical mass redistribution within the sensing volume, when cells respond to stimulation. Because of the poor lateral resolution of the biosensor, the lateral mass redistribution may be difficult to be resolved by these shifts. However, because of the finite width of the grating and laser beam, the diffracted light can be described using a plane wave distribution when illuminating the grating under angle $\alpha_o$ with a plane wave, as discussed in the RWLS theory section. This leads to a peak at $\beta_o$ with a PWHM of approximately $2\pi/L$, calculated from the optical uncertainty principle, when no any adlayer exists. Modeling using these equations led to interesting findings, which suggest that the shape of the resonant peaks (or spectra) carries valuable information about the lateral inhomogeneity of mass distribution. Such lateral inhomogeneity does not strongly perturb the cover medium refractive index, but significantly alters the shape of the resonant peaks.

It is well known that certain exogenous signals could lead to significant asymmetric lateral mass redistribution at the levels of both single cell and multiple cells. For example, distinct populations of cells could respond heterogeneously to compounds that are toxic to cells, while a single adherent cell could undergo uneven distribution of certain cellular targets or molecular assemblies during some cellular processes such as cell migration and invasion. We hypothesized that when occurring, the asymmetric lateral mass redistribution could also result in the change in the fine structure and shape of the resonant peaks.

d) Dynamic Mass Redistribution in Cell Signaling and Cell Physiology

Living cells consist of a complex and dynamic network of protein filaments, termed as cytoskeleton which extends throughout the cytoplasm of eukaryotic cells. The cytoskeleton involves in executing diverse cellular activities, for example, by providing tensile strength for maintaining cell shape, by providing the "track" or "docking sites" for signaling and trafficking, and by providing force for cell motion, intracellular transport and cell division. There are three kinds of cytoskeletal filaments: actin filaments, intermediate filaments and microtubules, each executing distinct biological functions. Among these filaments, actin filaments are mostly concentrated just beneath the plasma membrane, as they keep cellular shape, form cytoplasmatic protuberancies, and participate in some cell-to-cell or cell-to-matrix junctions, signal transduction and muscular contraction.

It is known that most of intracellular bio-macromolecules are highly organized by the matrices of filament networks and spatially restricted to appropriate sites in mammalian cells. Furthermore, the localization of cellular proteins is tightly controlled to regulate the specificity and efficiency of protein interactions, to spatially separate protein activation and deactivation mechanisms, and to determine specific cell functions and responses. In response to stimulation, there is often, sometimes significant, relocation of cellular proteins, depending on the nature of signaling pathway and its network interaction, cell status and the cellular context. The relocation of proteins and molecular assemblies is fundamental not only to cell signaling by enabling precise control in its amplitude, duration and kinetics, but also to cell functions such as migration, invasion, growth, cycling, differentiation, survival and death.

Perfect example is illustrated in G protein-coupled receptor (GPCR) signaling. GPCRs are a super family of membrane-bound proteins. In unstimulated cells, endogenous GPCRs primarily locate at the cell surface. After being exposed to ligands, cells respond with a series of spatial and temporal events which are tightly and precisely controlled by intracellular signaling and regulatory machineries. These events lead to ordered, directed, directional and dynamic redistribution of cellular contents during the GPCR signaling cycle. Monitoring the dynamic redistribution of cellular contents has provided insights into GPCR signaling and a powerful means for GPCR screens. For example, direct visualization of the relocation of β2-adrenoceptor-GFP conjugates after agonist stimulation initiated interest in this process as a direct screening strategy. One of these trafficking assays is the Transfluor technology from Xsira Pharmaceuticals Inc (formerly Norak Biosciences). This technology employs high resolution fluorescence imaging to monitor the intracellular location of fluorescently labeled arrestins in response to a compound. The re-localization of fluorescently labeled arrestins is viewed as an indication of agonism.

Many of these events occur within the bottom portion of the cells, which can be manifested by optical biosensors, resulting in an optical signal relating to dynamic mass redistribution (DMR). The DMR signals act as novel physiological responses of living cells. Theoretical analysis indicated that the optical signature, as indicated by the shift in incident angle or wavelength, is primarily sensitive to the vertical mass redistribution within the sensing volume (referred to DMR), while the optical output parameters relating to the shape (e.g., peak-width-at-half-maximum, intensity, and area) of the resonant peak are sensitive to the stimulation-induced lateral mass redistribution. Because of the exponential decay of the evanescence wave tail penetrating into the cell layer, a target or complex of certain mass contributes more to the overall response when the target or complex is closer to the sensor surface as compared to when it is further from the sensor surface. Furthermore, the relocation of a target or complex of certain mass towards the sensor surface results in increase in signal, whereas the relocation of a target or complex moving away from the surface leads to decrease in signal.

The DMR signals mediated through a particular target were found to depend on the cell status, such as degree of adhesion, and cell states (such as proliferating and quiescent state). Since the width or position of the resonant peak of a sensor is sensitive to the cell density and viability, the biological status of cells (e.g., cell viability, cell density, and degree of adhesion) that could significantly impact the assay results can be examined, resulting in reduced assay variability.

Three important aspects to qualify the suitability of a given approach for systems biology applications are the ability of multiplexing, of multi-parameter analysis, and of quantitative system-response profiles. Since optical biosensors are label-free and non-invasive, the biosensor-based cell assays are capable of multiplexing. For example, the agonist-induced activation of endogenous bradykinin $B_2$ receptor, P2Y receptors, as well as protease activated receptors (PARs) in A431 has been found to lead to similar Gq-type optical signatures (FIG. 66). Furthermore, since the optical biosensor offers an integrated response, the DMR signaling mediated through a particular target can also be used to profile its downstream signaling target. For example, the EGF-induced DMR in A431 can be used to profile the compounds that target one of its downstream targets: MEK1 (FIG. 44). These results suggested that the biosensor-based cell assay is multiplexing in nature.

Optical biosensors offer multi-parameters to analyze the ligand-induced DMR responses. These parameters include the shift in angle or wavelength of the reflected light which is sensitive to the vertical mass redistribution, and the parameters defining the shape of the resonant peak which are mostly sensitive to the lateral mass redistribution. The combination of these parameters could further provide detailed information on the action of ligands on the cells examined (examples are shown in FIG. 80 for reactive oxygen species signaling, in FIG. 84 for EGFR signaling, and in FIG. 85 for bradykinin $B_2$ signaling). Alternatively, since the biosensor is non-invasive, the biosensor-based cell assays can be easily integrated with other technologies, such as mass spectroscopy and fluorescence imaging. These technologies can further confirm the action of compounds or ligands on cells.

The DMR signal mediated through a particular target is an integrated and quantifiable signal that is a sum of contributions from mass redistribution occurring at different distances away from the sensor surface. Because of the complex nature of cell signaling, the activation of distinct cell signaling mediated through different targets might result in similar overall DMR signal. However, because of the participation of unique sets of cellular targets for a specific signaling event, the modulation profiles mediated by a predetermined set of selective modulators might provide a means to classify the specificity of cell signaling being activated by a particular stimulus. Therefore, the DMR response can be treated as a unique and perfect readout for systems biology studies of living cells (examples are shown in FIGS. 38-47 for EGFR signaling; or in FIGS. 71-79 for PAR signaling in A431 cells). These studies showed that the modulations of different targets result in distinct attenuations of the DMR signal induced by EGF. In response to epidermal growth factor (EGF) stimulation, the DMR response of quiescent A431 cells was found to be saturable to the concentration of EGF, and was able to be fully suppressed by a specific and potent EGFR tyrosine kinase inhibitor, AG1478. The effect of various known inhibitors/drugs on the DMR response of quiescent A431 cells linked the cell response to mainly the Ras/mitogen-activated protein (MAP) kinase pathway, which primarily proceeds through MEK.

5. Cell Assays

Disclosed are the methods and uses of optical free biosensors to perform any cell assay, such as an assay for cell death, an assay for cell proliferation, an assay for receptor activation or inhibition, an assay for cell membrane integrity, an assay for lipid signaling, an assay for cell signaling, an assay for reactive species signaling, an assay for evaluating the redox states of cells, an assay for study cross-communication between distinct targets, an assay for high throughput compound screening using endpoint measurements, and assay nuclear signaling or activity, or an assay for cytoskeleton rearrangement, for example. These assays incorporate the use of one or more biosensor output parameters that can be used to produce a signature for the assay or which can be used to make a determination from the assay as well as one or more steps.

A biosensor can produce an output which can be in different forms, such as pixels, or angular shift, or a wavelength shift, for example. The output can be in the form of a output data which is output information that is collected for a particular set of conditions, and can either be stored or analyzed in realtime. A biosensor when used produces an output of data, which typically can be represented in a graph form, such as response units versus time (see FIG. 6A as an example as well as many other figures disclosed herein). The response unit can be angular shift (in terms of degree) when an angular interrogation detection system is used, or wavelength shift (in terms of pico-meters when a wavelength interrogation detection system is used), or pixel position shift (in terms of pixel) when an angular interrogation detection system utilizing a CCD camera is used to collect the resonant band images of biosensors. Again, the response unit can be intensity of the incoupled light as a function of incoupling angle (See FIG. 6B) or wavelength, when a resonant peak spectrum of a given mode is used. In another embodiment, the response unit can be position in pixel or positional intensity when an angular interrogation detection system utilizing a CCD camera is used to collect the resonant band images of biosensors (See FIG. 6C). A biosensor output parameter or biosensor output data parameter is any characteristic of a biosensor output or output data respectively that can be measured and used to analyze the biosensor output or biosensor output data. In certain embodiments a biosensor output parameter can also be a characteristic that can be identified and used across multiple assays. The signature is any biosensor output parameter or combination of parameters that can be used as a diagnostic for a particular assay. For example, a signature could be the use of peak intensity magnitude after a stimulatory event, or it could be the position of the peak intensity after a stimulatory event, or it could be the position of the half maximal peak intensity. This signature can then be used to, for example, compare the effect of two different compounds on a culture of cells or the effect of a single compound on two different cultures of cells, rather than a comparison of the entire data output. Thus, a signature could occur at a single time point or a single wavelength or single wave angle, or an any combination, depending on what is be assayed. (See discussions above for response unit)

a) Biosensor Output Parameters

Figure 6A:
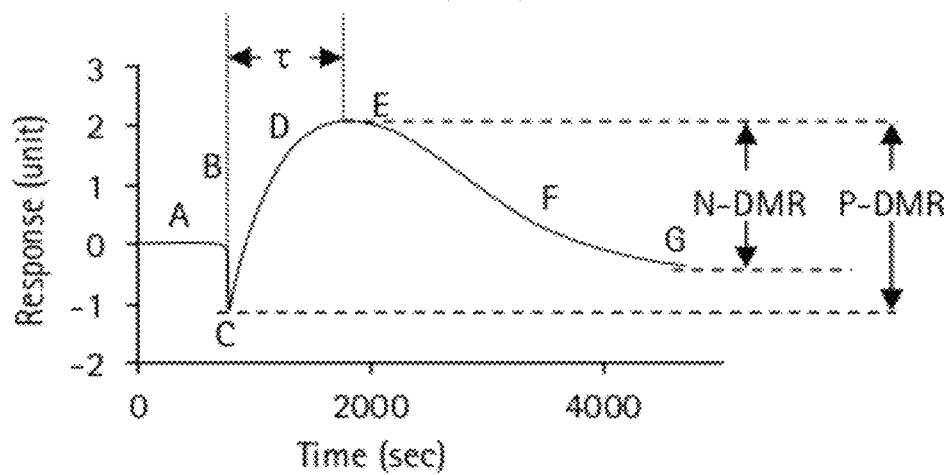
Figure 6B:
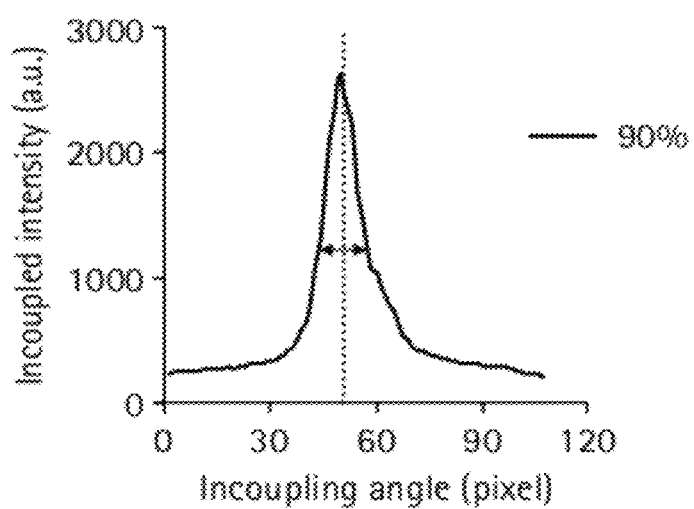
Figure 6C:
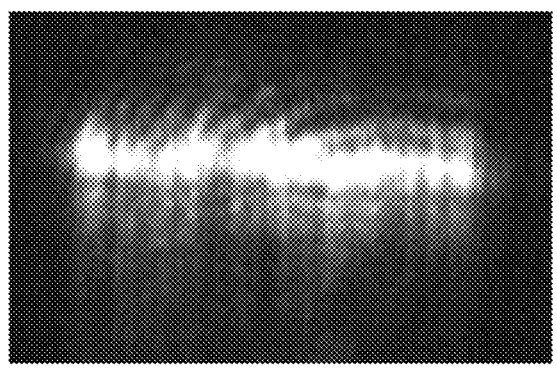

A number of different biosensor output parameters that can be used are illustrated in FIG. 6. For example, six parameters defining the kinetics of the stimulation-induced directional mass redistribution within the cells can be overall dynamics (i.e., shape), phases of the response (in this specific example, there are three main phases relating to the cell response: Positive-Directional Mass Redistribution (P-DMR) (FIG. 6A point C to D), net-zero Directional Mass Redistribution (net-zero DMR) (FIG. 6A point D to E) and Negative-Directional Mass Redistribution (N-DMR) (FIG. 6A point E to F to G)), kinetics, total duration time of each phase, total amplitudes of both P- and N-DMR phases, and transition time $\tau$ from the P- to N-DMR phase (FIG. 6A). Other biosensor output parameters can be obtained from a resonant peak (FIG. 6B). For example, peak position, intensity, peak shape and peak width at half maximum (PWHM) can be used (FIG. 6B). Biosensor output parameters can also be obtained from the resonant band image of a biosensor. The data was obtained using an arrayed angular interrogation system and illustrates 5 five additional features: band shape, position, intensity, distribution and width. All of these parameters can be used independently or together for any given application of any cell assays using biosensors as disclosed herein. The use of the parameters in any subset or combination can produce a signature for a given assay or given variation on a particular assay, such as a signature for a cell receptor assay, and then a specific signature for an EGF receptor based assay.

(1) Parameters Related to the Kinetics of Stimulation-Induced Directional Mass Redistribution There are a number of biosensor output parameters that are related to the kinetics of the stimulation-induced DMR. These parameters look at rates of change that occurs to biosensor data output as a stimulatory event to the cell occurs. A stimulatory event is any event that may change the state of the cell, such as the addition of a molecule to the culture medium, the removal of a molecule from the culture medium, a change in temperature or a change in pH, or the introduction of radiation to the cell, for example. A stimulatory event can produce a stimulatory effect which is any effect, such as a directional mass redistribution, on a cell that is produced by a stimulatory event. "The stimulatory event could be a compound, a chemical, a biochemical, a biological, a polymer. The biochemical or biological could a peptide, a synthetic peptide or naturally occurring peptide. For example, many different peptides act as signaling molecules, including the proinflammatory peptide bradykinin, the protease enzyme thrombin, and the blood pressure regulating peptide angiotensin. While these three proteins are distinct in their sequence and physiology, and act through different cell surface receptors, they share in a common class of cell surface receptors called G-protein coupled receptors (GPCRs). Other polypeptide ligands of GPCRs include vasopressin, oxytocin, somatostatin, neuropeptide Y, GnRH, leutinizing hormone, follicle stimulating hormone, parathyroid hormone, orexins, urotensin II, endorphins, enkephalins, and many others. GPCRs are a broad and diverse gene family that respond not only to peptide ligands but also small molecule neurotransmitters (acetylcholine, dopamine, serotonin and adrenaline), light, odorants, taste, lipids, nucleotides, and ions. The main signaling mechanism used by GPCRs is to interact with G-protein GTPase proteins coupled to downstream second messenger systems including intracellular calcium release and cAMP production. The intracellular signaling systems used by peptide GPCRs are similar to those used by all GPCRs, and are typically classified according to the G-protein they interact with and the second messenger system that is activated. For Gs-coupled GPCRs, activation of the G-protein Gs by receptor stimulates the downstream activation of adenylate cyclase and the production of cyclic AMP, while Gi-coupled receptors inhibit cAMP production. One of the key results of cAMP production is activation of protein kinase A. Gq-coupled receptors stimulate phospholipase C, releasing IP3 and diacylglycerol. IP3 binds to a receptor in the ER to cause the release of intracellular calcium, and the subsequent activation of protein kinase C, calmodulin-dependent pathways. In addition to these second messenger signaling systems for GPCRs, GPCR pathways exhibit crosstalk with other signaling pathways including tyrosine kinase growth factor receptors and map kinase pathways. Transactivation of either receptor tyrosine kinases like the EGF receptor or focal adhesion complexes can stimulate ras activation through the adaptor proteins Shc, Grb2 and Sos, and downstream Map kinases activating Erk1 and Erk2. Src kinases may also play an essential intermediary role in the activation of ras and map kinase pathways by GPCRs."

It is possible that some stimulatory events can occur but there is no change in the data output. This situation is still a stimulatory event because the conditions of the cell have changed in some way that could have caused a directional mass redistribution or a change in the cell or cell culture.

It is understood that a particular signature can be determined for any assay or any cell condition as disclosed herein. There are numerous "signatures" disclosed herein for many different assays, but for any assay performed herein, the "signature" of that assay can be determined. It is also possible that there can be more than one "signatures" for any given assay and each can be determined as described herein. After collecting the biosensor output data and looking at one or more parameters, or the signature for the given assay can be obtained. It may be necessary to perform multiple experiments to identify the optimal signature and it may be necessary to perform the experiments under different conditions to find the optimal signature, but this can be done. It is understood that any of the method disclosed herein can have the step of "identifying" or "determining" or "providing", for example, a signature added onto them.

(a) Overall Dynamics

One of the parameters that can be looked at is the overall dynamics of the data output. This overall dynamic parameter observes the complete kinetic picture of the data collection. One aspect of the overall dynamics that can be observed is a change in the shape of the curve produced by the data output over time. Thus the shape of the curve produced by the data output can either be changed or stay steady upon the occurrence of the stimulatory event. The direction of the changes indicates the overall mass distribution; for example, a positive-DMR(P-DMR) phase indicates the increased mass within the evanescent tail of the sensor; a net-zero DMR suggests that there is almost no net-change of mass within the evanescent tail of the sensor, whereas a negative-DMR indicates a net-deceased mass within the evanescent tail of the sensor. The overall dynamics of a stimulation-induced cell response obtained using the optical biosensors can consist of a single phase (either P-DMR or N-DMR or net-zero-DMR), or two phases (e.g., the two phases could be any combinations of these three phases), or three phases, or multiple phases (e.g., more one P-DMR can be occurred during the time course).

(b) Phases of the Response

Another parameter that can observed as a function of time are the phase changes that occur in the data output. A label free biosensor produces a data output that can be graphed which will produce a curve. This curve will have transition points, for example, where the data turns from an increasing state to a decreasing state or vice versa. These changes can be called phase transitions and the time at which they occur and the shape that they take can be used, for example, as a biosensor output parameter. For example, there can be a Positive-Directional Mass Redistribution (P-DMR), a net-zero Directional Mass Redistribution (net-zero DMR) or a Negative-Directional Mass Redistribution (N-DMR). The amplitude of the P-DMR, N-DMR, and the NZ-DMR can be measured as separate biosensor output parameters (See FIG. 6A and FIG. 7 for example).

(c) Kinetics

Another biosensor output parameter can be the kinetics of any of the aspects of data output. For example, the rate at the completion of the phase transitions. For example, how fast are the phase transitions completed or how long does it take to complete data output. Another example of the kinetics that can be measured would be the length of time for which an overall phase of the data output takes. Another example is the total duration of time of one or both of the P- and N-DMR phases. Another example is the rate or time in which it takes to acquire the total amplitudes of one or both of the P- and N-DMR phases. Another example can be the transition time τ from the P- to N-DMR phase (FIG. 6A, as well as other figures provide many examples of all of these types of kinetic parameters. The kinetics of both P-DMR and N-DMR events or phases can also be measured. For example, stimulation of human quiescent human epidermoid carcinoma A431 with epidermal growth factor (EGF) results in a dynamic response consisting of at least three phases, as shown in FIG. 6A and FIG. 7A. As evidenced in FIGS. 6A and 7, the higher the EGF concentration is, the greater are the amplitudes of both the P-DMR and the N-DMR signals, the faster are both the P-DMR and the N-DMR events, and the shorter is the transition time from the P-DMR to the N-DMR event. When the amplitudes of the P-DMR events showed a complicated relationship with the EGF concentrations, the amplitudes of the N-DMR signals were clearly saturable to EGF concentrations, resulting in an $EC_{50}$ of ~1.45 nM (See FIG. 7B). The transition time τ in seconds was found to decrease exponentially with the increasing concentration C of EGF (See FIG. 7C). In addition, the decay of the N-DMR signal can be fitted with non-linear regression. The one-phase decay constant K obtained was also saturable, resulting in a Kd of 5.76 nM (see FIG. 7D).

(2) Parameters Related to the Resonant Peak

Resonant peaks of a given guided mode are a type of data output that occurs by looking at, for example, the intensity of the light vs the angle of coupling of the light into the biosensor or the intensity of the light versus the wavelength of coupled light into the biosensor. The optical waveguide lightmode spectrum is a type of data output that occurs by looking at the intensity of the light vs the angle of coupling of the light into the biosensor in a way that uses a broad range of angles of light to illuminate the biosensor and monitors the intensity of incoupled intensity as a function of the angle. In this spectrum, multiple resonant peaks of multiple guided modes are co-occurred. Since the principal behind the resonant peaks and OWLS spectra is the same, one can use the resonant peak of a given guided mode or OWLS spectra of multiple guided modes interchangeably. In a biosensor, when either a particular wavelength of light occurs or when the light is produced such that it hits the biosensor at a particular angle, the light emitted from the light source becomes coupled into the biosensor and this coupling increases the signal that arises from the biosensor. This change in intensity as a function of coupling light angle or wavelength is called the resonant peak. (See FIG. 6B, for example). Distinct given modes of the sensor can give rise to similar resonant peaks with different characteristics. There are a number of different parameters defining the resonant peak or resonant spectrum of a given mode that can be used related to this peak to assess DMR or cellular effects. A subset of these are discussed below.

(a) Peak Position

When the data output is graphed the peak of the resonance peak occurs, for example, at either a particular wavelength of light or at a particular angle of incidence for the light coupling into the biosensor. The angle or wavelength that this occurs at, the position, can change due to the mass redistribution or cellular event(s) in response to a stimulatory event. For example, in the presence of a potential growth factor for a particular receptor, such as the EGF receptor, the position of the resonant peak for the cultured cells can either increase or decrease the angle of coupling or the wavelength of coupling which will result in a change in the central position of the resonant peak. It is understood that the position of the peak intensity can be measured, and is a good point to measure, the position of any point along the resonant peak can also be measured, such as the position at 75% peak intensity or 50% peak intensity or 25% peak intensity, or 66% peak intensity or 45% peak intensity, for example (all levels from 1-100% of peak intensity are considered disclosed). However, when one uses a point other than the peak intensity, there will always be a position before the peak intensity and a position after the peak intensity that will be at, for example, 45% peak intensity. Thus, for any intensity, other than peak intensity, there will always be two positions within the peak where that intensity will occur. The position of these non-peak intensities can be utilized as biosensor output parameters, but one simply needs to know if the position of the intensity is a pre-peak intensity or a post-peak intensity.

(b) Intensity

Just as the position of a particular intensity of a resonant peak can used as a biosensor output parameter, so to the amount of intensity itself can also be a biosensor output parameter. One particularly relevant intensity is the maximum intensity of the resonant peak of a given mode. This magnitude of the maximum intensity, just like the position, can change based on the presence of a stimulatory event that has a particular effect on the cell or cell culture and this change can be measured and used a signature. Just as with the resonant peak position, the resonant peak intensity can also be measured at any intensity or position within the peak. For example, one could use as a biosensor output parameter, an intensity that is 50% of maximum intensity or 30% of maximum intensity or 70% of maximum intensity or any percent between 1% and 100% of maximum intensity. Likewise, as with the position of the intensity, if an intensity other than the maximum intensity will be used, such as 45% maximum intensity, there will always be two positions within the resonant peak that have this intensity. Just as with the intensity position parameter, using a non-maximum intensity can be done, one just must account for whether the intensity is a pre-maximum intensity or a post-maximum intensity.

For example, the presence of both inhibitors and activators results in the decrease in the peak width at half maximum (PWHM) after culture when the original cell confluency is around 50% (at ~50% confluency, the cells on the sensor surface tend to lead to a maximum PWHM value); however, another biosensor output parameter, such as the total angular shift (i.e., the central position of the resonant peak) can be used to distinguish an inhibitors from an activators from a molecule having no effect at all. The PWHM is length of a line drawn between the points on a peak that are at half of the maximum intensity (height) of the peak, as exampled in FIG. 6B. The inhibitors, for example, of cell proliferation, tend to give rise to angular shift smaller than the shift for cells with no treatment at all, whereas the activators tend to give rise to a bigger angular shift, as compared to the sensors having cells without any treatment at all, when the cell densities on all sensors are essentially identical or approximately the same. The potency or ability of the compounds that either inhibit (as inhibitors) or stimulate (as activator) cell proliferation can be determined by their effect on the PWHM value, given that the concentration of all compounds are the same. A predetermined value of the PWHM changes can be used to filter out the inhibitors or activators, in combination with the changes of the central position of the resonant peak. Depending on the interrogation system used to detect the resonant peak of a given mode, the unit or value of the PWHM could be varied. For example, for an angular interrogation system, the unit can be degrees. The change in the PWHM of degrees could be 1 thousandths, 2 thousandths, 3 thousandths, 5 thousandths, 7 thousandths, or 10 thousandths, for example.

(c) Peak Shape

Another biosensor output parameter that can be used is the overall peak shape, or the shape of the peak between or at certain intensities. For example, the shape of the peak at the half maximal peak intensity, or any other intensity (such as 30%, 40%, 70%, or 88%, or any percent between 20 and 100%) can be used as a biosensor output parameter. The shape can be characterized by the area of the peak either below or above a particular intensity. For example, at the half maximal peak intensity there is a point that is pre-peak intensity and a point that is post-peak intensity. A line can be drawn between these two points and the area above this line within the resonant peak or the area below the line within the resonant peak can be determined and become a biosensor output parameter. It is understood that the integrated area of a given peak can also be used to analyze the effect of compounds acting on cells.

Another shape related biosensor output parameter can be the width of the resonant peak for a particular peak intensity. For example, at the width of the resonant peak at the half maximal peak intensity (HMPW) can be determined by measuring the size of the line between the pre-peak intensity point on the resonant peak that is 50% of peak intensity and the point on the line that is post-peak which is at 50% peak intensity. This measurement can then be used as a biosensor output parameter. It is understood that the width of the resonant peak can be determined in this way for any intensity between 20 and 100% of peak intensity. (Examples of this can be seen through out the figures, such as FIG. 6B).

(3) Parameters Related to the Resonant Band Image of a Biosensor

To date, most optical biosensors monitor the binding of target molecules to the probe molecules immobilized on the sensor surface, or cell attachment or cell viability on the sensor surface one at a time. For the binding event or cell attachment or cell viability on multiple biosensors, researchers generally monitor these events in a time-sequential manner. Therefore, direct comparison among different sensors can be a challenge. Furthermore, these detection systems whether it is wavelength or angular interrogation utilize a laser light of a small spot (~100-500 µm in diameter) to illuminate the sensor. The responses or resonant peaks represent an average of the cell responses from the illuminating area. For a 96 well biosensor microplate (e.g., Corning's Epic microplate), each RWG sensor is approximately 3×3 $mm^2$ and lies at the bottom of each well, whereas the sensor generally has a dimension of 1×1 $mm^2$ for a 384 well microplate format. Therefore, the responses obtained using the current sensor technology only represent a small portion of the sensor surface. Ideally, a detection system should not only allow one to simultaneously monitor the responses of live cells adherent on multiple biosensors, but also allow signal interrogation from relatively large area or multiple areas of each sensor.

Resonant bands through an imaging optical interrogation system (e.g., a CCD camera) are a type of data output that occurs by looking at, for example, the intensity of the reflected (i.e., outcoupled) light at the defined location across a single sensor versus the physical position. Reflected light is directly related to incoupled light. Alternatively, a resonant band can be collected through a scanning interrogation system in a way that uses a small laser spot to illuminate the sensor, and scan across the whole sensor in one-dimension or two-dimension, and collect the resonant peak of a given guided mode. The resonant peaks or the light intensities as a function of position within the sensors can be finally reconsisted to form a resonant band of the sensor. In a biosensor, when either a particular wavelength of light occurs or when the light is produced such that it hits the biosensor at a particular angle, the outcoupled light varies as a function of the refractive index changes at/near the sensor surface and this changes lead to the shift of the characteristics of the resonant band of each sensor collected by the imaging system. Furthermore, the un-even attachment of the cells across the entire sensor after cultured can be directly visualized using the resonant band (See the circled resonant band in FIG. 1, for example). In an ideal multi-well biosensor microplate, the location of each sensor is relative to normalize to other biosensors; i.e., the sensors are aligned through the center of each well across the row or the column in the microplate. Therefore, the resonant band images obtained can be used as an internal reference regarding to the cell attachment or cellular changes in response to the stimulation. Therefore, such resonant band of each sensor of a given mode provides additional parameters that can be used related to this band to assess DMR or cellular effects. A subset of these are discussed below.

(a) Band Shape

Another biosensor output parameter that can be used is the shape of the resonant band of each biosensor of a given mode. The shape is defined by the intensity distribution across a large area of each sensor. As shown in FIG. 1 and others therein, the shape can be used as an indicator of the homogeneity of cells attached or cell changes in response to stimulation across the large area (for example, as shown in FIG. 1, each resonant band represents responses across the entire sensor with a dimension of ~200 mm×3000 mm).

(b) Position

Similar to the position of the resonant peak of each sensor of a given mode, the position of each resonant band can be used as a biosensor output parameter. The intensity can be quantified using imaging software to generate the center position with maximum intensity of each band. Such position can be used to examine the cellular changes in response to stimulation or compound treatment.

(c) Intensity

Just as the position of the resonant band, the intensity of the outcoupled light collected using the imaging system can be used as a biosensor output parameter. The average intensity of the entire band or absolute intensity of each pixel in the imaging band can be used to examine the quality of the cell attachment and evaluate the cellular response.

(d) Distribution

The distribution of the outcoupled light with a defined angle or wavelength collected using the imaging system can be used as a biosensor output parameter. This parameter can be used to evaluate the surface properties of the sensor itself when no cells or probe molecules immobilized, and to examine the quality of cell attachment across the illuminated area of the sensor surface. Again, this parameter can also be used for examining the uniformity of compound effect on the cells when the cell density across the entire area is identical; or for examining the effect of the cell density on the compound-induced cellular responses when the cell density is distinct one region from others across the illuminated area.

(e) Width

Just like the PWHM of a resonant peak of a given mode, the width of the resonant band obtained using the imaging system can be used as a biosensor output parameter. This parameter shares almost identical features, thus the useful information content, to those of the PWHM value of a resonant peak, except that one can obtain multiple band widths at multiple regions of the illuminated area of the sensor, instead of only one PWHM that is available for a resonant peak. Similar to other parameters obtained by the resonant band images, the width can be used for the above mentioned applications.

All of these parameters can be used independently or together for any given application of any cell assays using biosensors as disclosed herein. The use of the parameters in any subset or combination can produce a signature for a given assay or given variation on a particular assay, such as a signature for a cell receptor assay, and then a specific signature for an EGF receptor based assay.

b) Cells and Cell Context Manipulation

Cells are the fundamental structural unit of biological systems. Thus, understanding cells is essential for understanding both sub-cellular phenomena such as cell biology, biochemistry, and molecular biology and multi-cellular phenomena such as physiology. By analyzing cells, biologists have learned many of the complex functional relationships among distinct target molecules. The target molecules could be any biological molecules, including DNA, RNA, lipid, protein, and carbohydrate, among others, and among assemblies of such molecules. Furthermore, biologists have learned the value of using cells to understand basic cell biology principles and to screen drug candidates for treating human disease and improving human health.

Cells may be analyzed, or used for an analysis, using optical biosensors. Cells to be assayed may be essentially any type of cell. Any type of cell can be assayed in any of the disclosed methods. Cells to be assayed can be either cells directly obtained from an organism or cells cultured in vitro. The cell having the target may be any cell from the germ line or somatic, totipotent or pluripotent, dividing or non-dividing, parenchyma or epithelium, immortalized or transformed, for example. To date, there are wide arrays of immortalized stable cell lines available. These stable cell lines are derived from many different organisms, tissues, and developmental stages. A sampling of this vast array is available from American Type Culture Collection and other cell repositories. Cells generally include any biological entity that is at least partially bounded by a membrane bilayer and is capable of replication and division into two or more entities, or is a descendant of such an entity.

Examples of cells may include eukaryotic cells, i.e., cells with a nucleus, including cells from animals, plants, fungi, yeast, and protozoans; anucleate or mutant derivatives or descendants thereof, such as reticulocytes and mature red blood cells, among others; enucleated derivatives thereof; and fusions between any the preceding. In addition, cells may include gametes, such as eggs, sperm, and the like. Cells also may include prokaryotic organisms, such as bacteria and archactacteria.

Suitable cells may be derived from any suitable organism, including any organism that is studied for research (such as basic, clinical, and biotechnology research, among others), drug design, drug discovery, and/or other economic, political, or humanitarian reasons. Exemplary organisms include mammals, such as apes, cats, cows, dogs, horses, humans, monkeys, mice, pigs, and sheep, among others. Exemplary organisms also include non-mammalian vertebrates, such as birds, reptiles, amphibians (e.g., frogs such as *Xenopus laevis*), and fish (e.g., kout, salmon, goldfish, and zebrafish), among others. Exemplary organisms also include nonmammalian invertebrates, such as species of *Drosophila* (e.g., *D. melanogaster* and *D. simulans*), nematodes (e.g., *C. elegans*), sea urchins (e.g., *Strongylocentrotus purpuratus*), and slime molds (e.g., *Dictyostelium discoideum*). Exemplary organisms also include single-celled eukaryotic organisms, such as yeast (e.g., *Saccharomyces cerevisiae, Schizosaccharomyces pombe, Pichia pastoris*, and *Candida albicans*) and protozoans (e.g., pathogenic and nonpathogenic protozoans). Exemplary organisms also include plants, such as *Arabidopsis thaliana*, rice, corn, potato, bean, loblolly pine, as well as nonvascular plants.

Suitable cells may be primary cells obtained directly from a wild-type, mutant, transgenic, chimeric zygote, morula, blastula, embryo, fetus, newborn, juvenile, adult, or other developmental stage of any organism. The primary cells may originate from distinct cell types, tissues, organs, or regions of the organism, or may be mixtures thereof. Examples include blood stem cells, B- and T-lymphocytes, red blood cells, neutrophils, eosinophils, mast cells, granulocytes, megakaryocytes, macrophages, adipose cells, glial cells, astrocytes, neuroblasts, neurons, skeletal myoblasts or myotubes, smooth muscle myoblasts, cardiac myoblasts, fibroblasts, osteoblasts, osteocytes, endocrine cells, exocrine cells, endothelial cells, keratinocytes, chondrocytes, cells derived from endoderm, mesoderm, or ectoderm, and/or extraembryonic derivatives, such as trophoblasts.

Suitable cells may be obtained from a tissue or tissues from any source. Tissue generally comprises any group of cells in temporary or stable spatial proximity in an organism, or a cultured explant thereof. This spatial proximity may occur naturally and/or artificially and may represent a native or normal state and/or an induced or diseased state, among others. Artificial proximity may include transplanted, implanted, and/or grafted tissue (including organ or tissue transplants, xenografts, allografts, and the like) and tissue moved within an individual organism, such as a skin graft, among others. Diseased tissue includes tissue that is abnormal due to a (1) genetic defect; (2) an environmental insult, such as a pollutant, a toxin, or radiation; (3) uncontrolled growth; (4) abnormal differentiation; (5) abnormal cell migration; (6) infection, such as with a virus, bacteria, protozoan, yeast, fungus, and/or parasite; or (7) any combination thereof.

An exemplary diseased tissue suitable for use in the invention is tumor material obtained surgically or from a fluid aspirate, for example, from a needle biopsy. Tissue may be any tissue from any wild-type, mutant, transgenic, or chimeric zygote, morula, blastula, embryo, fetus, newborn, juvenile, adolescent, or adult organism. Examples of suitable postnatal tissues include (1) muscle, including cardiac, smooth, and skeletal muscle; (2) neural tissue from the central or peripheral nervous system, such as spinal cord or brain; (3) other cardiac tissue; (4) kidney; (5) liver; (6) spleen; (7) any part of the digestive system, including esophagus, stomach, small and large intestines, and colon; (a) pancreas; (9) gall bladder; (10) circulatory system tissue, including heart, veins and arteries, and cells of the hematopoietic system; (11) immune tissue, such as thymus and lymph nodes; (12) adrenal glands; (13) bone; (14) cartilage; and (15) any epithelial tissue, such as mammary epithelium, among others. Tissue also includes natural and artificial combinations of any of the above.

Tissue may be at least partially or completely disaggregated into individual cells before use with optical biosensors or may be applied to the sensors whole or in sections.

Some applications of the invention are suited for clinical diagnosis using cells derived from a prenatal or postnatal human or other animal. Examples of prenatal cells include those obtained from amniotic fluid, a blastomere, chorionic villi, fetal blood, and other fetal tissue. Examples of postnatal cells include those obtained from a bone marrow aspirate' lymph, whole blood, blood serum, blood plasma, pleural effusion, skin biopsy, tumor biopsy, or a surgical procedure. Additional examples of postnatal cells include those obtained from other bodily fluids and/or secretions, such as urine, feces, saliva, mucus, phlegm, tears, perspiration, semen, spinal fluid, milk, sputum, and the like, or from tissue, as described above.

Rather than from primary cells and tissue, or cultured derivatives thereof, suitable cells may be obtained from established cell lines. These established lines may be produced by any suitable method, including viral, oncogenic, physical, chemical, mutagenic, spontaneous, and/or kansgenic transformation. In addition, cells may include characterized or uncharacterized derivatives of established cell lines that have been modified by any suitable method, such as genetic modification (e.g., by physical and/or chemical treatment, irradiation, transaction, infection, or injection) and/or epigenetic modification (e.g., by methylation or other molecular modification, kansposon function, chromosome imprinting, yeast mating type switching, and/or telomeric silencing).

The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands. Stem cells may be stem cells recently obtained from a donor, and in certain preferred embodiments, the stem cells are autologous stem cells. Stem cells may also be from an established stem cell line that is propagated in vitro. Suitable stem cells include embryonic stems and adult stem cells, whether totipotent, pluripotent, multipotent or of lesser developmental capacity. Stem cells are preferably derived from mammals, such as rodents (e.g. mouse or rat), primates (e.g. monkeys, chimpanzees or humans), pigs, and ruminants (e.g. cows, sheep and goats).

Generally each cell line has distinct characteristics based on its origin, genotype, method of immortalization, culture conditions, and environmental history. Thus, no single cell line is suitable for all experiments or compound screens. For example, the expression level of a particular target could be distinctly different from one type of cell to another type; in some cases, the signaling pathways through a particular target (e.g., EGFR) could significantly differ among different types of cells. Therefore, a modulator that generates effect through a particular target could lead to dramatically different cellular responses including mass redistribution are disclosed. For those reasons, a specific type of cells may be required to be re-engineered such that a particular target is controllably expressed or reduced or knockout, and in some cases, a particular signaling pathway is manipulated. There are many state-of-the-art technologies that can result in such re-engineered cells. For example, with the help of transfection reagents or other physical approaches, transfection of cells with the target gene or the target molecules can result in the increasing expression level of the specific target, whereas transfection of cells with an anti-target antibody, or antisense, anti-target gene oligonucleotides and their derivates, or peptide inhibitors, or interference RNA (RNAi) can lead to the suppression of the target molecules. In addition, there is need for new techniques for determination of cell signaling, or cellular responses dependent on cellular context. The dependence of cell signaling on the cellular context is perfectly exampled by receptor tyrosine kinase signaling. The biological outcome of signals generated at the cell surface in response to RTK stimulation is strongly dependent on cellular context. The same RTK will induce a totally different response when expressed in different cells or at different stages of differentiation of a particular cell lineage (see review in J. Schlessinger, "Cell signaling by receptor tyrosine kinases." Cell 2000,103,211-225). For instance, in early development, FGFR1 plays an important role in control of cell migration, a process crucial for mesodermal patterning and gastrulation. Stimulation of FGFR1 in fibroblasts on the other hand, leads to cell proliferation while stimulation of FGFR1 expressed in neuronal cells induces cell survival and differentiation. The most plausible explanation for these observations is that different cells express cell type-specific effector proteins and transcription factors that mediate the different responses. According to this view, RTKs and their signaling pathways are capable of feeding into multiple processes thus regulating the activity of different effector proteins and transcriptional factors in different cellular environments. A similar input can therefore generate a different output in a different cellular context. In other words, signaling cassettes that are activated by RTKs have evolved in order to relay information from the cell surface to the nucleus and other cellular compartments of the biological outcome of their activation.

The term "incubating" includes exposing cells to any condition. While "culturing" cells is often intended to that permit one or more cells to live and grow. Under certain conditions, incubating the cells under one or more conditions may actually kill one or more cells.

c) General Method Steps

A general method for performing the cell assays disclosed herein can be found in FIG. 8. In this general method, one can provide a label free optical biosensor (801). Then cells are directly be cultured on this biosensor (802) to a desired confluency. (From 1% confluent to 100% confluent and each percentage in between). Then a buffer solution can optionally be applied (803). Also a compound or compounds or composition to be tested can be applied to the cultured cells on the biosensor. This is a stimulant event. (804). Then using any of the biosensor output parameters described herein, the biosensor can be interrogated and the data collected so that the cell responses to the stimulant event (504) can be monitored.

Generally disclosed are methods for performing living cell-based assays using label free biosensors, such as, an optical label independent detection (LID) biosensor to monitor mass redistribution within living cells adherent on a surface of the optical LID biosensor. In general, there are a number of different steps that can occur within the disclosed methods. For example, the methods can comprise providing a label free optical biosensor, such as an optical LID biosensor. The methods generally also involve the culturing of cells on the biosensor as discussed herein. The culturing of the cells typically occurs in a cell medium that can cover the optical biosensor. In certain embodiments the cells can attach to surface of the biosensor, much as they would to a culture dish, for example. When the cells are cultured on the biosensor, they can be grown to any confluency as discussed herein, and then various assays can be performed on the cells. For example, the cells can be incubated with a test compound or set of test compounds or compositions, such as modulators, such as an agonist or antagonist of a receptor or an activator or repressor of a signal transduction pathway or potential modulators, agonists, antagonists, activators, or suppressors, to determine the effect of the compounds or compositions on the cells or on a particular target within the cells. A modulator is any molecule that either increases or decreases a particular event. An agonist is a molecule such as a compound or composition, which effects a receptor in way and that is related to the way the natural ligand effects the receptor. Typically this is to turn the receptor on or activate it. An antagonist is a molecule, such as a compound or composition, which effects a receptor in a way that causes the effect of the natural ligand to be reduced or eliminated. Typically an antagonist is an inhibitor or repressor of a receptor. It is understood that some classes of agonists can act in the absence of natural ligand or ligand analog, while others function in the presence of the ligand or ligand analog. For example, an antagonist could be a competitive inhibitor of the natural ligand or it could be a non-competitive inhibitor.

At any point, during the culturing of the cells, the cells can be assayed with the biosensor, wherein the biosensor is utilized, as designed, such as by providing light at a particular spectrum or at a particular angle. The output from the biosensor can be collected in a variety of ways including time dependent ways. For example, the step of interrogating the optical LID biosensor to obtain a time dependent optical response which indicates the mass redistribution within the living cells that enables one to monitor an agonist-induced GPCR activation within the living cells can be performed.

The step of applying a buffer solution at least once into the cell medium located on the surface of the optical LID biosensor solution can also be performed at any point during any of the methods. These buffers can be applied to stabilize the medium or the biosensor or cells. The buffer used generally is chosen for achieving optimal assay results based on the modulator-target interactions or stimulatory event-target interactions.

It is also understood that the methods can be used to screen for molecules that modulate (meaning either activate or suppress) a signal transduction pathway, modulate a particular cell surface receptor, such as a GPCR or an EGFR, within living cells.

It is also understood that in certain embodiments there can be incubation of more than one compound either in parallel or serially. For example, the biosensor-cell culture complex could be incubated with a known modulator, such as an agonist or antagonist, which produces a particular signature of a set of parameters, as discussed herein, and then another compound(s) or composition(s) could be incubated with the biosensor-cell-modulator mixture, and the effect of the compound on the modulator activity can be determined by looking for a change in the signature or in the output of the biosensor generally after interrogation. It is understood that all of the steps related to compounds or buffers can be done in increasing amounts to look at the effect of the concentration of the compositions or composition has on the biosensor output.

The methods can be performed with any biosensor as described herein, but a particular biosensor can be made into a self-referencing biosensor, which is a biosensor that is capable of not only collecting output data for the cell assay, but it can also collect control data for the data collected on the biosensor. This can be accomplished in a number of ways, including blocking a portion of the surface of the optical LID biosensor using a stamp that prevents attachment of the cultured cells and then placing the living cells in a cell medium to cover an unblocked portion of the surface of the optical LID biosensor so the living cells are able to attach to the unblocked portion of the surface of the optical LID biosensor; and then removing the stamp from the surface of the optical LID biosensor.

The variation on the self referencing method can be to remove the stamp after the first culture of cells has adhered to the biosensor and then placing a second cell medium to produce a second cell culture on the position of the biosensor that had been protected by the stamp. The second cells can be a different type of cell, or different stage of cell of the same type, etc. but they the second cell is culturing independent of the first. It is understood that this can be performed as many times as there are stamps. So for example, if there were four separate stamps that had been used on the biosensor, then if each of these removed serially and another cell population was provided to the sensor, one would culminate in 5 cultures of cells on the biosensor. Self referencing methods and systems allow for the reduction or eliminate unwanted sensitivity to ambient temperature, pressure fluctuations, and other environmental changes, and also provide confirmative information regarding to a particular target or type of cells.

It is understood that not only can the effect of multiple compounds on different types of cells be analyzed and the effect of a single compound on different types of cells be analyzed, but cells having different receptors, for example, and how they are modulated and compare to one another can also be analyzed. This can also be multiplexed by providing devices with multiple biosensors, such as a chamber having different biosensors.

It is also understood that, if for example, there are multiple different receptors on the different cells cultured on the biosensor, that molecules that are specific, such as specific antagonists could be provided, and then, for example, a compound or compounds could be tested. This type of method would provide information about which receptor antagonist, for example, was effected by which compound.

Disclosed are systems, comprising: an interrogation system; and an optical label independent detection (LID) biosensor, wherein said interrogation system emits an optical beam to said optical LID biosensor and receives an optical beam from said optical LID biosensor which enables said interrogation system to monitor mass redistribution within living cells located on a surface of the optical LID biosensor.

Also disclosed are systems, wherein said interrogation system is further capable of monitoring modulation of a cell, such as an agonist-induced G-protein coupled receptor (GPCR) activation, within the living cells after the following steps are performed: providing the optical LID biosensor; placing the living cells in a cell medium to cover the optical LID biosensor so the living cells are able to attach to the surface of the optical LID biosensor; applying a solution containing a compound into the cell medium located on the surface of the optical LID biosensor; and interrogating the optical LID biosensor to obtain a time dependent optical response which indicates the mass redistribution within the living cells that enables one to monitor the mass redistribution due to an agonist-induced GPCR activation within the living cells. Also disclosed are systems where applying a buffer solution at least once into the cell medium located on the surface of the optical LID biosensor solution.

It is understood that any of the method steps discussed herein can be applied to a system for performing the steps.

It is also understood that the optical output signals can be monitored in real time, but at distinct time intervals (for example, 1 sec, 3 sec, 5 sec, 10 sec, 15 sec, 30 sec, 60 sec, 2 min, 5 min, 10 min, 15 min, 30 min, 60 min, 2 hrs, 5 hrs, 10 hrs, 24 hrs).

It is also understood that only two points during the assay are measured before and after the compound addition to cells. The difference in terms of optical output parameters is analyzed.

d) Use of Biosensors for Cell Proliferation Assays

The characterizations of agents that either promote or retard cell proliferation are extremely important areas of cell biology and drug-discovery research. Several approaches have been used in the past. Trypan blue staining is a simple way to evaluate cell membrane integrity which is used as an indictor for cell survival, but the method requires counting dead cells under a microscope and cannot be adapted for high-throughput screening. Many cell proliferation assays estimate the number of cells either by incorporating 3H-thymidine or 5-bromo-2'-deoxyuridine (BrdU, a thymidine analog) into cells during proliferation (i.e., cell division), or by measuring total nucleic acid or protein content of lysed cells. Incorporation of 5-bromo-2'-deoxyuridine into newly synthesized DNA permits indirect detection of rapidly proliferating cells with fluorescently labeled anti-BrdU antibodies or certain nucleic acid stains (such as Hoechst 33342, TO-PRO-3 and LDS 751), thereby facilitating the identification of cells that have progressed through the S-phase of the cell cycle during the BrdU labeling period. Another one of the most popular assays is MTT cell proliferation assay. The colorimetric MTT assay is based on the conversion of the yellow tetrazolium salt (MTT) to insoluble purple formazan crystals due to the reduction by cellular mitochondrial dehydrogenases which only function in viable and metabolically active cells. After incubation of the cells with the MTT reagent for approximately 2 to 4 hours, a detergent solution is added to lyse the cells and solubilize the colored formazan crystals. The samples are read at a wavelength of 570 nm using a plate reader. The amount of color produced is directly proportional to the number of viable cells. Expansion in the number of viable cells resulted in an increase in the activity of the mitochondrial dehydrogenases, which leads to the increase in the amount of formazan dye formed.

Previous types of assays are time-consuming because of the requirement of lengthy incubation steps. For example, many conventional BrdU-based protocols require DNA denaturation in order for the BrdU epitope to become accessible to the anti-BrdU antibody. The DNA denaturation is typically accomplished with heat (>90° C.) or acid (2-4 M HCl). Such harsh treatments often make it difficult to perform multiparameter analysis because other cellular structures and antigens are not well preserved during these treatments. In addition, these conventional assays may be useful for assaying certain cell types; and different types of cells require different incubation protocols in order to achieve optimal assay results.

e) Characteristics for High Throughput Screening

Disclosed are methods that are suitable for high throughput screening of compounds that modulate or effect one or more signaling pathways in a cell or cell proliferation or cell death. These high throughput methods are based on the understanding that the biosensor output data can be assessed using a number of different parameters, as discussed herein. And that particular cells or particular receptors within cells or particular cell events such as death or proliferation or modulation of a signaling pathway can have a particular signature, as discussed herein. This signature can be made up of one or more biosensor output parameters as discussed herein. Importantly for high throughput methods, it is important that the there be a time point during the method where the collection of the biosensor output parameter data will be diagnostic of the state of the cell, i.e., a signaling pathway was activated or deactivated or the cell has dies or the cell is proliferating. This point can be where there is a combination of biosensor output parameters that are used to define the signature.

The high throughput methods can be used in devices with, for example, devices that have many biosensors, such up to 49 wells, or 96 wells or more. It is also understood that methods that can have a biosensor output parameter data collected within 1 hour, 30 min, 12 minutes, 11 minutes, 10 minutes, 9 minutes, 8 minutes, 7 minutes, 6 minutes, 5 minutes, 4 minutes, 3 minutes, 2 minutes, 1 minute, 59 seconds or at each second down to 1 second of a stimulatory event for the cell culture on the biosensor. It is also preferable that all of the collections for all of the biosensors, for example, complete plate of sensors, are completed in these times as well, but it is understood that this is not required.

Beside the characteristics associated with data collection duration and the numbers of samples examined in parallel, the data analysis and integrated presentations of the results that result in using the methods and systems disclosed herein can be, for example, resonant band images and predetermined time points which can be collected and presented in site.

(1) Cell Confluency

For the methods, and in particular for high throughput screening, one of the critical parameters of the methods disclosed herein is the number of starting cells used. The number of starting cells should be in a critical range such that the resulted density of cells on the waveguide substrate under normal culture condition can allow one to examine a change in the number of cells, both an increase as well as a decrease. It is understood that the greater the cell density, the more of an output signal that will arise from the biosensor, because of the fact that the more cells that are on the plate, the more DMR events that are being measured at any given time, such as after a stimulatory event. Thus the number of cells can change for example the characteristics of the resonant peak (e.g., intensity, PWHM, shape and/or position), and/or the features of the resonant band image (e.g., band shape, width, intensity, distribution, and/or position), and/or the amplitudes of the DMR event(s) (e.g., the P-DMR and/or the N-DMR). For example, the confluency can be 30-100%, 30-70%, 40-60%, 45% to 55% or about 50%, however, the confluency can be any percent between 30 and 100%, such as 38, or 57, or 63, or 88, or 75, or 95 or 99%. For different applications, the preferred confluency could be varied in order to achieve optimal performance. For example, for cell proliferation assays, in general, a preferred confluency is about 50%, but this can be slightly different for different cell types or different assays. Under these conditions, the PWHM is around maximal for cells cultured under normal conditions, so that modulators that interfere with cell proliferation can be evaluated in combination with the angular/wavelength shift or resonant peak/band position at the same time, no matter whether the modulators are promoters or inhibitors for cell profileration. Here both modulators result in a decrease in PWHM, but the promoters increase the angular shift while the inhibitors decrease the angular shift, compared to the cells without any treatment. For receptor assays or other applications relating to cell signaling and network interactions, the confluency of cells could vary from 30% to ~99%, depending on the cell events to be monitored. For example, for cell apoptosis studies the cell confluency could be in the range of ~10% to ~99%. For GPCR screens or EGFR screens, the cell confluency is preferably to be in the range of 50% to ~99%.

(a) Interfere with Cell Proliferation

The present methods allow one to detect compounds that affect cell proliferation in a short time, such as within 60 seconds, 50 seconds, 40 seconds, 30 seconds, 20 seconds, 10 seconds or at each second down to 1 second for a complete plate of sensors. In one embodiment, disclosed are methods for measuring the effect of compounds on cell proliferation, comprising: (a) providing a first and second optical-based label free biosensor; (b) placing a cell of a given seeding numbers in a medium on to the first said sensor, such that after an optimal culturing under cell growth condition the cells attached reach an optimal confluency; (c) placing the same cell of the same seeding numbers in said medium in the presence of a compound at a given concentration, (d) Culturing the cells under the same condition until the cell density of the said first sensor reaches the optimal density; (e) collecting the optical output parameters using an optical interrogation system. The optimal density is preferably between 40%-70%; most preferably 45%-55%. The optical interrogation system is preferably a parallel interrogation system or a scanning interrogation system. Disclosed herein are compounds, either inhibitors or activators modify the proliferation rate of a given type of cells, resulting in different number of cells attached onto the sensor substrate. The difference in density of attached cells gives rise to different optical waveguide lightmode spectra. Based on two parameters, angular shift and the PWMH, one can distinguish inhibitors versus activators.

f) Use of Biosensors for Cell Toxicity Screening

Drug discovery has become an industrialized process in which vast libraries of compounds are screened for activity against a chosen target. The wealth of active compounds that emerge from these primary screens has created a bottleneck in drug development. First-round hits often do not meet the safety and efficacy criteria required for human therapeutics, so sequential rounds of optimization are required before a product can be administered to humans. Optimization requires assays that test Absorption, Distribution, Metabolism, Elimination (Excretion), and Toxicity (ADME/Tox). ADME/Tox screening, representing a $3 billion market today, in the drug discovery and development setting is taking center stage given the large fraction of lead compound and drug failures associated with toxicity properties. Thirty percent of the total new drug attrition in the developmental pipeline is attributed to toxicity profiles and side effects. ADME/Tox screening could have prevented deaths caused by several drugs brought to the market or clinical practice (Zechnich, A. D. et al. (1994) West. J. Med. 160, 321-5). This surprising toxicity provides an excellent case study in light of the number of safe antihistamines currently on the market and the growing interest among pharmaceutical scientists in early ADME/Tox screening. Given the large fraction of lead compound and drug failures associated with toxicity properties, ADME/Tox screening is taking center stage in the drug discovery and development setting. The presumption that chemical libraries contain compounds with a spectrum of positive and negative effects forms the foundation of ADME/Tox screening. Beneficial features of a drug candidate include high specificity, low toxicity, good oral absorption and half-life, among others. The goal of early high-throughput ADME/Tox screening is to distinguish between "good" and "bad" compounds, in terms of toxicity, early in the discovery process. The identification of problems early in drug screening represents the single largest cost-saving opportunity in the pharmaceutical industry at the present time.

ADME/Tox screening is term that is generally used to describe the ensemble of those tests that are used to characterize a compound's properties with respect to absorption by the intestine, distribution to the organism, metabolism by the liver, excretion by the kidney, and toxicity profiles. Traditionally, deployment of ADME/Tox approaches in drug development has occurred in the latter stages of drug development—essentially late in the process subsequent to the initial phases of discovery of "hit compounds." Such a set-up was feasible when the number of drug discovery targets was few and the numbers of high-throughput screening assay points were relatively low across the pharmaceutical enterprise. With the changing paradigm in the drug discovery space, the number of drug targets is expanding and so is the volume of assay points performed in high-throughput screens. Therefore, it is imperative for the industry to quickly and efficiently triage, or identify, "potential hits," which might fail ADME and toxicity screening. In this manner, ADME/Tox screening needs to be performed earlier in the process of drug discovery and development, e.g., primary (high-throughput screening) and secondary screening. Furthermore, an integrated approach for predicting drug adsorption, toxicity and physiological effects would greatly benefit drug discovery and development processes.

(1) Real-Time Monitoring Compound Adsorption, Distribution and Toxicity

ADME/Tox screening includes testing a compound's properties with respect to absorption by the intestine, distribution to the organism, metabolism by the liver, excretion by the kidney, and toxicity profiles. Information relating to compound adsorption and toxicity during conventional HTS screening is generally discarded or missed; in addition, the effect due to compound adsorption and toxicity complicates data analysis. The increasing use of high content screening technology starts bridging toxicity screening with functional screening.

One aspect of the disclosed compositions, methods, and techniques is to eliminate the exiting gap between ADME/Tox screening and functional screening using cell-based assays in combination with label free optical-sensors.

In one embodiment, disclosed are methods for monitoring the compound adsorption and toxicity in real time, comprising: (a) providing an optical-based label free biosensor; (b) placing a cell in a medium, wherein the cell attaches onto the surface of the biosensor; (c) applying a solution containing a compound into the cell medium; (d) and monitoring the response of the cells cultured on the biosensor. The disclosed methods can also be characterized by (c) Optionally applying a buffer solution at least once into the cell medium. Furthermore, the disclosed methods can also incorporate more than one biosensor output parameter as discussed herein in the analysis. In fact, methods utilizing at least 1, 2, 3, 4, 5, 6, 7, 8, 9, 10, 11, 12, 13, 14, or 15, or more biosensor output parameters can be performed, and in certain embodiments it may be necessary to utilize more than one parameter to accurately obtain a signature for the assay or cell condition, for example. Also, in certain embodiments, the biosensor data output parameter(s) used for the signature can occur in less than 1 hour, 50 minutes, 40 minutes, 25 minutes, 10 minutes, 9 minutes, 8 minutes, 7 minutes, 6 minutes, 5 minutes, 4 minutes, 3 minutes, 2 minutes, 1 minute, 59 seconds or at each second down to 1 second after a stimulatory event or biosensor data output collection.

g) Use of Biosensors for Monitoring Cell Activities

Disclosed are compositions, methods, and techniques, related to the field of label free optical biosensors including waveguide grating-based biosensors. The compositions, methods, and techniques disclosed also relate to the field of cell-based assays. Because of the small penetration depth and the nature of the evanescent wave of the sensors that can be used, only the stimulation-induced DMR within the adlayer of cells that occurs in the vicinity of the sensors surface leads to a change in effective refractive index, which, in turn, results in angle shift of the reflected light from the sensor. The angular shift can be measured to obtain the kinetics of the DMR response signal. In addition, because of that, distinct cellular responses would contribute differently to the overall mass redistribution signals. For example, cell detachment from the extracellular matrices occurs at/near the sensor surface, and therefore can lead to significantly greater responses than those occurring inside the cells. Disclosed are methods that utilize optical biosensors to detect cell activities and compound-/stimulus-induced cellular changes based on the mass redistribution within the sensing volume of the sensors. For example, the disclosed compositions, methods, and techniques, relate to the use and the methods of use of optical-based biosensors for monitoring the binding of ligands to receptor tyrosine kinases (RTKs) and the sequential signaling events including internalization of signals, movement of molecules or assemblies in cells in real time, and/or cytoskeleton re-arrangement and cell morphological changes. Disclosed are methods for screening compounds or modulators that can interfere with one of these signaling events in living cells.

The present invention uses optical-based biosensors including waveguide based biosensors to monitor or investigate the binding of ligands to receptor tyrosine kinases (RTKs), a family of cell surface receptor, and several sequential signaling events in living cells. Disclosed are methods for screening compounds or modulators that could potentially interfere with these signaling events, e.g., binding, sequential phyosphorylation, internalization/cytoskeleton rearrangement and cell deadhension. In another embodiment, disclosed are methods to confirm the physiological or pharmacological effect of a compound against a specific receptor in living cells.

Disclosed are real time and label free functional receptor tyrosine kinase cell-based assays for compound screening and profiling. The disclosed methods allow one to study the kinetics of three major events in the receptor signaling pathway simultaneously: ligand binding, phosphorylation, and internalization/cytoskeleton rearrangement. This method according to the present invention also can be used to screen or classify compounds that can interfere with these signaling events. In again another embodiment, disclosed are methods to screen modulators for multiple targets in the signaling pathways that interfere with the DMR signal measured based on their unique characteristics, as defined by the optical output parameters.

Computational models of the EGF receptor system have been very useful in understanding complex interactions between different parts of the receptor pathway. However, there is only limited experimental data available for direct measurements of the kinetics of these signaling and trafficking in cells. Lacking the direct measurement of kinetics of signaling events limits the validation of these models. Therefore, methods and technologies that can simultaneously study the kinetics of cell signaling events are needed to gain further understanding the EGFR signaling.

(1) Mass Redistribution Monitoring

Disclosed herein, the adsorption, distribution and toxicity of a compound to a certain confluent cell layer near the cell-sensor interface can be monitored in real time. Because of the intrinsic limited-penetration sensing property (50-500 nM) (i.e., sensing volume) of optical-based biosensors, a mass redistribution that occurs within the volume where the sensor can sense results in a response change that is observable as an angular or spectral change in the reflected beam. This sensor response may be recorded as a function of time as well as solution composition changes. In this manner, the kinetics of any stimulatory event or effect caused by a stimulatory event that leads to a mass redistribution within the sensing volume can be analyzed. It should be understood that the confluency of cells to be assayed is important for high sensitivity detection. The higher the sensitivity required the more important the confluency of the cells allows for optimal detection as described here. The confluency of cells for mass redistribution monitoring induced by stimulatory event is preferably within the range of 30-100%. Alternatively it may be at 70-99%. Disclosed methods for distinct applications (cell proliferation, compound toxicity, cell apoptosis, compound adsorption and metabolism, cell signaling pathway activation, cell morphological changes, cell deadhension and movement, receptor and target (molecules or molecular assemblies) activation and movement, etc) may require distinct cell confluency (i.e., cell density) in order to achieve optimal assay results. Again, different types of cells as well as different target/signaling pathway activations might require different cell confluency for optimal cellular responses and functions. It should be understood that such confluency is not intent to limit the assay protocols or methods.

h) Cell Components and Biosensors

Biological cells, as shown in schematic drawing in FIG. 9, are complex structures with components ranging in size from nanometers to tens of microns. The cell, such as 1008 as shown in FIG. 10, typically has a cytoplasm (typical range 5-30 μM) that contains numerous organelles. Typically, the largest organelle is the nucleus, whose size can range between 3 and 10 μm. The nucleus contains DNA, RNA, proteins, and nucleic acid-protein complexes, such as DNA-protein or RNA-protein complexes. An important DNA-protein complex is chromatin. Mitochondria are small organelles comprised of a series of folded membranes with sizes typically ranging from 0.5-1.5 μm. Other cell components include endoplasmic reticulum (ER) (typically 0.2-1 μm), lysosomes (typically 0.2-0.5 μm), peroxisomes (typically 0.2-0.5 μm), endosomes (typically ~100 nm), and gogli, for example. Living cells, such as 1008, are highly dynamic and most organelles travel extensively within cells. For example, microtubules can transport organelles over long distances. A stimulus can result in the submicron movement of densely packed organelles in the very periphery of a sensor surface, such as 1010, on which the cells, such as 1008, are cultured; and such movement leads to mass redistribution, such as 1006, within the cell, such as 1008. The mass redistribution, such as 1006, can be detected by an optical biosensor, such as 1014; the signal relating to mass redistribution, such as 1006, is referred to as a directional mass redistribution (DMR) signal. Due to the limited range (tens to hundreds of nanometers) of the electromagnetic field propagating in the biosensors, such as the optical LID sensor 1014, that can extend into the surrounding media (e.g, adherent cell 1008) as an evanescent electromagnetic field, in certain situations, only a fraction of the mass redistribution, such as in 1006, can be detected because the penetration depth is insufficient to penetrate all the way through the cell or cells, if in cell layers, for example. The distance the electromagnetic field can extend is referred to as the penetration depth or sensing volume. In certain situations only the lower portion of the adherent cells that are within a certain distance to the biosensor surface, such as 1010, can be detected.

Cellular trafficking can occur, for example, when secretory organelles occupy their docking site beneath the plasma membrane, and if endocytic vesicles at the plasma membrane reach their processing stations in the cytosol. In either direction, organelles must typically penetrate the so-called actin cortex beneath the plasma membrane, a dense meshwork of actin filaments that is up to a few hundred nanometers thick. To the extent that actin filaments constantly assemble and disassemble, the meshwork is dynamic and permeable to organelles. Control mechanisms regulating the assembly and disassembly would also regulate the permeability of the actin cortex.

Exocytic vesicles can insert receptors into the plasma membrane and release ligands into the extracellular space. Endocytic vesicles carry receptors with bound ligand to internal processing stations. Caveolae are plasma-membrane-associated vesicles with a presumed role in cell signaling. Lipid rafts are thought to populate the plasma membrane as small floating islands in which select membrane proteins meet in private to exchange signals. Finally, there is the universe of membrane receptors, as disclosed herein. These can be embedded in large molecular complexes that continually recruit and release downstream effector molecules.

Transport of cellular components or extracellular stimuli not only occurs at the plasma membrane, but also occurs through signaling pathways within the cell and within multiple intracellular compartments and organelles. These events include (1) protein target or substrate recruitment to the nucleus, to the membrane, to the cytosol, throughout recycling pathways, to or from other organelles, uptake from extracellular space (ligand binding, gene transfection, infection and protein delivery); (2) redistribution of newly synthesized intracellular components within various functional compartments at defined microenvironments and with mediated release locations. These cellular events can lead to directional mass redistributions at certain times during signaling cycles.

(3). Multiple Penetration Depths for Cell Monitoring

Most or all of cell compartments are highly dynamic, and do their jobs in milliseconds to minutes and sometimes disperse soon thereafter. To observe signaling events mediated by single organelles and signaling complexes, traditionally in vivo methods are required to image single organelles, to detect molecules in small numbers and to report their function at high resolution in time and space. Fluorescence microscopy is a natural choice so far as some organelles may be stained specifically with dyes, and more and more proteins have been conjugated with fluorescent proteins such as green fluorescent protein (GFP) without impairing their function. However, most plasma membrane events involve interactions with cytosolic proteins that have been recruited to the plasma membrane transiently. Because even confocal microscopy looks into cells to a depth of nearly half a micron when focused on the plasma membrane, these and more conventional fluorescence microscopes show strong 'background' fluorescence from the cytosol that obscures the weaker fluorescence from small structures or molecular assemblies near the plasma membrane.

Upon stimulation, live cells can undergo a great number of cellular events, including but not limited to, ligand/compound binding to the receptor or intracellular targets, movements and translocation of cellular components, interaction of cellular signaling molecules, altered activities and even movement of cellular organelles or molecular assemblies, second messenger generation, cytoskeleton rearrangement and even dramatically cell morphological changes. For example, GPCRs participate in a wide array of cell signaling pathways. Ligand binding initiates a series of intracellular and cellular signaling events, including receptor conformational changes, receptor oligomerization, G protein activation (GDP-GTP exchanges on $G_\alpha$ subunit, $G_\alpha$ and $G_{\beta\gamma}$ disassociation, G protein decoupling from the receptor, generation of $G_\alpha$- and $G_{\beta\gamma}$-signaling complexes), and downstream signaling activation that leads to second messenger generation ($Ca^{2+}$ mobilization, inositoltriphosphate generation, and/or intracellular cAMP level modulation) and ultimately results in changes of specific gene expression. Ligand-mediated GPCR activation also leads to the desensitization of GPCRs from the cell surface and trafficking of many intracellular proteins, as well as changes in phenotypes, morphology and physical properties of the target cells. These changes could be static, long-lasting or dynamic (e.g., cycling or oscillation). Distinct signaling events exhibit significantly different kinetics ranging from milliseconds (e.g., GPCR conformational changes) to tens of seconds (e.g., $Ca^{2+}$ flux) to even tens of minutes (e.g., gene expression, or morphological changes). Although their characteristics (e.g., kinetics) are distinct, these events can lead to mass redistribution. Furthermore, the optical output parameters obtained using optical biosensors generally represent the overall average of responses due to a great number of cellular events, and distinct cellular events result in different contribution to the overall output parameters. The dependence of the overall DMR responses of the cell on the penetration depth would be extremely useful indicator where and when a DMR signal occurs.

Figure 11:
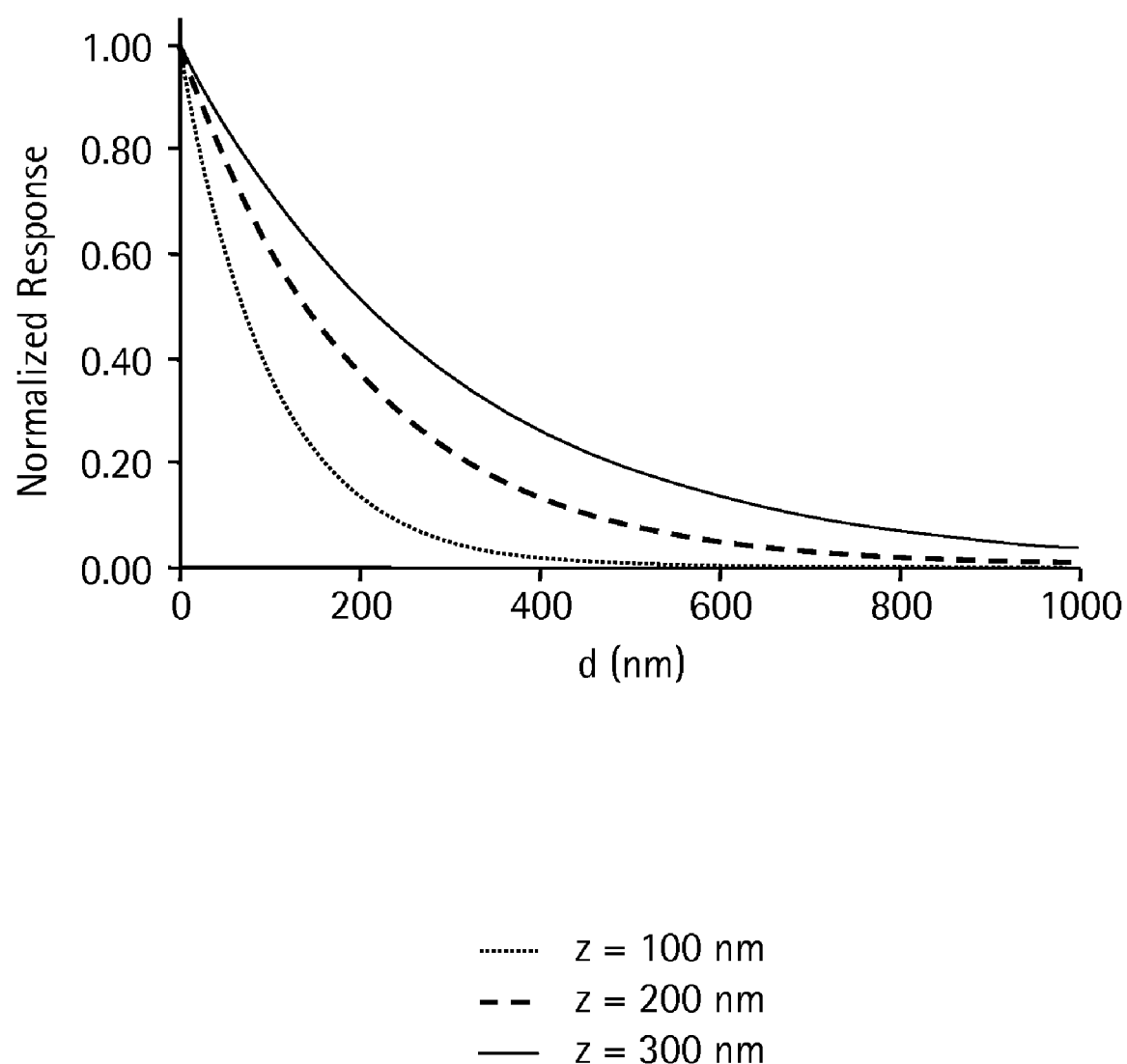
FIG. 11 shows the evanescent field (i.e, relative response) as a function of distance of a biological target away from the sensor surface for three types of sensors which have three distinct penetration depths: 100, 200, and 300 nm, respectively. This demonstrates the importance of variable penetration depths for cell sensing, especially for probing movements or a DMR event inside the cells.

As mentioned above, optical biosensors, depending on sensor structure and properties, give rise to a limited penetration depths into the cover medium (typically 50-500 nm nm), and can only detect the bottom part of tall cells (diameter of ~10 microns) or bacteria (diameter of ~1 micron). Therefore, the measured quantity is mainly related to the contact area between the organism and the surface, and near plasma membrane area, and the morphological changes near the sensor surface. In order to probe the movement or activities of different compartments or organelles inside cells which are far away from the plasma membranes, or refractive index of the whole organism, one need extend the penetration depth to reach these changes. FIG. 11 shows the behavior of evanescent wave of the sensor that depends on the penetration depth. This highlights the importance of penetration depth on cell monitoring. Since the optical output signals or parameters are an integrated and representative readout of stimulation-induced cell responses, multiple events such as receptor endocytosis or target complex movement or cell morphorological changes or cell deadhesion or movement could make distinct contributions to the overall responses obtained using optical biosensors. These events could occur at different locations relating to the sensor surface. Therefore, by using multiple penetration depths for monitoring the cell responses induced by same stimulatory event, the contributions of each event to the overall response and thus the mechanism of cell responses can be understood.

Disclosed are methods that can be used to monitor the cellular DMR signals in response to stimulation. In one embodiment, the methods involve the different modes of the sensors to measure the overall DMR signal of a particular type of cells in response to a specific stimulation. Different given modes of the sensors result in distinct penetration depths with altered sensitivity (e.g., $TM_0$ mode tends to give rise to longer penetration depth, such as 120 nm for a given sensor, than $TE_0$ mode does, such as ~90 nm for the same sensor. In another embodiment, disclosed methods can utilize at least two biosensors with different waveguide and grating structure and properties that result in different penetration depths for a given mode to measure the overall DMR signals of cells. In another embodiment, disclosed methods can use both conventional symmetry and reverse symmetry waveguide grating biosensors to measure the overall DRM signals of cells. The sensitivity of the trafficking signals or directional mass redistribution (DMR) signals to the penetration depth can be used as a signature for identifying a particular cellular trafficking event. The present methods that involve the modification of the biosensor configuration and structure, or "tuning" the penetration depths of a particular waveguide sensor, provides useful means to monitor or detect a particular cellular trafficking event with high sensitivity and intracellular compartment specificity. Particularly the use of multiple sensors with different penetration depths can be used to depict the signature of each cellular DMR or trafficking event. For a particular trafficking or DMR event, the present invention allows one to measure or detect the event with higher spatial resolution in Z-axis and higher sensitivity.

(4). Multiplexed Cell Assays Using Optical Biosensors

Standard screening campaigns, assaying a single target at a time, have been successful for identifying potent drug candidates. However, very little information about compound selectivity is generated. Currently, selectivity studies are conducted downstream in the drug discovery process; discarding compounds at this stage because of adverse binding makes the drug discovery process both expensive and time consuming. Multi-target screens that examine the activity of compounds against multiple targets in parallel are necessary to efficiently address compound selectivity early in the drug discovery process. Given these considerations, together with the increasing pace of target identification and expansion of compound libraries, novel technologies that are amenable to multi-target screening are needed.

Disclosed are methods that can be used for multi-target and multi-cell screening. In one embodiment, the present methods utilize the integrated optical output parameters as a means for screening compounds against multiple classes of targets or multiple family members of same class targets. For example, the activation of Ras/MAPK pathway in human A431 cells through EGFR mediated by EGF leads to a unique DMR signature; multiple classes of targets including EGFR, Src kinase, MEK1/2, dynamine, and actin filaments play distinct roles in the overall DMR signature. Again, in another example, in A431 cells, the activation of Ras/MAPK pathways can be mediated through several GPCR agonist-induced EGFR transactivation, and result in similar DMR signature as EGF-induced response; thus multiple family members of GPCR class targets can be screened and examined.

In another embodiment, the present invention discloses a method that sequentially cultures at least two types of cells onto distinct regions of a single sensor, which can be used for multiplexed cell assays using optical biosensors. Cells can be distinct types of cells, or physiological related, or disease related, or pathological related. Cells can also be originated from a same type of cells, one being unmodified, and one being genetically or the like re-engineered, such as a knockout or suppressed or over-expressed a particular target of interest. For example, Chinese hamster ovary (CHO) cells and their re-engineered CHO cells can be used. As shown in FIG. 12, a biosensor (1201) can be provided, and then a portion of this biosensor can be physically blocked (1202) so that even if cells are placed on the biosensor, the cells will not culture on this portion of the biosensor. One can then place a cell medium that has a cell type A and allow these to grow on the unblock region (1203). Then the blocked region of the biosensor can be unblocked and a second medium of cells of, for example, cell type B can applied such that cell type B becomes cultured on the region that had been blocked (805). A solution can then be provided that contains a molecule capable of giving a stimulatory event (1206). The biosensor can then be operated such that data from the two regions, the initial unblocked region and the region that had been blocked, can be collected and compared. The blocking can be achieved by placing a rubber stamp to cover a portion of the sensor, or by placing a cover plate having a given number of posts or columns. The end of each post or column can consist of an end made of soft materials such as rubber such that when the end of the column contacts with the part of the sensor surface without damage or deterioration of the sensor properties. The numbers and locations of the posts or columns fit with the given format of a sensor microplate. Alternatively, the blocking can be achieved by placing a device into the sensor microplate such that each sensor can be divided into at least two compartments. For example, the device can be a cover plate having a given number of microcolumns; in the end of each column (or the whole column) there can be a thin (typically 1 mm) wall made of flexible materials such as polymer. Once the column is placed into each well, the bottom of the microcolumn contacts with the center region of a sensor, and both sides contact with the inner wall of each well. The cover plate preferably contains a given numbers of fluid channels; each channel is associated with each microcolumn or the part of the microcolumn.

In again another embodiment, disclosed are methods that utilize physically separated multiple biosensors, and each biosensor can be used to host one type of cell. After initial cell attachment, a common culture medium can be applied to the chamber that contains the multiple biosensors. As shown in FIGS. 13 and 14, the method provides a modification of the disclosed methods related to the fact that the biosensor is located in a specific spot of a chamber, such as a well of microtiter plate. If a device is utilized that contains multiple well microplate having multiple compartments within each well and each compartment has a biosensor, then different types of cells can be placed in each of the different chambers, allowing for analysis of a different cell or set of conditions, for each well or biosensor (1302). Then optionally a common medium can be placed on each of the well to cover all biosensors or a different medium for each compartment can be applied with any combination between the two being disclosed (1303). The solution 1303, can contain a marker, such as a molecule that can create a stimulatory event, or a secondary solution can be applied containing one or more molecules for the stimulatory event (1304). The biosensor(s) can then be monitored and interrogated and the results from each compartment or sensor can be collected and compared (1305). In a particular embodiment, the present invention presents a unique type of biosensor microplate, as shown as an example in FIG. 14, a optical biosensor-embedded multi-compartment and multi-well microplate which each well contains four compartments, each compartment can have one waveguide grating substrate embedded. Each compartment can be used to host a single type of cells. Four compartments can be separated by inner walls, the height of the inner walls (preferably between 100 microns and 2 millimeters) is typically much lower than those of each well (which is the typical height of any given microplate), such that each well having four compartments can be used to examine simultaneously the effect of one drug candidate on the multiple targets or multiple types of cells. The compartments within a well can be separated by a physical barrier such that when a cell medium solution is applied to one compartment, and stays in the said compartment without cross-contamination with the adjacent compartments. It should be understood that the compartment could be 2, 3, 4, 5, 6 and more. Each well having a mutlicompartment can be separated by a higher physical barrier, such as plastic wall of a typical microplate, such that a common solution with relative large volume can be applied into each well to cover all compartments and used for a single assay.

In another embodiment, disclosed are methods that can utilize positional and surface-mediated transfection to generate multiple types of cells within a single sensor or multiple sensors within a single chamber or well. For a single sensor, a pre-determined region is chosen to deposit materials such that once cells are cultured and attached, cells can uptake the materials and therefore result in modified or re-engineered cells, distinct from the original cells that culture and attach to the other regions without the deposited materials. The materials can be preferably a target gene, or a antisense oligonucleotide and its derivates, or a antigene oliogonculeotide and its derivates, or an interference RNA (single-stranded, or double stranded, or any kind), or an antibody, or a protein, or a protein domain, or a drug, or a peptide. For different kinds of materials to be delivered or uptaken by the cells, specific transfection reagents can be used to reach optimal effect. Such methods or compositions can be achieved according as described in US2004/0023391A1 and U.S. Pat. No. 6,544,790, which are herein incorporated in their entireties, but at least for material related to methods for delivery to cells.

In another embodiment, disclosed are methods that can utilize positional and surface-mediated transfection to generate multiple types of cells within a single sensor or multiple sensors within a single chamber or well. For a single sensor, a pre-determined region is chosen to deposit materials such that once cells are cultured and attached, cells can uptake the materials and therefore result in modified or re-engineered cells, distinct from the original cells that culture and attach to the other regions without the deposited materials. The materials can be preferably a target gene, or an antisense oligonucleotide and its derivates, or a antigene oliogonculeotide and its derivates, or an interference RNA (single-stranded, or double stranded, or any kind), or an antibody, or a protein, or a protein domain, or a drug, or a peptide. For different kinds of materials to be delivered or uptaken by the cells, specific transfection reagents can be used to reach optimal effect. Such methods or compositions can be achieved according as described in US2004/0023391A1 and U.S. Pat. No. 6,544,790, which are herein incorporated in their entireties, but at least for material related to methods for delivery to cells. The deposition of the materials can be achieved using contact printing technologies (such as pin printing technologies), or stamping devices, or non-contact printing technologies such as dispenser devices or systems. For multi-biosensors within the same well separated by physical barriers, directly deposition of solution containing the materials can be achieved microplate dispenser. Such methods can be achieved according as described in, for example, U.S. Pat. Nos. 5,807,522 A, 6,101,946A, 5,731,152, 5,807,522, 5,601,980, 6,656,432 B1, EP0895082 B1 or U.S. Pat. No. 6,399,396 B1, which are herein incorporated in their entireties, but at least for material related to methods for delivery materials onto the surface of a substrate.

In another embodiment, disclosed are methods that can use position solution transfection techniques for cells located at different sensors within a well and but separated by physical barriers. These methods can use direct introduction of the materials mixed with transfection reagent into each compartment wherein cells are pre-cultured and attached to the sensor. For example, a DNA-containing transfection reagent solution is added into each compartment wherein cells have been placed onto the bottom substrate.

(5). Target Identification Using Optical Biosensors

Drug targets include mostly proteins that play a fundamental role in the on-set or progression of a particular disease. Until recently, pharmaceutical researchers have been limited to studying only approximately 500 biological targets (Drews, J., "Drug Discovery: A Historical Perspective" Science 2000, 287, 1960-1963). With the completion of the sequencing of the human genome, the number of available and potential biological targets is being expanded vastly. The numbers of potential targets uncovered through genomics-based methods have created an enormous need for target evaluation technologies. Traditional drug discovery methods, however, have and can address only a limited number of target families. This situation suggests that the conventional methods have become "boxed in." That is, the methods are unable to create as rapidly the numbers of novel drugs (e.g., three to five per year) that will be necessary to meet the business goals of the major pharmaceutical companies. The traditional methods are unlikely to provide breakthrough therapies for major diseases, such as cardiovascular diseases, neurodegenerative diseases, cancers, and type-2 diabetes, or other largely unmet medical needs. For these reasons, target evaluation has become one of the fastest growing and most critical fields of genomic research. Establishment of a stronger link between the target protein and the disease would lead to a lower failure rate when drugs proceed to clinical trials, and a shorter list of targets that have been proven to be valuable as drug targets would lead to greater success. In addition, a more rapid means of achieving better understanding of protein function would shorten the target evaluation process.

In drug discovery, target evaluation generally includes three major, critical stages: 1) target screening, 2) target identification, and 3) target validation. As the first and/or an early phase in target evaluation, the target screening stage involves identifying molecules that may be associated with a disease process (e.g., up-regulation of a particular gene identified through gene expression analysis). Target identification involves identifying molecules that clearly play a role in a disease process. As such, this type of approach provides a greater degree of certainty, but a possibility still exists that the identified targets will not be the best species or attach to the best binding sites to interfere with a disease process, or they may not be "druggable," meaning that the target is not suitable for drug target because it may not play a dominant role in a disease or cancer, or modification of the target by a drug could lead to adverse side effects. If all is successful, one may proceed to target validation, which is the process of determining which among the selected molecules leads to a phenotypic change when modulated, suggesting it may have value as a therapeutic target.

In one embodiment, disclosed are methods that can be used for target identification and evaluation based on mass redistribution monitored by optical biosensors. Mass redistribution, for example, associated with signaling pathway activations, cell motility and morphological changes can be used as a signature for disease association of a particular target, since many of these changes involve in tumor progression and migration. In one embodiment, the methods involve the comparison of the DMR responses of two types of cells mediated by a stimulatory event through a particular target. As shown in FIG. 15, an optical biosensor (1501) can be provided. Then, a cell medium containing a particular type of cell, cell A (1502) can be placed on the biosensor. Then a buffer solution (1503) can optionally be provided. A particular marker, which is a stimulatory event, such as a modulator or potential modulator of a particular pathway or receptor or cell can be added, for example in a solution (1504). The biosensor can then be used to monitor the cell response (1505). This same set of steps can be performed on a second biosensor (1506) and with a second cell type or cell culture (1507). After interrogation of the second biosensors (1510) the two responses (1505) and (1510) can be compared (1511).

FIG. 12 shows an alternative method for target identification and evaluation based on directional mass redistribution. A biosensor (1201) can be provided, and then a portion of this biosensor can be physically blocked (1202) so that even if cells are placed on the biosensor, the cells will not culture on this portion of the biosensor. One can then place a cell medium that has a cell type A and allow these to grow on the unblock region (1203). Then optionally the blocked region of the biosensor can be unblocked and a second medium of cells of, for example, cell type B such that cell type B becomes cultured on the region that had been blocked (1205). A solution can then be provided that contains a molecule capable of giving a stimulatory event (1206). The biosensor can then be operated such that data from the two regions, the initial unblocked region and the region that had been blocked, can be collected and compared (1207).

FIG. 13 shows an alternative method for target identification and evaluation based on directional mass redistribution. FIG. 13 provides a modification of the disclosed methods related to the fact that the biosensor is located in a specific spot of a chamber, such as a well of microtiter plate. If a device is utilized that contains multiple chambers, and multiple biosensors are used, then different types of cells can be placed on each of the different biosensors, allowing for analysis of a different cell or set of conditions, for each chamber or biosensor (1302). Then optionally a common medium can be placed on each of the chambers to cover all biosensors or a different medium for each chamber can be applied with any combination between the two being disclosed (1303). The solution 1303, can contain a marker, such as a molecule that can create a stimulatory event, or a secondary solution can be applied containing one or more molecules for the stimulatory event (1304). The biosensor(s) can then be monitored and interrogated and the results from each collected and compared (1305).

Similar to that shown in FIG. 2a, FIG. 10 provides a diagram that shows an exemplary label free biosensor along with the basic components. The optical LID system 1000 includes an interrogation system 1002 consisting of modules for controlling the light, electronics and other components for data generation, collection and analysis, and an optical LID biosensor 1004 that can be used to detect and monitor a mass redistribution. When the mass redistribution occurs aligned with the direction of the evanescent wave of the sensor, a signal termed as directional mass redistribution is generated and can be collected and analyzed. However, the mass redistribution occurs along or parallel to the sensor surface might be also be detected by the optical biosensor, as indicated by a number of output parameters such as the PWHM, resonant band width and shape, etc. For example, a translocation of molecules such as GPCR 1020 or molecular assemblies could occur starting from the cell surface facing the sensor to intracellular compartments such as endosome or ER. Such movement, as seen in the arrow numbered 1006 with the living cells 1008 (only one shown), generally leads to a decrease of mass within the sensing volume of the sensors as defined by the penetration depth. In a preferred embodiment, the interrogation system 1002 interrogates the optical LID biosensor 1004 (e.g., SPR sensor 1004, waveguide grating sensor 1004) so it can detect and monitor the mass redistribution within the living cell 1008. This can be done by emitting an optical beam 1012 which has the appropriate spectral or angular content as discussed herein, towards the optical LID biosensor 1004 such that when the optical beam 1012 is reflected by the sensing surface 1010, the resonant angle or wavelength response which identifies the mass redistribution becomes dominant in the reflected beam 1014. Thus, when there is a detectable mass redistribution within the living cell 1008, the optical LID biosensor 1004 can sense a response change which is observed as an angular or wavelength change in the reflected beam 1014. The optical response may be recorded as a function of time. In this way, the kinetic biosensor output parameter, or any other parameter, of any event that leads to a mass redistribution within the living cell 1008 can be analyzed, as discussed herein.

Referring to FIG. 16, there is shown a diagram where the optical LID system 1000 is used to monitor a stimulatory event, such as an agonist-induced translocation of G protein coupled receptors 1602 (GPCRs 1602) within a living cell 1008 (only one shown) located on the top surface 1010 of the optical LID biosensor 1014. In particular, the diagram illustrates an agonist induced and time-dependent optical response 1601 that partly is due to the translocation of a target GPCR 1602 within the living cell 1008. The cell is adherent on the top surface 1010 of the waveguide-based biosensor 1014. For clarity, the interrogation system 1002 is not shown in the portion labeled as "C".

As can be seen, the GPCR 1602 in the resting state resides at the cell surface 1604 (plasma membrane 1604), while the GPCR kinase 1606 (GRK 1606) and arrestin 1608 are uniformly distributed inside the cytosol of living cell 1008 (see diagram "A"). Upon agonist activation, the GPCR 1602 activates heterotrimeric G proteins composed of α, β, and γ subunits. The Gα and Gβγ subunits dissociate which causes the GRK 1606 to be recruited to the receptor 1602 at the plasma membrane 1604. Then, the GRK 1606 phosphorylates the carboxy terminus of the GPCR 1602. And, β-arrestin 1608, a relatively abundant intracellular protein, rapidly (within minutes) translocates within the cytoplasm to the activated GPCR 1602 at the plasma membrane 1604, binds the GRK-phosphorylated receptor, and uncouples the receptor from its cognate G protein. The β-arrestin 1608 then binds to the desensitized GPCR 1602 and translocates to clathrin-coated pits at the cell surface 1604 where the receptor 1602 is internalized in clathrin-coated vesicles (CCV) (see diagram "B"). Finally, the entire complex 1602 and 1606 is delivered to the endosome 1610 (endocytic vesicle 1610) (see diagram "C"). This process is known as translocation. For more information about GPCR translocation, reference is made to the following three articles: Pierce, K. L. et al. "Seven-transmembrane receptors." Nat. Rev. Mol. Cell. Biol. 2002, 3, 639-650, which are incorporated in their entireties at least for material related to translocation.

It should be appreciated that these translocation events lead to directional mass distribution (e.g., towards the cell surface or leaving the cell surface) within the living cells 1008 at a certain time, therefore resulting in different optical responses through a prolong period of time. Another possible biological event that can lead to directional mass distribution is the cell morphological changes due to the GPCR activation. The cell morphological changes involve the cytoskeleton rearrangement as well as cell adhesion changes. Cytoskeleton is a complex network of protein filaments that extends throughout the cytoplasm of eucaryotic cells and is involved in executing diverse activities in these cells. As well as providing tensile strength for the cells it also enables muscle contraction, carries out cellular movements and is involved in intracellular signaling and trafficking, cell division and changes in the shape of a cell. Activation of G-protein coupled receptors (GPCR) leads to at least two independent events that theoretically could exert an effect on the cytoskeleton rearrangement. The first event is the activation of the intracellular signaling pathway, and the second is a receptor-mediated endocytosis (i.e., translocation), which occurs after an agonist activation of the majority of GPCR. Activation of an intracellular signaling pathway after an agonist/GPCR binding then leads to two further sets of connected events. Processes in the first set lead to the activation of a secondary intracellular signaling pathway (G protein→effector→message), while the mechanisms of the second set regulate the degree of signaling within the cell by affecting the events in the first set. These mechanisms include phosphorylation/desensitization, internalization and down-regulation of membrane-bound receptors. It is assumed that both sets of events can lead to the rearrangement of actin filaments within the cell. For example, after the activation of GPCR, various forms of G proteins (e.g. $G_\alpha$ and $G_{\beta\gamma}$ can bind with F-actin filaments; and those and other signaling molecules can disassociate from actin filaments. The internalization process of membrane-bound receptors that occurs via receptor-mediated endocytosis could also be responsible for the dynamics of actin filaments.

Referring again to FIG. 16 and in accordance with the present invention, the different states associated with GPCR translocation within a living cell 1008 can be identified and monitored by analyzing the optical response 1601 from the optical LID system 1000. In fact, three different events can be identified when looking at the optical response 1601 shown in FIG. 16. The three major events that can be seen include: (1) a very large and sharp decrease in signal 1601 upon the addition of agonist, due to bulk index of refraction changes (i.e., in this example the compound solution has relatively lower refractive index than the cell medium. Thus compound addition results in a decreased LID signal); (2) a transition stage which has slow changes in the response signal 1601 and lasts almost 20 minutes: this stage can be related to the cell signaling pathway activation including, but not limited to, the phosphorylation of the activated receptors 1602 by GRKs 1606, arrestin binding, desensitization of the receptors 1602 to chathrin-coated pits, and/or other cellular responses; and (3) a slow decrease of response signal 1601 which lasts almost 50 minutes, corresponding to the translocation of the GPCR complexes 1602 and 1608 to the endosome 1602 or other cellular responses such as cytoskeleton rearrangement. In other cases, an additional event that immediately followed the initial step can be evident (e.g., FIG. 16); that is a rapid fluctuated response signal 1601, mainly due to the introduction and/or diffusion of the compound in the cell medium and/or recruitment of intracellular components to activated GPCRs at the cell surface. Details about how this test can be performed by the optical LID system 1002 are described below with respect to method 1700 shown in FIG. 17.

FIG. 18 shows an example of target identification using DMR. In FIG. 18, no matter whether CHO cells were cultured in a medium containing 10% fatal bovine serum (FBS) (data not shown) or 0.1% FBS (at least 16 hours) (1801), EGF stimulation did not result in significant DMR responses, except for a rapid change in signal that lasts typically less than 20 sec right after the introduction of a 50 μl EGF solution into the cell medium of 150 μl. This rapid change is due to a bulk index change. In contrast, when a stimulatory event occurs, such as the addition of EGF, EGF-induced responses of A431 cells strongly depend on the culture condition. EGF-treatment of A431 cells starved in 0.1% FBS for 20 hours gave rise to a time-dependent response (1802) that consists of three sequential phases, providing 3 biosensor output parameters: (i) a positive phase with increased signal (P-DMR) (Point C to D), (ii) a net-zero phase (Point D to E), and (iii) a decay phase with a decreased signal (N-DMR) (Point E to F to G), after the initial rapid phase of bulk index changes. In contrast, proliferating A431 cells (10% FBS) only gave rise to the P-DMR phase (1803), whereas A431 cells treated with 0.1% FBS for only 4 hours gave rise to similar responses (1804) but with altered kinetics and much smaller amplitudes, compared to those quiescent A431 cells. These results suggest that one can identify or evaluate a target (e.g., EGFR) in a given type of cells based on a marker-induced DMR response, such as using an activator or inhibitor of a cell signaling pathway (i.e., EGF in this particular sample).

i) Cell Signaling

Cell signaling can be monitored using the disclosed systems and methods. For example, referring to FIG. 17, there is shown a flowchart illustrating the basic steps of a method 1700 for monitoring in real time the mass redistribution due to an agonist-induced GPCR activation within living cells 1008 using an optical LID biosensor 1004 in accordance with the disclosed methods. The method 1700 includes the following steps: (a) providing an optical LID biosensor 1004 (step 1702); (b) placing a certain number of living cells 1008 in a medium which covers the optical LID biosensor 1004 such that the living cells 1008 attach onto the surface 1010 of the optical LID biosensor 1004 (step 1704); (c) optionally applying a buffer solution at least once into the cell medium (step 1706); (d) applying a solution containing a compound (agonist) into the cell medium (step 1708); and (e) interrogating the optical LID biosensor 1004 and monitoring the time dependent optical response 1601 of the living cells 1008 cultured on the optical LID biosensor 1004 (step 1710).

It should be appreciated that if step 1706 is performed and a buffer solution (the same buffer solution that is used to formulate the compound of interest) is applied to the living cells 1008 before applying the compound, any unwanted effect, due to the living cells 1008 responding to the environmental changes, can be minimized. This is possible because living cells 1008 that are cultured on the optical LID biosensor 1004 are alive and dynamic which means that they can sense changes in the surrounding medium compositions as well as temperature and can respond to those changes. However, as the living cells 1008 sense changes like the addition of a buffer then they tend to become resistant to those changes in the medium composition assuming no additional chemical is introduced.

It should also be appreciated that the real time method 1700 provides quantifiable information, and equally important, it provides the kinetics of the mass redistribution within cells due to GPCR activation. In contrast to traditional methods of screening GPCRs, this method 1700 is simpler to perform, more sensitive, label-independent and is applicable to all GPCRs 1002 without requiring prior knowledge of natural ligands or how a given receptor is coupled to downstream signaling pathways.

It should also be appreciated that in the step 1704 the number of cells should be optimized such that after a certain time cultured under optimal conditions the cells become adherent and reach high confluency (optionally larger than 75%) on the surface 1010 of an optical LID sensor 1004 in order to achieve high sensitivity.

Referring to FIG. 19, there is shown a flowchart illustrating the basic steps of a method 1900 for screening an agonist against a target GPCR 1002 based on mass redistribution within living cells 1008 using the optical LID biosensor 1004 in accordance with the present invention. The method 1900 includes the following steps: (a) providing the optical LID biosensor 1004 (step 1902); (b) placing a certain number of living cells 1008 in a medium which covers the optical LID biosensor 1004 such that the living cells 1008 attach onto the surface 1010 of the biosensor 1004 (step 1904); (c) applying a solution containing an antagonist with a known affinity at a certain concentration into the cell medium for a certain time until the optical LID biosensor 1004 becomes stabilized (step 1906); (d) applying a solution containing a compound (agonist) into the cell medium (step 1908) where the concentration of the compound is sufficiently high to compete off the receptor-bound antagonist; and (e) interrogating the optical LID biosensor 1004 and monitor the time dependent optical response 1601 of the living cells 1008 cultured on the optical LID biosensor 1004 (step 1910).

It should be appreciated that in this method 1900 by pre-applying the antagonist to one receptor in the living cells 1008, effectively enables one to screen the compounds for their agonism against this particular receptor. Moreover, it should be appreciated that this method 1900 is similar to the previous method 1800 except for one difference in that method 1900 requires pre-knowledge about the functionality of the compound for its cognate receptor in the living cells 1008. For instance, one needs to know whether the antagonist inhibits the activation of GPCR 1020, or whether the antagonist activates the GPCR 1020 which leads to translocation.

Referring to FIG. 20, there is shown a flowchart illustrating the basic steps of a method 2000 for screening an antagonist against a target GPCR 1020 based on mass redistribution within living cells 1008 using the optical LID biosensor 1004 in accordance with the present invention. The method 2000 includes the following steps: (a) providing an optical LID biosensor 1004 (step 2002); (b) placing a certain number of living cells 1008 in a medium which covers the optical LID biosensor 1004 such that the living cells 1008 attach onto the surface 1010 of the biosensor 1004 (step 2004); (c) applying a solution containing an agonist which has a known affinity at a certain concentration into the cell medium for a short time such that the translocation does not happen (step 2006); (d) after this short time, applying a solution containing a compound having a certain concentration into the cell medium (step 2008); and (e) interrogating the optical LID biosensor 1004 and monitoring the time dependent optical response 1601 of the living cells 1008 cultured on the optical LID biosensor 1004. It should be appreciated that like method 1900, this method 2000 requires pre-knowledge about the target GPCR 1020 in the living cells 1008 and also requires the pre-selection of an antagonist or angonist for pre-treating the living cell 1008 against this particular GPCR 1020.

It should be appreciated that the step 2006 and the step 2008 can be combined into one step; that is, the agonist known to the target GPCR in the cell can be added into together with a compound. It also should be appreciated that similar to the method 1700, the compound to be tested can be introduced first, followed by the addition of the known of agonist.

Each of the methods 1700, 1900 and 2000 can be further enhanced by using a self-referencing optical LID biosensor 1004. It is well known that the performance of the optical LID biosensor 1004 is generally affected by the designs and characteristics of the sensor, the optics, and by the environmental fluctuations including ambient temperature and pressure. A main advantage of using the self-referencing optical LID biosensor 1004 is that the top surface 1010 has both a reference region and a sample region which enables one to use the sample region to detect the mass redistribution in the living cells 1008 and at the same time use the reference region which does not have living cells 1008 attached thereto to reference out spurious changes that can adversely affect the detection of the mass redistribution within the living cells 1008.

In one embodiment, the self-referencing optical LID biosensor 1004 can be made in accordance with method 2100 shown in FIG. 21. This self-referencing optical LID biosensor 1004 can be created by using the following steps: (a) providing the optical LID biosensor 1004 (step 2102); (b) physically blocking one region (reference region) of the surface 1010 of the optical LID biosensor 1004 by using a soft stamp (e.g., rubber stamp) (step 2104); (c) placing a certain number of living cells in a growth medium which covers an unblocked region (sample region) of the optical LID biosensor 1004

(step 2106); and (d) removing the soft stamp after the living cells 1008 have attached to the unblocked region on the optical LID biosensor 1004 (step 2108). At this point, the living cell-based assay can be performed as described in methods 1800, 1900 and 2000. It should be appreciated that different methods can also be applied to create the self-referencing LID sensors for cell studies. For example, a physical barrier can be used to divide the sensor into two portions, and cells in a medium are only applied to cover one portion. After cell adhesion, the physical barrier can be removed.

Referring now to another feature of the disclosed methods, it is well known that multiplexed cell assays have become increasingly important, not only for increasing throughput, but also for the rich and confirmative information available from a single assay. As such, it is desirable for the present methods to be performed in a multiplexing fashion, performing multiple assays at a single time.

In one embodiment, the present methods can be enhanced to perform multiple living cell-based assays at the same time by using the method 2200 shown in FIG. 22. In accordance with method 2200 one can monitor mass redistribution due to agonist-induced GPCR activation within multiple types of the living cells 1008 by: (a) providing an optical LID biosensor 1004 (step 2202); (b) blocking a portion of the top surface 1010 of the optical LID biosensor 1004 by using a stamp that prevents the attachment of the living cells 1008 to that portion of the optical LID biosensor 1004 (step 2204); (c) placing a first type of living cells 1008 in a cell medium which covers the unblocked portion of the surface 1010 of the optical LID biosensor 1004 so the living cells 1008 are able to attach to the unblock portion of the surface 1010 of the optical LID biosensor 1004 (step 2206); (d) removing the stamp from the top surface 1010 of the optical LID biosensor 1004 (step 2208); (e) placing a second type of living cells 1008 in a cell medium which covers the optical LID biosensor 1004 so the second type of living cells 1008 are able to attach to the recently uncovered top surface 1010 of the optical LID biosensor 1004 (step 2210); (f) applying a solution containing a compound into the cell medium located on the top surface 1010 of the optical LID biosensor 1004 (step 2212); and (g) interrogating the optical LID biosensor 1004 to monitor time dependent optical responses 1601 which indicate mass redistributions within the two types of living cells 1008 on the optical LID biosensors 1004 (step 2214).

It should be appreciated that the two types of cells can be related; e.g., Chinese Hamster Ovary (CHO) cells versus engineered CHO cells containing an overexpressed target receptor. This approach not only enables multiplexed cell assays, but also provide confirmative results regarding to the compound effect on the target receptor by comparison of the optical responses of the same compound acting on two different cells, since two cells are identical except for the target receptor expression level.

In another embodiment, the present methods can be enhanced to perform multiple living cell-based assays at the same time using the method 2300 shown in FIG. 23. In accordance with method 2300 one can monitor the mass redistribution due to agonist-induced GPCR activation in multiple types of living cells 1008 by: (a) providing a chamber (microplate) containing an array of the optical LID biosensors 1004 (step 2302); (b) placing a first type of living cells 1008 in a cell medium which covers one or more of the optical LID biosensors 1004 so the first type of living cells 1008 are able to attach to the surfaces 1010 of the one or more optical LID biosensors 1004 (step 2304); (c) placing a second type of living cells 1008 in a cell medium which covers one or more of the remaining uncovered optical LID biosensors so the second type of living cells 1008 are able to attach to the surfaces 1010 of the one or more remaining uncovered optical LID biosensors 104 (step 2306); (d) applying a solution containing a compound into the cell mediums located on the top surfaces 1010 of covered optical LID biosensors 1004 (step 2310); and (e) interrogating the covered optical LID biosensors 1010 to monitor the time dependent optical responses 1601 which indicate mass redistributions within the living cells 1008 on each of the covered optical LID biosensors 1004 (step 2312).

It should be appreciated that arrays of different DNA vectors containing distinct target receptor genes in combination with transfection reagents can be deposited onto a LID sensor; a single type of cell is placed and overlaid with such array and uptakes the genes. Thus only cells overlaid on each spot area become transfected and therefore form a transfected cell cluster array (U.S. Pat. No. 6,544,790 B1 "Reverse transfection method"). Similarly, an array of functional receptor proteins can be complexed with protein delivery reagents and can be used in a similar transfected cell cluster array (US2004/0023391A1 "Methods and devices for protein delivery"). Both types of transfected cell arrays can be used for compound screening using the current technology.

In yet another embodiment, the present methods can be further enhanced to perform multiple target screens in a single type of cells at the same time by using method 2400 shown in FIG. 24. In accordance with method 2400 one can screen agonists against multiple GPCRs 1020 within a single type of living cells 1008 by performing the following steps: (a) providing a optical LID biosensor 1004 (step 2402); (b) placing the living cells 1008 in a cell medium which covers the optical LID biosensor 1004 so the living cells 1008 are able to attach to the surface 1010 of the optical LID biosensor 1004 (step 2404); (c) applying a solution containing a cocktail solution of antagonists (step 2406); (d) applying a solution containing a compound into the cell medium located on the top surface 1010 of the optical LID biosensor 1004 (step 2408); and (e) interrogating the optical LID biosensor 1004 to monitor a time dependent optical response 1601 which indicates mass redistributions within the living cells 1008 (step 24).

It should be appreciated that similar methods can be used to screen antagonist against multiple receptors in the same cell line by modifying the method 2400. Instead of a cocktail solution of antagonists in the step 2406, one can use a solution of compounds of interest; at the same time, a cocktail solution of agonists is used to replace the compound solution in the step 2408.

(1) Importance of Trafficking Kinetics Studies

Kinetics relating to cell signaling pathways and their associated cell activity and other cellular changes are extremely important for not only understanding cell biology and physiology, but they are also important for cell assay development and drug discovery. For example, the EGFR signaling network contains reactions ranging from almost instantaneous reactions (receptor phosphorylation after ligand binding) to reactions that occur over many minutes (vesicle formation or the sorting to lysosomes) or morphological changes in certain cell lines. Trafficking of the EGFR is regulated at multiple steps, including endocytosis, early endosomal sorting, and lysosome targeting. After internalization, the EGFR are either shuttled back to the plasma membrane or transported into late or multivesicular endosomes. The receptors in the late endosomes are further sorted to lysosomes for degradation or recycled back to the cell surface. The occupancy of the receptors dictates their ability to participate in each step of the sorting process. Although the principal hierarchy of the EGFR signaling cascade and its activation sequences is well known, the complicated kinetics network and critical signaling events that control such divergent cellular responses as cell growth, survival, or differentiation are poorly understood. Technologies that can measure the real time kinetics of cellular responses through ligand-mediated EGFR activation would greatly benefit understanding about the dynamics of signaling cascades and networks.

(2) G-protein Coupled Receptor Pathways

GPCRs belong to a family of cell surface receptors, and are among the most common targets that new drug compounds are designed against. Since GPCRs can transduce exogenous signals (i.e., the presence of stimuli such as a new drug) into intracellular response(s) makes them extremely valuable as drug targets and for the testing of new drugs.

GPCRs participate in a wide array of cell signaling pathways. Ligand binding initiates a series of intracellular and cellular signaling events, including receptor conformational changes, receptor oligomerization, G protein activation (GDP-GTP exchanges on $G_\alpha$ subunit, $G_\alpha$ and $G_{\beta\gamma}$ disassociation, G protein decoupling from the receptor, generation of $G_\alpha$- and $G_{\beta\gamma}$-signaling complexes), and downstream signaling activation that leads to second messenger generation ($Ca^{2+}$ mobilization, inositoltriphosphate generation, and/or intracellular cAMP level modulation) and ultimately results in changes of specific gene expression. Ligand-mediated GPCR activation also leads to the desensitization of GPCRs from the cell surface and trafficking of many intracellular proteins, as well as changes in phenotypes, morphology and physical properties of the target cells. These changes could be static, long-lasting or dynamic (e.g., cycling or oscillation). Distinct signaling events exhibit significantly different kinetics ranging from milliseconds (e.g., GPCR conformational changes) to tens of seconds (e.g., $Ca^{2+}$ flux) to even tens of minutes (e.g., gene expression, or morphological changes). Current GPCR assays include ligand-receptor binding, second messenger ($Ca^{2+}$, cAMP of IP3) assays, protein interaction assays, translocation assays and reporter gene assays. Since GPCR activation ultimately leads to protein trafficking and/or morphological changes, methods that can study the action of any compounds through the GPCRs on cell surface and the consequent events (e.g., trafficking and/or morphological changes) of the effected cells would be desired.

(3) Receptor Tyrosine Kinase (RTK) Signaling Pathways (a) Diversity of RTKs

A large group of genes in all eukaryotes encode for proteins that function as membrane spanning cell surface receptors. Membrane receptors can be classified into distinct families based upon the ligands they recognize, the biological responses they induce, and the primary structures they have. One large family of cell surface receptors is endowed with intrinsic protein tyrosine kinase activity. These receptor tyrosine kinases (RTKs) catalyze transfer of the phosphate of ATP to hydroxyl groups of tyrosines on target proteins. RTKs play an important role in the control of most fundamental cellular processes including the cell cycle, cell migration, cell metabolism and survival, as well as cell proliferation and differentiation.

Receptor tyrosine kinases (RTKs) belong to a super family of protein tyrosine kinases (PTKs). PTKs are a large and diverse multigene family. Their principal functions involve the regulation of multicellular aspects of the organism. Cell to cell signals concerning growth, differentiation, adhesion, motility, and death, are frequently transmitted through tyrosine kinases. In contrast, many of the serine/threonine kinase families, such as cyclin dependent kinases and MAP kinases, are conserved throughout eukaryotes and regulate processes in both unicellular and multicellular organisms. In humans, tyrosine kinases have been demonstrated to play significant roles in the development of many disease states, including diabetes and cancer. Historically, tyrosine kinases define the prototypical class of oncogenes, involved in most forms of human malignancies. Tyrosine kinase genes have also been linked to a wide variety of congenital syndromes. Tyrosine kinases contain highly conserved catalytic domains similar to those in protein serine/threonine and dual-specificity kinases but with unique subdomain motifs clearly identifying members as tyrosine kinases. Tyrosine kinase genes have been characterized in poriferans, cnidarians, nematodes, annelids, arthropods, echinoderms, and chordates, and others. The human tyrosine kinases may be grouped into 20 receptor and 10 non-receptor classes, based on either intron/exon structure or phylogenetic sequence analysis.

All receptor tyrosine kinases contain an extracellular ligand binding domain that is usually glycosylated, and involved in receptor dimerization. The ligand binding domain is connected to the cytoplasmic tyrosine kinase domain by a single transmembrane helix. The cytoplasmic domain contains a conserved protein tyrosine kinase (PTK) core and additional regulatory sequences that are subjected to autophosphorylation and phosphorylation by heterologous protein kinases. RTKs can be further classified into several subfamilies of receptors: insulin receptor (IR) family, epidermal growth factor (EGF) receptor family, PDGF receptor family, for example. The epidermal growth factor (EGF) family of receptor tyrosine kinases consists of four receptors, EGF-R (ErbB1), ErbB2 (Neu), ErbB3, and ErbB4.

(b) Dimerization of RTKs

With the exception of the insulin receptor (IR) family of RTKs, all known RTKs (e.g., epidermal growth factor (EGF) receptor, PDGF receptor) are monomers in the cell membrane. Ligand binding induces dimerization of these receptors resulting in autophosphorylation of their cytoplasmic domains. Members of the IR family are disulfide linked dimers of two polypeptide chains forming a 22 heterodimer. Insulin binding to the extracellular domain of the IR induces a rearrangement in the quaternary heterotetrameric structure that leads to increased autophosphorylation of the cytoplasmic domain.

Although all RTKs are activated by dimerization, different ligands induce the formation of different active dimeric states. Specific ligands define the dimer pair; the dimer pair, in turn, defines the signaling pathway. Structural studies of growth hormone (GH) in complex with GH receptor (GHR) and erythropoietin (EPO) in complex with EPO receptor (EPOR) show that these cytokines are bivalent, and one ligand binds simultaneously to two receptor molecules to form a 1:2 (ligand:receptor) complex. Receptor dimerization is further stabilized by additional receptor:receptor interactions. Only certain forms of receptor dimers with unique configurations of the extracellular and cytoplasmic domains of both RTKs and cytokine receptors lead to trans-autophosphorylation and PTK stimulation.

(c) EGFR

The EGR receptors, consisting of four members as mentioned above, belong to the tyrosine kinase family of receptors and are expressed in virtually all organs of mammals. EGF receptors play a complex role during embryonic and postnatal development and in the progression of tumors. Apart from their roles in growth and differentiation, EGFR receptors participate in transactivation processes and are involved in crosstalk with other receptors such as GPCRs.

(d) EGFR Signaling Pathways

The engagement of EGFR by its cognate ligand results in the generation of a number of intracellular signals (as shown in FIG. 38). Following ligand binding, the initial changes are receptor dimerization to form homo-dimers or hetero-dimers with other family members, activation of the kinase activity of the receptor, and autophosphorylation of the receptor on tyrosine residues of the cytoplasmic domain. Receptor autophosphorylation results in the creation of docking sites for a number of secondary signaling proteins bearing specific protein interaction domains such as the Src homology 2 (SH2) domain, which interact specifically with phosphorylated tyrosine residues. Each dimeric receptor complex will initiate a distinct signaling pathway by recruiting different SH2-containing effector proteins. As a consequence of this interaction, these secondary signaling proteins themselves may become activated and trigger a number of downstream signals. For example, the activated EGF-R dimer complexes with the adapter protein, Grb, coupled to the guanine nucleotide releasing factor, SOS. The Grb-SOS complex can either bind directly to phosphotyrosine sites in the receptor or indirectly through Shc. These protein interactions bring SOS in close proximity to Ras, allowing for Ras activation. This subsequently activates the ERK and INK signaling pathways that, in turn, activate transcription factors, such as c-fos, AP-1, and Elk-1, that promote gene expression and contribute to cell proliferation. One particular pathway that promotes cell proliferation involves the signaling proteins Shc, Grb2, Sos, Ras, Raf, MEK, ERK and ERK/MAPK, and is known as Ras/MAPK pathway.

(i) EGFR Signaling and Mass Redistribution

Ligands for EGFRs include EGF, TGF-α, amphiregulin, heparin-binding EGF-like growth factor, betacellulin, and epiregulin. The EGFR can be activated by the binding of any one of a number of different ligands, each of which appears to stimulate a somewhat different spectrum of biological responses. Furthermore, different EGFR ligands vary in their ability to bind to the receptor as a function of receptor microenvironment, such as intravesicular pH.

After binding, the activated EGFR is rapidly internalized by endocytosis. Receptor-mediated endocytosis allows the specific removal of cell surface receptors and their cargo from the plasma membrane and targets them to endosomes, where they are sorted for downregulation or recycling. After endocytosis, receptor-ligand complexes pass through several different compartments that vary in their intravesicular milieu. Receptor movement among cellular compartments (referred as trafficking) has a significant effect on the activity of the complexes. The different intracellular compartments also vary in their access to some of the substrates of the EGFR kinase. The conjoined relationship between substrate access and ligand-dependent activity in different endocytic compartments suggests that trafficking could function to "decode" the information unique to each ligand. Furthermore, the persistence of ligand-receptor interactions controls receptor trafficking. Thus, receptor endocytosis and degradation is an important mechanism for controlling the magnitude of the signal, the specificity of the response, and the duration of the response.

Ligand-induced internalization of the EGFR is a saturable process and increases in the level of EGFR expression beyond a certain threshold lead to impaired internalization of the receptor.

EGF receptors can be internalized by either an induced pathway or a constitutive pathway. The vesicles formed through the induced pathway are referred to as coated-pit mediated early endosome (EE) vesicles. All EE vesicles go through a sorting stage and can either return to the cell surface or merge into the late endosomes (LE). When an EE vesicle recycles back to the plasma membrane (PM), all of its receptors become part of the PM and any unbound ligand is released into the extracellular medium. Similarly, when an EE vesicle merges into the LE, all of its contents are transferred to the LE. The rates of recycling to the plasma membrane and of merging into the late endosome can depend on the type of EE vesicle. Endocytic vesicles are recycled back to the plasma membrane either at a very fast rate or after a time lag (i.e., slowly). Generally, the coated-pit EE vesicles recycle back to the plasma membrane slowly and, as a result, a considerable percentage of the coated-pit EE vesicles merge into the LE. In contrast, constitutive EE vesicles have a faster recycle rate and thus most of them return to the plasma membrane. The receptors go through a second stage of sorting in the LE and either are tagged for degradation and sent to the lysosome or are recycled back to the cell surface. A small vesicle breaks away from the sorting endosome at a certain rate. This vesicle either fuses to the lysosome for its contents to be degraded or it recycles back toward the plasma membrane. Mechanistically, receptors recycling from the late endosomes are likely to pass through the golgi. The net outcome of those endocytic processes leads to a directional mass re-distribution in cells after EGFR activation.

Depending on the cellular context of a specific cell line, ligand-induced EGFR activation could lead to distinct signaling pathways or multiple signaling pathways in which one becomes dominant compared to others. Furthermore, the expression level of EGFRs could vary from one to another cell line. Because of that, the mass redistribution within the cells mediated by ligand-induced EGFR activation could vary among different cell lines. For example, the human epidermoid carcinoma A431 cell is known to endogenously overexpress EGFRs (~1,700,000 copies per cell), and thus has been used as an ideal model for EGFR signaling (D. W. Barnes, "Epidermal growth factor inhibits growth of A431 human epidermoid carcinoma in serum-free cell culture," J. Cell. Biol. 1982, 93, 1-4). Upon the binding of EGF, EGFRs in the A431 cells become activated, and lead to various cellular responses through distinct pathways including the Ras/MAPK pathway. For example, stimulation of quiescent A431 cells with EGF at 37° C. ultimately leads to receptor endocytosis, refractile morphological changes and cell detachment from the extracellular matrices (Z. Lu, G. Jiang, P. Blume-Jensen, and T. Hunter, "Epidermal growth factor-induced tumor cell invasion and metastasis initiated by dephosphorylation and downregulation of focal adhesion kinase," Mol. Cell. Biol. 2001, 21, 4016-4031. and Y. Danjo and I. K. Gipson, "Actin 'purse string' filaments are anchored by E-cadherin-mediated adherens junctions at the leading edge of the epithelial wound, providing coordinated cell movement," J. Cell Sci. 1998, 111, 3323-3332). Again, receptor endocytosis is an important cellular process to attenuate the EGF signal, although some evidence suggests that EGF receptor complexes continue to signal in endosomal compartments. The endocytosis process involves multiple steps: recruitment of intracellular components to the activated receptors, subsequent internalization of the resulted complexes into endosomes, movement of the internalized receptor complexes among several intracellular compartments, and ultimately degradation and recycling back to the cell membrane. In addition, because of the size of those ligands, the density of cell surface receptors, and density and morphology of cell lines used (such as the A431 cell line) as well as the receptor trafficking after activation, there are a number of signaling events in RTK pathways that give rise to directional mass redistribution. For example, the binding of ligands to cell surface EGFRs leads to an increase of mass at the cell surface; the sequential autophosphorylation and intracellular components interacting with the activated EGFRs results in a net zero-change of mass redistribution for a short period of time. The trafficking of activated receptors leads to significant mass redistribution within different compartments of each cell.

Another possible resource for mass redistribution is due to cytoskeleton rearrangement. For example, the EGFR trafficking process is initiated by recruitment of the receptor into a clathrin-coated pit at the plasma membrane, a structure formed by assembly of clathrin and adaptors into a protein lattice on the membrane's cytosolic face. Polymerization of clathrin into a hexagonal array provides a scaffold for organizing the adaptors, which recognize sequence motifs in the cytoplasmic domains of internalized receptors. The actin cytoskeleton is believed to contribute to the formation of clathrin-coated pits, although the specific components that connect actin filaments with the endocytic machinery are unclear. Cortactin is an F-actin-associated protein, localizes within membrane ruffles in cultured cells, and is a direct binding partner of the large GTPase dynamin. Cortactin, together with actin and dynamin, are important components of the receptor-mediated endocytic machinery (Bajzer, Z., et al., "Binding internalization, and intracellular processing of proteins interacting with recycling receptors—a kinetic analysis", J. Biol. Chem. 1989, 264:13623-13631).

(ii) Constitutive Activity of EGFRs

It is thought that receptor monomers are in equilibrium with receptor dimers. A limited population of receptor dimers exist with quaternary structures of their extracellular and cytoplasmic domains in configurations that are compatible with trans-autophosphorylation and stimulation of PTK activity (active dimer). Ligand binding to the extracellular domain stabilizes the formation of active dimers and consequently PTK stimulation. It has been proposed that active dimers exist even in the absence of ligand binding since autophosphorylation of RTKs can be enhanced by inhibitors of protein tyrosine phosphatases or by receptor overexpression even in the absence of ligand binding. Experiments show that 2% of the unbound (ligand free) and 15% of the ligand-bound receptors on the plasma membrane get internalized per min. Furthermore, in quiescent A431 cells, obtained by culturing the cells in a medium containing relatively low concentrations of growth factors such as fetal bovine serum (FBS) (less than 0.5% in weight) or without any FBS, there is still some degree phosphorylation of the EGFR due to its constitutivity.

FIG. 7 shows that EGF stimulation lead to a strong dose-dependent dynamic response (See FIG. 7A); three major biosensor parameters defining the response are significantly changed as the concentration of EGF increases. The higher the EGF concentration goes, 1) the greater the amplitudes of both P-DMR and N-DMR signals, 2) the faster the kinetics of both P-DMR and N-DMR events is, and the 3) shorter the time resulting in the transition from the P-DMR to N-DMR event (the transition time $\tau$). When the amplitudes of the P-DMR events showed a complicate relationship with the EGF concentrations, the amplitudes of the N-DMR signals showed a strong and saturable dose dependence on EGF, resulting in an $EC_{50}$ of ~1.45 nM (see FIG. 7b). The transition time $\tau$ in seconds was found to decrease exponentially with the increasing concentration of EGF (see FIG. 7c): In addition, the decay of the N-DMR signal can be fitted with non-linear regression. The one-phase decay constant $\kappa$ obtained also gave rise to a typical saturable response with a Kd of 5.76 nM (see FIG. 7d). Those dose-dependent kinetics parameters (the transition time and the decay constant of the N-DMR phase) were in excellent agreement with the previous experimental data and computational predictions relating to kinetics of expression of the target gene, C-fos, in HeLa cells and of EGFR endocytosis (Schoeberl, B., C. Eichler-Jonsson, E. D. Gilles, and G. Muller. "Computational modeling of the dynamics of the MAP kinase cascade activated by surface and internalized EGF receptors". Nat. Biotech. 2000, 20:370-375). These results indicated that EGF-induced cell morphological changes and receptor endocytosis are DMR events and the DMR is an EGFR activation dependent event.

(e) PDGFR

Similar to EGFRs, platelet-derived growth factor (PDGF) has been shown to drive cellular responses including proliferation, survival, migration, and the deposition of extracellular matrix (ECM) and tissue remodeling factors. Knockout studies have demonstrated that many of these cellular responses to PDGFs are essential during mouse development. There are two ligands, PDGFa and PDGFb, and two receptors, PDGF receptor alpha and PDGF receptor beta (PDGFRα and PDGFRβ, respectively). PDGFb and PDGFRβ are essential for the development of support cells in the vasculature, whereas PDGFa and PDGFRα are more broadly required during embryogenesis, with essential roles in numerous contexts, including central nervous system, neural crest and organ development.

The PDGF signaling network consists of four ligands, PDGFA-D, and two receptors, PDGFRα and PDGFRβ. All PDGFs function as secreted, disulfide-linked homodimers, but only PDGFA and B can form functional heterodimers. PDGFRs also function as homo- and heterodimers, and in vitro assays have demonstrated that the ligands differ in their affinities for the, αβ and ββ receptors. All known PDGFs have characteristic 'PDGF domains', which include eight conserved cysteines that are involved in inter- and intramolecular bonds.

PDGFRs are receptor tyrosine kinases, just like EGFRs. Each receptor has five immunoglobulin repeats in the extracellular ligand-binding domain and a split tyrosine kinase domain in the cytoplasmic region. Upon ligand binding, PDGFRs dimerize, activating the tyrosine kinase domains, which then autophosphorylate several tyrosine residues in the receptor cytoplasmic domains. This creates docking sites for signaling proteins and adaptors that initiate signal transduction upon PDGFR binding. Both receptors can activate many of the same major signal transduction pathways, including the Ras-MAPK (mitogen activated protein kinase), phosphatidylinositol 3-kinase (PI3K) and phospholipase C pathways. However, the array of interacting proteins differs slightly between PDGFRα and PDGFRβ, resulting in some differences in their functional capabilities in vivo.

Similar to EGFR signaling, the activation of PDGFRs could also lead to significant mass redistribution which can be monitored and analyzed by optical biosensors.

(f) Other RTKs

Tyrosine kinases are primarily classified as receptor tyrosine kinase (RTK) e.g. EGFR, PDGFR, FGFR and the IR, and non-receptor tyrosine kinase (NRTK) e.g. SRC, ABL, FAK and Janus kinase. Besides EGFRs and PDGFRs, others receptor tyrosine kinases include insulin receptors, insulin-like growth factor I receptors (IFG-1R), nerve growth factor receptors (NGFRs), fibroblast growth factor receptors (FGFRs). Similarly, these RTKs are not only cell surface transmembrane receptors, but are also enzymes having kinase activity. The structural organization of the receptor tyrosine kinase exhibits a multidomain extracellular ligand for conveying ligand specificity, a single pass transmembrane hydrophobic helix and a cytoplasmic portion containing a tyrosine kinase domain. The kinase domain has regulatory sequence both on the N and C terminal end.

The NRTK are cytoplasmic proteins, exhibiting considerable structural variability. The NRTK have a kinase domain and often possess several additional signaling or protein-protein interacting domains such as SH2, SH3 and the PH domain. The tyrosine kinase domain spans approximately 300 residues and consists of an N terminal lobe comprising of a 5 stranded β sheet and one α helix, while the C terminal domain is a large cytoplasmic domain that is mainly α helical. ATP binds in the cleft in between the two lobes and the tyrosine containing sequence of the protein substrate interacts with the residues of the C terminal lobe. RTKs are activated by ligand binding to the extracellular domain followed by dimerization of receptors, facilitating trans-phosphorylation in the cytoplasmic domain whereas the activation mechanism of NRTK is more complex, involving heterologous protein-protein interaction to enable transphosphorylation.

(4) Cytoskeleton Modulation

Cytoskeleton is a unique and cellular "scaffolding" or "skeleton" contained within the cytoplasm. Cytoskeleton is a complex and dynamic network of protein filaments that extends throughout the cytoplasm of eukaryotic cells. Cytoskeleton is involved in executing diverse activities in cells. It maintains cell shape by providing tensile strength for the cells. It also enables some cell motion (using structures such as flagella and cilia), and plays important roles in both intra-cellular transport (the movement of vesicles and organelles, for example) and cellular division. The cytoskeleton is involved in intracellular signaling and trafficking by providing the "track" on which cells can move organelles, chromosomes and other things.

Eukaryotic cells are given shape and organized by the cytoskeleton. The long fibers of the cytoskeleton are polymers of subunits. The primary types of fibers comprising the cytoskeleton are microfilaments, microtubules, and intermediate filaments. (i) Microfilaments are twisted double strands consisting of a string of proteins, typically from 7 nm to 12 cm long. The protein is actin. Its function helps muscle contraction, cell shape, and movement in cytoplasm. (ii) Intermediate filaments are made of eight subunits in rope-strands. The proteins structure varies with different tissue types. This component helps maintain shape, support nerve cell extensions, and attach cells together. (iii) Microtubules are tubes made up of spiraling, two-part subunits. It is made of tubulin. It aids in chromosome movement, movement of organelles, and the movement of cilia and flagella. For example, in epithelial cells of the intestine, all three types of fibers are present. Microfilaments project into the villi, giving shape to the cell surface. Microtubules grow out of the centrosome to the cell pheriphery. Intermediate filaments connect adjacent cells through desmosomes.

(a) Cytoskeleton Structure

The cytoskeleton is a cellular "scaffolding" or "skeleton" contained, as all other organelles, within the cytoplasm. It is a dynamic structure that maintains cell shape, enables some cell motion (using structures such as flagella and cilia), and plays important roles in both intra-cellular transport (the movement of vesicles and organelles, for example) and cellular division. Eukaryotic cells contain three kinds of cytoskeletal filaments: actin filaments, intermediate filaments and microtubules (Janmey, P. A. (1998). The cytoskeleton and cell signaling: component localization and mechanical coupling. Physiol. Rev. 78, 763-781)) Actin filaments that are around 7 nm in diameter. This filament is composed of two actin chains oriented in a helicoidal shape. They are mostly concentrated just beneath the plasma membrane, as they keep cellular shape, form cytoplasmatic protuberancies (like pseudopods and microvillus), participate in some cell-to-cell or cell-to-matrix junctions and the transduction of signals. They are also important for cytokinesis and, along with myosin, muscular contraction. Intermediate filaments that are around 8 to 11 nanometers in diameter. They are the more stable (strongly bound) and heterogeneous constituents of the cytoskeleton. They organize the internal 3-dimensional structure of the cell (e.g., they are structural components of the nuclear envelope or the sarcomeres). They also participate in some cell-cell and cell-matrix junctions. Microtubules that are hollow cylinders of about 25 nm., formed by 13 protofilaments which, in turn, are polymers of alpha and beta tubulin. They have a very dynamic behavior, binding GTP for polymerization. They are organized by the centrosome. These filaments play key roles in intracellular transport (associated with dyneins and kinesins, they transport organelles like mitochondria or vesicles), and the mitotic spindle.

(b) Controlled Releasing of Biomaterials from Permeabilized Cells

Discussion regarding the controlled release of biomaterials from permaeabilized cells can be found in Negrutskii, B. S. and Deutscher, M. P. (1992) "A sequester pool of aminoacyl-tRNA in mammalian cells" Proc. Natl. Acad. Sci. USA 89, 3601-3604; Negrutskii, B. S., Stapulionis, R. and Deutscher, M. P. (1994) "Supramolecular organization of the mammalian translation system" Proc. Natl. Acad. Sci. USA 89, 3601-3604 which are herein incorporated in their entireties by reference and at least for material related to controlled release of biomaterials from permeabilized cells.

A living cell is a macromolecular assembly. Many studies have shown that endogenous macromolecules are highly organized within the cytoplasm of mammalian cells through direct binding to cytoskeletal elements. The cytoskeleton, particularly the actin microfilament network, plays an important role in maintaining this organization.

Permeabilized cells have been used to examine cell architecture. Treatment of the cells with many chemicals or biologicals can result in the pore formation in cell surface membrane which leads to permeabilized cells. These chemicals or biologicals include detergents such as saponin and filipin, or toxin such as digitonin or streptolysin O. Compared to other pore-forming reagents, however, saponin has the advantage when carefully titrated of causing minimal damage to internal membranes and leading to a very uniform population (>97%) of permeabilized cells. Saponin, a plant-derived glycoside, is well known for its ability to render the plasma membrane sufficiently porous to permit soluble proteins to diffuse away. Although the saponin-treated cells undergo the loss of some portions of biomacromolecules, the permeabilized cells resulted still retain the most of biological functions of living cells. This has been evidenced by the fact that protein synthesis in these permeabilized cells remains at a high level, despite the complexity of the process, which suggesting that this system has retained much of the original structural integrity of intact cells. This is because most macromolecules are sequestered as part of an organized cell structure, therefore being not released from these permeabilized cells. For example, components of the translation apparatus such as tRNA, aminoacyl-tRNA synthetases, and EF1 are normally tightly sequestered in permeabilized cells. Not only protein synthesis machinery is sequestered by the cytoskeleton, many other components of the cell are also stably or transiently associated with cellular structure; these transiently associated components can be partially released from permeabilized cells.

However, upon disruption of microfilaments there is a dramatic reduction of protein synthesis accompanied by release of these translation components from the cells. Also, many other sequestered biomacromolecules are released from these permeabilized cells after disrupting the cytoskeleton structure. These further released materials from the permeabilized cells result in a loss in mass; thus resulting in the changes in effective refractive index of the cell layer on the surface of an LID sensor which can be detected by LID sensors. Thus, the changes obtained using optical biosensors can be used as an indicator of modulators that interfere with the cytoskeleton structure.

Traditionally, methods to screen modulators that interfere with the cytoskeleton structure are mainly based on binding affinity measurements using in vitro assays, including actin binding protein assays, microtubule stabilization/destabilization assays, and actin/tubulin polymerization assay. Other methods are based on high resolution fluorescence imaging technique to directly visualize the intracellular cytoskeleton structure, or to measure the motility of cells after compound treatments, or to measure the activation of cytoskeleton-interacting maker proteins such as Cdc42 or Rho.

Disclosed herein are label-free detection methods using optical biosensors to screen modulators that interfere with cytoskeleton arrangement.

Disclosed are methods in the optical biosensor field and, in certain embodiments, to a system and method for using an optical label independent detection (LID) biosensor (e.g., waveguide grating-based biosensor) to monitor in real time compound-induced releasing of intracellular components that are sequestered by the cytoskeleton in permeabilized and functional cells. Disclosed are methods using chemicals or biologicals to generate permeabilized cells which permit soluble proteins to diffuse away. Disclosed are systems and methods for using a LID biosensor to screen modulators of cytoskeleton components using optical biosensors.

Unlike all the existing assay technologies for cytoskeleton arrangement, the disclosed methods provide a label-free and real time method to screen modulators that interfere with the cytoskeleton structure. In addition, unlike all the existing and cell-based assays for cytoskeleton arrangement, the present methods take advantage of permeabilized cells that retain most of the biological functions of living cells, but with significantly more simplicity than living cells. Unlike the fluorescence imaging-based assays that normally screen modulators against a single target, the present methods offer multiplexing capabilities, i.e. the capability to screen modulators that interfere with multiple targets within cells. Combined with a total internal reflection fluorescence imaging technique, the disclosed methods provide high information content screening, including kinetics, affinity, target(s) that are involved, as well as toxicity.

FIG. 25 shows an example of a method based on the measurement in real time of compound-induced releasing of intracellular components that are sequestered by the cytoskeleton in permeabilized and functional cells. The method involves the use of pore-forming reagents (e.g, saponin) to generate permeabilized cells which permit soluble proteins to diffuse away. It is known that treatment of the cells with many pore-forming reagents leads to permeabilized cells. Since intracellular macromolecules are highly organized within the cytoplasm of mammalian cells through direct binding to cytoskeletal elements, the permeabilized cells still retain most of the biological functions of living cells by sequestration of intracellular machinery through the cytoskeleton super-assembled structure, although the saponin-treated cells undergo the loss of some portions of biomacromolecules. However, upon disruption of microfilaments there is a dramatic reduction of protein synthesis accompanied by release of these translation components from the cells. Also, many other sequestered biomacromolecules are released from these permeabilized cells after disrupting the cytoskeleton structure. These further released materials from the permeabilized cells result in the loss in mass; thus resulting in the changes in effective refractive index of the cell layer on the surface of a LID biosensor which can be detected by LID biosensors. Thus, the changes obtained using optical biosensors can be used to screen modulators that interfere with the cytoskeleton structure. In one embodiment, the present methods can be used to screen modulators that interfere with the cytoskeleton structure using the method 2500 shown in FIG. 25. In accordance with method 2500 one can monitor the mass redistribution due to pore formation of cell surface membranes induced by pore-forming reagents such as saponin in living cells 1008 by: (a) providing an optical LID biosensors 1004 (step 2502); (b) placing cells 1008 in a cell medium onto the said sensor 1004 (step 2504); (c) Optionally applying a buffer solution (step 2506); (d) applying a solution containing a compound into the cell mediums located on the top surfaces 1010 of covered optical LID biosensors 1004 (step 2508); applying a solution containing a pore-forming reagent (step 2510); and (e) interrogating the covered optical LID biosensors 1010 to monitor the time dependent optical responses which indicate mass redistributions within the permeabilized cells 1008 (step 2512). A Pore-forming reagent is a chemical or biological compound or composition that can result in the formation of pores in cell surface membranes when the cells are exposed to the reagent.

Typically, measurements or assays relating to cell function or activities using optical biosensors, as disclosed herein, can be done in real time. Although a variety of optical output parameters can be used for cell monitoring and examination, the output parameters relating to the kinetics of stimulation-induced directional mass redistribution are two parameters for monitoring cell signaling and its consequences in real time.

Cell signaling pathways, including but not limiting to Ras/MAPK pathway, cAMP pathway, GPCR signaling pathways, RhoA pathway, Akt pathway, intregin pathways, GPCR attenuation pathways, G protein pathways, Ca pathways, phospholipase C pathway, cell transformation pathway, cell migration pathways, cell adhesion pathways, etc, can be associated with the DMR signals measured using optical biosensors. For example, activation of the MAPK kinase pathway has been identified as a mechanism that integrins use to regulate gene expression leading to cell shape changes during cell spreading or migration Epithelial cells respond to extracellular matrix (ECM) cause integrin-mediated FAK phosphorylation that in turn phosphorylates the surrounding proteins (paxillin, Fyn/shc, and src) and leads to signal amplification. FAK also binds PI-3 kinase and is upstream of the MAP kinase pathway. When MAPkinase or PI-3 kinase was inhibited, actin reorganization was blocked. Src phosphorylates p190RhoGAP, inactivating its GAP function that may allow RhoGTP to stay active longer, promoting further signal amplification. Activated RhoGTP binds to downstream kinases such as Rho-associated coiled coil-containing protein kinase (p160ROCK) and p140 diaphanous (p140-Dia) to increase actin polymerization and contraction. Actin reorganization assists integrin clustering, allowing more ECM binding that increase FAK phosphorylation and other signal transduction events. Because cell signaling pathways and their cellular consequences are strongly dependent on the cellular context, it should be understood that for a given cell type, the activation of a given signaling pathway through a specific and predetermined target may not lead to any DMR (meaning that a stimulation may only lead to a net-zero DMR phase), or in some cases, result in a distinct DMR response from that obtained using a different cell line. Furthermore, the activation of a particular signaling pathway mediated by a stimulus through distinct targets (e.g., a GPCR versus a RTK) might lead to identical or distinct DMR responses of a single type of cells. In other words, the DMR mediated by a stimulus through a specific target is an integrated and representative presentation of the interaction of numerous cell-signaling networks. Furthermore, the stimulus-induced cellular responses might also depend on cell conditions (e.g., proliferating versus quiescent states, or differentiating or non-differentiating, the state of cycles—G1 versus other states, etc.). In some cases, the cells attached on the sensor surface might have to be pre-treated in order to reach a desired state. For example, to study the activation of certain specific signaling pathways that are activated through stimulus-induced activation of certain targets and ultimately lead to cell growth and proliferation and/or differentiation, cells are preferably to be in a quiescent state. In order to reach quiescent state, cells at the proliferating state have to be pre-treated with a medium that has very little or not any growth factors or the like that stimulate cell growth and proliferation. A pre-treatment time is also critical to reach the desired state, because of the cellular function and dynamics.

Disclosed are methods that are specifically used to study the activation of cell signaling pathway(s) and its consequences, which require the pre-treatment of the cells to reach the quiescent state rather than the proliferating state. RTKs can be an example of this. In one embodiment, disclosed are methods for monitoring ligand binding and sequential signaling event in cells in real time, which comprises: (a) providing an optical-based label free biosensor; (b) placing cells having a receptor tyrosine kinase on the sensor surface; the cells are suspended in a medium containing certain concentration of serum which is required for the attachment and growth of the cells on the biosensor surface; (c) optionally starving the adherent cells in a medium containing no or low concentration of serum for certain time at 37° C.; (d) placing the biosensors having a layer of the cells into the detection system and monitoring the response; (e) optionally applying a buffer solution at least once into the cell medium for a certain amount of time; (f) optionally applying a solution containing a ligand to the RTK into the medium; and (g) monitoring the time dependent response of the layer of the adherent cells. The starvation treatment of the cells having a RTK is preferable for maximizing the cells response to ligands, because there are multiple growth factors found in serum. These growth factors include PDGF (platelet-derived growth factor), EGF, insulin, TGF-α, insulin-like growth factor I (IGF-I), and nerve growth factor (NGF). Medium with no or low concentrations (~0.5%) of serum or bovine serum albumin (BSA) can be used for starving the cells. The starvation time can typically involve an overnight starvation. It should be understood that such methods disclosed herein are not limited to RTK signaling studies; and can be applied to many other types of targets such as mitogenic GPCRs and their ligands.

In another embodiment, disclosed are methods for measuring or determining the expression level and cell—surface expression level of RTKs in cells, which comprises: (a) providing a microplate with multiple wells, each well having an optical-based label free biosensor embedded in the bottom; (b) providing multiple types of cells; (c) placing one type of cell suspended in a medium into at least one well; (d) culturing the cells in an appropriate medium for attachment and growth until a certain level of confluence is reached; (e) placing the microplate having biosensors, each biosensor covered by a layer of the cells into a detection system and monitoring the response; (f) applying a solution containing a ligand to the RTK into the medium; (g) monitoring and comparing the time dependent response of the layer of different types of cells. The different types of cells might require different growth medium. For same type of cells, different growth mediums can be applied for studying the effect of the medium on the cell surface expression level of the RTK of interest.

In another embodiment, disclosed are methods for determining the potency of ligands to RTKs using optical biosensors, which comprises: (a) providing a microplate with multiple wells, each well having an optical-based label free biosensor embedded in the bottom; (b) providing a certain number of cells having relatively high expression level of a RTK in a medium such that the cells become attached to each biosensor with a desired confluence; (c) exchanging the medium to starve the adherent cells for certain time; (d) placing the microplate having biosensors, each biosensor covered by a layer of the cells into a detection system and monitoring the response; (f) applying a solution containing a ligand at different concentrations into the medium covering each biosensor; (g) monitoring and comparing the dose- and time-dependent response of the cells. The dose-dependent binding and DMR signals as well as their corresponding kinetics can be used to determine the potency of ligands to the RTK of interest. It should be understood that such methods can also be used for determining the potency of an inhibitor against a downstream target that plays a significant role in the overall DMR signal due to the activation of the RTK or other signaling molecule, and subsequent cellular changes. For example, the EGF-induced DMR signal of quiescent A431 cells can be tuned or affected by downstream such as MEK1/2, or actin filament polyerization, or dynamin or receptor kinase activity, or upstream signaling molecules, such as certain GPCR agonists including carbachol. The potency of modulators that against targets can be also examined using their unique DMR signature or effect on the overall DMR signal obtained.

Also disclosed are methods to screen modulators that affect RTK signaling. The methods comprise: (a) providing an optical-based label free biosensor; (b) placing a certain number of cells having a RTK of interest in a medium to cover the biosensor such that the cells attach onto the surface of the biosensor; (c) monitoring the cell response using the biosensor; (d) applying a solution containing a compound at a certain concentration into the cell medium; (e) applying a solution containing a ligand to the RTK and continuously monitoring the time dependent response of the cells cultured on the biosensor.

(5) Assaying Cholesterol Transport

The correct intracellular distribution of cholesterol among cellular membranes is essential for many biological functions of mammalian cells, including signal transduction and membrane traffic. The prominent role of cholesterol in membrane trafficking is increasingly apparent. For example, depletion of plasma membrane-localized cholesterol inhibits clathrin-mediated endocytosis, but vesicular recycling seems unaffected. Since no direct measure of cholesterol is feasible, several indirect methods have been developed to study intracellular distribution of cholesterol and lipid signaling. Quenching emission from fluorescent sterols using membrane impermeant quenchers is used to determine the transbilyar distribution of cholesterol in plasma membranes. However, this approach is not ideal, in part because there may be quantitative differences in the properties of the fluorescent cholesterol analogs as compared with cholesterol. Furthermore, although cholesterol is poorly soluble in water, cholesterol can spontaneously desorb from membranes at an appreciable rate. Most often it will return to the same membrane, but it can also bind to whatever other hydrophobic binding sites are available.

The transport and distribution of newly synthesized cholesterol can be determined by introducing 3H-acetate into living cells and measuring the amount of 3H cholesterol in isolated membranes at different times. Radiolabeled cholesterol and cholesterol esters can be delivered by lipoproteins. Total cholesterol can be measured by direct chemical methods such as gas chromatography—mass spectrometry or by indirect methods such as assays based on cholesterol oxidase. In order for any of these methods of measuring cholesterol transport and distribution to be used, the various organelles of interest must be purified. It is generally quite difficult to obtain highly purified membrane fractions; and lengthy purification protocols may increase the risk of cholesterol transfer. These methods are most useful when organelles can be easily separated, as with the ER and the plasma membrane, but they can be very difficult to interpret when organelles such as endosomes and Golgi membranes are considered.

Filipin staining has been widely used to detect cholesterol in various membrane organelles in intact cells, due to that fact that this fluorescent detergent binds selectively to cholesterol but not to cholesterol esters. Filipin is a relatively weak fluorophore and can be detected by cooled charge-coupled device cameras. However, filipin staining can only provide qualitative information for cholesterol distribution, since its fluorescence intensity is not necessarily linearly related to cholesterol content. Another limitation is that cholesterol might redistribute during long incubations with filipin Thus, quantification of the intracellular cholesterol distribution from experiments using filipin is not possible.

Some specialized techniques, such as the cholesterol oxidase assay, have been developed to quantify cholesterol in the plasma membrane. This assay will overestimate the amount of cholesterol on the plasma membrane if the enzyme gains access to intracellular compartments (e.g., by endocytosis in living cells or by membrane breakage) or if cholesterol moves to the plasma membrane during the assay. While many methods have been developed to measure cholesterol distribution in cells, all of them are subject to various degrees of uncertainty in their interpretation. It is therefore necessary to compare results obtained by several different methods in order to get a reliable analysis of intracellular cholesterol distribution.

Cholesterol not only can be transported from one location or compartment to another in cells. It can also be excreted to outside the cells using a process called reverse cholesterol transport. The first step in reverse cholesterol transport is the efflux of free cholesterol from the plasma membrane of peripheral cells to an extracellular acceptor. This movement of cholesterol is governed by both cellular and extracellular factors. Many studies have focused on the extracellular acceptors of cellular cholesterol, specifically how modifications of these acceptors can positively enhance cholesterol efflux. It is generally believed that reverse cholesterol transport is mediated by high-density lipoprotein (HDL). With phospholipid-containing acceptors such as HDL, the rate-limiting step is the desorption of cholesterol molecules from the plasma membrane.

There are at least two pathways by which cholesterol can be removed from peripheral cells. Cholesterol acceptors, which already contain phospholipids, such as HDL particles or PL-apoA-1 disks, can remove cholesterol by diffusion via a concentration gradient between the membrane cholesterol donor and acceptor particle. The aqueous diffusion model is therefore a bi-directional mass transport model, which does not require the acceptor particle to bind or penetrate the cellular plasma membrane. The level of expression of the scavenger receptor B type 1 (SR-B1) is correlated with rates of cholesterol efflux to HDL or phospholipid particles. The ability of SR-B1 to stimulate cholesterol efflux appears independent of receptor-ligand binding and may reflect effects on the organization of membrane cholesterol domains that facilitate aqueous diffusion of cholesterol to acceptor particles.

Alternatively, lipid-poor cholesterol acceptors such as apoA-1 interact directly with the plasma membrane, simultaneously abstracting both cholesterol and phospholipid. Cholesterol efflux to lipid-free apoA-1 is largely dependent on expression of the ATP binding cassette transporter A1 (ABCA1). While its importance in apoA-1 mediated cholesterol efflux is clear, the exact function of ABCA1 in cholesterol export remains controversial, with recent studies suggesting roles as an apoA-1 receptor, an intracellular cholesterol transporter or in inducing modifications to membrane lipid distribution that favor apoA-1 docking at the cell surface.

The disclosed methods can be used to assay cholesterol transport and to, for example, screen for molecules that effect cholesterol transport, such as effluxing and uptake. FIG. 26 shows an example of a method to screen modulators that interfere with cholesterol effluxing. This method is based on the measurement in real time of the effect of compounds on cholesterol effluxing. Depletion of cholesterol content on cell surface or intracellular pool results in the disappearance of microvilli located in the cell surface, resulting in the flatness of cells adherent on a surface. The flatness of cells leads to a positive DMR phase with increased signal. Based on this biological effect, we use reagents, as markers, that can either extract cholesterol from the cell surface (e.g., methyl-beta-cyclodextrin (mβCD), or high density lipoproteins (HDLs)), or bind or sequester cholesterol on the cell surface (e.g., saponin at relatively low concentrations). The changes obtained using optical biosensors can be used as an indicator of modulators that interfere with the cholesterol effluxing. FIG. 27 provides a schematic of a cholesterol pathway.

The results in FIG. 28 showed that mβCD treatment of both A431 and HeLa cells gave rise to similar time-dependent responses obtained using LID biosensors. The difference between these two cell types is due to the distinct cholesterol content associated with the cell surface. The pretreatment of A431 cells with EGF significantly suppressed the mβCD-induced response. This is because the binding of EGF to EGFRs located at the cell surface results in a significant endocytosis of the receptor; and the receptor endocytosis causes the reduction of cell surface cholesterol content. Similarly, the pretreatment of A431 cells with H7, a protein kinase A, C and G inhibitor, also led to the suppression of the mβCD-induced response. This is because protein kinase is a critical regulator of cholesterol content on the cell surface.

(6) Assaying Reactive Species Signaling and Cell Redox States

Molecular oxygen (dioxygen; $O_2$) is essential for the survival of all aerobic organisms. Aerobic energy metabolism is dependent on oxidative phosphorylation, a process by which the oxidoreduction energy of mitochondrial electron transport (via a multicomponent NADH dehydrogenase enzymatic complex) is converted to the high-energy phosphate bond of ATP. $O_2$ serves as the final electron acceptor for cytochrome-c oxidase, the terminal enzymatic component of this mitochondrial enzymatic complex, which catalyzes the four-electron reduction of $O_2$ to $H_2O$. Partially reduced and highly reactive metabolites of $O_2$ may be formed during these (and other) electron transfer reactions. These $O_2$ metabolites include superoxide anion ($O_2$.) and hydrogen peroxide ($H_2O_2$), formed by one- and two-electron reductions of $O_2$, respectively. In the presence of transition metal ions, the even more reactive hydroxyl radical (OH.) can be formed. These partially reduced metabolites of $O_2$ are often referred to as "reactive oxygen species" (ROS) due to their higher reactivities relative to molecular $O_2$.

ROS have dual impacts on the cellular functions. ROS are initially considered as toxic by-products of metabolism with the potential to cause damage to lipids, proteins, and DNA. To protect against the potentially damaging effects of ROS, cells possess several antioxidant enzymes such as superoxide dismutase (which reduces $O_2$. to $H_2O_2$), catalase, and glutathione peroxidase (which reduces $H_2O_2$ to $H_2O$). Thus oxidative stress may be broadly defined as an imbalance between oxidant production and the antioxidant capacity of the cell to prevent oxidative injury. Oxidative stress has been implicated in a large number of human diseases including atherosclerosis, pulmonary fibrosis, cancer, neurodegenerative diseases, and aging.

Although ROS are generally considered to be toxic by-products of respiration, recent evidence suggests that the production of ROS might be essential participants in cell signaling and regulation. In mammalian cells, a variety of extracellular stimuli have been shown recently to induce a transient increase in the intracellular concentration of ROS, and specific inhibition of the ROS generation results in a complete blockage of stimulant-dependent signaling. The downstream effect of ROS production is the more or less reversible oxidation of proteins. Thiols, by virtue of their ability to be reversibly oxidized, are recognized as key targets of oxidative stress. Redox-sensitive proteins, which include protein tyrosine phosphatases (PTPs) as the active site cysteine, are the target of specific oxidation by various oxidants, including $H_2O_2$, and this modification can be reversed by intracellular reducing agents. The inhibition exerted by ROS on PTPs helps the propagation of receptor tyrosine kinase (RTK) signals mediated by protein tyrosine phosphorylation, generally associated with the proliferative stimulus.

The apparent paradox in the roles of ROS as essential biomolecules in the regulation of cellular functions and as toxic by-products of metabolism may be, at least in part, related to differences in the concentrations of ROS produced. When cellular production of ROS overwhelms its antioxidant capacity, damage to cellular macromolecules such as lipids, protein, and DNA may ensue.

The high reactivity and relative instability of ROS make them extremely difficult to detect or measure in biological systems. Thus assessments of ROS and free radical generation have largely been made by indirect measurement of various end products resulting from the interaction of ROS with cellular components such as lipids, protein, or DNA. Most methods for identification of specific ROS are based on reactions with various "detector" molecules (e.g., fluorogenic, chemiluminescent or chromogenic probes) that are oxidatively modified to elicit luminescent or fluorescent signals. Such methods could be complicated by the possibility of having multiple forms of reactive oxygen in the same cell. In addition, the nitric oxide radical may produce the same changes in the optical properties of the probe as do other reactive oxygen molecules. Quantitative analysis is also difficult because of: 1) the high intracellular concentration of glutathione, which can form thiyl or sulfinyl radicals or otherwise trap or reduce oxygen species; 2) the variable concentration of metals, which can either catalyze or inhibit radical reactions; and 3) the presence of other free radical-quenching agents such as spermine.

Disclosed are the methods to monitor in real time the effect of compounds on the $H_2O_2$-induced dynamic mass redistribution (DMR) in living cells. To study the ROS signaling, a wide array of well-known and specific modulators for various cellular targets was used to pretreat the cells for certain time (typically one hour). The ROS signaling networks then can be mapped out according to the effect of the modulators on the $H_2O_2$-induced DMR signals. To screen compounds that modulate the cellular redox states, cells are pretreated with compounds for long periods of time (typically overnight to days). The effect of compounds on the cellular redox states can be examined by the $H_2O_2$-mediated DMR signals.

Unlike all the existing assay technologies for ROS signaling and redox state, the present invention provides a label-free and real time method to screen modulators that interfere with the ROS signaling and its network interactions. The present invention also extends the applications of optical biosensor-based cell sensing.

Cellular production of ROS occurs from both enzymatic and nonenzymatic sources. Any electron-transferring protein or enzymatic system can result in the formation of ROS as "by-products" of electron transfer reactions. The enzymatic sources include:

(i) Cell metabolism in mitochondria. The generation of ROS in mitochondria accounts for ~1-2% of total $O_2$ consumption under reducing conditions. Due to high concentrations of mitochondrial SOD, the intra-mitochondrial concentrations of $O_2$. are maintained at very low steady-state levels, and is unlikely to escape into the cytoplasm. The potential for mitochondrial ROS to mediate cell signaling has gained significant attention in recent years, particularly with regard to the regulation of apoptosis. It has also been suggested that the mitochondria may function as an "$O_2$ sensor" to mediate hypoxia-induced gene transcription.

(ii) Lipid and protein biosynthesis in endoplasmic reticulum (ER). ER is another membrane-bound intracellular organelle that is primarily involved in lipid and protein biosynthesis. Smooth ER (lacking bound ribosomes) contains enzymes including cytochrome P-450 that catalyze a series of reactions to detoxify lipid-soluble drugs and other harmful metabolic products. cytochrome P-450 can oxidize unsaturated fatty acids and xenobiotics and reduce molecular $O_2$ to produce $O_2$. and/or $H_2O_2$.

(iii) ROS from nuclear membranes. Nuclear membranes contain cytochrome oxidases and electron transport systems that resemble those of the ER but the function of which is unknown. It has been postulated that electron "leaks" from these enzymatic systems may give rise to ROS that can damage cellular DNA in vivo.

(iv) $H_2O_2$ generation in peroxisomes. Peroxisomes are an important source of total cellular $H_2O_2$ production. They contain a number of $H_2O_2$-generating enzymes including glycolate oxidase, D-amino acid oxidase, urate oxidase, L—hydroxyacid oxidase, and fatty acyl-CoA oxidase. Peroxisomal catalase utilizes $H_2O_2$ produced by these oxidases to oxidize a variety of other substrates in "peroxidative" reactions. These types of oxidative reactions are particularly important in liver and kidney cells in which peroxisomes detoxify a variety of toxic molecules (including ethanol) that enter the circulation. Another major function of the oxidative reactions carried out in peroxisomes is oxidation of fatty acids, which in mammalian cells occurs in mitochondria and peroxisomes. Only a small fraction of $H_2O_2$ generated in these intracellular organelles appears to escape peroxisomal catalase.

(v) ROS from soluble enzymes. Soluble enzymes such as xanthine oxidase, aldehyde oxidase, dihydroorotate dehydrogenase, flavoprotein dehydrogenase and tryptophan dioxygenase can generate ROS during catalytic cycling.

(vi) ROS from small molecules. Auto-oxidation of small molecules such as dopamine, epinephrine, flavins, and hydroquinones can be an important source of intracellular ROS production. In most cases, the direct product of such autooxidation reactions is $O_2$.

(vii) ROS from plasma membrane associated enzymes. Plasma membrane-associated oxidases (e.g., phagocytic NADPH oxidase) have been implicated as the sources of most growth factor- and/or cytokine-stimulated oxidant production, although the precise enzymatic sources have yet to be fully characterized.

(viii) ROS from signaling. A variety of cytokines and growth factors that bind receptors of different classes have been reported to generate ROS in cells.

(ix) ROS from environment. Exogenous ROS can also be introduced in living cells. For example, exogenous $H_2O_2$ is capable of diffusing across the plasma membrane into the cells.

ROS regulates a large number of signaling pathways at multiple levels from receptor to nucleus. Cellular targets, although less clear, have been identified and broadened over the past decade. Receptor kinases and phosphatases may be targets of oxidative stress. Growth factor receptors are most commonly activated by ligand-induced dimerization or oligomerization that autophosphorylates its cytoplasmic kinase domain. Ligand-independent clustering and activation of receptors in response to ultraviolet light have also been well demonstrated, and this effect appears to be mediated by ROS. Exogenous $H_2O_2$ (usually in the millimolar range) has been shown to induce tyrosine phosphorylation and activation of the PDGF-, PDGF-, and EGF receptors. Lysophatidic acid-induced transactivation of the EGF receptor appears to be mediated by the intermediate formation of ROS. Because most growth factors and cytokines appear to generate ROS at or near the plasma membrane, phospholipid metabolites are potentially important targets for redox signaling. For example, the oxidized forms of diacylglycerol were more effective in activating PKC than its nonoxidized forms. In addition, PKC activation and protein tyrosine phosphorylation appear to be required for $H_2O_2$-induced PLD activation in endothelial cells and fibroblasts. Non-RTKs belonging to the Src family (Src kinases) and Janus kinase (JAK) family are also targets, at least, for exogenously added oxidants.

The ROS signaling also is able to trigger changes in intracellular $Ca^{2+}$ in a number of cell types including smooth muscle cells. Furthermore, the ROS signaling can participate in MAPK pathway. Exogenous oxidants can activate the ERK MAPK pathway. The mechanism(s) for this effect is unclear, and the precise molecular target(s) is unknown. Some studies suggest that ROS-mediated ERK activation may be an upstream event at the level of growth factor receptors, Src kinases, and/or p21Ras. Another potential mechanism for this effect may be oxidant-induced inactivation of protein tyrosine phosphatases (PTPs) and/or protein phosphatase A.

There are many other intracellular targets that have been identified as oxidation responsive molecules. These targets include NF-kB (a transcription factor that regulates the expression of a number of genes involved in immune and inflammatory responses), activator protein-1 (AP-1) (a transcriptional complex formed by the dimerization of Fos-Jun or Jun-Jun proteins), and other transcription factors in which DNA binding is regulated by similar redox mechanisms such as Sp-1, c-Myb, p53 and egr-1.

The ROS signaling primarily involves two general mechanisms of action: 1) alterations in intracellular redox state and 2) oxidative modifications of proteins.

In one embodiment, the present invention provides methods for the use of an optical biosensor to screen compounds that can interfere with the ROS signaling. The method involves the use of hydrogen peroxide as exogenous ROS to mediate mass redistribution within the bottom portion of cultured cell layer. The method comprise the following steps: Providing an optical label independent detection (LID) biosensor being capable of multi-optical output parameter measurements; Culturing cells onto the surface of the biosensor; Applying a modulator solution to the cells; Applying an exogenous reactive oxygen species solution to the cells; Monitoring said optical output parameters. The said modulator is selected from a pool of well-characterized modulators of cellular targets. The said modulator solution is applied and incubated for short period of time with said cells (e.g., 30 min, 60 min, 1 hr, 3 hrs, 6 hrs, 24 hrs, 2 days, 3 days, 5 days, etc). The said reactive oxygen species is hydrogen peroxide.

6. Additions to Label Free Cell Assays a) Two Part Assays Using Label Free Biosensors in Conjunction with Labeling Technology The disclosed label free biosensor cell based assays can also be used in conjunction with conventional label technologies (e.g. fluorescence) to provide multiparametric information on biological samples.

Label independent detection includes a suite of technologies that measure biomolecular events in a manner that does not require any of the analytes to be labeled. The two most popular technologies are based on mass spectroscopy (MS) and measurements of changes in refractive index (RI) using techniques such as surface plasmon resonance (SPR) or grating coupled waveguides as discussed herein. Disclosed herein is a system containing an instrument coupled to a optical biosensor containing dielectric coated optical gratings for simultaneous measurements of changes in refractive index and fluorescence (confocal or evanescent field).

While RI based label independent detection (RILID) methods offer significant advantages relative to labeled technologies, a limitation is that the event cannot be directly correlated to a particular species. For example, unlike fluorescence, binding of the desired protein and some undesirable protein qualitatively offer the same "type" of signal (change in index). The label free detection method itself is therefore non-specific in nature. To offset this ambiguity, RILID methods have been coupled to MS to enable the identification of the bound species.

RILID measurements can be made in real time, and is typically focused by its ability to typically detect events within ~200 nm or less of the substrate surface and lateral resolution of ~10 µm. Fluorescence enables the labeling of multiple species (with different fluorescent dyes or particles), and can be used in the evanescent mode (using total internal reflectance fluorescence or grating coupled waveguides) which enables detection within ~200 nm or the confocal mode which enables detection within ~10 µm, and has excellent lateral resolution (down to ~300 nm in the far field or <100 nm in the near field). Disclosed is the use of RILID as another "channel" for bio-detection using a combination of the two technologies, label free biosensors and labeling, both of which share time and space resolution but one which is species specific in nature (labeling, i.e. fluorescence) and one that is species non-specific in nature (label free biosensors, RILID). This combination is inherently powerful as it enables one to dissect complex bio-detection events such as those encountered while studying biological pathways within cells.

For example, the binding of a ligand to a receptor (e.g. a GPCR) can induce cellular cascades that may result in a complex change in refractive index profile with time. One or more of these cascades can be probed by fluorescence using different reporter systems or labeling at the cellular, organelle (e.g. using organelle specific dyes to probe the ER, Golgi, or nucleus), protein (e.g. translocation of GFP-(β-arrestin) or DNA level (gene expression using fluorescence in-situ hybridization, FISH). Correlation of the LID signal to multi-color fluorescence in time and space can offer vital clues about the pathway. Moreover, certain fluorescent reporters and/or labels are often mutually incompatible. The disclosed methods allow analysis of the correlation and can enable assay development such that the need for one or more fluorescent reporters is removed because that information is available through RILID.309. Disclosed are multimode detection systems utilizing planar waveguide-based biosensors. This system not only monitors the refractive index changes, indicated by changes in wavelength or angle of reflected lights induced by a net change in bio-mass upon binding and subsequent activation and cellular responses, but also changes in fluorescence (or chemiluminescence, bioluminescence, phosphorescence or electro-luminescence, etc). Also provided are detection systems that provide ultra-high content assays for use in drug discovery and fundamental research.

Current bioanalytical techniques are typically uniparametric in nature. As a result, outputs from multiple different assays are iteratively put together to guide decisions about drug discovery (or diagnosis). This process can be both time consuming and misleading. Multiparametric detection seeks to obtain information on several fronts using combinations of analytical techniques that provide clues about multiple steps in a pathway (or multiple pathways) and their modulation by potential drug compounds. Multiparametric detection is distinct from multiplexing in that multiplexing implies the simultaneous detection of binding to or activation of multiple biological species using one technique (or combinations, e.g. combinations of radioactive and fluorescent labels) to monitor the same step in the pathway. Multiparametric detection, in conjunction with multiplexed assays (e.g. reverse transfection arrays) offer the possibility of multiple types of information on multiple samples simultaneously. Grating coupled waveguides are uniquely advantageous in terms of a platform for multiparametric detection by enabling both RILID and fluorescence.

III. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular receptor is disclosed and discussed and a number of modifications that can be made to a number of molecules including the receptor are discussed, specifically contemplated is each and every combination and permutation of receptor and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed in herein or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, the disclosed cells, are also disclosed. Thus, the products produced using the combinatorial or screening approaches that involve the disclosed compositions, such as, the disclosed cells, are also considered herein disclosed.

It is understood that the disclosed methods for identifying molecules as discussed herein can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Oligonucleotide molecules with a given function, catalytic or ligand-binding, can be isolated from a complex mixture of random oligonucleotides in what has been referred to as "in vitro genetics" (Szostak, TIBS19:89, 1992). One synthesizes a large pool of molecules bearing random and defined sequences that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interactive processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, the disclosed cells, are also disclosed. Thus, the products produced using the molecular modeling approaches that involve the disclosed compositions, such as, the disclosed cells, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57 (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

2. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

IV. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant GA (1992) Synthetic Peptides: A User Guide. W. H. Freeman and Co., N.Y. (1992); Bodansky M. and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed. Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

V. Methods of Using the Compositions

1. Methods of Using the Compositions as Research Tools

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

VI. Illustrations of Certain Embodiments

Disclosed is a method to test a stimulatory event's effect on a cell comprising providing a label free biosensor, culturing a cell on the biosensor, providing a stimulatory event to the cultured cell, collecting biosensor output data from the biosensor.

Also disclosed is a method to screen compounds that affect cell viability or proliferation based on inhomogeneity of cells on the surface of a biosensor.

A method to screen modulators that affect a stimulatory event's effect on a cell comprising providing a label free biosensor, culturing a cell on the biosensor, incubating with a solution containing a compound for a specific and predetermined time, providing a stimulatory event to the cultured cell, collecting biosensor output data from the biosensor.

Also disclosed is a method for analyzing a cell comprising providing a detection system, provide a plurality of biosensors, placing cells in medium, culturing the cells on the biosensor to a confluency of at least 70%, applying a compound solution, measuring the angle or wavelength of incidence that coupling in the biosensor occurs, wherein, the measurement occurs in less than 10 minutes.

Also disclosed is a method for monitoring a compound toxicity, comprising: (a) providing an optical-based label free biosensor; (b) placing a cell in a medium, wherein the cell attaches onto the surface of the biosensor; (c) applying a solution containing a compound into the cell medium; (d) and monitoring the response of the cells cultured on the biosensor.

Also disclosed is a method for monitoring the effect of a compound on a cell comprising, (a) incubating the cell with the compound, wherein the cell is attached to a label free biosensor, (b) identifying the effect the compound has on the cell, wherein the step of identifying comprises observing and analyzing the output of the label free biosensor.

Also disclosed is a method for monitoring the effect of a compound on a cell comprising, (a) incubating the cell with the compound, wherein the cell is attached to a label free biosensor, (b) identifying the effect the compound has on the cell, wherein the step of identifying comprises observing the output of the label free biosensor, and wherein the output is compared to a signature output.

Also disclosed is a method for monitoring the compound adsorption and toxicity in real time, comprising the steps: (a) providing an optical-based label free biosensor; (b) placing a certain number of cells in a medium to cover the biosensor such that the cells attach onto the surface of the biosensor; (c) applying a solution containing a compound into the cell medium; (e) and monitoring the time dependent response of the cells cultured on the biosensor.

Also disclosed is a method of identifying a state of a cell, the method comprising the steps, (a) culturing the cell on a surface of a biosensor forming a cell-biosensor composition, (b) assaying the cell-biosensor composition, wherein the step of assaying comprises identifying an inhomogeneity of the surface where the cell is cultured.

Also disclosed is a method for high throughput screening of compound toxicity on cells using a biosensor, comprising the steps of: (a) providing a biosensor; (b) placing cells into each well to cover the biosensor such that the cells attach and reach high confluency onto the surface of the biosensor; (c) applying a compound solution into the cell medium of each well; (d) collecting optical waveguide lightmode spectra at a certain time, (e) comparing the PWHM of each compound with a control well wherein the cells are not exposed to any compound, wherein the toxicity of compounds can be evaluated using a single data point.

Also disclosed is a method to evaluate compound toxicity comprising, (a) providing an optical based label free biosensor attached to a microplate with wells; (b) placing cells into each well along with a cell medium, wherein the cells cover the biosensor such that the cells attach onto the surface of the biosensor; (c) applying a compound solution into the cell medium of each well; (d) collecting images of a $TM_0$ mode resonance angular band of the whole sensor area of each well at a designated time.

Also disclosed is a method for high throughput screening of a compound for the compound's effect on cell proliferation using optical biosensors, comprising (a) providing a biosensor; (b) bringing a cell in contact with the biosensor forming a cell-biosensor composition such that after a period of time for cell growth the cell confluency reaches 45%-55%, (c) incubating the compound with the cell-biosensor composition, forming a compound-cell-biosensor complex, (d) collecting the output of the biosensor, (d) obtaining a PWHM from the output, (e) comparing the PWHM of each compound-cell-biosensor complex with a control wherein the cell-biosensor composition is not exposed to the compound, wherein a decrease in the PWHM indicates the compound has an effect on the cell.

Also disclosed is a method for monitoring ligand binding and a sequential signaling event in cells in real time, which comprises: (a) providing an optical-based label free biosensor; (b) placing cells having a receptor tyrosine kinase (RTK) on the sensor surface; the cells are suspended in a medium containing certain concentration of serum which is required for the attachment and growth of the cells on the biosensor surface; (c) optionally incubating the cells with a medium without serum or other growth factors, or without any serum or other growth factors for overnight in order to reach quiescent states of the cells; (d) placing the biosensors having a layer of the cells into the detection system and monitoring the response; (e) monitoring the time dependent response of the layer of the adherent cells before and after addition of a solution containing a stimulus or sequential addition of two solutions, the first one containing a compound and the second one containing a ligand or marker, separated by a specific period of time.

Also disclosed is a method for measuring or determining the expression level and cell-surface expression level of receptor tyrosine kinases (RTK) in cells, which comprises: (a) providing a microplate with multiple wells, each well having an optical-based label free biosensor embedded in the bottom; (b) providing multiple types of cells; (c) placing one type of cell suspended in a medium into at least one well; (d) culturing the cells in an appropriate medium for attachment and growth until a certain level of confluence is reached; (e) placing the microplate having biosensors, each biosensor covered by a layer of the cells into a detection system and monitoring the response; (f) applying a solution containing a ligand to the RTK into the medium; (g) monitoring and comparing the time dependent response of the layer of different types of cells.

Also disclosed is a method for determining the potency of ligand's to an RTK which comprises: (a) providing a microplate with multiple wells, each well having an optical-based label free biosensor embedded in the bottom; (b) providing a certain number of cells having relatively high expression level of an RTK in a medium such that the cells become attached to each biosensor with a desired confluence; (c) exchanging the medium to starve the adherent cells for certain time; (d) placing the microplate having biosensors, each biosensor covered by a layer of the cells into a detection system and monitoring the response; (f) applying a solution containing a ligand at different concentrations into the medium covering each biosensor; (g) monitoring and comparing the dose- and time-dependent response of the cells.

Also disclosed is a method for screening modulators that affect receptor tyrosine kinase (RTK) signaling comprising: (a) providing an optical-based label free biosensor; (b) placing a certain number of cells having a RTK of interest in a medium to cover the biosensor such that the cells attach onto the surface of the biosensor; (c) monitoring the cell response using the biosensor; (d) applying a solution containing a compound at a certain concentration into the cell medium; (e) applying a solution containing a ligand to the RTK and continuously monitoring the time dependent response of the cells cultured on the biosensor.

Also disclosed is a method for analyzing cytoskeleton arrangement in cells the method comprising providing an optical label independent detection (LID) biosensor and monitoring release of bio-materials from cells adherent on a surface of the optical LID biosensor.

Also disclosed is a method for analyzing cytoskeleton rearrangement comprising, providing the optical LID biosensor; placing the living cells in a cell medium to cover the optical LID biosensor so the living cells are able to attach to the surface of the optical LID biosensor; applying a solution containing a pore-forming reagent into the cell medium located on the surface of the optical LID biosensor; and interrogating the optical LID biosensor to obtain a time dependent optical response which indicates the loss of biomaterials from the cells.

Also disclosed is a method of analyzing cytoskeleton structure comprising providing the optical LID biosensor; placing living cells in a cell medium to cover the optical LID biosensor so the living cells are able to attach to the surface of the optical LID biosensor; applying a solution containing a compound into the cell medium located on the surface of the optical LID biosensor; applying a solution containing a pore-forming reagent solution into the cell medium located on the surface of the optical LID biosensor; and interrogating the optical LID biosensor to obtain a time dependent optical response which indicates the loss of biomaterials from the cells that enables one to screen modulators capable of interfering with the cytoskeleton structure within cells.

Also disclosed is a method of analyzing cytoskeleton structure comprising providing the optical LID biosensor; placing the living cells in a cell medium to cover the optical LID biosensor so the living cells are able to attach to the surface of the optical LID biosensor; applying a solution containing a pore-forming reagent solution into the cell medium located on the surface of the optical LID biosensor; applying a solution containing a compound into the cell medium located on the surface of the optical LID biosensor; and interrogating the optical LID biosensor to obtain a time dependent optical response which indicates the loss of biomaterials from the cells that enables one to screen modulators capable of interfering with the cytoskeleton structure within cells.

Disclosed are methods to test the effect of a stimulatory event on a cell comprising providing a label free biosensor, incubating a cell on the biosensor, providing a stimulatory event to the incubated cell, collecting biosensor output from the biosensor.

Also disclosed are methods of identifying a state of a cell, the method comprising culturing the cell on a surface of a label free biosensor forming a cell-biosensor composition, and assaying the cell-biosensor composition, wherein the assaying comprises identifying an inhomogeneity of the surface where the cell is cultured.

Also disclosed are methods that can include methods wherein incubating a cell involves culturing the cell, wherein a stimulatory effect is identified from the biosensor output.

Also disclosed are methods that can include methods wherein the cell is cultured to 20-99% confluency, wherein the cell is cultured to 30-80% confluency, wherein the cell is cultured to 40-65% confluency, wherein the cell is cultured to 70-99% confluency, and wherein the cell is cultured to 80-95% confluency.

Also disclosed are methods that can include methods wherein the cell is an adherent cell, wherein the cell is in contact with the biosensor, wherein the cell attaches to the biosensor.

Also disclosed are methods that can include, wherein the stimulatory event comprises adding a compound to the cell culture, wherein the compound modulates a cell signaling pathway of the cell, wherein the modulation activates the cell signaling pathway, wherein the modulation suppresses the cell signaling pathway, wherein the compound modulates a cell surface receptor on the cell, wherein the compound is an agonist of the receptor, and wherein the compound is an antagonist of the receptor.

Also disclosed are methods that can include methods wherein the cell surface receptor is an ion channel, a receptor tyrosine kinase, a cytokine receptor, an integrin receptor, a $Na^+/H^+$ exchanger receptor, or an immune receptor, wherein the cell surface receptor is a G protein coupled receptor (GPCR), Epidermal growth factor receptor, (EGFR), Platelet derived growth factor receptor (PDGFR), Fibroblast growth factor receptor (FGF), or Vascular endothelial growth factor receptor (VEGFR), wherein the compound modulates a cytoskeleton component within the cell, wherein the compound destabilizes the cytoskeleton structure, wherein the compound stabilizes the cytoskeleton structure, wherein the compound modulates an intracellular enzyme, an intracellular kinase, an intracellular organelle, an intracellular protein, or an extracellular matrix, wherein the compound is added in a compound solution.

Also disclosed are methods that can include further comprising determining if the compound is toxic to the cell.

Also disclosed are methods that can include methods wherein a plurality of compounds are tested to screen for compounds that are toxic to the cell, wherein the level of toxicity of the compound is monitored via the biosensor output.

Also disclosed are methods that can include, wherein the cell is monitored via the biosensor output for an effect of the compound.

Also disclosed are methods that can include methods wherein absorption of the compound is monitored via the biosensor output.

Also disclosed are methods that can include methods wherein the biosensor can penetrate the cell to a depth of 100 nm, wherein the biosensor can penetrate the cell to a depth of 100 nm, 200 nm, 300, or 500 nm, wherein the biosensor can receive data from multiple depths of penetration within the cell, wherein the depths of penetration are up to 500 nm.

Also disclosed are methods that can include methods wherein the state of the cell is identified using the biosensor output.

Also disclosed are methods that can include further comprising determining if the stimulatory event affects cell viability or proliferation.

Also disclosed are methods that can include methods wherein a plurality of compounds are tested to screen for compounds that are toxic to the cell, wherein the effect of the compound on the cell is monitored, wherein the compound is an anticancer compound.

Also disclosed are methods that can include methods wherein collecting biosensor output from the biosensor comprises collecting a biosensor output parameter.

Also disclosed are methods that can include methods wherein the biosensor output parameter is a parameter related to the kinetics of the biosensor output.

Also disclosed are methods that can include methods wherein the biosensor output parameter comprises analyzing the overall kinetics of the biosensor output, wherein the analyzing of the overall kinetics comprises analyzing the rate of change from one phase to another phase at the completion of a phase transition, wherein the analyzing of the overall kinetics comprises analyzing the length of time it takes to complete output of the biosensor output, wherein the analyzing of the overall kinetics comprises analyzing the length of time for which an overall phase of the output of the biosensor output takes, wherein the analyzing of the overall kinetics comprises analyzing the total duration of a P-DMR phase, wherein the analyzing of the overall kinetics comprises analyzing the total duration of an N-DMR phase, wherein the analyzing of the overall kinetics comprises analyzing the rate for attaining the total amplitude of the P-DMR, wherein the analyzing of the overall kinetics comprises analyzing the rate for attaining the total amplitude of the N-DMR, wherein the analyzing of the overall kinetics comprises analyzing the rate to go from a N-DMR to a P-DMR, wherein the analyzing of the overall kinetics comprises analyzing the transition time t from a P-DMR phase to a N-DMR phase, a net-zero phase to a P-DMR phase, a net-zero to a N-DMR phase, a net-zero to a P-DMR phase, a P-DMR phase to a net-zero phase, a N-DMR phase to a net zero, or a P-DMR to a net-zero.

Also disclosed are methods that can include methods wherein the biosensor output parameter comprises analyzing the phases of the biosensor output, wherein the analyzing the phases comprises analyzing a phase transition, wherein the analyzing the phases comprises analyzing a Positive-Directional Mass Redistribution (P-DMR) signal, wherein the analyzing the phases comprises analyzing a Negative-Directional Mass Redistribution (N-DMR) signal, wherein the analyzing the phases comprises analyzing a net-zero Directional Mass Redistribution (net-zero DMR), wherein the analyzing the phases comprises analyzing the shape of a Positive-Directional Mass Redistribution (P-DMR) signal, wherein the analyzing the phases comprises analyzing the amplitude of a Positive-Directional Mass Redistribution (P-DMR) signal, wherein the analyzing the phases comprises analyzing the shape of a Negative-Directional Mass Redistribution (N-DMR) signal, and wherein the analyzing the phases comprises analyzing the amplitude of a Negative-Directional Mass Redistribution (N-DMR) signal.

Also disclosed are methods that can include methods wherein the biosensor output parameter comprises the overall dynamics of the biosensor output, wherein the analyzing overall dynamics comprises analyzing the shape of the complete curve produced by the biosensor output.

Also disclosed are methods that can include methods wherein the biosensor output parameter is a parameter related to the resonant peak.

Also disclosed are methods that can include methods wherein the biosensor output parameter comprises analyzing the intensity of the light versus the angle of incidence at which the light is coupled into the biosensor.

Also disclosed are methods that can include methods wherein the biosensor output parameter comprises analyzing the intensity of the light versus the wavelength of light at which the light is coupled into the biosensor.

Also disclosed are methods that can include methods wherein the biosensor output parameter comprises analyzing the peak position.

Also disclosed are methods that can include methods wherein analyzing the peak position comprises analyzing the position of the half maximal peak intensity occurring before the position of the maximal intensity.

Also disclosed are methods that can include methods wherein analyzing the peak position comprises analyzing the position of the half maximal peak intensity occurring after the position of the maximal intensity.

Also disclosed are methods that can include methods wherein the biosensor output parameter comprises analyzing the intensity of a point on the resonant peak.

Also disclosed are methods that can include methods wherein analyzing the intensity of the resonant peak comprises analyzing the intensity of the maximal intensity.

Also disclosed are methods that can include methods wherein analyzing the intensity of the resonant peak comprises analyzing the intensity of the half maximal peak intensity that occurs on the resonant peak prior to the peak intensity.

Also disclosed are methods that can include methods wherein analyzing the intensity of the resonant peak comprises analyzing the intensity of the half maximal peak intensity that occurs on the resonant peak after the peak intensity.

Also disclosed are methods that can include methods wherein the method further comprises collecting a second biosensor output parameter.

Also disclosed are methods that can include methods wherein the second biosensor output parameter comprises analyzing peak position.

Also disclosed are methods that can include methods wherein the biosensor output parameter comprises analyzing the peak shape.

Also disclosed are methods that can include methods wherein analyzing the peak shape comprises determining the area beneath the resonant peak.

Also disclosed are methods that can include methods wherein the area beneath the resonant peak only includes the area above a line drawn between the half maximal intensity points occurring on the resonant peak.

Also disclosed are methods that can include methods wherein analyzing the peak shape comprises analyzing the width of the resonant peak at the half maximal intensity points.

Also disclosed are methods that can include methods wherein the biosensor output parameter is a parameter related to the resonant band image.

Also disclosed are methods that can include methods wherein the resonant band image is obtained by illuminating the biosensor with a light spot across the biosensor and imaging in-coupled light intensity distribution across the biosensor.

Also disclosed are methods that can include methods wherein the in-coupled light intensity distribution is imaged with a CCD camera.

Also disclosed are methods that can include methods wherein the parameter related to the resonant band image is the band shape, the band position, the band intensity, or the light intensity distribution.

Also disclosed are methods that can include methods wherein the peak width at half maximum (PWHM) in combination with the position of the maximum intensity are analyzed.

Also disclosed are methods that can include further comprising incubating the cultured cell with a compound.

Also disclosed are methods that can include further comprising determining if the compound affects the effect of the stimulatory event on the cell.

Also disclosed are methods that can include further comprising determining the affect of the compound on the effect of the stimulatory event on the cell.

Also disclosed are methods that can include methods wherein one or more additional compounds are screened to determining if the compounds affect the effect of the stimulatory event on the cell.

Also disclosed are methods that can include methods wherein biosensor output is collected for less than 10 minutes, and wherein biosensor output is collected for less than 5 minutes, 1 minute, 30 seconds, 10 seconds, 5 seconds, or 1 second.

Also disclosed are methods that can include methods wherein biosensor output is collected for a time substantially the same as the biological diffusion limit for the stimulatory effect.

Also disclosed are methods that can include further comprising providing a detection system.

Also disclosed are methods that can include methods wherein a plurality of label free biosensors are provided, wherein a cell is cultured on each of two or more of the biosensors, wherein a stimulatory event is provided to the two or more biosensors, wherein biosensor output is collected from the two of more biosensors.

Also disclosed are methods that can include methods wherein a multiplicity of penetration depths of the cell are monitored.

Also disclosed are methods that can include methods wherein each biosensor has one of the penetration depths.

Also disclosed are methods that can include methods wherein the biosensor outputs from the two or more biosensors are collected simultaneously.

Also disclosed are methods that can include methods wherein the cells are cultured simultaneously.

Also disclosed are methods that can include methods wherein the stimulatory events are provided to the two or more biosensors simultaneously.

Also disclosed are methods that can include methods wherein a plurality of different cells types is incubated on the plurality of biosensors.

Also disclosed are methods that can include methods wherein the plurality of cells comprises at least two cells that are different because at least one of the cells has been genetically engineered.

Also disclosed are methods that can include methods wherein each cell type within the plurality of cell type is detected by a different biosensor of the plurality of biosensors.

Also disclosed are methods that can include methods wherein the cell is cultured to a confluency of at least 70%.

Also disclosed are methods that can include methods wherein the cell comprises a plurality of cells.

Also disclosed are methods that can include further comprising applying a buffer solution to the cell, wherein the buffer solution is compatible with the type of cell and type of stimulatory event.

Also disclosed are methods that can include methods wherein collecting biosensor output comprises exposing the biosensor to light at varying angles of incidence and measuring the angle of incidence at which the light becomes in-coupled.

Also disclosed are methods that can include methods wherein collecting biosensor output comprises exposing the biosensor to light of varying wavelengths and measuring the wavelength at which the light becomes in-coupled.

Also disclosed are methods that can include methods wherein the cell is in a proliferating state, in a quiescent state, in a differentiated state, or in a specific cell cycle state.

Also disclosed are methods that can include methods wherein the cell is in a proliferating state by culturing the cell with a growth medium.

Also disclosed are methods that can include methods wherein the cell is in a quiescent state by culturing the cell with a starvation medium.

Also disclosed are methods that can include further comprising analyzing the biosensor output.

Also disclosed are methods that can include methods wherein the monitoring occurs continuously with a sampling rate of 1 second, 3 seconds, 5 seconds, 10 seconds, 20 seconds, 30 seconds, 1 minute or 5 minutes.

Also disclosed are methods that can include further comprising identifying the effect of the stimulatory event on the cell.

Also disclosed are methods that can include methods wherein identifying the effect comprises comparing the biosensor output to a signature output.

Also disclosed are methods that can include methods wherein the signature output comprises a dynamic mass redistribution response comprising at least one of the phases: positive-DMR, negative-DMR and net-zero DMR phases.

Also disclosed are methods that can include methods wherein the cell arises from a cell line.

Also disclosed are methods that can include methods wherein the cell line is a genetically engineered variant cell line.

Also disclosed are methods that can include methods wherein the stimulatory event comprises adding a compound to the cell culture, wherein the effect is an effect on absorption, distribution, metabolism, or toxicity of the compound on the cell.

Also disclosed are methods that can include methods wherein the stimulatory event comprises adding a compound to the cell culture, wherein determining the effect of the compound comprises a functional assessment of the effect of the compound on the cell and identification of the effect of the compound on absorption, distribution, metabolism, excretion, or toxicity on the cell.

Also disclosed are methods that can include methods wherein the output of the biosensor is correlated with a change in mass redistribution with the cell.

Also disclosed are methods that can include methods wherein the output of the biosensor is observable as an angular or spectral change in a reflected beam of the biosensor.

Also disclosed are methods that can include methods wherein collecting the biosensor output comprises monitoring the time dependent response of the cultured cell.

Also disclosed are methods that can include methods wherein the cells reached at least 80% confluence.

Also disclosed are methods that can include methods wherein the biosensor is embedded in a microplate.

Also disclosed are methods that can include methods wherein the cells are grown on the biosensor for at least 1 hour, 5 hours, 10 hours, 16 hours, 24 hours, 36 hours, a week, or two weeks.

Also disclosed are methods that can include methods wherein the biosensor is capable of differentiating between an area of the biosensor surface in contact with a viable cell, an area of the biosensor surface in contact with a cell that has been affected by a stimulatory event, and an area of the biosensor surface contacting no cell.

Also disclosed are methods that can include methods wherein the affected cell has ejected a portion of its intracellular components or is a dead cell.

Also disclosed are methods that can include further comprising incubating the cell-biosensor composition with a compound.

Also disclosed are methods that can include methods wherein the compound is a chemical, a biochemical, a biological molecule, a drug, or a polymer.

Also disclosed are methods that can include methods wherein the assaying is performed after incubating with the compound.

Also disclosed are methods that can include methods wherein the assaying occurs in less than or equal to 60 seconds, 45 seconds, 30 seconds, 15 seconds, 10 seconds, 5 seconds, 4 seconds, 3 seconds, 2 seconds, or 1 second.

Also disclosed are methods that can include methods wherein the inhomogeneity is determined by collecting biosensor output from the biosensor, wherein the biosensor output comprises a resonant peak of a guided mode having a maximum intensity, and comparing the width of the peak at half-maximum intensity (PWHM).

Also disclosed are methods that can include methods wherein the guided mode is a transverse magnetic mode.

Also disclosed are methods that can include methods wherein the biosensor is in a singular or multiplexed format.

Also disclosed are methods that can include methods wherein when the biosensor is in a multiplexed format, wherein the biosensor is embedded in one or more wells of a microplate.

Also disclosed are methods that can include methods wherein there is one biosensor in one well of a microplate.

Also disclosed are methods that can include methods wherein there are multiple biosensors in one well of a microplate, wherein the biosensors are physically separated with or without a barrier.

Also disclosed are methods that can include methods wherein the biosensors are physically separated with a barrier, wherein the barrier that defines the compartment within the well is lower than the barrier defining the well in the microplate.

Also disclosed are methods that can include methods wherein the biosensor is an optical waveguide biosensor.

Also disclosed are methods that can include methods wherein the biosensor is an optical waveguide grating biosensor.

Also disclosed are methods that can include methods wherein a cell is cultured in each of two or more wells, wherein a stimulatory event is provided to the two or more wells, wherein the stimulatory event comprises adding a compound to the two or more wells, wherein biosensor output is collected from the two of more wells, wherein the PWHM of two or more of the wells is compared with a control well, wherein a stimulatory event is not provided to the control well.

Also disclosed are methods that can include methods wherein the biosensor output is collected at a rate greater than 1, 2, 3, 4, 5, 10, 15, 30, 45, or 60 second(s) per well.

Also disclosed are methods that can include methods wherein the biosensor output is a rate greater than 60, 30, 15, 10, 7, 5, 4, 3, 2, or 1 well(s) per minute.

Also disclosed are methods that can include methods wherein the PWHM of the wells is compared at a rate greater than 1, 2, 3, 4, 5, 10, 15, 30, 45, or 60 second(s) per well.

Also disclosed are methods that can include methods wherein the PWHM of the wells is compared a rate greater than 60, 30, 15, 10, 7, 5, 4, 3, 2, or 1 well(s) per minute.

Also disclosed are methods that can include methods wherein the toxicity of the compounds can be evaluated using a single data point.

Also disclosed are methods that can include methods wherein the biosensor output are time-dependent PWHM changes.

Also disclosed are methods that can include methods wherein the biosensor is an optical biosensor.

14 Also disclosed are methods that can include methods wherein the biosensor is an optical based biosensor.

Also disclosed are methods that can include methods wherein the biosensor is a label free biosensor Also disclosed are methods that can include methods wherein the biosensor is attached to a system for culturing cells.

Also disclosed are methods that can include methods wherein the system is a plate.

Also disclosed are methods that can include methods wherein the plate is a plate with a plurality of wells.

Also disclosed are methods that can include methods wherein the plate is a microplate.

Also disclosed are methods that can include methods wherein a cell is cultured in each of two or more wells, wherein a microplate is comprised of the wells, wherein the biosensor output is images of a $TM_0$ mode resonance angular band of the whole sensor area of each well at a designated time.

Also disclosed are methods that can include methods wherein the cells reach 70% confluency.

Also disclosed are methods that can include methods wherein the stimulatory event comprises adding a compound to two or more of the wells, wherein the width of the $TM_0$ mode resonance angular band is compared with the width of the $TM_0$ mode resonance angular band of a well having compound added to the $TM_0$ mode resonance angular band of a well with no compound added.

Also disclosed are methods that can include methods wherein the biosensor is a waveguide-based biosensor.

Also disclosed are methods that can include methods wherein the waveguide-based biosensor is a $Nb_2O_5$-based optical biosensor.

Also disclosed are methods that can include methods wherein the cells are adherent cells.

Also disclosed are methods that can include methods wherein the cells are grown to a confluency of 30%, 50%, or 90%.

Also disclosed are methods that can include methods wherein the biosensor output is an optical waveguide light-mode spectra (OWLS), a resonant peak of a guided mode, or a resonant band image of a guided mode.

Also disclosed are methods that can include methods wherein a decrease in the PWHM indicates that the compound is toxic to the cell.

Also disclosed are methods that can include methods wherein the broadening of the PWHM indicates that the compound is toxic to the cell.

Also disclosed are methods that can include methods wherein the splitting of the PWHM indicates that the compound is toxic to the cell.

Also disclosed are methods that can include methods wherein resonance band broadening indicates the compound is toxic to the cell.

Also disclosed are methods that can include methods wherein the cells reached a confluency of at least 70%.

Also disclosed are methods that can include methods wherein a decrease in the PWHM indicates the compound has an effect on the cell.

Also disclosed are methods that can include methods wherein the biosensor is attached to a microplate.

Also disclosed are methods that can include methods wherein the biosensor is embedded in the bottom of each well of the microplate.

Also disclosed are methods that can include methods wherein the biosensor is an optical-based label free biosensor.

Also disclosed are methods that can include methods wherein the cell-biosensor is covered with the compound.

Also disclosed are methods that can include methods wherein the compound is in solution.

Also disclosed are methods that can include methods wherein the number of starting cells allows for an analysis of either an increase in proliferation or a decrease in proliferation.

Also disclosed are methods that can include methods wherein the number of cells reach a confluency between 30-70% in the absence of compound.

Also disclosed are methods that can include methods wherein the number of cells reach a confluency between 40-60%.

Also disclosed are methods that can include methods wherein the number of cells reach a confluency between 45-55%.

Also disclosed are methods that can include methods wherein the number of cells reach a confluency of 50%.

Also disclosed are methods that can include methods wherein the number of cells cultured on the biosensor before incubation with the compound comprises at least 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 30,000, 35,000, 40,000, 45,000, 50,000, 55,000, 60,000, 65,000, or 70,000 cell(s).

Also disclosed are methods that can include methods wherein the biosensor output is collected at a single time point.

Also disclosed are methods that can include methods wherein the biosensor output collected is a spectra.

Also disclosed are methods that can include methods wherein the biosensor output collected is an image of $TM_0$ mode resonance angular band of the whole individual biosensor area.

Also disclosed are methods that can include methods wherein the biosensor output collected is an image of $TM_0$ mode resonance angular band of the whole individual biosensor area.

Also disclosed are methods that can include methods wherein the biosensor output comprises total angular shift, wherein a decrease in the total angular shift indicates the compound is an inhibitor of cell proliferation.

Also disclosed are methods that can include methods wherein the biosensor output comprises total angular shift, wherein an increase in the total angular shift indicates the compound is an inhibitor of cell proliferation.

Also disclosed are methods that can include methods wherein the biosensor output comprises the intensity of incoupled light, wherein the intensity of incoupled light is plotted as a function of the angle of incidence of light.

Also disclosed are methods that can include methods wherein the cells are cultured on the biosensor for at least 1 hour, 5 hours, 10 hours, 16 hours, 24 hours, 36 hours, a week, or two weeks.

Also disclosed are methods that can include methods wherein the biosensor output comprises a coupling mode.

Also disclosed are methods that can include methods wherein the coupling mode is a transverse magnetic mode ($TM_0$).

Also disclosed are methods that can include methods wherein the $TM_0$ mode is plotted as a function of initial cell seeding numbers.

Also disclosed are methods that can include methods wherein the cell has a receptor tyrosine kinase (RTK), wherein the cell is suspended in a medium containing serum at a concentration that allows for the attachment and growth of the cell on the biosensor surface, wherein the cell adheres to the biosensor surface.

Also disclosed are methods that can include further comprising starving the adherent cell by culturing the cell in starvation medium at 37° C., wherein the starvation medium is a medium containing low concentration of serum.

Also disclosed are methods that can include further comprising applying a buffer solution at least once into the medium.

Also disclosed are methods that can include methods wherein the stimulatory event comprises applying a ligand to the RTK into the medium.

Also disclosed are methods that can include methods wherein the medium lacks PDGF (platelet-derived growth factor), EGF, insulin, TGF-α, insulin-like growth factor I (IGF-I), and nerve growth factor (NGF).

Also disclosed are methods that can include methods wherein the starvation medium has a concentration less than about 0.1% of serum or fetal bovine serum (FBS).

Also disclosed are methods that can include methods wherein the time-dependent response occurs for at least 1, 2, 3, 4, 5, 6, 7, 8, 9, 10, 11, 12, 13, 14, 15, 16, 17, 18, 19, 20, 21, 22, 23, 24, 36, or 48 hours.

Also disclosed are methods that can include methods wherein the biosensor is embedded in the bottom of a microplate having a plurality of wells, wherein a different type of cell is cultured in each of two or more wells, wherein a stimulatory event is provided to the two or more wells, wherein the stimulatory event comprises adding a ligand to the RTK to the two or more wells, wherein biosensor output is collected from the two of more wells, wherein the biosensor output is the time-dependent response of the different types of cell.

Also disclosed are methods that can include methods wherein the different types of cell require different culture conditions.

Also disclosed are methods that can include methods wherein the expression level or cell-surface expression level of the RTK is measured or determined in the different types of cells.

Also disclosed are methods that can include further comprising incubating the cultured cell with a compound and determining if the compound modulates signaling of the RTK.

Also disclosed are methods that can include methods wherein the cell has a relatively high expression level of the RTK, wherein the biosensor is embedded in the bottom of a microplate having a plurality of wells, wherein a cell is cultured in each of two or more wells, wherein a stimulatory event is provided to the two or more wells, wherein the stimulatory event comprises adding a ligand to the RTK to the two or more wells, wherein a different concentration of the ligand to the RTK is added to the two or more cells, wherein biosensor output is collected from the two of more wells, wherein the biosensor output is the dose- and time-dependent response of the cells in the different wells.

Also disclosed are methods that can include methods wherein the dose- and time-dependent response of the cells is compared.

Also disclosed are methods that can include methods wherein the potency of the ligand is determined.

Also disclosed are methods that can include further comprising analyzing the biosensor output for release of biomaterials from the cell, whereby the state of the cytoskeleton in the cell is analyzed.

Also disclosed are methods that can include methods wherein the release of biomaterials from the cell is dependent on a pore-forming reagent-induced permeability of the cells.

Also disclosed are methods that can include further comprising applying a pore-forming reagent to the cell culture.

Also disclosed are methods that can include methods wherein the biosensor output is a time dependent optical response.

Also disclosed are methods that can include methods wherein said pore-forming reagent is a chemical or biological compound that can result in the pore formation in cell surface membranes.

Also disclosed are methods that can include methods wherein the pore-forming reagent is saponin, digitonin, filipin, or streptolysin O.

Also disclosed are methods that can include further comprising applying a compound to the cell culture following application of the pore-forming reagent to the cell culture.

Also disclosed are methods that can include methods wherein one or more additional compounds are screened to determining if the compounds are capable of interfering with the cytoskeleton structure within cells.

Also disclosed are methods that can include further comprising applying a compound to the cell culture prior to application of the pore-forming reagent to the cell culture.

Also disclosed are methods that can include methods wherein one or more additional compounds are screened to determining if the compounds are capable of interfering with the cytoskeleton structure within cells.

Also disclosed are methods that can include further comprising the step of detecting a label with a device capable of detecting the label.

Also disclosed are methods that can include methods wherein the label is a fluorescent label, a radioactive label, or a phosphorescent label.

Also disclosed are methods that can include methods wherein the step of detecting the label occurs simultaneously with the step of monitoring the biosensor.

Also disclosed are methods that can include methods wherein the biosensor has two regions, the first one having no material-containing mixture deposited and the second one having material-containing mixture deposited, such that when the cells are incubated onto the sensor, the cells overlaid the second region become transfected by the materials.

Also disclosed are methods that can include methods wherein the material is a target gene, a target protein, a fusion protein of the target protein and a tag protein, a RNAi against the target, an antibody against the target, an antisense oligonucleotide and its derivates, an antigene oligonucleotide and its derivates.

Also disclosed are methods that can include methods wherein the tag protein is a His-tag, a GFP protein or one a derivate.

Also disclosed are methods that can include methods wherein the material is complexed with a reagent such that the cells can uptake the material, when the cells adhere onto the material-presenting region of the sensor.

Also disclosed are methods that can include methods wherein the regions are formed by selectively depositing the material-containing mixture onto one half of the sensor surface along the grating structure.

Also disclosed are methods of determining a state of a living cell comprising observing the dynamic mass redistribution of the cellular contents, wherein the step of observing occurs on a resonant waveguide grating biosensor.

Also disclosed are methods for testing a compounds effect on a cell comprising, culturing cells on a biosensor, first washing the cells, starving the cells, incubating the compound with the cell, and recording a signal with a biosensor.

Also disclosed are methods 605 further comprising the step of rinsing with a buffer after the step of starving, or wherein the cells are grown to greater than 90% confluency, or wherein the cells are washed wash twice, or wherein starving cells comprises culturing them only in DMEM, or wherein starving the cells occurs 1, 2, 3, 4, 5, 6, 7, 8, 9, 10, 11, 12, 13, 14, 15, 16, 17, 18, 19, 20, 21, 22, 23, 24, 25, 30, 35, 40 hours, or wherein starving the cells occurs overnight, or wherein the rinsing buffer comprises 1× regular Hank's balanced salt solution, 20 mM HEPES buffer, pH 7.0 in the presence of 2.5 mM probenicid, or wherein the signal is a calcium signal, or wherein calcium signal was recorded was recorded over 6 minutes with a 6 sec interval, or wherein the biosensor comprises a HTS7000 BioAssay Reader, or wherein the method occurs at room temperature, or wherein the biosensor is a Corning® Epic™ angular interrogation system, or wherein the biosensors is used in transverse magnetic mode, or wherein the biosensor is used in p-polarized $TM_0$ mode, or wherein the compounds were diluted in rinsing buffer, or wherein the rinsing buffer comprises 1× regular Hank's balanced salt solution, 20 mM HEPES buffer, pH 7.0, or wherein the starving of the cells occurs in a buffer lacking FBS, or wherein the compound is in a solution wherein the solution has less than 0.05% DMSO, or wherein the step of starving takes place at 37 degrees celcius, or wherein the step of starving further takes place under air/5% $CO_2$, or wherein cell is pretreated with a compound solution lacking the compound before incubating the compound solution with the cells, until a steady phase is reached, or wherein the biosensor identifies a change in a pixel density of the central position of the resonant band, or wherein the biosensor measures the angular shift of the resonant band, or further comprising the step of plotting the biosensor data as a function of time, or wherein an increased signal (P-DMR) means an increase in the amount of bio-molecules within the sensing volume and a decreased signal (N-DMR) means a decrease in the amount of biomolecules within the sensing volume, or wherein the method identifies a signature for the cell and compound, or wherein the signature comprises a P-DMR phase followed by a subsequent N-DMR phase, wherein the P-DMR phase occurs at a rate higher than the rate of decay of the N-DMR phase, or wherein the signature comprises a P-DMR phase until it the P-DMR phase reaches an evaluated plateau, or wherein the signature comprises two consecutive P-DMR events, wherein the first P-DMR phase to an elevated level occurs at a rate greater than the rate the second P-DMR phase occurs to a second elevated level, or wherein the signature does not include any DMR signal above the noise level, or further comprising the step of plotting the signal from the biosensor as a function of the compound concentration.

The cell can be cultured to 20-99% confluency, 30-80% confluency, 40-65% confluency, 70-99% confluency, and 80-95% confluency. The cell can be adherent cell. Adherent cells are cells that can adhere on the surface of a biosensor. The stimulatory event can comprise adding a compound to the cell culture. The compound can modulate a cell signaling pathway of the cell. The modulation can activate the cell signaling pathway. The modulation can suppress the cell signaling pathway. The compound can modulate a cell surface receptor on the cell. The compound modulation can be an agonist of the receptor. The compound modulation can be an antagonist of the receptor. The cell surface receptor can be a G protein coupled receptor (GPCR), an ion channel, a receptor tyrosine kinase, a cytokine receptor, an integrin receptor, a $Na^+/H^+$ exchanger receptor, and an immune receptor. The receptor tyrosine kinase can be an epidermal growth factor receptor (EGFR), a platelet derived growth factor receptor (PDGFR), a fibroblast growth factor receptor (FGF), an insulin receptor, a vascular endothelial growth factor receptor (VEGFR).

The compound can modulate a cytoskeleton component within the cell. The modulator can destabilize the cytoskeleton structure. The modulator can stabilize the cytoskeleton structure. The compound can modulate an intracellular enzyme, an intracellular kinase, an intracellular organelle, or an intracellular protein. The compound can modulate an extracellular matrix.

The step of collecting biosensor output data from the biosensor can comprise collecting a biosensor output data parameter. The biosensor output data parameter can be a parameter related to the kinetics of the stimulatory event. The biosensor output parameter can comprise analyzing the overall kinetics of the biosensor output data. The analyzing of the overall kinetics can comprise analyzing the rate of the completion of the phase transitions. The analyzing of the overall kinetics can comprise analyzing the length of time it takes to complete data output. The analyzing of the overall kinetics can comprise analyzing the length of time for which an overall phase of the data output takes. The analyzing of the overall kinetics can comprise analyzing the total duration of time of a P-DMR phase. The analyzing of the overall kinetics can comprise analyzing the total duration of time of an N-DMR phase. The analyzing of the overall kinetics can comprise analyzing the rate for acquiring the total amplitude of the P-DMR. The analyzing of the overall kinetics can comprise analyzing the total length of time it takes for the total amplitude of the N-DMR. The analyzing of the overall kinetics can comprise analyzing the total length of time it takes for the total amplitude of the P-DMR. The analyzing of the overall kinetics can comprise analyzing the transition time τ from a P- to N-DMR phase.

The biosensor output parameter can comprise analyzing the phases of the biosensor output data. The analyzing the phase can comprise analyzing a phase transition. The analyzing the phase can comprise analyzing a Positive-Directional Mass Redistribution (P-DMR) signal. The analyzing the phase can comprise analyzing a Negative-Directional Mass Redistribution (N-DMR) signal. The analyzing the phase can comprise analyzing a net-zero Directional Mass Redistribution (net-zero DMR). The analyzing the phase can comprise analyzing the shape of a Positive-Directional Mass Redistribution (P-DMR) signal. The analyzing the phase can comprise analyzing the amplitude a of Positive-Directional Mass Redistribution (P-DMR) signal. The analyzing the phase can comprise analyzing the shape of a Negative-Directional Mass Redistribution (N-DMR) signal. The analyzing the phase can comprise analyzing the amplitude a of Negative-Directional Mass Redistribution (N-DMR) signal.

The biosensor output parameter can comprise the overall dynamics of the biosensor output data. The analyzing overall dynamics can comprise analyzing the shape of the complete curve produced by the output data. The biosensor output data parameter can be a parameter related to the resonant peak. The biosensor output parameter an comprise analyzing the intensity of the light versus the angle of incidence wherein the light is coupled into the biosensor. The biosensor output parameter can comprise analyzing the intensity of the light versus the wavelength of light wherein the light is coupled into the biosensor. The biosensor output parameter can comprise analyzing the peak position. Analyzing the peak position can comprise analyzing the position of the half maximal peak intensity occurring before the position of the peak intensity. Analyzing the peak position can comprise analyzing the position of the half maximal peak intensity occurring after the position of the peak intensity.

The biosensor output parameter can comprise analyzing the intensity of a point of the resonant peak. Analyzing the intensity of the resonant peak can comprise analyzing the intensity of the peak intensity. Analyzing the intensity of the resonant peak can comprise analyzing the intensity of the half maximal peak intensity that occurs on the resonant peak prior to the peak intensity. Analyzing the intensity of the resonant peak can comprise analyzing the intensity of the half maximal peak intensity that occurs on the resonant peak after the peak intensity.

The method can further comprise a second biosensor output parameter. The second biosensor output parameter can comprise analyzing peak position. The biosensor output parameter can comprise analyzing the peak shape. Analyzing the peak shape can comprise determining the area beneath the resonant peak. The area beneath the resonant peak can include only the area above a line drawn between the half maximal intensity points occurring on the resonant peak. Analyzing the peak shape can comprise analyzing the width of the resonant peak at the half maximal intensity points. The biosensor output data parameter can be a parameter related to the resonant band image. The resonant band image can be collected by illuminating the sensor with a light spot that across the sensor in combination with a receive system to image the in-coupled light intensity distribution across the sensor. The receive system can be a CCD camera. The parameter relating to the resonant band image can be the band shape, the band position, the band intensity, or the light intensity distribution.

The PWHM in combination with the position of the maximum intensity can be analyzed. The biosensors can be analyzed simultaneously. The time for collecting a data point from each well biosensor can be done in less than 1 hour, 30 min, 5 min, 1 min, 30 sec, 10 sec, 5 second, 2 seconds, 1 second, and where it is biological diffusion limited. The cell can be at a proliferating state by culturing the cell with a growth medium, or a quiescent state by culturing the cell with a starvation medium, or a differentiated state, or a specific cell cycle state. A starvation medium is any medium which decreases the cell proliferation capacity of a culture of cells.

The method can further comprise the step of applying a buffer solution at least once into the cell medium, wherein the buffer solution used can be based on the optimal assay according to the nature of cell type and of target-compound interaction. The monitoring can occur in continuous fashion with a sampling rate of 1 sec, 3 sec, 5 sec, 10 sec, 20 sec, 30 sec, 1 minute, or 5 minutes, 30 minutes. The signature output can comprise a dynamic mass redistribution response comprising at least one of the three phases: positive-DMR, negative-DMR and net-zero DMR phases. The cell can arise from a cell line or a genetically engineered variant cell line. The effect of the compound can be determined for an analysis of the adsorption, distribution, metabolism and toxicity of the compound on a cell. The effect can comprise a functional assessment of the compound on the cell and identifies the effect of the adsorption, distribution, metabolism, excretion and toxicity on the cell.

The output of the biosensor can be correlated with a change in mass redistribution with the cell. The output of the biosensor can be observable as an angular or spectral change in a reflected beam of the biosensor. The method can further comprise applying a buffer solution at least once into the cell medium. The compound can be an anticancer compound, or a potential anticancer compound. There can be at least $10 \times 10^5$ cells on the biosensor. The cells can reach at least 80% confluence. The biosensor can be embedded in a microplate. The cells can be grown on the biosensor for at least 1 hour, 5 hours, 16 hours, 24 hours, 36 hours, a week, or two weeks. The biosensor can be capable of differentiating between an area of the biosensor surface in contact with a viable cell. The effected cell can have ejected a portion of its intracellular components, or can be a dead cell.

The method can further comprise incubating the cell-biosensor composition with a compound. The compound is a chemical, a biochemical, a biological, a drug, or a polymer. The method can further comprise performing the assay step after incubating with the compound. The assaying can occur in less than or equal to 60, 45, 30, 15, 10, 5, 4, 3, 2, or 1 second(s). The inhomogeneity can be determined by collecting an output which produces a resonant peak of a guided mode having a maximum intensity and comparing the width of the peak at half-maximum intensity (PWHM). The guided mode can be transverse magnetic mode.

The biosensor can be in a singular or multiplexed format. When the biosensor is in a multiplexed format, the biosensor can be embedded in some of wells of a microplate. There can be one biosensor in one well of a microplate. There can be multiple biosensors in one well of a microplate, in which biosensors can be physically separated with or without a barrier. When there is a physically barrier, the barrier defining the compartment within a well can be lower that that defining the well in a microplate. The biosensor can be an optical waveguide biosensor. The biosensor can be an optical waveguide grating biosensor.

The method can further comprise collecting time-dependent PWHM changes. The optical waveguide lightmode spectra can be a resonant peak of a guided transverse magnetic mode. The biosensor can be an optical biosensor. The biosensor can be an optical based biosensor. The biosensor can be a label free biosensor. The biosensor can be attached to a system for culturing cells. The system can be a plate. The plate can be a plate with a plurality of wells. The plate can be a microplate. The cells can reach 70% confluency.

The method can further comprise the step of obtaining the width of the $TM_0$ mode resonance angular band and comparing the width of the $TM_0$ mode resonance angular band of a well having a compound applied to the $TM_0$ mode resonance angular band of a well with no compound applied. The biosensor can be a waveguide-based biosensor. The waveguide-based biosensor can be a $Nb_2O_5$-based optical biosensor. The cells can be adherent cells. The cells can be grown to a confluency of 30%, 50%, or 90%. The output can be an optical waveguide lightmode spectra (OWLS), or a resonant peak of a guided mode, or a resonant band image of a guided mode. A change in the PWHM can indicate that the compound is toxic to the cell. The broadening of the PWHM can indicate that the compound is toxic to the cell. The splitting of the PWHM can indicate that the compound is toxic to the cell. Resonance band broadening can indicate the compound is toxic to the cell. The cells can reach a confluency of at least 70%. The biosensor can be attached to a microplate. The biosensor can be embedded in the bottom of each well of the microplate. The biosensor can be an optical-based label free biosensor. The cell-biosensor can be covered with the compound. The compound can be in solution. The number of starting cells can allow for an analysis of either an increase in proliferation or a decrease in proliferation. The number of cells can reach a confluency between 30-70% in the absence of compound. The number of cells can reach a confluency between 40-60%. The number of cells can reach a confluency between 45-55%. The number of cells can reach a confluency of 50%. The number of cells cultured on the biosensor before incubation with the compound can comprise at least 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 30,000, 35,000, 40,000, 45,000, 50,000, 55,000, 60,000, 65,000, or 70,000 cell(s).

The output can be collected at a single time point. The output collected can be a spectra. The output collected can be an image of $TM_0$ mode resonance angular band of the whole individual biosensor area. The output collected can be an image of $TM_0$ mode resonance angular band of the whole individual biosensor area. The method can further comprise obtaining an output providing total angular shift, wherein a decrease in the total angular shift can indicate the compound is an inhibitor of cell proliferation. The method can further comprise obtaining an output providing total angular shift, wherein an increase in the total angular shift can indicate the compound is an inhibitor of cell proliferation. The output collected can obtain the intensity of incoupled light and plots this a function of the incident angle of light. The cells can be cultured on the biosensor for at least 1 hour, 5 hours, 10 hours, 16 hours, 24 hours, 36 hours, or overnight.

The output can comprise a coupling mode. The coupling mode can be a transverse magnetic mode ($TM_0$). The $TM_0$ mode can be further plotted as a function of initial cell seeding numbers. The method can further comprise starving the adherent cells in a medium containing low concentration of serum for certain time at 37° C. The method can further comprise applying a buffer solution at least once into the cell medium for a certain amount of time. The method can further comprise applying a solution containing a ligand to the RTK into the medium. The cell culture medium can lack PDGF (platelet-derived growth factor), EGF, insulin, TGF-α, insulin-like growth factor I (IGF-I), and nerve growth factor (NGF). The starvation medium can have a concentration less than about 0.1% of serum or bovine serum albumin (BSA). The collection of the biosensor output can occur for at least 1, 2, 3, 4, 5, 6, 7, 8, 9, 10, 11, 12, 13, 14, 15, 16, 17, 18, 19, 20, 21, 22, 23, 24, 36, or 48 hours. The different types of cells can require different culture conditions. The monitoring release of bio-materials from cells can be dependent on a pore-forming reagent-induced permeability of the cells. The pore-forming reagent can be a chemical or biological that can result in the pore formation in cell surface membranes. The pore-forming reagent can be saponin, digitonin, filipin, or streptolysin O.

VII. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Biosensor-based Cell Toxicity Screening

Profiling compounds by virtue of their cytotoxic and antiproliferative effects is often used to profile potential anticancer agents. One such phenotype is the compromise in plasma membrane integrity when cells are exposed to cytotoxic agents, including dimethyl sulfoxide (DMSO). Using a waveguide-based biosensor technique, the feasibility for monitoring the effect of DMSO on both Chinese hamster ovary (CHO) and A431 cells was examined. Approximately $10 \times 10^5$ cells were placed into each well of a Corning Epic® LID microplate. These cells were cultured in serum medium for overnight to ensure that the cells became adherent to the substrate surface and reach at least 80% confluence. The response of cells to DMSO at different concentrations (1%, 2%, 5%, 10%, 15%, 18% and 20%) was examined. Higher concentrations of ~≧25% of DMSO result in bulk index changes which are beyond the maximum dynamic range of the sensor used and the signal was lost. At least two sets of experiments were carried out for each cell line.

a) Materials and Methods

All cell lines were purchased from American Type Cell Culture. DMSO was obtained from Sigma Chemical Co. (St. Louis, Mo.). The Live/DEAD cell viability reagent kit for animal cells was obtained from Molecular Probes (Eugene, Oreg.).

Both A431 and CHO-K1 cells were grown in Dulbecco's modified Eagle's medium (DMEM) supplemented with 10% fetal calf serum, 100 µg/ml penicillin, and 100 µg/ml streptomycin. For cell culture, $\sim 10 \times 10^5$ cells, either A431 or CHO-K1, were suspended in 200 µl medium were placed in each well of a 96 well Corning Epic Biosensor microplate, and were cultured at 37° C. in air/5% $CO_2$ for overnight. Before the assays, the cells were washed once with the corresponding medium. During the assays, the cells in 100 µl medium were subject to two 25 µl HBSS buffer solutions containing 20 mM HEPES, pH 7.4, each separated by at least 15 minutes before 50 µl DMSO solution was applied. During all these steps, a parallel angular interrogation system was used to monitor the real time kinetics of cellular responses.

After assays, the corresponding resulting cells were immediately subject to Live/DEAD staining using the protocol recommended by the supplier. After staining, fluorescence microscopy (a Zeiss Axioplan fluorescence microscope) was used to visualize the morphology and fluorescence distribution of treated and un-treated cells.

b) Results

Results showed that cells that had adhered to the biosensor gave rise to a similar response curve. As shown in FIG. 29, the DMSO-induced dose-response and time-dependent response curve of a CHO cell layer indicates that at a DMSO concentration of <20%, the response is almost featureless, except that there is a gradual decrease after introduction of DMSO solution. It is noted that there is an initial and rapid increased phase, which is due to bulk index change right after the DMSO at all concentratios was introduced. However, when the concentration of DMSO reaches 20%, there are four events that can be observed: (A) a great response signal due to the bulk index change right after the introduction of DMSO solution; (B) a small decreased signal, probably due to the mixing of two fluids in the well; (C) a slow and steady increased signal probably because DMSO at those concentrations penetrates and replaces the biofluid inside the cells; and (D) a prolonged and decreased signal due to the loss of proteins or other biological molecules of cells caused by the toxicity of high concentrations of DMSO and the resulting lost integrity of the cell surface membranes. It is known that the refractive index values are: 1.3328 for the aqueous buffer medium used in this study 1.437 for DMSO, and ~1.5 for proteins. In addition, there is about 70% (weight) for biofluid, which consist primarily of water with a refractive index of 1.3328, inside cells. Another 30% includes proteins, DNA, RNA, lipid molecules. It is also known that when the concentration of DMSO is lower than 10%, cell membranes are not significantly affected by DMSO during the duration of experiments; however, when the concentration of DMSO is between 10% and 20%, there is increasing percentage of cell membranes which are compromised. At higher concentration, nearly all cell membranes have been compromised (Beske, O., et al., "A novel encoded particle technology that enables simultaneous interrogation of multiple cell types", J. Biomol. Screening. 2004, 9, 173-185).

Similar dose response curves have been observed for DMSO acting on A431 cells (FIG. 30). The different behavior for the event B between CHO cells and A431 cell lines is likely due to the different attachment and morphology of the two types of cells on the substrate. CHO cells tend to spread much less than A431 cells, resulting in a thinner layer of A431 cells attached on the substrates, which means that the biofluid exchange event (Event C) should be less pronounced than the biological redistribution event, when the lost of materials from effected cells that account for most of the event D are similar to both cell lines.

2. Example 2

HT Screening Compound Toxicity with Optical Sensor a) Methods for High Throughput Screening Compound Toxicity One aspect according to the present invention is to provide methods that are suitable for high throughput screening compound toxicity and apoptosis using label free optical-sensors. The present methods allow one to detect, compound toxicity within a couple of seconds for a whole plate.

The principal of the present methods lies in the fact that toxicity of a given compound could lead to cell leakage, and even death. This, in turn, results in the inhomogeneity of the sensor surface wherein the cells are cultured. During the toxicity studies, the biosensors sense three types of area: area having viable cell, area having dead or dying cells (in which the dead cells tend to loss their intracellular components, leading to the altered refractive index), and no-cell area. The inhomogeneity formation could cause changes in the PWHM of the resonant peak of a given guided mode or the width and distribution of the resonant band image, which all are dependent on the cell density. In special cases wherein the cells cultured on the film surface are oriented or have certain type of preferred structure, or wherein the cells at certain areas are sensitive to toxic compounds, the compound toxicity could lead to the occurring of fine structures such as shoulders (which lead to resonant peak and band broadening) and even splitting of resonance peaks.

Considering that the cells are pre-cultured on waveguide sensor plates and reach high confluency (>75%), the sensors sense mostly the live cells with a refractive index of ~1.37, as well as the cover medium with a refractive index of ~1.33. The PWHM of the $TM_0$ peak is relatively low. After a toxic compound is added, the cells start to be affected. The affected cells undergo both physical and physiological changes (i.e., morphology, shape, and intracellular component rearrangement). Ultimately the affected cells die. At certain time after compound treatment, there are mixed populations of cells: live cells, affected cells and dead cells. Therefore, as the time increases after compound treatment, the PWHM of the $TM_0$ peak starts to increase from its relatively low level, reach its maximum at certain time, and start its decay to original low level again with a decreased overall response (i.e., angular or wavelength shift). The kinetics to reach its maximum is dependent on cell line and mechanism of the compounds acting on the cells. This process is inverse to the cell attachment and spreading processes.

In one embodiment, the present invention provides a method for high throughput screening compound toxicity on cells using optical biosensors, which comprises of (a) Provide a microplate that there is an optical-based label free biosensor embedded in the bottom of each well; (b) Place cells into each well to cover the biosensor such that the cells attach and reach high confluency onto the surface of the biosensor; (c) Apply a compound solution into the cell medium of each well; (e) Collect optical waveguide lightmode spectra at certain time. Comparing the PWHM of each compound with a control well wherein the cells are not exposed to any compound solution, the toxicity of compounds can be evaluated using the single data point. If necessary, time-dependent PWHM changes can be also recorded to study the kinetics.

In another embodiment, the present invention provides alternative methods to evaluate compound toxicity, which comprises of: (a) Provide a microplate that there is an optical-based label free biosensor embedded in the bottom of each well; (b) Place cells into each well to cover the biosensor such that the cells attach and reach desired confluency onto the surface of the biosensor; (c) Apply a compound solution into the cell medium of each well; (e) Collect images of $TM_0$ mode resonance angular band of the whole sensor area of each well at certain time. Comparing the widths of the resonant bands of sensors that have been treated with a compound solution with that of a control well wherein the cells are not exposed to any compound solution; the toxicity of compounds can be evaluated.

Profiling compounds by virtue of their cytotoxic and antiproliferative effects is often used to profile potential anticancer agents. One such phenotype is the compromise in plasma membrane integrity when cells are exposed to cytotoxic agents, including dimethyl sulfoxide (DMSO). Using a waveguide-based biosensor technique, the feasibility for monitoring the effect of DMSO on both Chinese hamster ovary (CHO) and A431 cells was examined using the high throughput methods.

FIG. 31A shows the intensity of the incoupled light as a function of the incident angle for a layer of CHO cells with different confluencies (30%, 50% and 90%) cultured on $Nb_2O_5$-based optical waveguide biosensors. The coupling mode is transverse magnetic ($TM_0$) mode. FIG. 31B shows the width of the peak at half-maximum (PWHM) of the $TM_0$ mode is calculated and plotted as a function of CHO cell confluency. As the confluency of cells increases, the PWHM increases, reaches at maximum at around 50% confluency, and starts decrease to starting value. It is worthy noting that there is small shoulder peak for the incoupled peak for cells at all confluency level, but not for the sensors that have no cells attached. This is probably due to the fact that CHO cells prefer to attach onto the grating sensor surfaces with preferred orientation (see FIG. 35A).

FIG. 32 shows the $TM_0$ mode resonant peak of a layer of CHO cells with two different confluencies, 5% (Left) and 75% (right), respectively, cultured on a waveguide grating sensor. The resonant peak spectra were recorded at different times after addition of DMSO (with a final concentration of 18%). For cell density below ~25%, there is no change in the PWHM value over time. However, when the confluency of cells on sensors is high (>70%), there is an initial increase in PWHM followed by decreasing PWHM value. Besides the broadening of resonance peak, there is the occurrence of fine structure such as shoulders and even splitting of the resonance peak at the time of ~25 min after DMSO treatment. Interestingly, the broadening or shape changes of the resonant peaks in response to DMSO treatment is a dynamic process, suggesting that the DMSO-induced cell responses are consistent with certain cellular signaling pathways, such as apoptosis.

FIG. 33 shows the $TM_0$ mode resonance band images of the whole sensors covered by a layer of CHO cells at different confluencies. The images are taken after 25 min treatment with buffer (column 2), and with 18% DMSO (column 1). The images suggest that (i) the cells treated with buffer solution do not result in any changes in the resonance band of the whole sensors no matter what the confluency of the cells is; and (ii) the cells treated with 18% DMSO give rise to the confluency dependent resonance band broadening. When the confluency of cells is above 70%, there is DMSO-induced resonance band broadening. These results suggest that the broadening of the resonance band broadening can be used as a signature for compound toxicity; and cell density or confluency is important in order to make this type of evaluation valid. Similar to the resonant peak spectra, the broadening or shape changes of the resonant band images in response to DMSO treatment is a dynamic process, suggesting that the DMSO-induced cell responses might be related to certain cellular signaling pathways, such as apoptosis. More importantly, the resonant band images for all 96 sensors within a microplate can be collected within 3 seconds, suggesting that the present method based on resonant band images or spectra offers an ultra-high throughput technique for cell toxicity evaluation and compound toxicity screening.

FIG. 34 shows the $TM_0$ mode resonance band images of the whole sensors covered by a layer of CHO cells at same confluency (~95%). The images are taken after 25 min treatment with buffer (6 wells in column 2), and with different concentrations of DMSO (6 wells in column 1, and 6 wells in column 3, as indicated in the FIG. 34). The results show that the toxicity effect of DMSO is dependent on the concentration; only higher concentrations cause significant cell toxicity, as indicated by the changes in band shape. A particularly interesting finding is that when the concentration of DMSO used is ~15%, there is a second resonance band appearing, probably due to the preferred orientation of CHO cells cultures on the sensors. The CHO cells seem align with the grating structure under culture conditions (see FIG. 35). These results were found to be consistent with and thus confirmed by conventional Live/DEAD cell staining methods (data not shown).

3. Example 3

High Throughput Proliferation Assays

FIG. 36A shows the intensity of the incoupled light as a function of the incident angle for CHO cells cultured onto waveguide grating sensor surfaces when the different seeding numbers of cells are used for culture under normal growth condition for 36 hours. The coupling mode is transverse magnetic ($TM_0$) mode. FIG. 36B shows the width of the peak at half-maximum (PWHM) using $TM_0$ mode is calculated and plotted as a function of initial seeding cell numbers. As the initial seeding number of cells increases, the PWHM increases, reaches at maximum at between 20000 and 30000 initial seeding cells (the corresponding confluency is around 50%), and starts decreasing to a starting value. It is worthy noting that there is an obvious shoulder peak for the incoupled peak for cells at all confluency levels, but not for the sensors that have no cells attached. Again, this is likely due to the fact that CHO cells prefer to attach onto the grating sensor surfaces with preferred orientation (See FIG. 35). Interestingly, the results shown here are consistent with those obtained using different seeding numbers of cells to reach different cell densities after a fixed period of time (see FIG. 31), suggesting that the present method is reproducible.

FIG. 37 shows the TM0 mode resonance band images of the whole sensors covered by CHO cells, after cultured on the waveguide grating sensors for 36 hours; different wells host different initial seeding numbers of cells. The shape and position of the TM0 mode resonance band images of the whole sensors is observed to be dependent on initial seeding cell numbers, suggesting that the sensors are sensitive to cell density; the proliferation rate of CHO cells depends on initial seeding cell numbers, as confirmed by cell density analysis using fluorescence microscopy after stained with Live/Dead® cell kit from the Molecular Probes. The corresponding confluencies are 5%, 30%, 55%, 75% and 95% for the initial seeding number of 10000, 20000, 30000, 40000 and 50000 cells, respectively.

4. Example 4

Cell Signaling Pathway Studies Using Biosensors a) Materials and Methods

All cell lines were purchased from American Type Cell Culture. All chemicals were obtained from either Sigma Chemical Co. (St. Louis, Mo.), or Tocris Chemical Co. (St. Louis, Mo.).

Both A431 and CHO-K1 cells were grown in Dulbecco's modified Eagle's medium (DMEM) supplemented with 10% fetal calf serum, 100 µg/ml penicillin, and 100 µg/ml streptomycin. For cell culture, certain numbers of cells ($2 \times 10^5$ to $1 \times 10^6$), either A431 or CHO-K1, were suspended in 200 ml medium were placed in each well of a 96 well Corning Epic Biosensor microplate, and were cultured at 37° C. in air/5% CO2 for certain time until the cell density reached ~90% and above (unless specified). The resulted cells were termed as "profilerating" cells. The "quiescent" cells were obtained by culturing the profilerating cells of desired confluencies with a medium containing no or little (~0.1% fetal bovine serum (FBS)) for at least 16 hours.

The cells, either proliferating or quiescent cells, were either directly used for assays or washed once with the corresponding medium (both result in no obvious difference in cell responses). During the assays, the cells in 100 µl medium were subject to two 25 µl HBSS buffer containing 20 mM HEPES, pH 7.4, each separated by at least 15 minutes before 50 µl stimulus-containing solution was applied. During all these steps, a parallel angular interrogation system was used to monitor the real time kinetics of cellular responses. For compound effect studies, a modified protocol was used which starts with 50 µl medium, and subject to sequential treatment: 25 µl HBSS buffer twice (each separated by at least 15 minutes), 50 µl compound solution and finally 50 µl stimulus-containing solution.

The sensors used were 96 well Corning Epic® biosensor microplates (as shown in FIG. 1 and FIG. 2a), and used directly for cell culture. The detection system used can be that of U.S. patent application Ser. No. 10/602,304, filed Jun. 24, 2003 having publication no. US-2004-0263841, published Dec. 12, 2004 and U.S. patent application Ser. No. 11/019, 439, filed Dec. 21, 2004, and U.S. patent application For "OPTICAL INTERROGATION SYSTEM AND METHOD FOR 2-D SENSOR ARRAYS" by N. Fontaine, et al., filed on Mar. 31, 2005, all of which are herein incorporated in their entireties by reference but at least for biosensors and their uses.

b) Results (1) Real Time Monitoring the Ligand Binding and Sequential Signaling Events of RTKs FIG. 6A shows a time-dependent response of a layer of quiescent or starved A431 cells (monitored using optical biosensor) before and after addition of 8 nM EGF. The A431 cell line is a cancer cell line having endogenously over-expressed EGFRs. A431 cells in a Dulbecco's modified Eagle's medium (DMEM) medium containing 10% fetal calf serum (FCS) were applied to each well of a microplate which has a waveguide biosensor in the bottom of each well. The cells were cultured overnight at 37° C., the serum medium was exchanged with a medium containing only 0.1% serum, and the cells were continuously cultured for another 18 hours. The whole time course was obtained at room temperature (~20° C.). After addition of EGF (A), EGF-treatment of quiescent A431 cells, obtained by being cultured in 0.1% fetal bovine serum (FBS) for 18 hours, gave rise to a time-dependent response that consists of three distinct, sequential phases: (i) a positive phase with increased signal (P-DMR) (Point C to D in FIG. 6A), (ii) a net-zero phase (Point D to E), and (iii) a decay phase with a decreased signal (N-DMR) (Point E to F to G). It was noted that there is a rapid response change in signal, lasting for less than 20 sec (Point B to C in FIG. 6A), which occurs upon the introduction of a 50 ml EGF solution into the well. This rapid change is due primarily to a bulk index change, which temporarily overwhelms any DMR signal. The measured P-DMR signal is mainly due to the recruitment of intracellular components to activated EGFRs and the flatness of the cells due to the invagination of plasma membranes after EGFR activation, whereas cell detachment and receptor internalization are two major contributors to the N-DMR event. However, the P-DMR event might also involve non-cell function-related events, including solution diffusion and temperature differences between the cell medium and the compound solution.

The kinetics of the above-mentioned steps in the response curve is consistent with that of ligand binding, phosphorylation and trafficking events of EGF-induced EGFR signaling reported in the literature (B. Schoeberl, C. Eichler-Jonsson, E. D. Gilles, G. Muller, "Computational Modeling of the Dynamics of the MAP Kinase Cascade Activated by Surface and Internalized EGF Receptors," Nat. Biotech. 20, 370 (2002). Biological and biochemical studies have shown that at 37° C., EGF-bound receptors can be internalized into early endosomes within ~5-20 min which locate at nearly the inner face of cell membranes. Afterwards, these EGFRs in complexation with other components are transferred to late endosomes (20-60 min) and lysosomes (>60 min) for degradation of which both are located relatively far away from the inner face of the cell membranes (i.e., during the trafficking, these receptors move away from the sensor surface). There is a continual flux of receptors and ligand through different compartments; and multiple steps dictate their overall dynamic distribution. EGF-bound receptors only spend a relatively short time at the cell surface (~3 min) owing to rapid internalization.

(2) Methods to Measure the Expression Level and Cell-Surface Expression Level of EGFR The A431 cell, endogenously over-expressing epidermal growth factor receptors (EGFRs) (~1,700,000 copies per cell), is a well-studied model for EGFR signaling (A. Glading, P. Chang, D. A. Lauffenburger, and A. Wells, "Epidermal growth factor receptor activation of calpain is required for fibroblast motility and occurs via an ERK/MAP kinase signaling pathway," J. Biol. Chem. 2000, 275:2390-2398). Stimulation of quiescent A431 cells with EGF at room temperature or 37° C. ultimately leads to receptor endocytosis, refractile morphological changes and cell detachment from the extracellular matrices (Z. Lu, G. Jiang, P. Blume-Jensen, and T. Hunter, "Epidermal growth factor-induced tumor cell invasion and metastasis initiated by dephosphorylation and downregulation of focal adhesion kinase," Mol. Cell. Biol. 2001, 21, 4016-4031). Thus, EGF stimulation results in significant mass redistribution within the A431 cells, as measured in real time using the arrayed interrogation system (see FIG. 6A, FIG. 18). Results showed that EGF-induced DMR responses of A431 cells strongly depend on the culture condition. EGF-treatment of A431 cells cultured in 0.1% FBS for 20 hours gave rise to a time-dependent response that consists of three distinct, sequential phases: (i) a positive phase with increased signal (P-DMR) (Point C to D in FIG. 6A), (ii) a net-zero phase (Point D to E), and (iii) a decay phase with a decreased signal (N-DMR) (Point E to F). However, A431 cells treated with 0.1% FBS for only 4 hours gave rise to similar response but with altered kinetics and much smaller amplitudes, compared to the quiescent A431 cells. Conversely, proliferating A431 cells (cultured with 10% FBS) only gave rise to a P-DMR event in response to EGF stimulation. Furthermore, no significant responses were observed for either quiescent or proliferating Chinese hamster ovary (CHO) cells, consistent with the fact that CHO cells do not endogenously express EGFR (E. Livneh, R. Prywes, O. Kashle, N. Reiss, I. Sasson, Y. Mory, A. Ullrich, and J. Schlessinger, "Reconstitution of human epidermal growth factor receptors and its deletion mutants in cultured hamster cells," J. Biol. Chem. 1986, 261, 12490-12497.). These results suggested that the EGF-induced DMR signals are EGFR dependent.

FIG. 39 summarizes the P-DMR and N-DMR signals for these three types of cells. The results show that there is no clear P-DMR nor B-DMR signal when CHO cells were incubated with EGF, consistent with the fact that CHO cells do not express EGFR. In contrast, the P-DMR and N-DMR signals induced by EGF stimulation are 3.08, and 2.34, respectively, for quiescent A431 cells. However un-starved (i.e., proliferating) A431 cells gave rise to much smaller P-DMR signals with no obvious N-DMR. These results confirm the fact that serum growth medium affects the cell surface expression level of EGFRs; higher serum medium results in lower cell surface EGFR expression due to the fact that the serum contains EGF and many other growth factors.

(3) Methods to Determine the Potency of Ligands to RTKs

As shown in FIG. 7, stimulations with EGF at different concentrations all led to a similar response (FIG. 7A); however, three major parameters defining the response displayed a clear tendency to the concentrations of EGF used. The higher the EGF concentration is, (i) the greater are the amplitudes of both the P-DMR and the N-DMR signals, (ii) the faster are both the P-DMR and the N-DMR events, and (iii) the shorter is the transition time $\tau$ from the P-DMR to the N-DMR event. The P-DMR event involves cell function-related and other contributions. The possible contributors include, but are not limited to, cell flatness in response to treatment, cell membrane invigination, recruitment of intracellular components and cytoskeleton remodeling, and to less extent, EGF binding. Non-cell function-related events, including solution diffusion and temperature differences between the cell medium and the compound solution, might also complicate the analysis. Because of those, we had observed a complicated relationship of the overall P-DMR amplitudes with the EGF concentrations. When the amplitudes of the P-DMR events showed a complicated relationship with the EGF concentrations, the amplitudes of the N-DMR signals were clearly saturable to EGF concentrations, resulting in an $EC_{50}$ of ~1.45 nM (FIG. 7B). The transition time $\tau$ in seconds was found to decrease exponentially with the increasing concentration C of EGF (FIG. 7C):

$$\tau(C)=946*e^{-0.144C}+1130$$

In addition, the decay of the N-DMR signal can be fitted with non-linear regression. The one-phase decay constant $\kappa$ obtained was also saturable, resulting in a $K_d$ of 5.76 nM (FIG. 7D). The results indicated that (i) the EGF-induced DMR signal is dependent on EGFR activation; (ii) the optical biosensors can be used to determine the potency of the ligands based on the ligand-induced mass redistribution signals.

(4) Methods to Screen Modulators that Affect RTK Signaling at Different Stages

FIG. 40 shows the effect of pre-treatment with different compounds on the time-dependent response of 8 nM EGF-induced signaling for a layer of starved A431 cells. FIG. 41 summarizes the net changes of binding and DMR signals under different conditions. The results showed that cell permeable dynamin inhibitory peptide (DIP) (Burke, P., et al., "Regulation of epidermal growth factor receptor signaling by endocytosis and intracellular trafficking", Mol. Biol. Cell. 2001, 12:1897-1910) totally blocks the N-DMR signal, but slightly increases the P-DMR signal with much slower kinetics. DIP is a cell permeable inhibitor of the GTPase dynamin that competitively blocks binding of dynamin to amphiphysin, preventing endocytosis ((Burke, P., et al., "Regulation of epidermal growth factor receptor signaling by endocytosis and intracellular trafficking", Mol. Biol. Cell. 2001, 12: 1897-1910). These observations suggest that the N-DMR signals involve receptor translocation and its associated cell morphology changes, because the EGF-induced EGFR internalization occurs mainly through dynamin-dependent pathways and involves the cytoskeleton rearrangement, and the coupling of dynamin with activated EGFRs affects the affinity of EGF binding. The total P-DMR signal in the presence of DIP is 50% more than that in the absence of DIP; suggesting that during the P-DMR phase (from C to D in FIG. 6A) there are some activated EGFRs that have been internalized. It is known that EGF-bound receptors only spend a relatively short time at the cell surface (~3 min) at 37° C. owing to rapid internalization. In addition, it has been estimated that during trafficking, 48.7% and 96.2%, respectively, of the formed coated- and smooth-pit EE recycle back to the cell surface; i.e., receptor internalization through clathrin-coated pits is sufficient to account for the majority of endocytosis. Therefore, receptor internalization through the coated-pit EE vesicles is the dominant mechanism of receptor accumulation within cells, and this is particularly true when ligand is present in the system.

The pretreatment of starved A431 cells by wortmannin has no obvious effect on both the P-DMR and N-DMR signals as well as their kinetics. Wortmannin is a potent, selective, cell permeable and irreversible inhibitor of phosphatidylinositol 3-kinase (PI 3-kinase) with an $IC_{50}$ of 2-4 nM (Powis, et al, "Wortmannin, a potent and selective inhibitor of phosphatidylinositol-3-kinase", (1994) Cancer Res. 54 2419). This suggests that the blocking of the PLC-gamma pathway does not affect both events of the cells in response to EGF stimulation.

The pretreatment of starved A431 cells with growth hormone (GH), PD98059 and PP1 (also See FIG. 43) not only significantly reduced both the binding and DMR signals, but also results in a decrease in the kinetics of both P-DMR and N-DMR events. PD 98059 is a specific inhibitor of mitogen-activated protein kinase kinase (MAPKK/MEK) and acts by binding to the inactivated form of MEK, thereby preventing its phosphorylation by cRAF or MEK kinase ($IC_{50}$=2-7 µM) (Alessi, et al., "PD 98059 is a specific inhibitor of the activation of mitogen-activated protein kinase kinase in vitro and in vivo", Nov. 17, 1995, J. Biol. Chem., Vol. 270, No. 46, pg. 27489-27494). The blocking of the MAPKKs by PD98059 possibly reduces the magnitude of the signal, and the duration of the response of the cells having EGFR to EGF binding. PP1 is a potent inhibitor of Src-family tyrosine kinases, and inhibits p561ck and p59fynT ($IC_{50}$ of 5 and 6 nM, respectively) and also moderately inhibits p38, CSK, PDGF receptors, RET-derived oncoproteins, c-Kit and Bcr-Abl (Liu et al, Structural basis for selective inhibition of Src family kinases by PP1", (1999) Chem.Biol. 6, 671). Epidermal growth factor (EGF) binding to its receptor causes rapid phosphorylation of the clathrin heavy chain at tyrosine 1477, which lies in a domain controlling clathrin assembly. EGF-mediated clathrin phosphorylation is followed by clathrin redistribution to the cell periphery and is the product of downstream activation of SRC kinase by EGF receptor (EGFR) signaling. In cells lacking SRC kinase, or cells treated with a specific SRC family kinase inhibitor, EGF stimulation of clathrin phosphorylation and redistribution does not occur, and EGF endocytosis is delayed. These are consistent with the current observations.

Growth hormone (GH) is a four-helix bundle protein that shares structural similarity with a large class of hormones and cytokines, including prolactin and various interleukins and colony stimulating factors (Huang, Y., et al., "Growth hormone-induced phosphorylation of epidermal growth factor (EGF) receptor in 3T3-F442A cells", J. Biol. Chem. 278, 18902-18913). GH exerts its profound somatogenic and metabolic regulatory effects by interacting with the GH receptor (GHR), a cell surface glycoprotein member of the cytokine receptor superfamily. Recent studies suggest that there is cross-talk between the GHR and members of the EGFR family, examples of seemingly disparate types of signaling receptors (a cytokine receptor and a family of tyrosine kinase receptors, respectively). GH causes phosphorylation of epidermal growth factor receptor (EGFR; ErbB-1) and its family member, ErbB-2. This GH-induced EGFR tyrosine phosphorylation was shown to require JAK2, but not EGFR, kinase activity. GH causes a decrease in basal and EGF-induced ErbB-2 tyrosine kinase activation and tyrosine phosphorylation, suggesting that GH causes an ERK pathway-dependent phosphorylation of ErbB2 that renders it desensitized to activation in response to EGF. Fluorescence microscopy studies indicated that EGF-induced intracellular redistribution of an EGFR-cyan fluorescent protein chimera was markedly reduced by GH co-treatment. This is also consistent with the current observations (Huang, Y., et al., "Growth hormone-induced phosphorylation of epidermal growth factor (EGF) receptor in 3T3-F442A cells", J. Biol. Chem. 278, 18902-18913).

(5) Dose Dependent Suppression of the EGF-Induced Responses of Quiescent A431 Cells Induced by AG1478

FIG. 42 shows a dose dependent suppression of the EGF-induced responses of quiescent A431 cells induced by AG1478. To confirm that these DMR events are dependent on receptor phosphorylation, a potent and specific EGFR kinase inhibitor tyrphostin AG1478 was used. The A431 was pre-starved in a medium without any FBS for 20 hours, resulting in significantly faster kinetics for the P-DMR event and shorter transition time than those starved in 0.1% FBS medium for the same period of time (FIG. 42A). The pretreatment of A431 cells with AG1478 at different concentrations for one hour resulted in a dose-dependent suppression of the EGF-induced response, yielding a typical inhibition curve with an $IC_{50}$ of ~194 nM when the amplitude of the N-DMR signal was plotted as the function of AG 1478 (FIG. 42 a and b). However, pretreatment of A431 with 0.5% dimethyl sulfoxide had a little effect on the EGF-induced response (data not shown). These data indicate that EGFR kinase phosphorylation is required for the EGF-induced DMR changes; and the DMR signals obtained using optical biosensors can be used to determine the potency of modulators that play an important role in the DMR event measured.

(6) The Effect of Ras/MAPK Pathway Modulators on 32 nM EGF-Induced Response of the Quiescent A431 Cells EGF regulates cell proliferation and differentiation, and uses, at least in part, mitogen-activated protein kinases as downstream signals. Furthermore, ERK activation seems to represent a global, negative signal downstream of EGFR activation, which may be important in deadhesion. Thus, the effect of inhibitors targeting Ras-MAPK pathways, including MEK inhibitors U0126, p38 MAPK inhibitor SB203580 and SB20219, and a JNK inhibitor SP600125, were examined (see FIG. 44). U0126 significantly compressed the amplitudes of both the P-DMR and N-DMR signals with a delayed time τ. This suggests that inhibition of MEK1/2 prevents cell detachment and movement that leads to the N-DMR signals, consistent with previous studies. However, the endocytosis of activated EGFR could still occur when the MEK1/2 were inhibited. Since the endocytosis occurs away from the sensor surface compared to the cell detachment and movement, the endocytosis should contribute significantly less to the overall response. Therefore, the EGF-induced responses of those quiescent A431 pretreated with MEK1/2 inhibitor is consistent with receptor endocytosis. This was further supported by the kinetics of the responses which are consistent with computational modeling results. In contrast, both SB203580 and SB20219 only led to a partial attenuation, whereas SP600125 had little effect on the EGF-induced response. These results indicate that in quiescent A431 cells EGF simulation of the DMR responses involve the Raf-MEK pathway, and proceeds through MEK.

(7) The Effect of Protein Kinase Inhibitors on 32 nM EGF-Induced Response of the Quiescent A431 Cells The effect of protein kinase inhibitors on the EGF-induced response was examined since EGFR signaling involves a variety of other protein kinases. Pretreatment of A431 with 1 µM wortmainnin (a potent and selective PI3K inhibitor), 1 µM KT 5720 (a potent and selective inhibitor of protein kinase A), 10 µM KT5823 (a selective inhibitor of protein kinase G), and 10 µM KN 62 (a selective inhibitor of CaM kinase II) had little effect on the response. In contrast, GF 109203x(a selective inhibitor of protein kinase C) exhibited partial attenuation on the response (see FIG. 45). These results indicate that protein kinase C, but not PI3K, protein kinase A and CaM II, alters the ability of EGF to stimulate the DMR changes.

(8) The Effect of Cytoskeleton Modulators on 32 nM EGF-Induced Response of the Quiescent A431 Cells.

Since the trafficking of targets and morphological changes of cells in response to EGF stimulation requires the re-modeling of cytoskeleton structure, the effect of cytoskeleton modulators on the EGF-induced DMR response was examined (see FIG. 46). Pretreatment of A431 with actin filament disruption agents, either cytochalasin B or latrunculin A, totally abolished the N-DMR signal, and resulted in the prolonged P-DMR phase with significantly slow kinetics. The two toxins perturb actin assembly and disassembly by distinct mechanisms: cytochalasin B caps actin filaments and ultimately leads to actin filament disassembly, while latrunculin A sequesters actin monomers and causes actin filament disassembly. However, neither a stabilizing polymeric F-actin agent phalloidin or microtubule disrupters vinblastine and nocodazole (data not shown), had hardly any effect on the EGF-induced response. These results confirm that the movement of cells resulting in the N-DMR signal is not due to reorganization of preexisting actin but, rather, actin polymerization, and is independent of microtubule assembly. In contrast, since the trafficking of intracellular proteins requires actin filaments, the P-DMR signal is at least partially due to the recruitment of intracellular components to the activated receptors. Extra evidence came from the effect of the cell membrane permeable dynamin inhibitory peptide (DIPC). Pretreatment of A431 with DIPC at 50 µM gave rise to similar response to those pretreated with cytochalasin B and latrunculin A, but with faster kinetics.

(9) The Effect of Phosphodiesterase Inhibitors on 32 nM EGF-Induced Response of the Quiescent a431 Cells Cyclic AMP (cAMP) has served as a paradigm of an intracellular second messenger, and regulates a myriad of cellular functions, such as metabolism, contractility, motility, and transcription in virtually all cell types. Previous studies showed that cAMP pathways crosstalk with and attenuate growth factor-stimulated MAP kinase activity that depends on the cellular context. Since phosphodiesterases (PDE) regulate the cAMP levels in cells, the role of PDEs on the EGF-induced response was studied using PDE inhibitors cilostamide, milrinone, Ro 20-1724, R(−)-rolipram and Zard-averine (each at 10 µM). None of these inhibitors had an obvious effect on the responses (see FIG. 47), suggesting that cAMP is not involved in the overall DMR response. Previous studies have shown that protein kinase A can antagonize the activity of Raf-1 and thus regulate Ras-MAPK pathway through modulating PDE activities. However, in quiescent cells Raf-1 exhibits a constitutive phosphorylation which is not sensitive to a PKA inhibitor, consistent with our observations that a PKA inhibitor KT5720 (FIG. 45) and PDE4 inhibitors Ro 20-1724 and R-(−)-rolipram had little effect on the EGF-induced DMR signals.

(10) EGF Induced EGFR Internalization, Cell Morphology Changes, and Directional Mass Redistribution in A431 Cells at Room Temperature (22° C.)

Figure 48A:
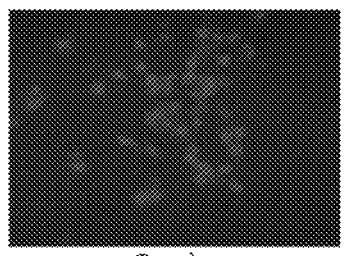
Figure 48B:
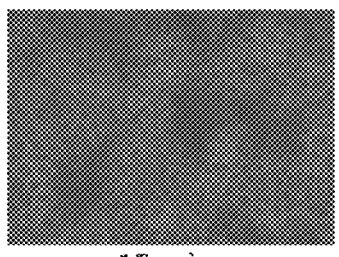
Figure 48C:
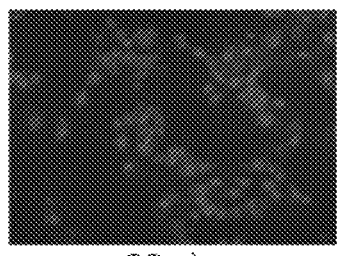
Figure 48D:
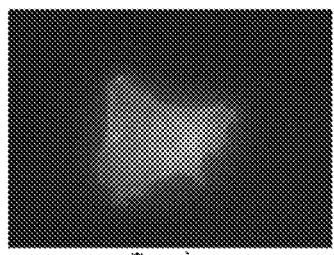
Figure 48E:
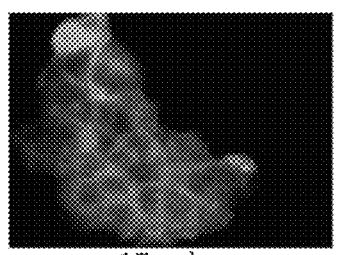
Figure 48F:
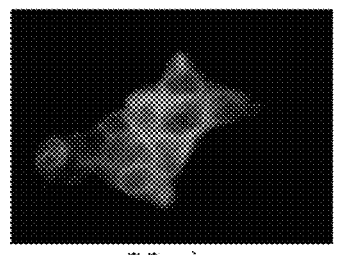

Stimulation of A431 cells with EGF at room temperature triggers EGFR activation through receptor dimerization and sequent autophosphorylation that ultimately leads to receptor endocytosis (see FIG. 48A-C, refractile morphological changes (see FIG. 48D), and directional mass redistribution (see FIG. 2A, FIG. 18 and others). By selectively removing the surface-bound tetramethylrhodimine-labeled EGF (TMR-EGF) using acid stripping method, the extent of EGFR internalization was examined and found to be dependent on cell culture condition. Much higher cell surface and internalized receptors were found in quiescent cells than those in proliferating cells. The EGF-induced morphological changes of quiescent cells were visualized by Texas red-phalloidin staining after fixation. Previous studies showed that the A431 at 37° C. exhibits time-dependent refractile morphological changes and detachment from the extracellular matrix upon EGF treatment. Consistent with these studies, actin remodeling started to change after ~15 minutes of EGF treatment, and this change became more dramatic at longer stimulation, as indicated by the rim of filamentous actin at the edge of the cell.

(11) Schematic Drawing Shows One Possible Mechanism for EGF-Induced DMR Signals—Receptor Endocytosis Potential roles for the actin cytoskeleton in endocytosis. The model in FIG. 49 depicts how the cortical actin cytoskeleton can be involved in different steps of the endocytic process implicating potential functional roles for molecules at the interface of endocytosis and cytoskeletal organization. Following the receptor activation by its cognate ligand (e.g., EGF), there are three major steps in receptor endocytosis: (FIG. 49A) 1) spatial organization of the endocytic machinery. Cytoskeletal structures may organize or constrain the lateral mobility of the machinery for endocytosis. Deformation and invagination of the plasma membrane may be supported by the cytoskeleton. (FIG. 49B) 2) The cortical actin barrier underlying the plasma membrane might need to be dissolved. Actin polymerization may provide force to drive membrane fission during endocytic vesicle formation, and (FIG. 49C) 3) Actin polymerization may promote the movement of newly formed endocytic vesicles into the cytoplasm by forming a comet tail.

5. Example 5

Method to Screening Modulators for Cytoskeleton

The pore-forming regents include detergents such as saponin and filipin, or toxin such as digitonin or streptolysin O. It is well known that treatment of the cells with these reagents can result in the pore formation in cell surface membrane; the resulted permeabilized cells can release a certain amount of intracellular material, mainly soluble proteins. However, there are a great number of bio-materials that still stay with these permeabilized cells due to the sequestration by directly binding or association with the cytoskeleton structure. As a matter of fact, these permeabilized cells retain many of the biological functions of living cells such as protein synthesis. Treatment of the cells with a compound that can disrupt the cytoskeleton structure can result in releasing significantly more bio-materials from these permeabilized cells.

Cytoskeleton is a complex and dynamic network of protein filaments that extends throughout the cytoplasm of eukaryotic cells. Cytoskeleton is involved in executing diverse activities in cells. It maintains cell shape by providing tensile strength for the cells. It also enables some cell motion (using structures such as flagella and cilia), and plays important roles in both intra-cellular transport (the movement of vesicles and organelles, for example) and cellular division. The cytoskeleton is involved in intracellular signaling and trafficking by providing the "track" on which cells can move organelles, chromosomes and other things.

FIG. 50 presents the dose-dependent responses of CHO cells adherent on the surface of a LID sensor in response to saponin as a function of time. After the addition of saponin at different concentrations, a different response is evident. At low concentration, there is almost no response. When the concentration of saponin is above ~20 ug/ml, there is a decreased signal followed by an increased response. The initial increased signal can be most likely due to the flattening out of the cells on the surface of the sensor, resulting in a mass increase within the sensing volume of the sensor; whereas the decreased signal most likely reflects the loss of bio-materials from the cells; another possibility is due to the rearrangement of cellular components and/or morphology changes that lead to a net-decreased mass within the sensing volume of the sensor. At the highest concentration tested, there is no initial increased signal; conversely there is only a decreased signal with significant greater response than those at lower concentrations.

The permeability of the cells treated with higher concentration of saponin can be evidenced by the fluorescence images of CHO cells stained with Texas Red ® phalloidin after treated with different concentrations of saponin (data not shown). Texas Red-X phalloidin is a high-affinity probe for F-actin that is made from a mushroom toxin conjugated. Staining using Texas Red® phalloidin requires that cells are permeable, generally done after formaldehyde-fixation. This is because the fluorescent phalloidin conjugates are not permeant to most live cells, although unlabeled phalloidin can penetrate the membranes of cells. The strong fluorescence inside the cells treated with high concentrations of saponin indicates the pore formation and the cells are permeable. Based on this study, the concentration of saponin at 67 ug/ml was chosen for compound screening.

FIG. 51 shows the saponin-induced and time-dependent responses of CHO cells after being pre-treated with different compounds. Results show that these compounds can be mainly classified into four categories: (i) compounds (e.g., cytochalasin B) that cause increased loss of biomaterials, as evidenced by increased kinetics and amplitudes of the N-DMR signal; (ii) compounds (e.g., dynamin inhibitory peptide, brefeldin A) that show no effect on a saponin-induced response; (iii) compounds (e.g., phalloidin) that delay the loss of biomaterials in saponin-treated cells, but with similar total changes after longer time; and (iv) compounds (e.g., vinblastine) that block the saponin-induced loss of biomaterials from the cells. These observations are consistent with the known properties of these compounds. Cytochalasin B caps actin filaments preventing assembly and, owing to the dynamic nature of actin filaments, ultimately leads to actin filament disassembly. In contrast, phalloidin binds to F-actin and promotes actin polymerization. Vinblastine inhibits microtubule assembly by binding tubulin and induces self association in spiral aggregates. Dynamin inhibitory peptide (DIPC) and brefeldin A are non-binders to actin or other filaments. These results also suggest that actin filaments, but not other filaments, provide the most of sequestered sites for bio-macromolecules.

Staining with Texas Red-phalloidin after saponin-treatment reveals that cytochalasin B-pretreated cells give rise to similar staining pattern compared to those pretreated with other compounds (data not shown). This can be due to limited fluorescence resolution available. However, phalloidin-pretreated cells give rise to significantly lower staining. This is because the unlabeled phalloidin blocks F-actin staining by labeled phallotoxins.

6. Example 6 Systems and Methods for Performing G Protein Coupled Receptor (GPCR) Cell Assays Using Label Free Optical Biosensors FIGS. 52-60 provide various graphs and charts indicating the results of several different experiments that were conducted to show that the optical LID system can be used to monitor mass redistributions, such as GPCR translocations, within living cells. These translocations can be located on a surface of an optical LID biosensor as disclosed herein. The particular data shown in FIGS. 52-60 was obtained using an optical waveguide grating sensor system and LID microplates ($Nb_2O_5$ plates), manufactured by Corning Incorporated. FIG. 52 is a graph that shows several agonist-induced responses within chinese hamster ovary cells 108 (CHO 1008) that were monitored by the optical LID system 1000. It is known that CHO cells 1008 endogenously express beta adrenergic receptors, alpha2-adrenergic receptors, P2Y receptors, as well as beta-arrestin and GRKs. It is also known that muscarinic receptors are endogenously expressed at very low level in the CHO cells 1008. In this experiment, approximately ~$5 \times 10^4$ CHO cells 1008 were placed within each well of a microplate that contained an array of optical LID biosensors 1004. The CHO cells 1008 were then cultured in 150 µl serum medium for 24 hours to ensure that the CHO cells 1008 became adherent to the substrate surface 1010. The graph shows the optical responses of the CHO cells to four different compounds which were examined: (1) ATP (100 µM), agonist for P2Y receptors; (2) clonidine (10 µM), agonist for alpha2-adrenergic receptors; (3) epinephrine (100 µM), agonist for beta adrenergic receptors; and (4) oxotremorine M (10 µM), agonist for muscarinic receptors. Since muscarinic receptors are endogenously expressed at very low level in CHO cells, oxotremorine M, agonist for muscarinic receptors, served as a control. Each of these agonists was directly applied to a different one of the wells which contained the serum medium. The optical responses were then collected by the optical LID system.

The results showed that these adherent CHO cells gave rise to similar kinetics and transitions as shown by the optical responses after the introduction of the three agonists: ATP, clonidine, and epinephrine. Oxotremorine M caused almost no cell response. In FIG. 53, a kinetics analysis of the later stage of the process revealed that all three agonists (ATP, epinephrine, clonidine) resulted in a similar slow process. The changes for the Stage 3 as shown in FIG. 16, caused by those agonists, are shown in the graph in FIG. 54. The similar changes might reflect the fact that beta-arrestin, a critical component for GPCR translocation, could be the limiting factor in the CHO cells, given that the size of clathrin-coated pits and beta-arrestin are similar. FIG. 55 is a graph that shows the results from an experiment which indicates the ligand- and time-dependent response of a monolayer of living CHO cells on wave-guide biosensors. The agonists which were used included: (1) clonidine; (2) oxotremorine M; (3) NECA; and telenzepine, an antagonist for M1 receptor, is also used.

FIG. 56 is a graph that shows the results from an experiment which indicates the ligand- and time-dependent response of monolayer of living CHO cells 108 with stably overexpressed rat muscarinic receptor subtype 1 (M1) on wave-guide biosensors 104. The agonists which were used included: (1) clonidine; (2) oxotremorine M; and (3) NECA; and telenzepine, an antagonist for M1 receptor, is also used. FIG. 57 is a graph that shows the results from an experiment which indicates the ligand-induced total change in response of monolayer of living CHO cells without (CHO) and with stably overexpressed rat muscarinic receptor subtype 1(M1CHO) on wave-guide biosensors 104. Results shown in FIGS. 52 and 54-56 indicated that (1) there are alpha2 adrenergic receptors expressed in both CHO and M1-CHO cells; and their agonist (clonidine) induced mass redistribution signals; (2) there is relatively low or almost no M1 receptor expressed in CHO cells, but high in M1-CHO cells since its agonist (oxotremorine M) but not its antagonist (telenzepine) results in significantly larger responses in M1-CHO cells.

FIG. 58 is a graph that shows the results from an experiment which indicates the effect of pre-incubation of a dynamin phosphorylation inhibitor (dynamin inhibitory peptide, DIP) on oxotremorine M-induced time-dependent response of a monolayer of living CHO cells without and with stably overexpressed rat muscarinic receptor subtype 1 (M1CHO) on wave-guide biosensors. Results show that the pre-incubation of cells with DIP almost totally eliminates the oxotremorine M-induced mass distribution responses in both cell lines, suggesting that oxotremorine M-induced mass distribution is dynamin-dependent. The dynamin-dependency is common for most of agonist-induced GPCR translocation.

FIG. 59 is a graph that shows the results from an experiment which indicates the effect of pre-incubation of a dynamin phosphorylation inhibitor (dynamin inhibitory peptide, DIP) on clonidine-induced time-dependent response of a monolayer of living Chinese Hamster Ovary (CHO) cells without and with stably overexpressed rat muscarinic receptor subtype 1 (M1CHO) on wave-guide biosensors. Results show that the pre-incubation of both cell lines with DIP almost totally eliminates the clonidine-induced mass distribution response, suggesting that clonidine-induced mass distribution is also dynamin-dependent.

FIG. 60 is a graph that shows the results from an experiment which indicates the effect of pre-incubation of a dynamin phosphorylation inhibitor (dynamin inhibitory peptide, DIP) on NECA-induced time-dependent response of a monolayer of living CHO cells 108 without and with stably overexpressed rat muscarinic receptor subtype 1 (M1CHO) on wave-guide biosensors 104. Results showed that the pre-incubation of both cells with DIP has little effect on NECA-induced response, suggesting that NECA results in mass redistribution signals in both cell lines through a dynamin-independent pathway. FIG. 61 shows the results of a GPCR agonist-induced directional mass redistribution within adlayer of quiescent A431 cells. Three GPCR agonists, bradykinin (100 nM), carbachol (10 µM) and clonidine (1 µM), induced time-dependent responses of quiescent A431 cells, in comparison with that induced by EGF (8 nM). (F) Pretreatment of A431 with 10 µM AG1478 on the GPCR agonist- and EGF-induced responses.

FIG. 62 shows a schematic drawing shows the mechanism of EGF-induced EGFR activation and GPCR agonist-induced EGFR transactivation. The EGFR has been found to be a critical downstream element of signaling systems, including those employed by mitogenic G protein-coupled receptors (GPCRs), cytokine receptors, integrins and membrane-depolarizing or stress-inducing agents. Previous studies have shown that A431 endogenously expresses bradykinin $B_2$ receptor, muscarinic receptor(s), and alpha 2 adrenergic receptor(s). Stimulation of quiescent A431 with GPCR agonists, bradykinin, clonidine and carbachol, results in two distinct DMR response curves. Carbachol and clonidine stimulation led to responses with almost identical features as those induced by low concentrations (2-8 nM) of EGF. As expected, pretreatment of A431 with AG1478 at 10 µM totally abolished the N-DMR phase, and significantly reduced the kinetics of the P-DMR phase. In contrast, bradykinin stimulation results in an extremely rapid P-DMR phase (within 100 sec), and a much shorter transition time τ. The pretreatment of A431 with AG1478 can only partially attenuate the response. Consistent with those previous studies by others, (i) stimulation with GPCR agonists could crosstalk with Ras-MAPK pathways through distinct mechanisms which depend on the context of specific cells, (2) the GPCR agonist-induced EGFR transactivation can be examined using the resulted signatures of the Ras/MAPK activation. Since the GPCR agonist-triggered EGFR transactivation leads to comparable DMR signals as EGF stimulation, the transactivation acts as a signaling amplification mechanism such that one can study GPCR signaling and screen agonists and antagonists against an endogenous target GPCR in its native environment. The distinct kinetics of the DMR responses in response to different GPCR agonists indicates that distinct GPCRs may transactivate the Ras/MAPK pathway through distinct mechanisms, possibly depending on the G proteins the receptor coupled and the cell context.

In FIG. 62 epidermal growth factor receptor (EGFR) signaling pathways are shown. Members of the EGFR family contain a cytoplasmic tyrosine kinase domain, a single transmembrane domain, and an extracellular domain that is involved in ligand binding and receptor dimerization. Binding of ligand to EGFR leads to formation of homodimers or heterodimers of the receptor with other family members. Each dimeric receptor complex will initiate a distinct signaling pathway by recruiting different Src homology 2 (SH2)-containing effector proteins. Dimerization results in autophosphorylation initiating a diverse array of downstream cellular signaling pathways. The activated EGF-R dimer complexes with the adapter protein, Grb, coupled to the guanine nucleotide releasing factor, SOS. The Grb-SOS complex can either bind directly to phosphotyrosine sites in the receptor or indirectly through Shc. These protein interactions bring SOS in close proximity to Ras, allowing for Ras activation. This subsequently activates the ERK and INK signaling pathways that, in turn, activate transcription factors, such as c-fos, AP-1, and Elk-1, that promote gene expression and contribute to cell proliferation. EGF=epidermal growth factor, EGFR=epidermal growth factor receptor, Shc=src homology domain consensus, grb2=growth factor receptor-bound protein 2, SOS=mammalian son of sevenless, Raf=Ras activated factor, MEK=MAP kinase kinase, MAPK=mitogen activated protein kinase, PI3K=phosphatidylinositol 3' kinase, PIP2=phosphatidyl inositol 3,4-diphosphate, PIP3=phosphatidyl inositol 3,4,5 triphosphate, PLCγ=phospholipase-γ, DAG=diacyl glycerol, IP3=inositol 3,4,5 triphosphate, PKC=protein kinase C. In FIG. 61 GPCR agonist induced EGFR transactivation is shown. Activation of Src family kinases by GPCR-stimulated transactivation of receptor tyrosine kinases. The best understood mechanism of crosstalk between GPCRs and receptor tyrosine kinases involves the GPCR-stimulated proteolytic release of ligands, such as HB-EGF, following activation of membrane-associated ADAM family MMPs. Transactivated EGF receptors (EGFR1/2) recruit Shc and the Grb2/mSos complex, allowing them to serve as platforms for the GPCR-induced assembly of a Ras activation complex. Transactivation of EGF receptors accounts for GPCR-stimulated activation of the cRaf-1, MEK1/2, ERK1/2 MAP kinase cascade in many systems. Src family kinases are activated in response to EGF receptor activation, and play an essential downstreammole in this form of GPCR signaling. In addition, some evidence suggests that Src plays a role in the poorly understood process of GPCR-stimulated MMP activation, particularly in the Gβγ subunit-dependent pathway 7. Example 7

Multimode Detection Methods

Grating coupler biosensors are evanescent-wave sensors based on the resonant coupling of light into a waveguide by means of a diffraction grating. (See discussion of different biosensors herein). An example, of a biosensor, the grating coupler sensor, typically consists of the combination of a guiding multilayer and of a diffraction grating. Typically, a four layer waveguide biosensor consists of a thin film of a high refractive index ($n_F$) material with a thickness of $d_F$ (e.g., $Nb_2O_5$ of index about 2.36) on a substrate of lower index ($n_s$) (e.g., 1737 glass, Corning code with an index about 1.50) than the film, but higher than the cover medium being the biological solution with index around 1.35 ($n_c$). The substrate is preferably transparent in order to permit light incidence from the substrate side. An adlayer of biologicals, immobilized on the waveguide film, with a refractive index around 1.4 ($n_A$) and a thickness $d_A$. The biologicals immobilized include, but not limited to, antibodies, antigens, receptors, peptides, phages, "single-stranded" DNA(RNA)-sections, genes, gene sections, targets, proteins, binding proteins, enzymes, inhibitors, nucleic acids, nucleotides, oligonucleotides, allergens, pathogens, carbohydrates, metabolites, hormones, active ingredients, molecules with low molecular weight, lipids, signal, cells, and bacteria.

The guided waves or modes in planar waveguide are $TE_m$ (transverse electric or s-polarized) and $TM_m$ (transverse magnetic or p-polarized), where m=0, 1, 2, . . . is the mode number. A laser illuminates the waveguide at varying angles and light is coupled into the waveguide only at specific angles determined by the effective refractive index of the guided mode. The laser light coupled propagates parallel to the surface in the plane of a waveguide film creating an electromagnetic field in the liquid adjacent to the interface. A given mode type propagates only as a guide wave if two conditions need to be fulfilled: (a) the refractive index of the waveguide film has to be at least 1% larger than the surrounding substrate and cover medium refractive indices; and (2) the thickness of the waveguide film is larger than a well-defined value, call the cut-off thickness $d_C$.

The waveguide grating biosensors consist of at least one waveguide grating structure unit or of at least one sensor location. The biosensors can be associated with a microplate, each well containing at least one waveguide grating structure.

Disclosed are methods wherein an analyte(s) in a sample is either unlabeled or labeled. When the analyte(s) is labeled, it can be labeled in any fashion, such as the moiety attached to the analyte(s) can emit fluorescence, chemiluminescence, bioluminescence, phosphorescence or electro-luminescence on excitation with light (with a wide and/or narrow excitation spectrum) or chemical/electrochemical activation. When the analytes themselves are not labeled, a labeled binding partner that can bind to specific binding site(s) of the immobilized probe molecules with desired affinity are used as a reference ligand. The reference ligand is used to determine relative activities or affinities of analytes against the probe molecules.

The label-independent detection of a binding of an analyte(s) and/or the reference ligand to immobilized probe molecules located at the grating area is based on the changes in wavelength or angle of reflected lights due to the refractive index changes (e.g., see U.S. Pat. Nos. 4,815,843, or 5,479, 260). The label-dependent detection of binding of the reference ligand or the competitive binding of the analytes against the reference ligand to the probe molecules is based on the changes in color (e.g., fluorescence, chemiluminescence, or bioluminescence, phosphorescence or electro-luminescence, etc).

The labeled dependent detection can be achieved by two distinct exemplary methods. In the first method, the waveguide grating substrate is used to propagate light within the waveguide film and at the same time generate an evanescent wave penetrating the side of the probe molecules immobilized. The penetrated evanescent wave results in excitation of the labeled analytes or the labeled reference ligand, with different efficiency that is dependent on the distance between the labeled molecules and the waveguide film surface. The closer the labeled molecules are to the surface, the higher the efficiency of the excitation. Particularly, the evanescent field excitation provides an enhanced excitation probability/efficiency of the surface-bound fluorophores along the entire planar waveguiding surface (Budach, W.; Abel, A. P.; Bruno, A. E.; Neuschafer, D.; "Planar Waveguides as High-Performance Sensing Platforms for Fluorescence-Based Multiplexed Oligonucleotide Hybridization Assays" Anal. Chem. 1999, 71(16): 3347-3355. and Edmiston, P. L.; Lee, J. E.; Wood, L. L.; Saavedra, S. S. "Dipole Orientation Distributions in Langmuir-Blodgett Films by Planar Waveguide Linear Dichroism and Fluorescence Anisotropy" J. Phys. Chem.1996, 100: 775-784.). This is in contrast to luminescence detection principles based on confocal microscopy, where the light source is focused to a defined volume element leading to a strong local electrical field (i.e., epifluorescence). By doing this, the waveguide grating structure becomes the core component for both detections: label-independent detection based on changes in the refractive index in the propagation media of the evanescent field due to specific molecular adsorption at the sensor surface, and label-dependent detection based on changes in color (intensity, intensity distribution, total internal reflection fluorescence intensity, etc) which offer superior sensitivity, because of the fact that the evanescent wave decays exponentially as the distance of a target or a target complex whether it is labeled or unlabeled is increased.

For this approach, the special sensor design is required for simultaneously coupling the light into the waveguide and exciting the fluorescence moiety when the fluorescence-based detection is targeted. A given sensor with a unique structure (e.g., grating structure, periods, depths, properties and thickness of the waveguide film, configurations of the sensor, etc) tends to allow a laser of specific wavelength to be coupled into the sensor at near the normal angle. This normal angle coupling is preferred for cell sensing, since cells are covered with medium as well as most liquid handling devices prefer the liquid changes at the normal angle. However, fluorescent molecules to be excited generally require specific light sources with a particular range of wavelength. For example, Cy3 requires the excitation light being in the range of 530-560 nm. In order to detect the DMR signal as well as fluorescence using same light source, the sensor need to be modeled such that it allows the coupling of the same light source into the waveguide. Thus the evanescent wave of the propagated light can be used to excite the fluorescence molecules within the penetration depth or sensing volume.

The second method involves a separate excitation light source to specifically excite the bound labeled analytes or reference ligand(s), and a separate emission detection device to collect the emission light. This approach has less stringent requirements relating to waveguide sensor design, and can be applied to a wide range of different sensor designs.

8. Example 8

Profiling of Endogenous GPCRs in A431 Cells

Dynamic redistribution of cellular contents, equivalent to dynamic mass redistribution (DMR), is common to many cellular processes including the signaling through G protein-coupled receptors (GPCRs) in response to stimulation. The DMR can be manifested by resonant waveguide grating (RWG) biosensors, and the resultant DMR signal offers a novel and integrated readout for sensing living cells under real physiological conditions. Upon investigating the DMR signals of quiescent A431 cells mediated through the activation of endogenous GPCRs using the RWG biosensors in combination with a panel of GPCR agonists, a unique DMR signature was identified for each class of GPCRs, based on the G protein(s) with which the receptor is coupled (i.e., Gq, Gs and Gi). The DMR signals were dependent on the doses of agonists and the expression levels of endogenous receptors. The dose-dependent switching from one type of DMR signal to another was observed for a small set of GPCR agonists. Together with its ability to map the network interactions and regulation of GPCR signaling, the label-free and non-invasive biosensors enable real time kinetic measurements, thus allowing them to be used for GPCR drug discovery and deorphanization.

G-protein-coupled receptors (GPCRs) are a superfamily of membrane proteins that share common structural motifs with seven transmembrane spanning domains, an extracellular N-terminus and an intracellular C-terminus. GPCRs have been implicated in the development and progression of major diseases such as cardiovascular, respiratory, gastrointestinal, neurological, psychiatric and metabolic disorders. GPCRs represent the single largest family of druggable targets in human genome and have been proven to be the most productive area for small molecule drug discovery, as illustrated by the fact that GPCRs account for ~50% of the current drug targets with more than $60 billion in sales in 2000. Considering that the current GPCR-based drugs only target ~25% of the approximately 200 known GPCRs, and there are ~140 newly classified orphan receptors, GPCRs are a target class that offers ample opportunities for drug discovery.

A diverse array of exogenous stimuli including light, ions, neurotransmitters and hormones modulate the physiology and pathophysiology of cells through GPCRs. The activation of GPCRs mediated by agonists triggers the dynamic interaction with their associated G proteins and other regulatory proteins, which governs the cascade of intracellular responses. GPCRs can be divided into three groups, distinguished by their coupled G-protein subtype: $G_q$, $G_s$ and $G_i$. The ligand-induced cellular events mediated through a GPCR typically start with changes in receptor conformation and oligomerization state, followed by G protein activation (GDP-GTP exchanges on $G_\alpha$ subunit, $G_\alpha$ and $G_{\beta\gamma}$ disassociation, G protein decoupling from the receptor, generation of $G_\alpha$- and $G_{\beta\gamma}$-signaling complexes), and downstream signaling activation that leads to second messenger generation ($Ca^{2+}$ mobilization, inositoltriphosphate generation, and/or intracellular cAMP level modulation). Subsequently, GPCR signaling leads to expression of specific genes and desensitization of GPCRs from the cell surface through endocytosis; many of which involve dynamic trafficking of numerous intracellular proteins. Ultimately, the phenotypes, morphology and physical properties of the target cells are altered. The signaling and regulatory machineries generally take a timely and precisely controlled action that governs the cellular responses. As a result, almost all GPCR signaling are common in the sense that there are ordered and regulated dynamic redistribution of cellular contents during the signaling cycle. Monitoring the dynamic redistribution of cellular contents should will insights in GPCR signaling and a powerful means for GPCR screens.

a) Materials and methods (1) Materials

688. Adenosine amine cogener (ADAC), anandamide, ATP, interleukin-8 (IL-8), interferon-γ-inducible protein-10 (IP-10), oleoyl-L-α-lysophosphatidic acid (LPA), NECA, nocodazole, thrombin, trypsin, and UK14304 were purchased from Sigma Chemical Co. (St. Louis, Mo.). A-77636, BRL 54443, clonidine, epinephrine, HTMT dimaleate, isoprenternol, oxotremorine M, oxymetazoline, and SKF38392 were obtained from Tocris Chemical Co. (St. Louis, Mo.). Fluo-3 was obtained from Molecular Probes (Eugene, Oreg.). Angiotensin II, apelin 1-17, apelin 1-13, bombesin, bradykinin, DAMGO, dynorphin A, endothelin-1, galanin, GLIGKV-amide, GLIGLR-amide, glucagon, α-melanocyte stimulating hormone (α-MSH), motilin, neurokinin A, neuromedin N, neuropeptide Y, neurotensin, nociceptin, SFFLR-amide, substance P, urotensin II, and YFLLNRP-amide were obtained from Bachem (King of Prussia, Pa.). Corning® Epic™ 96 well and 384 well biosensor microplates were obtained from Corning Incorporated (Corning, N.Y.), and cleaned by exposure to high intensity UV light (UVO-cleaner, Jelight Company Inc., Laguna Hills, Calif.) for 6 minutes before use.

Human epidermoid carcinoma A431 cells (American Type Cell Culture) were grown in Dulbecco's modified Eagle's medium (DMEM) supplemented with 10% fetal bovine serum (FBS), 4.5 g/liter glucose, 2 mM glutamine, and antibiotics. ~3–7.5×10$^4$ cells at passage 3 to 5 suspended in 200 µl the DMEM medium containing 10% FBS were placed in each well of a 96 well microplate. Similarly ~1–2×10$^4$ cells in 50 µl the growth medium were placed in each well of a 384 well microplate. After cell seeding, the cells were cultured at 37° C. under air/5% CO$_2$ until ~95% confluency was reached (~2-4 days).

(2) Fluo-3 Ca$^{2+}$ Mobilization Assay—

A431 at passage 3 to 5 were grown in Costar™ 96 well clear cell culture microplates until ~95% confluency, washed twice and starved overnight with the DMEM only, washed with 1×HBSS (1× regular Hank's balanced salt solution, 20 mM HEPES buffer, pH 7.0) in the presence of 2.5 mM probenicid, and labeled in the same buffer containing 4 µM Fluo-3 for 1 hour at room temperature. The cells were then washed twice with buffer, maintained with 100 µl 1×HBSS containing 2.5 mM probenicid. The assay was initiated by transferring 100 µl GPCR agonist solution to the cell plate, and calcium signal was recorded over 6 minutes with a 6 sec interval using HTS7000 BioAssay Reader (PerkinElmer Life Science, Boston, Mass.). The assays were carried out at room temperature in order to allow direct comparison with optical sensing data.

(3) Dynamic Mass Redistribution (DMR) Optical Biosensor Assays

A Corning® Epic™ angular interrogation system with transverse magnetic or p-polarized TM$_0$ mode was used for all studies. Several extra actions were taken to minimize the unwanted effects. First, to minimize the bulk index changes when a compound solution is introduced, 1×HBSS buffer without any probenecid was used to dilute all the compounds, whereas the DMEM buffer only was used to starve the cells. Secondly, to facilitate the cell responses as well as to rapidly reach a steady state when the sensor plates having cells were placed in the system at room temperature, the cells were pre-starved with the DMEM buffer without any FBS for a prolonged period of time (typically 20±2 hours), and the quiescent cells were directly used for assays without any wash. Thirdly, the DMSO concentrations in all compound solution were minimized to below 0.05%, although higher concentrations of DMSO can be used in the disclosed assays.

For kinetics measurements, the cultured cells (~95% confluency) were starved for about 20 hours with DMEM alone at 37° C. under air/5% CO$_2$. Afterwards, the sensor microplate containing cells was placed into the optical system, and the cell responses were recorded before and after addition of a solution at room temperature. For compound studies, the cells in each well were pretreated with a compound solution of 50 µl or the 1×HBSS until a steady phase (i.e., no obvious mass redistribution) was reached (generally within one hour), before GPCR agonist solution of 50 µl was introduced. All studies were carried out at room temperature with the lid of the microplate on except for a short period of time (seconds) when the solution was introduced, in order to minimize the effect of temperature fluctuation and evaporative cooling. The unit of the responses indicated herein was a change in pixel of the central position of the resonant band of each sensor as imaged by a CCD camera; 1 unit equals to ~5.82×10$^{-4}$ refractive index changes, based on an experimental normalization protocol, which uses the concentration-dependent responses of both glycerol and dimethyl sulfoxide. It is understood that other units can be determined based on operating parameters and the needs of the assay as disclosed herein.

b) Results and Discussions (1) Endogenous GPCRs and Their Signaling in A431 Cells A431 cells were used as a model system to study the ligand-induced optical signatures of all three major types of GPCRs—G$_q$, G$_s$, and G$_i$-coupled receptors—under real physiological conditions. The approach was primarily based on known endogenous receptors in A431, in combination with random screening using a small library of well-known agonists against many other different types of GPCRs. It is highly possible that a particular GPCR could transduce signals through more than one types of G proteins with which the receptor is coupled, and even through other non-G protein signaling pathways.

The known endogenous GPCRs in A431 cells include bradykinin B$_2$ receptor, β$_2$ adrenergic receptor, adenosine receptors A$_1$, A$_{2A}$ and A$_{2B}$, histamine receptor H$_1$, protease activated receptors PAR$_1$, and PAR$_2$, purinergic receptors P2Y$_1$, P2Y$_4$, P2Y$_6$ and P2Y$_{11}$, LPA receptors LPA$_1$, LPA$_2$ and LPA$_3$, and bombesin receptor BRS$_1$. RT-PCR studies done by others have shown that A431 endogenously expresses at least four family members of P2Y receptors—P2Y$^1$ (relatively low), P2Y$_4$, P2Y$_6$ and P2Y$_{11}$, although other studies suggested that P2Y$_2$ is also endogenously expressed.

Among these receptors, B$_2$, P2Y receptors, PAR receptors, LPA$_2$ and LPA$_3$, and BRS$_1$ receptors are primarily G$_q$-coupled receptors, whereas A$_{2A}$, A$_{2B}$, and β$_2$ are G$_s$-coupled receptors. Little is known for the signaling pathways of H$_1$ receptors in A431. Interestingly, there are only few of literature reports for endogenous G$_i$-coupled receptors in A431. One example is A, receptor. Although LPA$_1$ is known to primarily lead to signaling through $G_i$ pathway, there is no any literature report for the signaling mechanism of $LPA_1$ in A431.

(2) Optical Signatures of the Activation of Endogenous GPCRs in A431

The panel of agonists were used individually to stimulate quiescent A431 cells. The dose-dependent and kinetic responses were recorded and analyzed. In a typical kinetic measurement, the angular shift of resonant lights of each sensor induced by an agonist is monitored in real time and plotted as a function of time. An increased signal (P-DMR) means an increase in the amount of bio-molecules within the sensing volume (~120 nm); conversely, a decreased signal (N-DMR) means a decrease in the amount of bio-molecules within the sensing volume. The sensing volume, also known as penetration depth, is an intrinsic property of the coupled light within the waveguide film, which creates an evanescent wave extending into the cell layer and the medium.

FIG. 63 showed four classes of optical responses of A431 cells mediated by GPCR agonists. As shown in FIG. 63a, the first class of optical signatures exhibited two major phases—a P-DMR phase with a rapid increased signal (point A to B in FIG. 63a) and a subsequent N-DMR phase with a slowly decayed signal (point B to C in FIG. 63a). Agonists that result in such type of optical signature include $B_2$ receptor agonist bradykinin, P2Y receptors agonist ATP, and PAR agonists thrombin, trypsin, GLIGLR-amide, GLIGKV-amide and SFFLR-amide. The conventional $Ca^{2+}$ mobilization assays using Fluo-3 showed that all of these agonists triggered a dose-dependent elevation of intracellular $Ca^{2+}$ level, as measured with the change in fluorescence intensity of Fluo-3 in cells. Together with the detailed analysis of cellular mechanisms for bradykinin-mediated A431 responses, these results suggested that this type of optical signature is attributed to the activation of $G_q$-coupled receptors, which leads to rapid $Ca^{2+}$ mobilization and downstream signaling events.

Figure 63A:
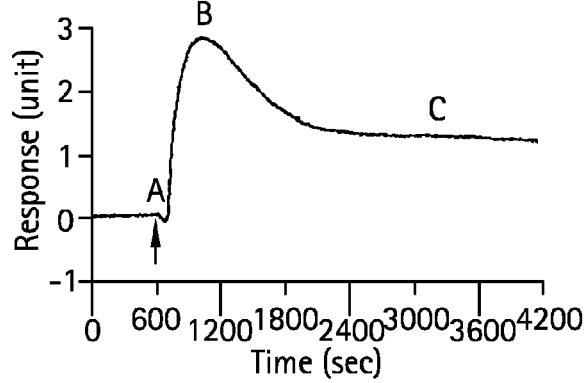
Figure 63B:
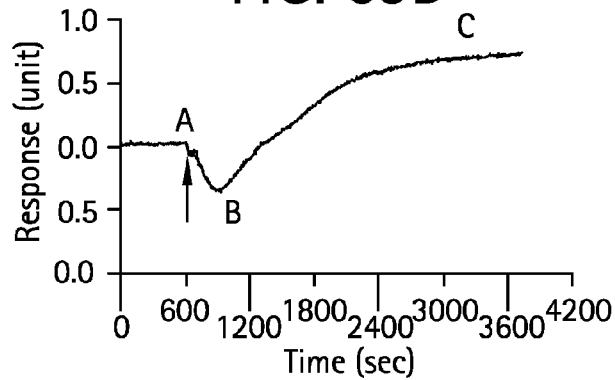

The second class of optical signatures exhibited one major phase (FIG. 63b)—a P-DMR phase with a slowly increased signal until it reaches an evaluated plateau (point B to C in FIG. 63b). In many cases there is an initial phase with a slowly decreased signal and small amplitude, which occurs right after the introduction of agonist solution (point A to B in FIG. 63b). The time to complete the initial phase generally is much longer than those induced by the introduction of compound solutions (seconds). When a compound solution was added, the unmatched refractive indices between the compound solution and the DMEM medium if any would result in a rapid phase relating to the bulk index change. Agonists that result in such type of optical signature include $\beta_2$ agonists epinephrine and isoprenternol, and $A_{2A}$ and $A_{2B}$ agonist NECA. The conventional $Ca^{2+}$ mobilization assays showed that all of these agonists did not trigger any significant changes in intracellular $Ca^{2+}$ level (data not shown). On the other hand, either of the two adenylate cyclase activators forskolin and NKH447 resulted in an optical signature that is similar to those induced by either $\beta_2$ or $A_2$ agonists (FIG. 64). Both chemicals are known to activate adenylate cyclase, leading to the increase in the intracellular level of cAMP—a second messenger in $G_s$-coupled receptor signaling. The pretreatment of quiescent cells with 10 μM forskolin or NKH447 completely abolished the DMR responses mediated by epinephrine (FIG. 65), indicating that both compounds resulted in a cellular response sharing same downstream signaling pathway(s) with these agonists. These results suggested that this type of optical signature is attributed to the activation of $G_s$-coupled receptors, which leads to accumulation of intracellular cAMP and downstream signaling events.

Figure 63C:
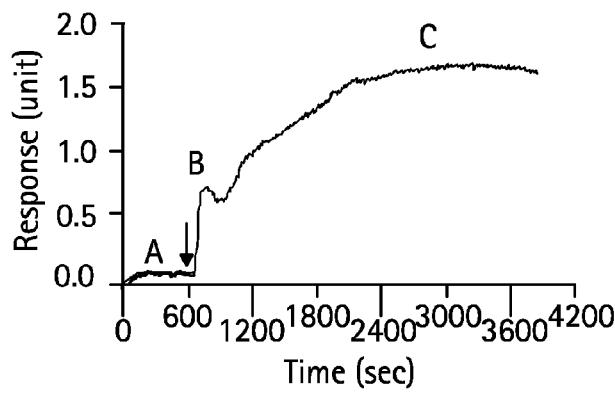

The third class of optical signatures exhibited two consecutive P-DMR events (FIG. 63c)—a rapid P-DMR phase that leads to an elevated level (point A to Bin FIG. 63c), and a subsequent P-DMR phase with a slowly increased signal until it reaches another elevated plateau (point B to C in FIG. 63c). Among these agonists that target known endogenous GPCRs, only LPA receptor agonist LPA at the doses below about 500 nM resulted in this type of optical signature. Other agonists that also triggered this type of response include MC receptors α-MSH. This type of optical signature can be attributed to the activation of $G_i$-coupled receptors, since it shares unsurprised similarity to that of $G_s$-coupled receptors. Both $G_i$ and $G_s$ signaling lead to the modulation of intracellular cAMP but in an opposite way.

The fourth class of optical signature did not exhibited any significant DMR signals (FIG. 63d), which was similar to that induced by the HBSS alone. Each agonist was examined typically at five different doses between 1 nM and 10 μM, and at least two independent experiments were carried out to ensure the results. Agonists that fall into this category include A-77636, $SCH_{23390}$ and SKF38392 (DRD1), anandamide (CNR1 and CNR2), Angiotensin II (AGTR1), apelin 1-17 and apelin 1-13 (AGTRL1), BRL 54443 (HTR1E/F), clonidine and UK14304 (ADRA2A, B and C), DAMGO and dynorphin A (OPRM1 and OPRK1), endothelin-1 (EDNRA and EDNRB), galanin (GALR1 and GALR2), glucagon (GCGR), interleukin-8 (CXCR1), IP-10 (CXCR3), motilin (MOTR), substance P (TACR1), neurokinin A (TACR2), neuromedin N and neurotensin (NTSR1), neuropeptide Y (NPY1, 2, 4, 5, 6R), nociceptin (OPRL1), oxymetazoline (ADRA1A), and urotensin II (GRP14). The targeted receptor(s) of these agonists were indicated in the parentheses. That no significant DMR signals resulted from these agonists indicated that there are no or relatively low expression levels of their corresponding receptor(s) in A431 cells. The little DMR signals resulted from IL-8 stimulation (data not shown) suggested that relatively low level of endogenous CXCR1 is expressed in A431 cells. Another possibility is that there is low-constitutive secretion of IL-8 from A431 cells.

Bombesin receptor subtype 1 ($BRS_1$) was also previously reported to endogenously express in A431 cells. Fluo-3 assays showed that bombesin led to a maximum increase in intracellular $Ca^{2+}$ level of 20±5% (n=5; data not shown), suggesting that bombesin triggers $G_q$-signaling. As expected, the stimulation of quiescent A431 with bombesin led to a dose-dependent $G_q$-type optical signature (data not shown), but with much smaller amplitudes than those mediated by bradykinin, ATP or either of PAR agonists. The apparent $IC_{50}$ was found to be approximately 1 nM. The small amplitude of the DMR signals induced by bombesin suggested the relatively low expression of BRS1 in A431.

(3) Determination of Agonist Efficacies to Activate Endogenous GPCRs in A431

Next, the efficacies of these agonists that result in significant DMR signals were examined. Since in some cases more than one subfamily receptors are endogenously expressed in A431, and a particular agonist could activate multiple of subfamily receptors with different efficacies, a 5× concentration series of agonist solution was initially used to examine the cellular responses. In most cases a 2× concentration series of agonist solutions were further used to accurately determine the $EC_{50}$ value of the agonist. The amplitudes of DMR signals were plotted as a function of agonist concentration, and analyzed with Prism to calculate the $EC_{50}$.

FIG. 66 summarized the dose-dependent responses induced by agonists that target endogenous $G_q$-coupled receptors. Since analysis of the amplitudes of both P-DMR and N-DMR signals as a function of agonist concentration result in almost identical $EC_{50}$, only the P-DMR signals were plotted and the resultant efficacies of agonists were discussed. All saturation curves fit well with one-binding site non-linear regression, leading to an apparent $EC_{50}$. The apparent $EC_{50}$ value was found to be 2.2±0.6 µM (n=3), 10.0±1.2 nM (n=3), and 9.6±2.0 unit/ml (n=3) for ATP, bradykinin and thrombin, respectively. In comparison, the $EC_{50}$ values of these agonists were also determined using $Ca^{2+}$ flux assays (data not shown) and found to be consistent with those obtained with the optical biosensor assays. Extracellular ATP has been shown to be a potent agonist of both ionotropic P2X and G protein-coupled P2Y receptors. Because the RWG biosensor is most sensitive to the redistribution of cellular bio-macromolecules rather than ions and the ATP-mediated optical signatures are similar to those induced by bradykinin and PAR agonists, it was reasoned that endogenous P2Y receptors primarily account for the DMR signals induced by ATP. On the other hand, $B_2$ but not $B_1$ receptor is endogenously expressed in A431 and $B_2$ receptor accounts for most of the physiological and pathophysiological action of bradykinin. Thrombin is an agonist for $PAR_1$, and SLIGLR-amide and SLIGKV-amide are $PAR_2$-specific agonists. However, SFFLR-amide and trypsin apparently activate both $PAR_1$ and $PAR_2$.

FIG. 67 summarized the dose-dependent responses induced by agonists that activate endogenous $G_s$-coupled receptors. Here the amplitudes of the slowly increased P-DMR signals were plotted as a function of agonist concentration. The apparent $EC_{50}$ value was found to 21.5±1.2 nM (n=3), and 6.0±1.4 nM (n=3) for NECA and epinephrine, respectively. NECA is an agonist for $A_{2A}$, $A_{2B}$, and $A_1$ receptors with an affinity of 20, 330, and 14 nM, respectively. Coexisting $A_1$ and $A_2$ adenosine receptors with opposite actions on adenylate cyclase activity has been described in several cell lines including A431. In A431, adenosine evoked a biphasic response in which low doses (<~10 µM) produced inhibition of colony formation through $A_1$ receptor but higher concentrations (up to 100 µM) progressively reversed this inhibition through $A_2$ receptor. Such dual effect thus affords the opportunity for reciprocal control and fine-tuning the signaling pathways. Since NECA has similar affinities to $A_1$ and $A_{2A}$, the optical signatures induced by NECA indicated that $G_s$ signaling is dominated. To further discriminate the effect, adenosine amine cogener (ADAC), an adenosine receptor selective agonist with an affinity of 0.85, 210, and 285 nM to $A_1$, $A_{2A}$, and $A_3$ receptor, were used respectively. We were particularly interested in high doses of ADAC. Results showed that at high doses (>50 nM) ADAC stimulated a typical $G_s$-type optical signature in a dose-dependent manner, with an apparent and effective $EC_{50}$ of 3.7±1.1 µM (n=3). On the other hand, since A431 endogenously expresses high numbers of $β_2$ receptor (~40,000 copies per cell), the epinephrine-induced DMR signals observed are specific to the activation $β_2$. Epinephrine binds to $β_2$ with a $EC_{50}$ of 5-20 nM.

FIG. 68A shows the dose-dependent responses induced by α-MSH. Here the total responses of two P-DMR events were plotted as a function of agonist concentrations. The apparent $EC_{50}$, value was found to 9.0±1.6nM (n=3) for α-MSH, consistent with the literature values. FIG. 68B shows the saturation curve of quiescent a431 cells induced by α-MSH, plotted as the DMR signal amplitudes at 1 hr poststimulation as a function of α-MSH doses.

Figure 63D:
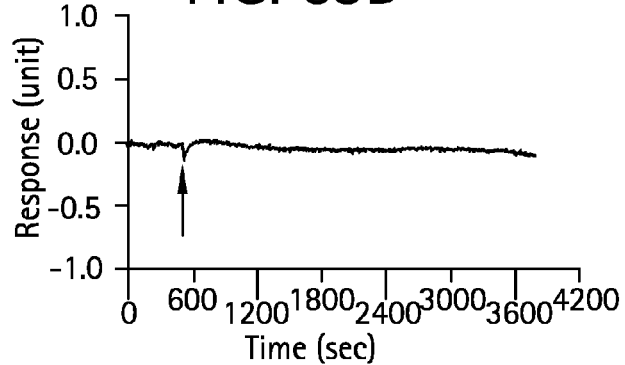

We here systematically examined the optical signatures of quiescent A431 cells stimulated with a panel of agonists that target a wide variety of GPCRs. The choice of agonists was partly based on the known endogenous GPCRs in A431. The results showed that the optical signatures mediated by those agonists fall into three major categories (FIGS. 63a,b and c), besides the fourth type of optical signatures that is similar to that treated with the vehicle (i.e., HBSS) only (FIG. 63d). Three different strategies were employed to clarify the cellular signaling mechanisms account for these optical signatures. First, the conventional second messenger assays (i.e., Fluo-3 assays) were used to classify the agonists for their ability to cause $Ca^{2+}$ mobilization. Second, two adenylyl cyclase (AC) activators, forskolin and NKH447, were used to stimulate the quiescent A431 cells. The similarity between GPCR agonist-mediated and adenylate cyclase activator-mediated optical signatures was examined and used to point out the $G_s$-mediated signaling. Third, a systematic mapping of the effect of a panel of well-known modulators on the optical signatures induced by a specific agonist was carried out to investigate its cellular mechanisms and signaling network interactions. Based on these studies, the three major classes of optical signatures were assigned to three classical types of GPCR signaling: $G_q$-, $G_s$-, and $G_i$-signaling. Because of the limit information of endogenous $G_i$-coupled receptors in A431 cells, the $G_i$-type optical signature need to be further confirmed, although the dose-dependent responses induced by HTMT strongly supported such indication.

Except of IL-8, all agonists that target all known endogenous GPCRs in A431 had led to significant DMR responses. Their efficacies determined with the RWG biosensors were consistent with either Fluo-3 assay results if applicable or literature reports, suggesting that the MRCAT can be used to accurately determine the agonist efficacies.

(4) Signature Switching of Agonist-Mediated Cell Responses—

GPCR signaling is complicated, depending on the cellular states and context, the selectivity of agonists, and the expression level and type of the receptor. Depending on the cellular states and context, the activation of a particular GPCR could trigger the cellular responses through more than one type of G proteins. For example, the activation of endogenous bradykinin $B_2$ receptor induced by bradykinin mediates the cellular signaling through both $G_q$ and $G_s$-pathways in A431 cells; both signaling pathways cross-regulate each other. It was found herein that the signaling mediated through $B_2$ receptor is dependent on the cellular status of A431 cells as well as the doses of bradykinin. In proliferating states, low doses (<100 nM) of bradykinin preferably trigger $G_s$-mediated signaling, when high doses (>100 nM) of bradykinin favors $G_q$-signaling. One the other hand, bradykinin between 0.5 nM and about 100 nM mediated both $G_s$ and $G_q$-pathways, when it was used to stimulate the quiescent A431 cells obtained with 0.1% FBS for about 20 hours. Conversely, the fully quiescent A431, obtained with the DMEM medium in the absence of any FBS or other growth factors for about 20 hours, responded to bradykinin at all doses with predominantly $G_q$-signaling (data not shown).

It was identified that a few of the agonists including LPA and HTMT triggered DMR signals that exhibited relatively complicated dose-dependence. FIG. 69 showed the dose-dependent responses induced by LPA. The fully quiescent A431 cells responded to LPA stimulation with typical $G_i$-type optical signature at low doses of LPA, and progressively switched to $G_q$-type optical signature at high doses of LPA. One possibility is that LPA at low doses preferably activated $LPA_1$ receptor that leads to $G_i$-mediated signaling. When the concentration of LPA increases, the endogenous $LPA_2$ and $LPA_3$ receptors become activated, leading to the $G_q$-mediated signaling.

FIG. 70 showed the dose-dependent optical signals induced by HTMT. HTMT is an agonist of $H_1$ and $H_2$ receptors. At low doses (<~40 nM), HTMT dose-dependently resulted in a typical $G_i$-type optical signature (FIG. 70b). As the concentration of HTMT continues to increase up to around 80 nM, the optical signature relating to DMR started to decrease and became almost steady (i.e., no obvious DMR). Further increase in the concentration of HTMT resulted in the switching to a typical $G_s$-type optical signature (FIG. 70b). The amplitude of the P-DMR signals was plotted as a function of HTMT concentration, and clearly showed the switching (FIG. 73c). Since $G_s$ signaling leads to the accumulation of intracellular cAMP and $G_i$ signaling causes the opposite effect, it is reasonable to speculate that HTMT activates both $G_s$ and $G_i$-signaling pathways with different efficacies, possibly through distinct receptors. The delicate balance between $G_s$ and $G_i$ signaling determines the net cellular responses, at least in terms of dynamic mass redistribution as monitored by the RWG biosensor.

9. Example 9

Probe the Cross-Communication Between Different Targets

It is common that there is cross-communication among distinct targets, and even more common among the members of a subfamily of targets. For example, EGFR can be trans-activated by certain GPCR agonists. Again, an activator of one target (e.g., GPCR) can activate other closely related target.

Protease activated receptors (PARs) comprise a novel family of G protein-coupled receptors (GPCRs) which to date include PAR1, PAR2, PAR3 and PAR4. Instead of being activated through reversible ligand binding, PARs utilize a unique proteolytic mechanism for activation. Serine proteases such as thrombin and trypsin site-specifically cleave the receptor within the extracellular N-terminal exodomain. The activating cleavage site is the residue 41-42 (R↓SFLLRN), 36-37(R↓SLIGKV), 38-39 (K↓TFRGAP) and 47-48 (R↓GYPGQV) in humans for PAR1, PAR2, PAR3 and PAR4, respectively. The cleavage unmasks a new N-terminus, which in turn acts as a tethered ligand sequence. The tethered ligand domain binds intramolecularly to and activates the receptor, thus initiating signaling. The proteases that activate PARs include coagulation factors (e.g. thrombin, coagulation factors VIIa and Xa), proteases from inflammatory cells (mast cell tryptase, neutrophil cathepsin G) and enzymes from epithelial tissues (trypsins). Three of the four PARs (PAR1, PAR3, and PAR4) are activated principally by thrombin, while PAR2 is activated by trypsin-like proteases such as mast cell tryptase and coagulation Factor Xa. Synthetic peptides (PAR-activating peptides or PAR-APs), corresponding to the first five or six amino acids of the tethered ligand sequences, can directly activate PARs, except for PAR3. Since these synthetic peptides function as receptor agonists independently of proteolysis, PAR-APs are useful for studying the physiological and pathophysiological functions of PARs.

PARs are found in a large variety of normal and malignant tissues and cells including skin, platelets, endothelial cells, gastrointestinal tract, brain and lungs. Most cell types express multiple PARs. One example is A431 cells which endogenously express PAR1 and PAR2. However, little is known for the signaling pathways of PARs in A431 cells, although epideriomoid carcinoma cells express several serine proteases including human airway trypsin-like protease that may be potential PAR activators.

a) Materials and Methods (1) Regents—

Thrombin, trypsin, latrunculin A, cytochalasin B, phalloidin, nocodazole, methyl-β-cyclodextrin (mβCD), α-cyclodextrin (αCD), N-benzoyl-L-arginine ethyl ester (BAEE) and epidermal growth factor (EGF) were purchased from Sigma Chemical Co. (St. Louis, Mo.). KN-62 and GF109203x were obtained from Tocris Chemical Co. (St. Louis, Mo.). Fluo-3 and Texas Red-phalloidin (TR-phalloidin) was obtained from Molecular Probes (Eugene, Oreg.). SFFLR-amide, GLIGKV-amide, GLIGLR-amide, bradykinin, and YFLLNRP-amide were obtained from Bachem (King of Prussia, Pa.). Corning® Epic™ 96 well biosensor microplates were obtained from Corning Inc (Corning, N.Y.), and cleaned by exposure to high intensity UV light (UVO-cleaner, Jelight Company Inc., Laguna Hills, Calif.) for 6 minutes before use.

(2) Cell Culture

Human epidermoid carcinoma A431 cells (American Type Cell Culture) were grown in Dulbecco's modified Eagle's medium (DMEM) supplemented with 10% fetal bovine serum (FBS), 4.5 g/liter glucose, 2 mM glutamine, and antibiotics. ~3–7.5×10$^4$ cells at passage 3 to 5 suspended in 200 µl the DMEM medium containing 10% FBS were placed in each well of a 96 well microplate, and were cultured at 37° C. under air/5% $CO_2$ until ~95% confluency was reached (~2-4 days).

(3) Fluo-3 $Ca^{2+}$ Mobilization Assay

A431 at passage 3 to 5 were grown in Costar™ 96 well clear cell culture microplates until ~95% confluency, washed twice and starved overnight with the DMEM only, washed with 1×HBSS (1× regular Hank's balanced salt solution, 20 mM HEPES buffer, pH 7.0) in the presence of 2.5 mM probenicid, and labeled in the same buffer containing 4 µM Fluo-3 for 1 hour at room temperature. The cells were then washed twice with buffer, maintained with 100 µl 1×HBSS containing 2.5 mM probenicid. The assay was initiated by transferring 50 µl PAR agonist solution to the cell plate, and calcium signal was recorded over 6 minutes with a 6 sec interval using HTS7000 BioAssay Reader (PerkinElmer Life Science, Boston, Mass.). The assays were carried out at room temperature in order to allow direct comparison with optical sensing data.

(4) Dynamic Mass Redistribution (DMR) Optical Biosensor Assays

Corning® Epic™ angular interrogation system with transverse magnetic or p-polarized $TM_0$ mode was used for all studies. After culturing, the cells (~95% confluency) were starved for about 20 hours with DMEM alone, washed twice and maintained with 100 µl DMEM. Afterwards, the sensor microplate containing cells was placed into the optical system, and the cell responses were recorded before and after addition of a solution. For compound studies, the cells in each well were pretreated with a compound solution of 50 µl or the 1×HBSS until a steady phase (i.e., no obvious mass redistribution) was reached (generally within one hour), before PAR agonist solution of 50 µl was introduced. The compound or PAR agonist solutions were made in 1×HBSS in order to match the refractive index between the cell medium and compound solution, thus minimizing the unwanted effect of bulk index change due to the introduction of compound solution which can temporarily overwhelms any DMR signal as it occurs. All studies were carried out at room temperature with the lid of the microplate on except for a short period of time (~seconds) when the solution was introduced, in order to minimize the effect of temperature fluctuation and evaporative cooling. The unit of the responses indicated throughout this paper was a change in pixel of the central position of the resonant band of each sensor as imaged by a CCD camera; 1 unit equals to ~5.82×10⁻⁴ refractive index changes, based on an experimental normalization protocol, which uses the concentration-dependent responses of both glycerol and dimethyl sulfoxide.

(5) Fluorescence Imaging

Cells were grown on Corning® Epic™ 96 well biosensor microplates, starved for overnight with serum-free DMEM medium, chased with either trypsin or thrombin for certain time, fixed with 4% paraformaldehyde, permeabilized in phosphate-buffered saline (PBS) containing 0.2% Triton, and blocked with 1% bovine serum albumin (BSA). Afterwards, cells were incubated with 0.5 µM Texas Red-labeled phalloidin for 1 h at room temperature, and washed. After final washes and mounting, cells were examined with a 40× objective, equipped in a Zeiss Axioplan fluorescence microscope.

b) Results (1) PAR Agonists Mediate Elevation of Intracellular $Ca^{2+}$ in A431 Cells In quiescent A431 cells, thrombin, trypsin, PAR1-AP(SF-FLR-amide), and PAR2-APs (GLIGKV-amide and GLIGLR-amide) all induced a rapid and transient increase in intracellular $Ca^{2+}([Ca^{2+}]_i)$ in a concentration-dependent manner, as measured with the increase of Fluo-3 fluorescence intensity. The saturation curves mediated by all PAR agonists seem fit very well with one-site binding, based on non-linear regression and Scatchard analysis. The $EC_{50}$ was found to be 6±1 unit/ml (equivalent to 60±10 nM), 5.0±0.4 µM, 45.7±5.8 nM, 2.5±0.3 µM, and 3.8±0.4 µM for thrombin, SFFLR-amide, trypsin, SLIGLR-amide, and SLIGKV-amide, respectively. The maximal $[Ca^{2+}]_i$ elevation induced by thrombin, SFFLR-amide, trypsin, SLIGKV-amide, and SLIGLR-amide was found to be 48.2±3.5%, 74.3±3.9%, 100±6.3%, 52±6.3%, and 64±3.7%, respectively (FIG. 71). The maximal $[Ca^{2+}]_i$ elevation obtained with trypsin was approximately 2 fold as high as that obtained with thrombin. On the other hand, the maximal $[Ca^{2+}]_i$ elevation obtained with trypsin was also much higher than those obtained with two PAR2-APs. Furthermore, stimulation of A431 with a mixture of SFFLR-amide (20 µM) and SLIGKV-amide (20 µM) induced a $[Ca^{2+}]_i$ elevation of 102±5.4%, similar to that obtained with 200 nM trypsin alone. Interestingly, a PAR1 specific partial agonist YFLLRNP at concentrations up to 160 µM did not induce any significantly elevation of $[Ca^{2+}]_i$, but the pretreatment of cells with 80 µM YFLLRNP suppressed the $[Ca^{2+}]_i$ elevation mediated by 200 nM trypsin (48.3±4.5%, n=5). YFLLRNP at appropriate concentrations (<~10004) was found to selectively activate the $G_{12/13}$ signaling cascade through PAR1 resulting in platelet shape change, without stimulating the $G_q$ or $G_i$ signaling pathways in human platelets. These results suggest that trypsin can activate PARs other than PAR2. The concentrations required to induce a maximal response were 40 unit/ml, 20 µM, 400 nM, 20 µM, and 20 µM for thrombin, SFFLR-amide, trypsin, SLIGKV-amide, and SLIGLR-amide, respectively.

(2) PAR Agonists Mediate the Reorganization of Actin Filaments in A431 Cells

The activation of PARs are known to lead to the reorganization of cytoskeleton structure in several cell lines such as LNCaP, possibly through the activation of the Rho family proteins. The effect of PAR agonists on the cytoskeleton structure of cells at high confluency (>90%) was investigated because of the unique design of our optical sensing system which uses a band of light (a dimension of 200×3000☐m Note: this is the current configuration in our angular interrogation; the size of light used for illumation is typically in the range of ~50☐m to 5 mm) to illuminate each biosensor (meaning that the optical signature relating to DMR is an average of all cells within the illuminating area). Stimulation of quiescent A431 cells at confluency of ~95% with either thrombin or trypsin induced the reorganization of actin filaments, as showed by the Texas Red® X-phalloidin staining pattern (data not shown). Resting A431 cells showed a typical staining pattern—the actin filaments appear mostly elongated and evenly distribute throughout the cytoplasm. Cells treated with 100nM trypsin or 40unit/ml thrombin triggered significant cytoskeletal reorganization after about 10 min (data not shown), and become obvious after about 30 min. The actin filaments became predominately concentrated around the rim of the cells 30 min after being stimulated with either thrombin or trypsin. These results demonstrated that both thrombin and trypsin mediate the reorganization of actin filaments in A431 cells.

(3) PAR Agonists Mediate Significant Dynamic Mass Redistribution in A431 Cells

Disclosed herein it was demonstrated that either one of the five PARs agonists examined results in a $G_q$-type optical signature, which all are saturable to agonist concentration. Similar to the $Ca^{2+}$ mobilization results, the saturation curves of PAR agonist-mediated DMR signals obtained with the optical biosensor assays also fitted very well with one-site binding model, based on the non-linear regression and Scatchard analysis. It is worth noting that for trypsin, the DMR signals induced by trypsin at low doses (<2000 nM) were focused on because trypsin at high doses (>2000 nM) leads to significant cell detachment from the surface of the biosensors (data not shown).

Since many important aspects of cell activities including trafficking, signaling and morphological changes require the rearrangement of cytoskeleton structure, the roles of cytoskeletal modulation in the PAR agonist-induced optical responses (FIG. 72) were investigated. Pretreatment of A431 with latrunculin A completely blocked either thrombin- or trypsin-mediated DMR signal, while cytochalasin B was much less effective in suppressing the responses. It is known that the two agents utilize distinct mechanisms to cause actin disassembly: cytochalasin B caps actin filaments, while latrunculin A sequesters actin monomers. Such a difference may lead to distinct abilities for each toxin to modulate the receptor signaling by either affecting the endocytosis or the assembly of signaling machineries. Conversely, neither a stabilizing polymeric F-actin agent phalloidin nor a microtubule disrupter nocodazole had significant effect on both thrombin- and trypsin-mediated responses.

PAR intracellular signaling leading to Rho activation that regulates the cytoskeletal reorganization appears to involve two major signal transduction pathways: the $G_q$-coupled pathway resulting in phosphoinositol hydrolysis and calcium-dependent Rho activation, and the calcium-independent direct activation of Rho through $G_{12/13}$-coupled p115Rho-GEF. Thus the effect of modulators that target $Ca^{2+}$ signaling was examined. The modulators used were a potent PKC inhibitor GF109203x and a potent $Ca^{2+}$/calmodulin-dependent protein kinase II (CaMKII) inhibitor KN-62 (FIG. 73). GF109203x had no obvious effect on both thrombin- and trypsin-mediated DMR signal. However, KN-62 pretreatment affected the DMR signal mediated by thrombin and trypsin differently. When KN-62 slightly suppressed the thrombin-mediated DMR signal, it almost completely abolished the trypsin-mediated DMR signal. To examine the possibility of KN-62 directly inhibiting the trypsin activity, the BAEE hydrolyisis assay was used. Results showed that the presence of KN-62 has no any obvious effect on the trypsin activity (data not shown).

The effect of PAR1 specific partial agonist YFFLRNRP which is previously shown to activate $G_{12/13}$ resulting in the cell shape change, but not $G_q$-mediated $Ca^{2+}$ signaling in human platelets was also examined. YFFLRNP only at high doses stimulated significant DMR signals (data not shown). YFFLRNP dose-dependently suppressed the DMR signals mediated by thrombin-, SFFLR-amide- and trypsin (FIG. 74). At the highest dose examined, YFFLRNP almost completely blocked the thrombin-mediated DMR, but only partially attenuated both SFFLR-amide and trypsin-mediated DMR. Conversely, YFFLRNP has no obvious effect on the PAR2-AP GLIGKV-mediated DMR signal. Collectively, these results suggested that the cytoskeletal reorganization is mainly resulted from the $G_q$-mediated $Ca^{2+}$ signaling through PAR2 activation, but a $Ca^{2+}$-independent mechanism through PAR1 activation.

(4) Receptor Desensitization and Cross Desensitization of PAR Agonists

Since A431 endogenously expresses at least PAR1 and PAR2, and either thrombin or trypsin potentially activates more than one receptors, the desensitization and cross desensitization of receptors in response to subsequent stimulation of various combinations of PAR agonists, as evaluated by the extent of $[Ca^{2+}]_i$ elevation with Fluo-3 or the DMR signal with optical biosensors was examined. The intervals were 6 min for $Ca^{2+}$ mobilization assays, and about 1 hour for DMR optical assays.

FIG. 75 summarized the main results of $[Ca^{2+}]_i$ in A431 sequentially stimulated in various combinations of PAR agonists. Once A431 cells were stimulated with trypsin, the subsequent application of other PAR agonists (40 unit/ml thrombin, 20 µM SFFLR-amide, 20 µM GLIGKV-amide, 20 µM GLIGLR-amide, or 200 nM trypsin) induced almost no $[Ca^{2+}]_i$ elevation (FIG. 75a-c, data not shown). Conversely, neither of PAR agonists examined had any effect on the $[Ca^{2+}]_i$ elevation mediated with subsequent stimulation with bradykinin, an agonist for $B_2$ receptor which is endogenously expressed in A431 cells (exampled in FIG. 79d), suggesting that the inhibition of the response to PAR agonists by the preceding stimulation with trypsin was not due to the non-specific digestion of the membrane proteins. On the other hand, the preceding stimulation with 40 unit/ml thrombin totally blocked the $[Ca^{2+}]_i$ elevation mediated by 40 unit/ml thrombin, but slightly suppressed the trypsin-induced $[Ca^{2+}]_i$ elevation, whereas the preceding stimulation with SFFLR-amide, GLIGKV-amide or GLIGLR-amide significantly attenuated but not completely eliminates the trypsin-induced $[Ca^{2+}]_i$ elevation (FIG. 79e-g; data not shown). Furthermore, after the preceding stimulation with thrombin, PAR2-AP SLIGKV-amide induced the $[Ca^{2+}]_i$ elevation (48.5±3.8%) similar to that obtained without the preceding stimulation (52.0±6.3%). Conversely, the preceding stimulation with thrombin only partially block the $[Ca^{2+}]_i$ elevation induced by SFFLR-amide (32±4.3%), consist with the previous observations done by others that SFFLR-amide may activate both PAR1 and PAR2. [Blackhart, B. D.; Emilsson, K.; Nguyen, D.; Teng, G. W.; Martelli, A. J.; Nysted, S.; Sundelin, J.; Scarborough, R. M. J. Biol. Chem. 1996, 271, 16466-16471]. Thus trypsin desensitized the responsiveness to both PAR1-AP and PAR2-APs, whereas thrombin did not desensitize the responsiveness to PAR2-APs.

FIG. 76 summarized the main results of DMR responses of A431 sequentially stimulated in various combinations of PAR agonists, as monitored in real time using the RWG biosensors. The preceding stimulation with trypsin completely eliminated the DMR signal induced by either trypsin (data not shown) or thrombin (FIG. 76a), while it significantly suppressed the DMR signal induced by either of three PAR-APs (SFFLR-amide, GLIGKV-amide, GLIGLR-amide) (FIG. 76b-c, data not shown). Conversely, trypsin pretreatment has little effect on the DMR mediated by bradykinin (FIG. 76d). On the other hand, the preceding stimulation with thrombin, SFFLR-amide, GLIGKV-amide or GLIGLR-amide significantly suppresses but not completely eliminates the trypsin-induced DMR signal (FIG. 76e-g; data not shown). Furthermore, after the preceding stimulation with thrombin, two PAR2-APs (SLIGKV-amide and SLIGLR-amide) induced the DMR signal similar to that obtained without the preceding stimulation (data not shown). In summary, these results indicated that thrombin primarily activates PAR1, while trypsin activates both PAR1 and PAR2.

(5) The $[Ca^{2+}]_i$ Elevation and DMR Signals Mediated by Both Thrombin and Trypsin are Sensitive to Cholesterol Level in Cells Since cell cholesterol level is important to many cell functions including GPCR signaling, the effect of cholesterol depletion by mβCD on both intracellular $Ca^{2+}$ elevation and DMR responses mediated by thrombin and trypsin was examined. The pretreatment of quiescent A431 cells with mβCD led to a dose-dependent suppression of $[Ca^{2+}]_i$ elevation mediated by either trypsin or thrombin (data not shown). Both dose-dependent suppression curves fit very well with the one-phase decay non-linear regression; consistent with the fact that mβCD results in the rapid effluxing of cell membrane cholesterol molecules. On the other hand, the inactive cyclodextrin steroisome αCD up to 8 mM had no effect on both trypsin and thrombin-induced responses (data not shown).

Similarly, the pretreatment of A431 with mβCD also led to a dose-dependent alteration of the optical signatures induced by thrombin or trypsin (FIG. 77). Unlike the suppression of thrombin-mediated DMR by mβCD that exhibited dose-dependence similar to that measured with $Ca^{2+}$ mobilization, the suppression of trypsin-mediated DMR by mβCD showed complicate nature—a slow decayed attenuation to increased doses of mβCD. This difference suggested that the trypsin-mediated DMR signals involve more complicated cellular mechanisms than that induced by thrombin. Conversely, the inactive cyclodextrin steroisome αCD up to 8 mM had little effect on both agonist-induced DMR responses. However, high doses of αCD (>10 mM) resulted in significant amounts of cells detached from the surface of the biosensors (data not shown). The functional recovery of PARs after cholesterol depletion with mβCD was also examined. This experiment was based on the timely recovery of cell surface cholesterol in the mβCD-treated cells after the removal of medium containing mβCD. To do so, the quiescent A431 cells were treated with 5 mM mβCD for 15 minutes to ensure the removal of cell surface cholesterol content, followed by washing the treated cells three times with the DMEM medium only. The cells were then maintained with 100 µl the medium, and placed into the optical systems. After incubation for 15 minutes to allow cells reaching reasonably steady state, a 100 µl solution of thrombin at 80 unit/ml was added to each well at specific time. The optical responses were recorded throughout the assays. As shown in FIG. 78, resulted showed that the thrombin-induced DMR signals were dependent on the time after the cell surface cholesterol was removed. The thrombin-induced DMR signals progressively recovered until it reaches to the original level obtained without cholesterol removal. The time-dependent recovery of the thrombin-induced optical signatures strongly implied that the formation of cholesterol-assisted microdomains is dynamic and reversible, and cholesterol concentration at the cell membranes is important in regulating the PAR signaling.

(6) The Cross-Communication Between EGFR and PARs

Figure 79C:
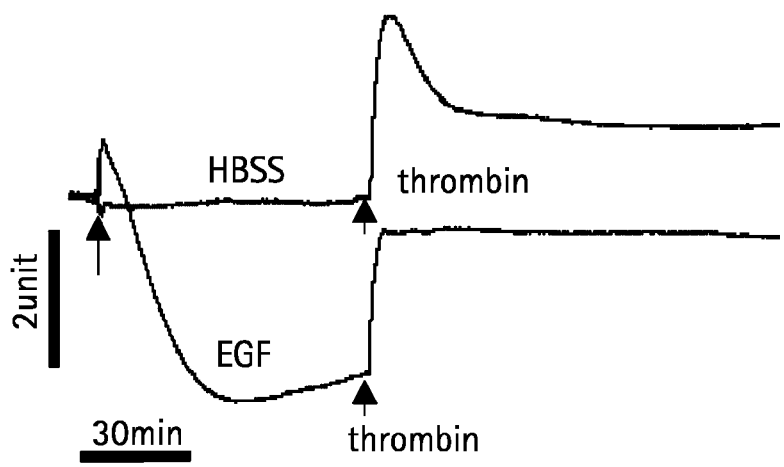
Figure 80A:
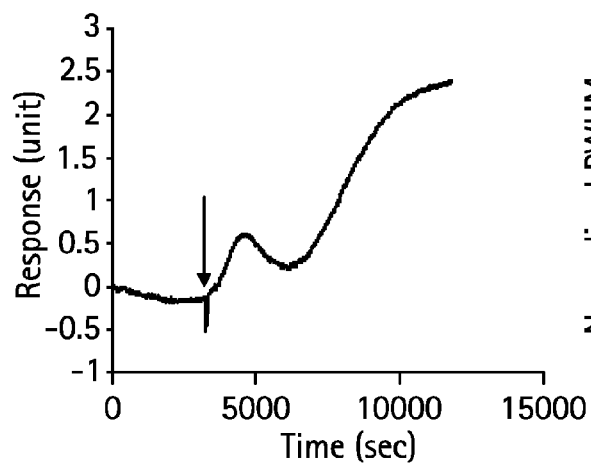
Figure 80B:
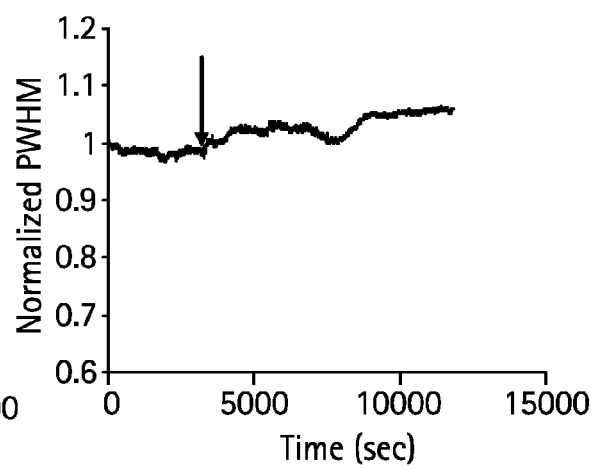
Figure 80C:
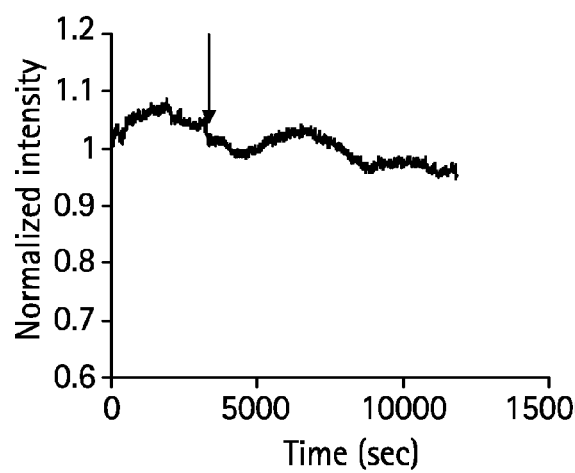
Figure 80D:
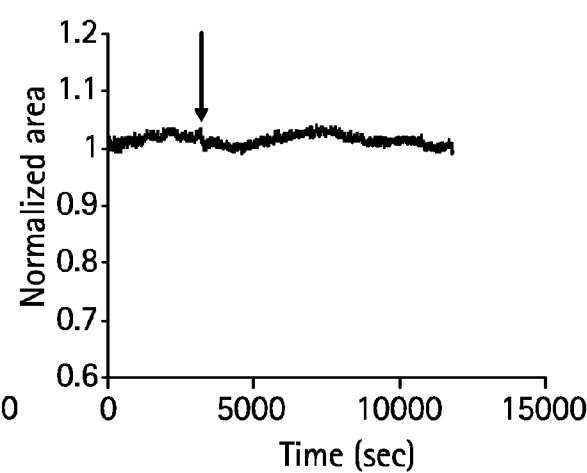

Since certain GPCR agonists transactivate EGFRs, the effect of EGF on PAR signaling was examined. The preceding stimulation with EGF had little effect on the $[Ca^{2+}]_i$ elevation mediated by trypsin (FIG. 79a) or thrombin (data not shown). However, at 100 nM which fully activating EGFRs, EGF totally blocked the N-DMR event, but only attenuated the P-DMR event for the DMR responses mediated by trypsin (FIG. 79b), or thrombin (FIG. 79c). These results suggested that there may be cross-communication between EGFR and PARs, at least in terms of regulating the actin filament reorganization.

In summary, to elucidate the molecular mechanisms of PAR signaling in A431 cells, five PAR agonists (thrombin, PAR1-AP FLLLR-amide, trypsin, PAR2-APs GLIGLR-amide and GLIGKV-amide) and one PAR1 specific partial agonist YFLLRNP was used to stimulate A431 cells. The cellular responses including changes in $[Ca^{2+}]_i$ level and dynamic mass redistribution were examined. Three lines of evidence supported that thrombin primarily activates PAR1, while trypsin activates both PAR1 and PAR2. First, the dose-dependence and saturability of $[Ca^{2+}]_i$ elevation and DMR signal to either of PAR agonists examined suggested the presence of PAR1 and PAR2 signaling in A431 cells. Compared to those mediated by other PAR agonists, the greater $[Ca^{2+}]_i$ elevation and DMR signals mediated by trypsin suggested that trypsin might activate receptor(s) other than PAR2. The $[Ca^{2+}]_i$ elevation mediated by a mixture of SFFLR-amide and GLIGKV-amide is similar to that mediated by trypsin alone, further strengthening the possibility that trypsin activates both PAR1 and PAR2 in A431 cells. The second evidence is from the observations that the preceding stimulation with trypsin almost completely blocked the $[Ca^{2+}]_i$ elevation mediated by either one of all PAR agonists, but not bradykinin (a $B_2$ receptor agonist), thus suggesting that along with PAR2, PAR1 was cleaved and activated by trypsin. On the other hand, the preceding stimulation with thrombin attenuated only slightly the $[Ca^{2+}]_i$ elevation, but significantly the DMR signal mediated by trypsin. Interestingly, the prolonged preceding stimulation (~1 hr) with trypsin totally inhibited the DMR response of A431 cells mediated by thrombin, suggesting that no intact thrombin-activated receptor(s) recovers after one hour continuous stimulation with trypsin. However, unlike the $[Ca^{2+}]_i$ measurement, the prolonged preceding stimulation with trypsin only partially suppressed the DMR signals mediated by all three PAR-APs, implying that there might some portions of PAR2 receptors being recovered. SFFLR-amide is known to be able to activate both PAR1 and PAR2. It is also known that receptor proteolysis and phosphorylation regulate the activities of PARs through receptor internalization and the inhibition of intracellular signal transduction. Depending on the cellular context, the recovery of functional receptors at the cell surface could take from tens of minutes to hours. The third line of evidence came from the effect of YFFLRNP. The preceding stimulation with YFFLRNP dose-dependently suppressed the DMR signals mediated by thrombin, SFFLR-amide or trypsin, but not a PAR2-AP SLIGKV-amide. At the highest dose (729 µM), YFFLRNP totally blocked the DMR signal mediated by thrombin, but only partially suppressed those induced by SFFLR-amide or trypsin. Collectively, these results suggested that beside PAR2, trypsin might also activate PAR1 in A431 cells. It is reported that PAR1, PAR3 and PAR4 serve as thrombin receptor, while trypsin is able to activate PAR1 and PAR4, besides PAR2.

The actin filament staining with Texas Red-X-phalloidin, together with the dynamic mass redistribution as manifested by the RWG biosensor, supported the roles of the activation of PAR1 and PAR2 in the cytoskeletal reorganization of A431 cells. The activation of PAR1 has been shown to lead to cytoskeletal reorganization in several types of cells including platelets and LNCaP cells. The stimulation of A431 cells with either thrombin or trypsin triggered significant rearrangement of actin filaments from the randomized distribution of elongated actin filaments to concentrated filaments near the rim of the cells. Furthermore, all PAR agonists examined also induced dramatic mass redistribution within the bottom portion of adherent cells on the surface of the biosensors. The ability of actin filament disruption agents latrunculin A and cytochalasin B, but not actin polymerization-prompting agent phalloidin or microtubule disruption agent nocodazole, to selectively attenuate the DMR signals mediated by thrombin or trypsin suggested the roles of actin filament rearrangement in the DMR responses, thus the roles of PAR signaling in the cytoskeletal reorganization in A431 cells. In human platelets, which undergo extensive spreading and shape change when exposed to thrombin, PAR1 has been shown to activate RhoA through p115Rho-GEF, a GTP exchange factor (GEF) that associates with the PAR1-coupled G-proteins, $G_{12/13}$. In A431 cells, YFFLRNP, a PAR1 specific partial agonist that is reported to specifically activate $G_{12/13}$ but not $G_q$, was found to be able to induce a DMR signal similar to other PAR agonists (data not shown). Furthermore, the pretreatment of A431 cells with YFFLRNP dose-dependently attenuated the DMR signals mediated by thrombin and SFFLR-amide, but not PAR2-AP GLIGKV-amide. These results suggested that the activation of PAR1 in A431 might also trigger the cytoskeletal reorganization through $G_{12/13}$. On the other hand, the trypsin-mediated cytoskeletal reorganization may be resulted from both $G_{12/13}$- and $G_q$-dependent pathways, since the trypsin-mediated DMR signal was sensitive to a CaMKII inhibitor KN-62 as well as the PAR1 specific partial agonist YFFLRNP. One possibility is that trypsin induced the cytoskeletal reorganization depending on the $G_q$ signaling pathway through the activation of PAR2, but the $G_{12/13}$ signaling pathway through the activation of PAR1.

Together with other lipids including sphingolipids and saturated phospholipids, cholesterol at the cell surface tends to assemble microdomains, which function to selectively compartmentalize numerous signaling proteins. The treatment of cells with mβCD but not its inactive steroisomer αCD attenuated PAR signaling including $Ca^{2+}$ mobilization and dynamic mass redistribution induced by thrombin and trypsin. The effect of the preceding stimulation with EGF suggested that the transactivation of EGFR by cholesterol depletion at least accounts for the attenuation of the N-DMR event mediated by thrombin or trypsin. Furthermore, the ability of cholesterol depletion to attenuate the $Ca^{2+}$ mobilization implicated that cholesterol in the plasma membrane regulates the signaling of both PAR1 and PAR2 through $G_q$-signaling pathway. It is known that cholesterol extraction leads to the loss of compartmentalization of PtdIns 4,5-$P_2$, and $G_q$, two important molecules for PAR signaling. The suppression of $Ca^{2+}$ mobilization by cholesterol depletion might be a direct result of delocalization of PtdIns and $G_q$. As discussed above, the DMR signals mediated through PARs may involve other pathways independently of $G_q$ pathway. However, the ability of cholesterol removal to fully block the DMR signal mediated by trypsin and thrombin suggested that cholesterol depletion might also impair other signaling pathways, such as $G_{12/13}$. These findings agreed with the previous observations done by others that the membrane raffling in A431 cells requires cholesterol. Interestingly, the functional recovery experiments showed that the cholesterol-assembled micro domains are dynamic and reversible.

The $Ca^{2+}$ signaling and dynamic mass redistribution by trypsin, thrombin, or PAR-APs suggested that thrombin mediates PAR1 signaling, and trypsin activates both PAR1 and PAR2 in A431 cells. The activation of both PAR1 and PAR2 leads to the reorganization of cytoskeleton structure, but possibly through distinct mechanisms. The $G_q$ and $Ca^{2+}$-dependent mechanism is assigned to the PAR2-mediated cytoskeletal rearrangement, while other signaling pathways including $G_{12/13}$ might contribute to the PAR1-mediated rearrangement. Furthermore, cholesterol at the cell surface plays important roles in regulating the PAR signaling in A431. These findings suggest that PAR signaling might be important to tumor invasion and metastasis. The present study strongly augments the great potentials of the RWG biosensors in deciphering the cell signaling and its network interaction.

10. Example 10

Study of Reactive Oxygen Species Signaling and Cell Redox States

ROS regulates a large number of signaling pathways at multiple levels from receptor to nucleus. Cellular targets, although less clear, have been identified and broadened over the past decade. Receptor kinases and phosphatases may be targets of oxidative stress. Growth factor receptors are most commonly activated by ligand-induced dimerization or oligomerization that autophosphorylates its cytoplasmic kinase domain. Ligand-independent clustering and activation of receptors in response to ultraviolet light have also been well demonstrated, and this effect appears to be mediated by ROS. Exogenous $H_2O_2$ (usually in the millimolar range) has been shown to induce tyrosine phosphorylation and activation of the PDGF- and EGF receptors. Lysophatidic acid-induced transactivation of the EGF receptor appears to be mediated by the intermediate formation of ROS. Because most growth factors and cytokines appear to generate ROS at or near the plasma membrane, phospholipid metabolites are potentially important targets for redox signaling. For example, the oxidized forms of diacylglycerol were more effective in activating PKC than its nonoxidized forms. In addition, PKC activation and protein tyrosine phosphorylation appear to be required for $H_2O_2$-induced PLD activation in endothelial cells and fibroblasts. Non-RTKs belonging to the Src family (Src kinases) and Janus kinase (JAK) family are also targets, at least, for exogenously added oxidants.

In this study, all optical responses were monitored with a wavelength interrogation system. The RWG biosensor is comprised of three major components for bioassay applications: an Epic™ sensor microplate, an RWG detector, and a liquid handling system. The sensor microplate consists of a glass bottom plate attached to a plastic holy plate of a given SBS format (e.g., 96-well or 384-well), which enables high throughput screening. In a 96 well Epic™ sensor microplate, each well contains one RWG sensor of approximately 3×3 mm². The RWG sensor consists of a thin film of dielectric material on the grating presenting glass substrate.

The wavelength interrogation detector system is centered on integrated fiber optics. A broadband light source, generated through a fiber optic and a collimating lens at nominally normal incidence through the bottom of the microplate, is used to illuminate a small region of the grating surface. A detection fiber for recording the reflected light is bundled with the illumination fiber. A series of 8 illumination/detection heads are arranged in a linear fashion, so that reflection spectra are collected from all 8 wells within the same column of a microplate at once. With the spatial-controlled movement, the whole plate is moving across the illumination/detection heads so that each sensor can be addressed multiple times, and each column be addressed in sequence. A series of spectra of the reflected lights are collected and used for analysis. Since this detection system measures the wavelength shift of the reflected lights induced by the cell response in response to stimulation, this approach is referred to the wavelength interrogation system.

Figure 84B:
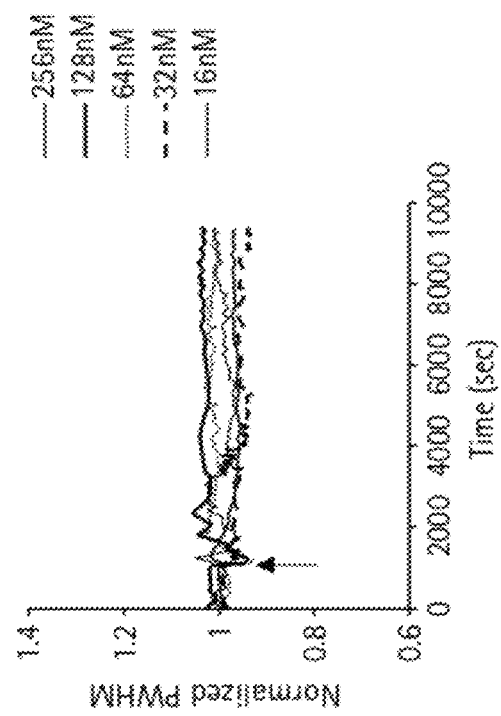
Figure 84D:
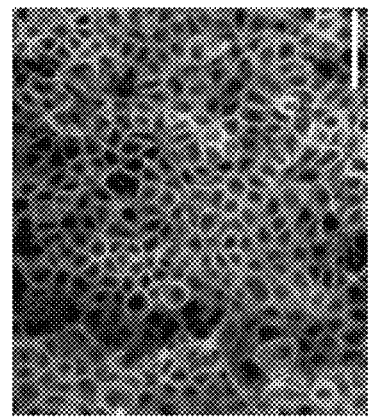
Figure 84A:
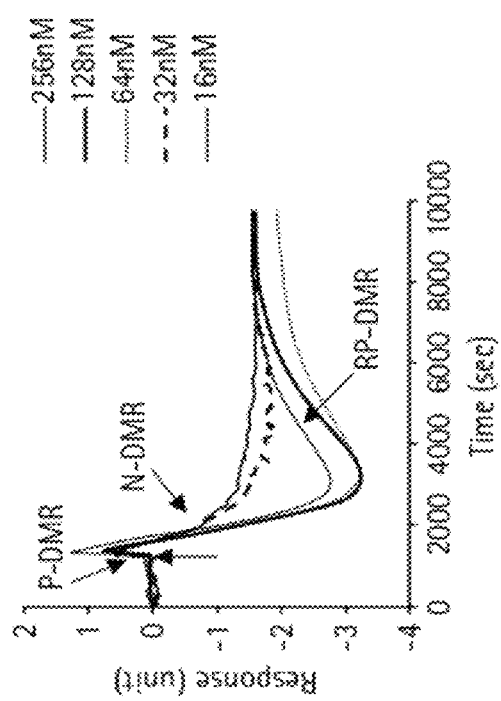
Figure 84C:
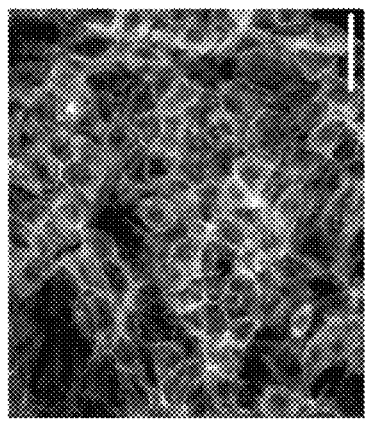

FIG. 80 presented multi-optical output parameters of quiescent A431 cells in response to 1 mM $H_2O_2$, as monitored by the angular interrogation system. The stimulation by $H_2O_2$-triggered significant mass redistribution within the sensing volume of the sensors (FIG. 84A). The DMR signal consists of two major events: an initial peak that comprises of three phases—an increased mass signal (P-DMR), a transition phase, and a decreased mass signal (N-DMR); and a prolonged and increased mass signal that ultimately leads to a plateau. On the other hand, the stimulation by $H_2O_2$ also slightly increased the PWHM of the resonant peak of $TM_0$ mode, indicating the increased inhomogeneity of mass distribution within the bottom portion of cell layer. Consistent with the PWHM, the peak intensity also slightly decreased over time after the stimulation, while the integrated area remained almost constant.

FIGS. 81A and 81B show the dynamic mass redistribution signal of quiescent A431 cells in response to $H_2O_2$ at different doses, as monitored by the shift in the wavelength with the wavelength interrogation system. As shown in FIGS. 81A and 81B the optical signatures of $H_2O_2$ stimulation depend strongly on its doses. When the concentration of $H_2O_2$ is at or below about 8 mM, the cells respond to $H_2O_2$ with a typical curve that consists of two major events: an initial peak and a prolonged increased mass signal. However, when the concentration of $H_2O_2$ is at or above 16 mM (FIG. 81B), the cells respond to $H_2O_2$ with distinct characteristics: an initial increased mass signal followed by a somewhat steady transition state and ultimately a decreased mass signal. The later decreased mass signal is well consistent with the observations with Live/Dead cell staining (data not shown), which indicated that the cells treated with high doses of $H_2O_2$ undergo apoptosis—a process leading to the loss of cellular mass.

FIG. 82 showed the effect of src kinase modulators on the cell responses mediated with 1 mM $H_2O_2$. Results showed that two specific src kinase inhibitors, PP1 and PP2, significantly suppressed the $H_2O_2$-mediated cell responses, whereas the negative control, PP3, did not affect the responses. These suggested that Src kinase involves in the $H_2O_2$-mediated DMR signal; and optical biosensors can be used to screen modulators that affect ROS signaling.

FIG. 83 showed the effect of different redox states of quiescent A431 cells on the $H_2O_2$-mediated DMR signal. The different redox states were achieved by using different initial seeding numbers of cells in combination with different culturing time. The low redox cells was achieved by culturing 75,000 cells per well for 3 days culturing under normal conditions and subsequently overnight starvation with 0% fetal bovine serum (FBS), while the high redox cells was achieved by culturing 10,000 cells per well for 10 days culturing under normal conditions and subsequently overnight starvation with 0% FBS. The cell densities were similar (~95%), as examined with light microscopy. As shown in FIG. 83, two different redox states of cells responded to 4 mM $H_2O_2$ differently. $H_2O_2$ triggered a typical DMR signal for the low redox state of cells, which ultimately increased the mass within the bottom portion of cells. However, $H_2O_2$ at the same concentration mediated a DMR signal of the high redox state of cells with a characteristic of cells undergoing apoptosis (i.e., ultimately lost in mass within the cells). These results indicated that optical biosensors can be used to differentiate the redox states of cultured cells, and to screen modulators that affect the redox states of cells.

11. Example 11

Analysis of Multiple Optical Output Parameters for Cell Assays

Multiple optical output parameters were recorded in real time and in parallel for several well-studied cell responses and processes, including adhesion and spreading, detachment, as well as signaling of cells through EGFR or bradykinin $B_2$ receptor. These optical readouts include the shift in the incident angle, as well as three parameters defining the shape of the resonant peaks: intensity, PWHM and area. Because of its high sensitivity and information content, only $TM_0$ mode was used for all data collection and analysis.

a) The Shape of the $TM_0$ Peak

As shown in FIG. 31, the shape and position of the $TM_0$ peak for cultured CHO cells was found to be dependent on the cell confluency. As the cell confluency increases, the resonant peak shifts towards the direction of high incident angles. The PWHM value, a parameter defining the peak shape, also exhibited a dependence on the cell confluency (FIG. 31b). The PWHM value reached its maximum at the cell confluency of about 50%; the maximum PWHM was about 35% higher than those in the absence or presence of cell monolayer with high density above 75%. It is worthy noting that these data were obtained after cells became fully spread after ~2 days culturing in a growth medium.

The $TM_0$ peak of adherent CHO cells was also found to be sensitive to DMSO—a toxic compound when high doses are used. As shown in FIG. 32a, the shape and position of the $TM_0$ peak exhibited dynamic changes when proliferating cells, obtained in 10% FBS, was treated with 18% DMSO. After treated with DMSO, both the intensity and area of the peak increases throughout the time monitored (about 3 hours). However, the peak position (i.e., the incident angle) showed dynamic characteristics: the incident angle initially shifts towards an increase in mass (e.g., 25 min), and then a decrease in mass (e.g., 40 and 120 min). Similarly, the peak shape initially became broadened and showed a complicate fine structure (e.g., 25 min), and eventually became narrow (e.g., 40 and 120 min). The appearance of complicate peak structures has been used as an implication of large-scale irregular inhomogeneity of mass at or near the sensor surface, thus indicating that during certain period after treatment with DMSO, the biosensor senses the increased surface inhomogeneity. The live/dead staining pattern of CHO cells, obtained 25 min after the DMSO treatment, showed that there were mixed populations of cells: viable, dead and affected cells (FIG. 32b), implying that the CHO cells seem respond heterogeneously to the DMSO treatment. These results suggested that the shape of the $TM_0$ peak is useful to examine the heterogeneous lateral mass distribution within the sensing volume.

(b) Cell Adhesion and Spreading

The adhesion and spreading of cells at surfaces were well studied using optical imaging techniques, as well as optical biosensors such as SPR and RWG. Cells start to interact with a surface by initial contact or attachment where cells generally retain the round shape they possessed in suspension. Subsequently, attached cells undergo morphological changes known as spreading—a process that the cells increase their area in contact with the surface. Both attachment and spreading are dependent on the nature of the surface and of the medium in which the cells are suspended. Since cell adhesion and spreading obviously leads to both vertical and horizontal mass redistribution within the sensing volume, we first characterized the adhesion and spreading of A431 cells in 5% FBS in the absence and presence of vincristine. Vincristine is a plant alkaoid that inhibits microtubule assembly by binding to tubulin.

We studied the adhesion and spreading of A431 cells in 5% FBS in the absence and presence of vincristine at room temperature (25° C.). Results show that in the absence of vincristine, the shift in the incident angle exhibited three major phases (data not shown). Following the addition of cell solution, there is an immediate and rapid increased signal, which is probably resulted from three events: the increased bulk index from the addition of the cell solution, the immobilization of serum proteins onto the sensor surface, and the sedimentation of cells and subsequent contact of cells with the surface. Afterwards, a prolonged increased signal occurred, indicating the slow process of cell spreading. Ultimately a saturated level was reached. The saturated level (16.8±0.6 unit, n=3) was much lower than those of fully spread cells at similar density (22.6±1.0 unit, n=3). On the other hand, the normalized PWHM value was also found to be dynamic with distinct characteristics (data not shown). After the cell solution was added, the PWHM value started to increase. About 20 min later, the PWHM began to decay back to its original level within about 2 hours, followed by a slowly continuous increase until it reached a plateau. The PWHM at the endpoint was about 25% higher than that at the starting point, which indicated that the cells were still not fully spread, even after 20 hours assaying with the biosensor under ambient condition. This was confirmed by light microscopy images (data not shown). These results suggested that (i) at room temperature A431 cells seem not be able to reach optimal degree of adhesion; (ii) the cells interact with the surface through multiple steps, each has its own characteristics; and (iii) the spreading step clearly increases the mass within the sensing volume, which means increased contact of the cell with the surface.

The presence of 100 nM vincristine significantly altered the optical signatures. The presence of vincristine suppressed not only both the initial and total responses, but also reduced the kinetics of cell spreading (data not shown). The total change in the incident angle in the presence of vincristine was about 20% less than that in the absence of vincristine. Interestingly vincristine also altered the dynamic features of the PWHM value (data not shown). Unlike in the absence of vincristine, the PWHM initially decreased and remained low for about 3 hours, and subsequently increased until it reached a plateau, indicating that vincristine primarily affects the initial steps during the cell adhesion and spreading processes. These results suggested that the biosensor is not only able to provide insights for the interaction of cells with the surfaces, but also to differentiate compounds for their ability to alter cell adhesion and spreading processes.

(c) EGFR Signaling

As discussed above, rich information had been obtained through analysis of the modulation of the EGF-induced DMR signals by a variety of known modulators. Results showed that the DMR in quiescent A431 cells mediated by EGF required EGFR tyrosine kinase activity, actin polymerization, and dynamin activity, and mainly proceed through MEK. The optical signatures of EGFR signaling mediated by EGF using parallel multi-parameter measurements were characterized. As shown in FIG. 84a, the cell responses, as manifested by the angular shift, induced by high doses of EGF were particularly interesting. When stimulated with high doses of EGF above 32 nM, a novel phase of DMR signal was observed for quiescent A431 cells. Besides an initial rapid P-DMR with increased signal followed by a short transition phase and a long decay N-DMR with decreased signal, there is a partial recovery RP-DMR phase with increased signal before the cells ultimately reaches a plateau which exhibits similar level to those induced by either 16 nM or 32 nM. One possibility is that after stimulated with high doses of EGF the cells underwent a detachment process, followed by a partial re-attachment process.

Since EGF mediates asymmetric lateral redistribution of certain cellular targets such as PI3K that is important for EGF-induced cell migration, parameters defining the shape of the resonant peak were monitored in parallel. However, all three parameters seem to remain constant after stimulated with EGF at different doses (FIG. 85b; only the PWHM was presented), indicating that EGF stimulation does not increase inhomogeneity of lateral mass distribution within the bottom portion of cells. This is contradictory to the staining pattern of actin filaments with TR-phalloidin (FIGS. 85c and d). These images showed that EGF mediated significant rearrangement of actin filaments in lateral dimensions. The inability to detect any inhomogeneity of lateral mass redistribution triggered by EGF suggested that the asymmetric redistribution might mainly occur outside the sensing volume.

b) Bradykinin $B_2$ Receptor Signaling

Bradykinin $B_2$ receptor is a G protein-coupled receptor, and accounts for most of the physiological and pathophysiological action of bradykinin (BK). Bradykinin (BK) appears to act as a mediator of a wide variety of physiological and pathophysiological responses including mitogenic and antimitogenic effects. A431 cells endogenously express bradykinin $B_2$ receptor, but not $B_1$ receptor. Disclosed herein the optical signatures of quiescent A431 cells in response to BK stimulation were characterized, and it was found that A431 cells responded to BK stimulation with dynamic mass redistribution; its kinetics, amplitudes and duration depend on the cell culture conditions, the dose of BK, and the cellular context. As showed in FIG. 86, BK stimulation of quiescent A431 cells results in a rapid increase in PWHM, followed by a slow decay back to the original level, while the peak intensity gave rise to a dynamic response that is inverse to those of the PWHM and the angular shift. Furthermore, the changes in both parameters are also BK dose-dependent, and their dynamics and kinetics exhibited similarity to the DMR signals previously reported. These results suggested that compared to EGF-mediated cell responses, BK stimulation leads to more significant asymmetric redistribution of cellular contents, which, in turn, increases the inhomogeneity of lateral mass distribution within the bottom portion of cells.

In summary, the RWG biosensors provided rich information content for probing living cells. Theoretical analysis revealed that the optical signatures measured are integrated responses and can be used for readouts for examining cells in their native environments without the need of labels. Several cell responses and processes including adhesion and spreading, detachment and cell signaling through EGFR and bradykinin $B_2$ receptor had been investigated systematically. Parallel and kinetic measurements of multiple optical output parameters led to identification of unique signatures for stimulation-mediated dynamic mass redistribution in both vertical and lateral dimensions within the bottom portion of cells. Cell adhesion and spreading had been found to involve multiple steps; vincristine was found to be able to modulate the cell adhesion and spreading by interfering with its initial steps. Unexpectedly, EGF did not trigger obvious asymmetric lateral mass redistribution, at least within the bottom portion of cells This suggested that the EGF-induced asymmetric distribution of cellular contents, an important process for cell migration, occurs in the top portion of cells, rather than in the bottom portion of cells. However, increasing the penetration depth of the biosensor (such as reverses waveguide configuration) should be able to allow one to detect such lateral redistribution. Nonetheless, the multiparameter monitoring should add more dimensions that allow one to distinguish the cellular events induced by the stimulation.

Interestingly, the activation of $B_2$ receptor in A431 induced by bradykinin triggered both vertical and lateral mass redistribution.

12. Example 12

High Throughput Screening of Compounds Against Endogenous GPCRs Using Endpoint Measurements Disclosed are methods that are suitable for high throughput screening of compounds that modulate or effect one or more signaling pathways in a cell or cell proliferation or cell death. These high throughput methods are based on the understanding that the biosensor output data can be assessed using a number of different parameters, as discussed herein. And that particular cells or particular receptors within cells or particular cell events such as death or proliferation or modulation of a signaling pathway can have a particular signature, as discussed herein. This signature can be made up of one or more biosensor output parameters as discussed herein. Importantly for high throughput methods, it is important that the there be a time point during the method where the collection of the biosensor output parameter data will be diagnostic of the state of the cell, i.e., a signaling pathway was activated or deactivated or the cell has dies or the cell is proliferating. This point can be where there is a combination of biosensor output parameters that are used to define the signature.

The ligand-induced DMR signals typically proceed for a prolonged period of time (~tens of minutes). Thus kinetic measurements do not seem amenable for high throughput (HT) screening applications. However, based on the overall dynamics and well-characterized kinetics of the DMR signal induced by a particular ligand, one can readily develop endpoint measurements for HTS applications. Based on the optical signature of two GPCRs: bradykinin $B_2$ receptor in A431 cells, and protease activated receptor subtype 1 (PAR1) in CHO cells, two endpoint measurements were used to develop high throughput screening methods.

FIG. 86 showed the wavelength shift between two time points during the assay as a function of compounds. The two time points were right before the compound addition (the baseline point), and 5 minutes after the compound addition (the measured point). The difference between two endpoints reflects the total amplitude of the P-DMR event mediated by bradykinin—a bradykinin $B_2$ receptor agonist. The $B_2$ receptor is endogenously expressed in A431 cells. The cells become quiescent before the bradykinin stimulation. In this example, a 384 well Coring Epic biosensor plate was used. Each well contains A431 cells with a confluency of ~90%. Half of the wells were treated with bradykinin at 100 nM, whereas other half of the wells were treated with the buffer HBSS only. Results showed that cells treated with 100 nM bradykinin result in a total change in wavelength of about 800 pm, where the cells treated with HBSS buffer only respond with a much small amplitude (about −10 pm). The assay window is quite large (~810 pm), and assay variability is small (~6% in CV for the cells treated with bradykinin)

FIG. 87 showed the wavelength shift between two time points during the assay as a function of compounds. The two time points were right before the compound addition (the baseline point), and 5 minutes after the compound addition (the measured point). The difference between two endpoints reflects the total amplitude of the P-DMR event mediated by thrombin—a PAR1 receptor agonist. Here a different cell line—CHO cells was used. The PAR1 receptor is endogenously expressed in CHO cells. The cells become partially quiescent by culturing the cells in the DMEM medium for 4 hours before the thrombin stimulation. In this example, a 384 well Coring Epic biosensor plate was used. Each well contains CHO cells with a confluency of ~90%. Half of the wells were treated with thrombin at 40 unit/ml, whereas other half of the wells were treated with the buffer HBSS only. Since the agonist-induced activation of both $B_2$ in A431 and PAR1 in CHO cells leads to Gq signaling, the significance of this assay results is that the Gq-type optical signature is at least universal in both cell lines. By using similar endpoint measurements, one is able to screen GPCR modulators against different endogenous targets in different cells.

FIG. 88 showed the wavelength shift between two time points during the assay as a function of thrombin concentration. The two time points were right before the compound addition (the baseline point), and 5 minutes after the compound addition (the measured point). The CHO cells were treated with thrombin at different doses. Results showed that by using the endpoint measurements, the cells dose-dependently responded to thrombin stimulation, leading to an apparent $EC_{50}$ of 12.5 unit/ml. This assay results suggested that the endpoint measurements not only enable high throughput screening of GPCR modulators, but also enable the determination of agonism and the efficacies of GPCR agonists for endogeneous GPCRs in real physiological conditions Unlike conventional methods which assay a discrete cell response or a particular labeled target, the biosensor-based cell assay is applicable to large-scale and multiple target-based selection of potential ligands. Once a unique DMR signature is identified and linked to a particular signaling pathway through a specific class of target in a cell line at specific states, a library of compounds are screened. The compounds can be classified into distinct categories based on their optical signatures. Such a screen is useful for compound classification.

Alternatively, since a compound resulting in a given type of optical signature could be an agonist to a same class of endogenous receptors such as Gq-coupled receptors. The effect of preceding stimulation with such a compound on a receptor-specific agonist-induced DMR signal can be examined and used as an indication of target specificity. Such a screen is useful for target-based screening.

The identification of an appropriate lead structure is a key step in drug discovery. Once a lead structure is selected, the action of it on living cells can be studied systematically using the disclosed optical biosensors. For example, panels of well-known modulators of a set of targets in signaling pathways can be used to study the modulation profiles on the lead structure-induced DMR signal, thus linking the action of the lead structure to a specific target or a signaling pathway. Once the linkage is established, biosensors can then be used to optimize the lead structure. Since cell signaling through a target is complex, lead structures can be further optimized such that they only selectively modulate a specific oligomerization state of a receptor, or a specific pathway or a state of cells.

What is claimed is:

1. A method to test the effect of a stimulatory event on a cell comprising:
   providing a RWG (Resonant Wave Guide Grating) label-free biosensor system including a light source, and a label independent detector;
   incubating a cell on the biosensor, wherein the cell has a labeled molecule that is part of a signaling cascade;
   providing a stimulatory event to the incubated cell;
   collecting from within the cell, at the cell surface, or a combination thereof, the DMR (Directional Mass Redistribution) biosensor output from the biosensor;
   analyzing the DMR to determine the effect of the stimulatory event on the cell;
   detecting a change in the labeled molecule with a label detector; and
   dissecting the biological pathway of the stimulatory event induced DMR by the detected change in the labeled molecule,
   wherein the change in the labeled molecule is the concentration of the labeled molecule, the location of the labeled molecule, or a combination thereof.

2. The method of claim 1, wherein the label labeled molecule comprises a fluorescent label, a radioactive label, or a phosphorescent label.

3. The method of claim 1, wherein detecting the labeled molecule occurs simultaneously with collecting label-free biosensor output.

4. The method of claim 1, wherein the labeled molecule is a labeled protein, a labeled DNA, an organelle specific dye molecule, or a labeled analyte.

5. The method of claim 1, wherein the labeled molecule is excited using the same light source that is used to generate and detect the DMR signal, and the labeled molecule is detected with a separate emission detection device, when the label of the labeled molecule is a fluorescent or phosphorescent label.

6. The method of claim 1, wherein the labeled molecule is excited with an excitation light source different from the light source used to interrogate and detect the DMR signal, and the labeled molecule is detected with a separate emission detection device when the label is a fluorescent or phosphorescent label.

7. The method of claim 1, wherein the label of the labeled molecule is radioactive, and the label is detected with a radioactivity counter.

8. The method of claim 1, wherein detecting the labeled molecule with a label detector includes multiparameteric detection of the effect of the stimulatory event on the incubated cell.

9. A method of determining a state of a living cell having a labeled molecule comprising:
   observing the dynamic mass redistribution (DMR) of the cellular contents with a resonant waveguide grating biosensor system including a light source, and a label independent detector;
   observing a change in the labeled molecule with a label detector; and
   determining the state of the cell by comparing the characteristics of the DMR with the observed change in the labeled molecule,
   wherein the change in the labeled molecule is the concentration of the labeled molecule, the location of the labeled molecule, or a combination thereof.

* * * * *